United States Patent
Adams et al.

(10) Patent No.: US 11,161,819 B2
(45) Date of Patent: Nov. 2, 2021

(54) SUBSTITUTED TETRAHYDROISOQUINOLINE COMPOUNDS USEFUL AS GPR120 AGONISTS

(71) Applicant: Merck Sharp & Dohme Corp., Rahway, NJ (US)

(72) Inventors: Gregory L. Adams, Vincentown, NJ (US); Jason M. Cox, East Windsor, NJ (US); John S. Debenham, Scotch Plains, NJ (US); Scott Edmondson, Clark, NJ (US); Eric J. Gilbert, Scotch Plains, NJ (US); Yan Guo, Westfield, NJ (US); Yu Jiang, East Windsor, NJ (US); Hubert Josien, Jersey City, NJ (US); Hyunjin M. Kim, Livingston, NJ (US); Ping Lan, Plainsboro, NJ (US); Shouwu Miao, Edison, NJ (US); Christopher W. Plummer, Hoboken, NJ (US); Murali Rajagopalan, Edison, NJ (US); Unmesh Shah, Neshanic Station, NJ (US); Zhongxiang Sun, Princeton, NJ (US); Quang T. Truong, Morganville, NJ (US); Feroze Ujjainwalla, Hoboken, NJ (US); Francisco Velazquez, Clinton, NJ (US); Srikanth Venkatraman, Edison, NJ (US); Takao Suzuki, Shanghai (CN); Nengxue Wang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/935,565

(22) Filed: Jul. 22, 2020

(65) Prior Publication Data
US 2020/0347020 A1 Nov. 5, 2020

Related U.S. Application Data

(63) Continuation of application No. 16/096,710, filed as application No. PCT/US2017/033451 on May 19, 2017, now abandoned.

(30) Foreign Application Priority Data

May 25, 2016 (WO) ............... PCT/CN2016/083265

(51) Int. Cl.
| C07D 217/04 | (2006.01) |
| C07D 401/04 | (2006.01) |
| C07D 401/12 | (2006.01) |
| C07D 413/04 | (2006.01) |
| C07D 417/12 | (2006.01) |
| C07D 417/14 | (2006.01) |

(Continued)

(52) U.S. Cl.
CPC .......... *C07D 217/04* (2013.01); *A61K 9/4858* (2013.01); *A61K 31/472* (2013.01); *A61K 31/4725* (2013.01); *A61K 45/06* (2013.01); *A61P 3/04* (2018.01); *A61P 3/06* (2018.01); *A61P 3/10* (2018.01); *A61P 29/00* (2018.01); *C07D 217/22* (2013.01); *C07D 401/04* (2013.01); *C07D 401/06* (2013.01); *C07D 401/12* (2013.01); *C07D 413/04* (2013.01); *C07D 417/04* (2013.01); *C07D 417/06* (2013.01); *C07D 417/12* (2013.01); *C07D 417/14* (2013.01)

(58) Field of Classification Search
CPC .................................................... C07D 217/04
See application file for complete search history.

(56) References Cited

U.S. PATENT DOCUMENTS

| 4,717,724 A | 1/1988 | Schaper |
| 5,071,837 A | 12/1991 | Doherty et al. |

(Continued)

FOREIGN PATENT DOCUMENTS

| EP | 1113007 A1 | 7/2001 |
| WO | 2002046164 A1 | 6/2002 |

(Continued)

OTHER PUBLICATIONS

Wislicenus, J. "Adolph Strecker's Short Textbook of Organic Chemistry" 1881, Spottiswoode: London, pp. 38-39.*

(Continued)

*Primary Examiner* — David K O'Dell
(74) *Attorney, Agent, or Firm* — Baerbel R. Brown; Catherine D. Fitch

(57) ABSTRACT

The present invention relates to a compound represented by formula (I):

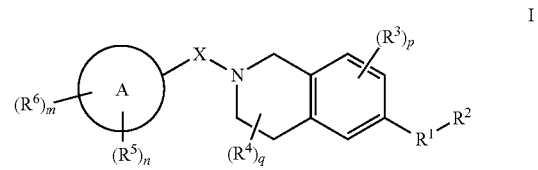

and pharmaceutically acceptable salts thereof are disclosed as useful for treating or preventing diabetes, hyperlipidemia, obesity, NASH, inflammation related disorders, and related diseases and conditions. The compounds are useful as agonists of the G-protein coupled receptor GPR120. Pharmaceutical compositions and methods of treatment are also included.

17 Claims, No Drawings

(51) Int. Cl.
*C07D 401/06* (2006.01)
*C07D 417/04* (2006.01)
*A61K 31/4725* (2006.01)
*C07D 417/06* (2006.01)
*C07D 217/22* (2006.01)
*A61K 45/06* (2006.01)
*A61K 31/472* (2006.01)
*A61K 9/48* (2006.01)
*A61P 3/04* (2006.01)
*A61P 3/06* (2006.01)
*A61P 3/10* (2006.01)
*A61P 29/00* (2006.01)

(56) References Cited

U.S. PATENT DOCUMENTS

| | | | |
|---|---|---|---|
| 5,089,471 | A | 2/1992 | Hanson et al. |
| 2005/0165049 | A1 | 7/2005 | Hulme et al. |
| 2007/0093515 | A1* | 4/2007 | Arrington ............... A61P 25/08 514/266.21 |
| 2009/0012097 | A1* | 1/2009 | Epple ........................ A61P 1/00 514/252.18 |
| 2009/0082389 | A1 | 3/2009 | Schnatterer |
| 2010/0216827 | A1 | 8/2010 | Ma et al. |
| 2015/0274672 | A1 | 10/2015 | Chelliah et al. |

FOREIGN PATENT DOCUMENTS

| | | | |
|---|---|---|---|
| WO | 2004103997 | A1 | 12/2004 |
| WO | 2005005392 | A1 | 1/2005 |
| WO | 2007022280 | A1 | 2/2007 |
| WO | 2007089557 | A2 | 8/2007 |
| WO | 2008109336 | A1 | 9/2008 |
| WO | 2009047240 | A1 | 4/2009 |
| WO | 2010048207 | A2 | 4/2010 |
| WO | 2013019682 | A1 | 2/2013 |
| WO | 2014059232 | A2 | 4/2014 |
| WO | 2014165815 | A2 | 10/2014 |
| WO | 2016001875 | A1 | 1/2016 |
| WO | 2016001876 | A1 | 1/2016 |
| WO | 2016109515 | A1 | 7/2016 |

OTHER PUBLICATIONS

American Chemical Society RN 1029720-61-3 Registry (STN) Jun. 22, 2008.
American Chemical Society RN 1458775-32-0 Registry (STN) Oct. 15, 2013.
American Chemical Society RN 1538454-34-0 Registry (STN) Feb. 6, 2014.
Buzard, Daniel, et a., Discovery and characterization of potent and selective 4-oxo-4-(5-(5-phenyl-1,2,4-oxadiazol-3-yl)indolin-1-yl)butanoic acids as S1P1 agonists, Bioorganic & Medicinal Chemistry Letters, 2011, p. 6013-6018, vol. 21.
Cintra, Dennys, E. et al., Unsaturated Fatty Acids Revert Diet-Induced Hypothalamic Inflammation in Obesity, PLoS ONE, 2012, p. 1-15, vol. 7, Issue 1.
Harris, Robert M. et al, The Fit for Purpose Development of SIP1 Receptor Agonist GSK2263167 Using a Robinson Annulation and Saegusa Oxidation to Access an Advanced Phenol Intermediate, Organic Process Research and Development, 2013, 1239-1246, 17.
Hirasawa, Akira, et al., Free fatty acids regulate gut incretin glucagon-like peptide-1 secretion through GPR120, Nature Medicine, 2005, p. 90-94, vol. 11, No. 1.
Ichimura, Atsuhiko, et al., Dysfunction of lipid sensor GPR120 leads to obesity in both mouse and human, Nature, 2012, p. 350-357, vol. 483.
International Search Report for PCT/CN2016083265 dated Feb. 17, 2017, 19 pages.
International Search Report for PCT/US2017/033451 dated Aug. 14, 2017, 12 pages.
Oh, Da Young, et al, GPR120 is an Omega-3 Fatty Acid Receptor Mediating Potent Anti-Inflammatory and Insulin Sensitizing Effects, Cell, 2010, p. 687-698, vol. 142, No. 5.
Online "http://www.chembridge.com/ordering/terms/" Jan. 9, 2013, 2 Pages.
Online "https://web.archive.org/web/20100109114027/http://www.allichemllc.com/services" dated Jan. 9, 2010, accessed Jan. 7, 2020.
Pubchem, Compound Molport-004-371-564, Create Date: May 28, 2009.
Pubchem, Compound-2-Phenyl-1,2,3,4-Tetrahydroisoquinoline, Create Date: Oct. 26, 2006.
Sawa, Yoichi, et al, 1,2,3,4-Tetrahydro-4, 4-dimethylisoquinoline Derivatives, Yakugaku Zasshi, 1976, 401-406, 96-4.
STN-Chemical database registry# RN 414885-04-4 entry for 1,2,3,4-Tetrahydro-2-[(3-methoxyphenyl)methyl] isoquinoline SR Chemical Library Supplier: Chem Bridge Corporation ED Entered STN: May 13, 2002, 1 page.
Talukdar, Saswata, et al., Targeting GPR120 an dother fatty acid-sensing GPCRs ameliorates insulin resistance and inflammatory diseases, Trends in Pharmacological Sciences, 2011, p. 543-550, vol. 32, No. 9.

* cited by examiner

SUBSTITUTED TETRAHYDROISOQUINOLINE COMPOUNDS USEFUL AS GPR120 AGONISTS

This application is a continuation of Application No. U.S. Ser. No. 16/096,710, filed Oct. 26, 2018, co-pending herewith, which is a U.S. National Phase application under 35 U.S.C. § 371 of PCT Application PCT/US17/033451, filed May 19, 2017, which claims priority from and the benefit of PCT Application PCT/CN16/083265, filed May 25, 2016.

BACKGROUND OF THE INVENTION

The present invention relates to substituted chromane derivatives that are useful in the pharmaceutical field. The compounds act as GPR120 receptor function regulating agents (modulators), which are useful as drugs for treating and/or preventing diabetes, obesity, hyperlipidemia, and inflammation related disorders.

GPR120, a G protein-coupled receptor, causes intracellular signaling through binding with unsaturated long chain fatty acids, such as alpha-linoleic acid, to induce various biological reactions. Actions of GPR120 and its ligand(s) have been reported to promote secretion of glucagon-like-peptide-1 ("GLP-1") functions to reduce blood glucose level in gastrointestinal cell lines (see Nature Medicine, 2005, 11(1), 90-94). GLP-1, which is a peptide hormone, has been found to induce insulin secretion depending on a blood glucose level. GLP-1 is also suggested to be efficacious for delaying the apoptosis of beta cells in type II diabetes mellitus.

GPR120 is expressed in adipocytes. GPR120 has been found to be increasingly expressed by adipose differentiation induction. In addition, actions of GPR120 and its ligand have been reported to suppress lipolysis in adipose-differentiated cells. A high blood lipid level is known to be one of the causes of insulin resistance. Suppression of lipolysis by a GPR120 agonist is thus expected to decrease the levels of free fatty acids in blood to normalize blood lipid levels, resulting in improvement in insulin resistance.

GPR120 is also expressed in the pituitary gland, and a GPR120 ligand is reported to suppress adrenocorticotropic hormone secretion. Adrenocorticotropic hormone promotes glucocorticoid secretion downstream thereof to induce action such as promotion of gluconeogenesis in the liver, inhibitory action against glucose uptake in muscle and peripheral tissue, lipolysis in adipose tissue or release of fatty acids or glycerol. Accordingly, GPR120 is considered to exhibit hypoglycemic action or blood lipid lowering action via suppression action against adrenocorticotropic hormone secretion even in the center.

Recently, GPR120 has been shown to play a role in obesity in both mice and humans. GPR120 knockout mice fed a high fat diet developed obesity; glucose intolerance and fatty liver with decreased adipocyte differentiation and lipogenesis and enhanced hepatic lipogenesis. In the study, insulin resistance in such mice was associated with reduced insulin signaling and enhanced inflammation in adipose tissue. In humans, GPR120 expression in adipose tissue is significantly higher in obese individuals than in lean controls (See Ichimura, et al., Nature, 2012, 483, 350-54; and Cintra, et al., Plos One, 2012, 7(1), 1-15).

GPR120 has also been shown to play a role in inflammation. Wild-type mice treated with omega-3 fatty acids inhibited macrophage-induced tissue inflammation and enhanced systemic insulin sensitivity. However, this effect was not observed in GPR120 knockout mice (See Oh, et al., Cell, 2010, 142, 687; and Talukar, et al., Trends in Pharmacological Sciences, 2011, 32 (9), 543-550).

In light of the above description, a compound having GPR120 agonist activity is considered to be useful as an agent for treating and/or preventing diabetes mellitus, obesity, hyperlipidemia, fatty liver (including non-alcoholic steatohepatitis or NASH), and inflammation related disorders.

SUMMARY OF THE INVENTION

The present invention relates to compounds represented by formula I:

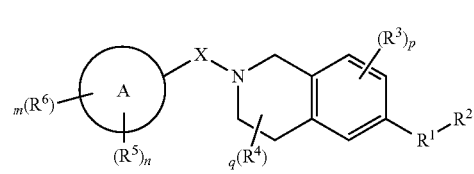

as well as pharmaceutically acceptable salts thereof, and pharmaceutical compositions comprising a compound of formula I.

The present invention further relates to methods of treating diabetes, obesity, hyperlipidemia, NASH, inflammation related disorders, and related diseases and conditions, comprising administering a compound of formula I to a patient in need thereof.

DETAILED DESCRIPTION OF THE INVENTION

The present invention relates to compounds represented by formula I:

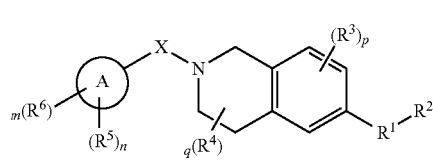

or a pharmaceutically acceptable salt thereof, wherein:
X is
  (1) bond,
  (2) $(C_{1-2})$alkyl, or
  (3) halo$(C_{1-2})$alkyl;
ring A is
  (1) aryl,
  (2) 5- or 6-membered heteroaryl containing 1, 2, or 3 heteroatoms independently selected from N, O and S, or
  (3) 9- or 10-membered fused heteroaryl containing 1, 2, or 3 heteroatoms independently selected from N, O, and S;
$R^1$ is
  (1) bond,
  (2) $(C_{1-6})$alkyl,
  (3) —O—$(C_{1-6})$alkyl-, or
  (4) $(C_{3-6})$cycloalkyl,
$R^2$ is
  (1) hydrogen,
  (2) hydroxy, (3) COOH,
(4) tetrazole,
(5) hydroxyisoxazole,
(6) triazole,
(7) C(O)NH$_2$,
(8) C(O)NHC
(9) C(O)NHC$_{3-6}$cycloalkyl,
(10) C(O)NHC$_{2-5}$cycloheteroalkyl,
(11) C(O)NH-aryl,
(12) C(O)NH-heteroaryl,
(13) SO$_2$C$_{1-6}$alkyl,
(14) SO$_2$C$_{3-6}$cycloalkyl,
(15) SO$_2$C$_{2-5}$cycloheteroalkyl,
(16) SO$_7$-aryl, or
(17) SO$_2$-heteroaryl $R^3$ is
(1) hydrogen,
(2) halogen.
(3) cyano, or
(4) (C$_{1-3}$)alkyl;

$R^4$ is
(1) hydrogen,
(2) (C$_{1-3}$)alkyl,
(3) halo(C$_{1-3}$)alkyl, or
(4) halogen;

R is
(1) cyano,
(2) (C$_{1-3}$)alkyl,
(3) halo(C$_{1-3}$)alkyl,
(4) (C$_{1-3}$)alkoxy,
(5) halo(C$_{1-3}$)alkoxy, or
(6) halogen;

$R^6$ is
(1) (C$_{1-3}$)alkoxy,
(2) halo(C$_{1-3}$)alkoxy,
(3) halo(C$_{1-3}$)alkyl,
(4) (C$_{3-6}$)cycloalkyl,
(5) (C$_{3-6}$)cycloalkyl-O—,
(6) (C$_{3-6}$)cycloalkyl-S—,
(7) (C$_{3-6}$)cycloalkyl-(C$_{1-2}$)alkyl-,
(8) (C$_{3-6}$)cycloalkyl-halo(C$_{1-2}$)alkyl-,
(9) phenyl,
(10) 5- to 6-membered heteroaryl-O— wherein the heteroaryl contains 1, 2, or 3 heteroatoms independently selected from N, O and S, or
(11) 5- to 6-membered heteroaryl- wherein the heteroaryl contains 1, 2, or 3 heteroatoms independently selected from N, O and S, wherein alkyl, cycloalkyl, phenyl and heteroaryl are unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halogen;
n is 0, 1, 2 or 3;
m is 0 or 1;
p is 0, 1, 2 or 3; and
q is 0; 1, or 2.

In one embodiment of the present invention, X is a bond, (C$_{1-2}$)alkyl, or halo(C$_{1-2}$)alkyl.

In another embodiment of the present invention, X is a bond, or (C$_{1-2}$)alkyl.

In another embodiment of the present invention, X is a bond, or CH$_2$.

In another embodiment of the present invention, X is a bond.

In another embodiment of the present invention, X is CH$_2$.

In another embodiment of the present invention, ring A is aryl, 5- or 6-membered heteroaryl containing 1, 2, or 3 heteroatoms independently selected from N, O and S, or 9- or 10-membered fused heteroaryl containing 1, 2, or 3 heteroatoms independently selected from N, O, and S. In a class of this embodiment, ring A is phenyl, pyridine, pyrimidine, pyrazole, pyrazine, isothiaozole, or benzisoxazole.

In another embodiment, ring A is 5- or 6-membered heteroaryl containing 1, 2, or 3 heteroatoms independently selected from N, O and S, or 9- or 10-membered fused heteroaryl containing 1, 2, or 3 heteroatoms independently selected from N, O, and S. In a class of this embodiment, ring A is pyridine, pyrimidine, pyrazole, pyrazine, isothiaozole, or benzisoxazole.

In another embodiment, ring A is 5- or 6-membered heteroaryl containing 1, 2, or 3 heteroatoms independently selected from N, O and S. In a class of this embodiment, ring A is pyridine, pyrimidine, pyrazole, pyrazine, or isothiaozole.

In another embodiment, ring A is 9- or 10-membered fused heteroaryl containing 1, 2, or 3 heteroatoms independently selected from N, O, and S. In a class of this embodiment, ring A is benzisoxazole.

In another embodiment, ring A is aryl. In a class of this embodiment, ring A is phenyl.

In another embodiment of the present invention, $R^1$ is a bond, (C$_{1-6}$)alkyl, —O—(C$_{1-6}$)alkyl-, or (C$_{3-6}$)cycloalkyl. In a class of this embodiment, $R^1$ is a bond, CH$_2$CH$_2$, CH$_2$CH$_2$CH$_2$, CH(CH$_3$)CH$_2$, CH$_2$CH(CH$_3$), CH$_2$CH$_2$CH$_2$CH$_2$, CH(CH$_3$)CH$_2$CH$_2$CH$_2$, OCH$_2$CH$_2$, OCH$_2$CH$_2$CH$_2$, OCH$_2$CH$_2$CH$_2$CH$_2$, or cycloalkyl.

In another embodiment of the present invention, $R^1$ is a bond, —O—(C$_{1-6}$)alkyl-, or (C$_{3-6}$)cycloalkyl. In a class of this embodiment, $R^1$ is a bond, OCH$_2$CH$_2$. OCH$_2$CH$_2$CH$_2$, OCH$_2$CH$_2$CH$_2$CH$_2$, or cycloalkyl.

In another embodiment of the present invention, $R^1$ is a bond.

In another embodiment of the present invention, $R^1$ is —O—(C$_{1-6}$)alkyl-, or (C$_{3-6}$)cycloalkyl. In a class of this embodiment, $R^1$ is OCH$_2$CH$_2$, OCH$_2$CH$_2$CH$_2$, OCH$_2$CH$_2$CH$_2$CH$_2$, or cycloalkyl.

In another embodiment of the present invention, $R^1$ is —O—(C$_{1-6}$)alkyl-. In a class of this embodiment, $R^1$ is OCH$_2$CH$_2$, OCH$_2$CH$_2$CH$_2$, or OCH$_2$CH$_2$CH$_2$CH$_2$.

In another embodiment of the present invention, $R^1$ is (C$_{3-6}$)cycloalkyl. In a class of this embodiment, $R^1$ is cyclopropyl.

In another embodiment of the present invention, $R^1$ is (C$_{1-6}$)alkyl. In a class of this embodiment, $R^1$ is CH$_2$CH$_2$, CH$_2$CH$_2$CH$_2$, CH(CH$_3$)CH$_2$, CH$_2$CH(CH$_3$), CH$_2$CH$_2$CH$_2$CH$_2$, or CH(CH$_3$)CH$_2$CH$_2$CH$_2$.

In another embodiment of the present invention, $R^1$ is a bond,

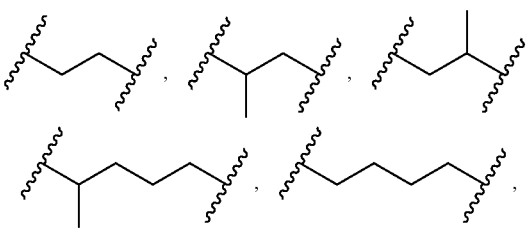

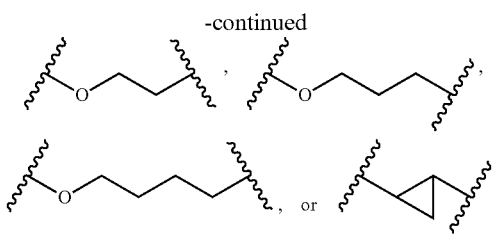

In another embodiment of the present invention, $R^2$ is hydrogen, hydroxy, COOH, tetrazole, hydroxyisoxazole, triazole, C(O)NH$_2$,C(O)NHC$_{1-6}$alkyl, C(O)NHC$_{3-6}$cycloalkyl, C(O)NHC$_{2-5}$cycloheteroalkyl, C(O)NH-aryl, C(O)NH-heteroaryl, SO$_2$C$_{1-6}$alkyl, SO$_2$C$_{3-6}$cycloalkyl, SO$_2$C$_{2-5}$cycloheteroalkyl, SO$_2$-aryl, or SO$_2$-heteroaryl.

In another embodiment of the present invention, $R^2$ is hydrogen, hydroxy, COOH, tetrazole, hydroxyisoxazole, or triazole.

In another embodiment of the present invention, $R^2$ is hydrogen, hydroxy, COOH, or tetrazole.

In another embodiment of the present invention, $R^2$ is hydrogen, hydroxy, or tetrazole.

In another embodiment of the present invention, $R^2$ is hydrogen.

In another embodiment of the present invention, $R^2$ is hydroxyl.

In another embodiment of the present invention, $R^2$ is tetrazole.

In another embodiment of the present invention, $R^2$ is COOH.

In another embodiment of the present invention, $R^3$ is hydrogen, halogen, cyano, or (C$_{1-3}$)alkyl. In a class of this embodiment, $R^3$ is hydrogen, F, Cl, cyano, or CH$_3$.

In another embodiment of the present invention, $R^3$ is hydrogen, halogen, or (C$_{1-3}$)alkyl.

In a class of this embodiment, $R^3$ is hydrogen, F, Cl, or CH$_3$.

In another embodiment of the present invention, $R^3$ is hydrogen, or halogen. In a class of this embodiment, $R^3$ is hydrogen, F, or Cl. In another class of this embodiment, $R^3$ is hydrogen, or F.

In another embodiment of the present invention, $R^4$ is hydrogen, (C$_{1-3}$)alkyl, halo(C$_{1-3}$)alkyl, or halogen.

In another embodiment of the present invention, $R^4$ is hydrogen, or (C$_{1-3}$)alkyl. In a class of this embodiment, $R^4$ is hydrogen, or CH$_3$.

In another embodiment of the present invention, $R^4$ is (C$_{1-3}$)alkyl. In a class of this embodiment, $R^4$ is CH$_3$.

In another embodiment of the present invention, $R^4$ is hydrogen.

In another embodiment of the present invention, $R^5$ is cyano, (C$_{1-3}$)alkyl, halo(C$_{1-3}$)alkyl, (C$_{1-3}$)alkoxy, halo(C$_{1-3}$)alkoxy, or halogen.

In another embodiment of the present invention, $R^5$ is cyano, (C$_{1-3}$)alkyl, halo(C$_{1-3}$)alkyl, (C$_{1-3}$)alkoxy, or halogen. In a class of this embodiment, $R^5$ is cyano, CH$_3$, CF$_3$, CHF$_2$, OCH$_3$, F, or Cl.

In another embodiment of the present invention, $R^5$ is cyano or halogen. In a class of this embodiment, $R^5$ is cyano, F, or Cl.

In another embodiment of the present invention, $R^6$ is halo(C$_{1-3}$)alkoxy, halo(C$_{1-3}$)alkyl, (C$_{3-6}$)cycloalkyl, (C$_{3-6}$)cycloalkyl-O—, (C$_{3-6}$)cycloalkyl-S—, (C$_{3-6}$)cycloalkyl-(C$_{1-2}$)alkyl-, phenyl, 5- to 6-membered heteroaryl-O— wherein the heteroaryl contains 1, 2, or 3 heteroatoms independently selected from N, O and S, or 5- to 6-membered heteroaryl- wherein the heteroaryl contains 1, 2, or 3 heteroatoms independently selected from N, O and S, wherein alkyl, cycloalkyl, phenyl and heteroaryl are unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halogen. In a class of this embodiment of the present invention, $R^6$ is OCF$_3$, CF$_3$, cyclopropyl, cyclobutyl-O—, cyclobutyl-S—, cyclobutyl-CH$_2$—, phenyl, thiazolyl-O—, pyridyl-O—, pyrazinyl-O—, or thienyl, wherein cyclopropyl, cyclobutyl, phenyl, thiazolyl, pyridyl, pyrazinyl and thienyl are unsubstituted or substituted with 1-3 substituents selected from OCH$_3$, CHF$_2$, CH$_3$, F, and Cl.

In another embodiment of the present invention, $R^6$ is (C$_{3-6}$)cycloalkyl, (C$_{3-6}$)cycloalkyl-O—, (C$_{3-6}$)cycloalkyl-S—, (C$_{3-6}$)cycloalkyl-(C$_{1-2}$)alkyl-, phenyl, 5- to 6-membered heteroaryl-O— wherein the heteroaryl contains 1, 2, or 3 heteroatoms independently selected from N, O and S, or 5- to 6-membered heteroaryl- wherein the heteroaryl contains 1, 2, or 3 heteroatoms independently selected from N, O and S, wherein cycloalkyl, phenyl and heteroaryl are unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halogen. In a class of this embodiment of the present invention, $R^6$ is cyclopropyl, cyclobutyl-O—, cyclobutyl-S—, cyclobutyl-CH$_2$—, phenyl, thiazolyl-O—, pyridyl-O—, pyrazinyl-O—, or thienyl, wherein cyclopropyl, cyclobutyl, phenyl, thiazolyl, pyridyl, pyrazinyl and thienyl are unsubstituted or substituted with 1-3 substituents selected from OCH$_3$, CHF$_2$, CH$_3$, F, and Cl.

In another embodiment of the present invention, $R^6$ is halo(C$_{1-3}$)alkoxy, or halo(C$_{1-3}$)alkyl, wherein alkyl is unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halo. In a class of this embodiment, $R^6$ is halo(C$_{1-3}$)alkoxy, or halo(C$_{1-3}$)alkyl. In another class of this embodiment, $R^6$ is OCF$_3$, or CF$_3$.

In another embodiment of the present invention, $R^6$ is (C$_{3-6}$)cycloalkyl-O—, wherein cycloalkyl is unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halogen. In a class of this embodiment, $R^6$ is cyclobutyl-O—, wherein cycloalkyl is unsubstituted or substituted with 1-3 substituents selected from OCH$_3$, CHF$_2$, CH$_3$, F, and Cl. In another class of this embodiment, $R^6$ is cyclobutyl-O—, wherein cycloalkyl is unsubstituted or substituted with 1-3 substituents selected from OCH$_3$.

In another embodiment of the present invention, $R^6$ is

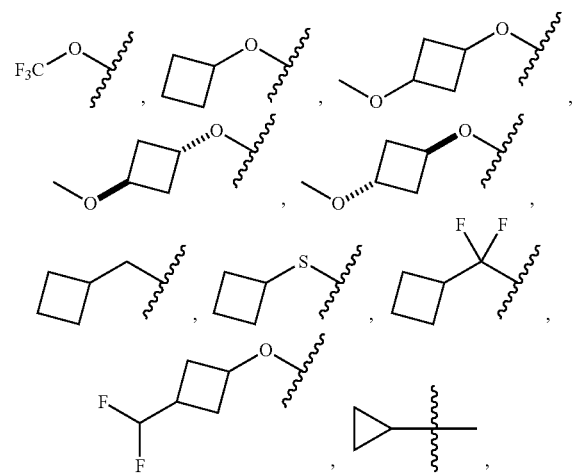

-continued

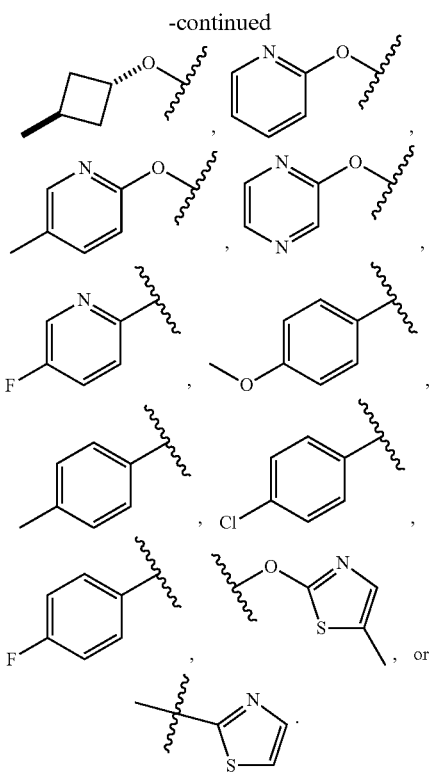

In another embodiment of the present invention, n is 0, 1, 2 or 3. In a class of this embodiment, n is 1, 2 or 3. In another class of this embodiment, n is 0, 1, or 2. In another class of this embodiment, n is 1, 2 or 3. In another class of this embodiment, n is 0, 1 or 2. In another class of this embodiment, n is for 3. In another class of this embodiment, n is 0. In another class of this embodiment, n is 1. In another class of this embodiment, n is 2. In another class of this embodiment, n is 3.

In another embodiment of the present invention, m is 0 or 1. In a class of this embodiment, in is 0. In another class of this embodiment, m is 1.

In another embodiment of the present invention, p is 0, 1, 2 or 3. In a class of this embodiment, p is 1, 2 or 3. In another class of this embodiment, p is 0, 1, or 2. In another class of this embodiment, p is 0 or 2. In another class of this embodiment, p is 1 or 2. In another class of this embodiment, p is 0 or 1. In another class of this embodiment, p is 0. In another class of this embodiment, p is 1. In another class of this embodiment, p is 2. In another class of this embodiment, p is 3.

In another embodiment of the present invention, q is 0, or 2. In a class of this embodiment, q is 0 or 1. In another class of this embodiment, q is 1 or 2. In another class of this embodiment, q is 0 or 2. In another class of this embodiment, q is 0. In another class of this embodiment, q is 1. In another class of this embodiment, q is 2.

In one embodiment, ring A is phenyl, pyridinyl, pyrimidinyl, pyrazinyl, pyrazolyl, thiazolyl, isoxazolyl, or benzo[d]isoxazolyl. In a class of this embodiment, ring A is pyrimidinyl, pyridinyl, pyrazinyl, thiazolyl, isoxazolyl, pyrrolyl, or pyrazolyl, or benzo[d]isoxazolyl. In another class of this embodiment, ring A is pyridinyl, pyrazinyl, thiazolyl, isoxazolyl, pyrrolyl, or pyrazolyl, or benzo[d]isoxazolyl. In another class of this embodiment, ring A is pyridinyl, pyrazinyl, thiazolyl, isoxazolyl, pyrrolyl, or pyrazolyl. In another class of this embodiment, ring A is benzo[d]isoxazolyl. In another class of this embodiment, ring A is phenyl. In another class of this embodiment, ring A is pyrimidinyl. In another class of this embodiment, ring A is pyridinyl. In another class of this embodiment, ring A is pyrazinyl. In another embodiment, ring A is pyrazolyl. In another embodiment, ring A is thiazolyl. In another embodiment, ring A is isoxazolyl. In another embodiment, ring A is benzo[d]isoxazolyl.

In one class of this embodiment, $R^2$ is hydrogen.

In one subclass of this class, $R^1$ is a bond. In one sub-subclass of this subclass, X is a bond. In one sub-subclass of this subclass, X is $(C_{1-2})$alkyl.

In one subclass of this class, $R^1$ is $(C_{1-6})$alkyl. In one sub-subclass of this subclass, X is a bond. In one sub-subclass of this subclass, X is $(C_{1-2})$alkyl.

In one subclass of this class, $R^1$ is —O—$(C_{1-6})$alkyl-. In one sub-subclass of s subclass, X is a bond. In one sub-subclass of this subclass, X is $(C_{1-2})$alkyl.

In one subclass of this class, $R^1$ is $(C_{3-6})$cycloalkyl. In one sub-subclass of this subclass, X is a bond. In one sub-subclass of this subclass, X is $(C_{1-2})$alkyl.

In one subclass of this class, $R^1$ is $(C_{1-6})$alkyl or —O—$(C_{1-6})$alkyl-. In one sub-subclass of this subclass, X is a bond. In one sub-subclass of this subclass, X is $(C_{1-2})$alkyl.

In one class of this embodiment, $R^2$ is hydroxy.

In one subclass of this class, $R^1$ is a bond. In one sub-subclass of this subclass, X is a bond. In one sub-subclass of this subclass, X is $(C_{1-2})$alkyl.

In one subclass of this class, $R^1$ is $(C_{1-6})$alkyl. In one sub-subclass of this subclass, X is a bond. In one sub-subclass of this subclass, X is $(C_{1-2})$alkyl.

In one subclass of this class, $R^1$ is —O—$(C_{1-6})$alkyl-. In one sub-subclass of this subclass, X is a bond. In one sub-subclass of this subclass, X is $(C_{1-2})$alkyl.

In one subclass of this class, $R^1$ is $(C_{3-6})$cycloalkyl. In one sub-subclass of this subclass, X is a bond. In one sub-subclass of this subclass, X is $(C_{1-2})$alkyl.

In one subclass of this class, $R^1$ is $(C_{1-6})$alkyl or —O—$(C_{1-6})$alkyl-. In one sub-subclass of this subclass, X is a bond. In one sub-subclass of this subclass, X is $(C_{1-2})$alkyl.

In one class of this embodiment, $R^2$ is COOH.

In one subclass of this class, $R^1$ is $(C_{1-6})$alkyl. In one sub-subclass of this subclass, X is a bond. In one sub-subclass of this subclass, X is a bond.

In one subclass of this class, $R^1$ is ethyl. In one sub-subclass of this subclass, X is a bond. In one sub-subclass of this subclass, X is a bond.

In one subclass of this class, $R^1$ is a bond. In one sub-subclass of this subclass, X is a bond. In one sub-subclass of this subclass, X is $(C_{1-2})$alkyl.

In one subclass of this class, $R^1$ is $(C_{1-6})$alkyl. In one sub-subclass of this subclass, X is a bond. In one sub-subclass of this subclass, X is $(C_{1-2})$alkyl.

In one subclass of this class, $R^1$ is —O—$(C_{1-6})$alkyl-. In one sub-subclass of this subclass, X is a bond. In one sub-subclass of this subclass, X is $(C_{1-2})$alkyl, In one subclass of this class, $R^1$ is $(C_{3-6})$cycloalkyl. In one sub-subclass of this subclass, X is a bond. In one sub-subclass of this subclass, X is $(C_{1-2})$alkyl.

In one subclass of this class, $R^1$ is $(C_{1-6})$alkyl or —O—$(C_{1-6})$alkyl-. In one sub-subclass of this subclass, X is a bond. In one sub-subclass of this subclass, X is $(C_{1-2})$alkyl, In one class of this embodiment, $R^2$ is hydroxyisoxazole or triazole. In one class of this embodiment, $R^2$ is hydroxyisoxazole. In one class of this embodiment, $R^2$ is triazole.

In one class of this embodiment, R² is C(O)NH₂, C(O)NHC₁₋₆alkyl, C(O)NHC₃₋₆cycloalkyl, C(O)NHC₂₋₅cycloheteroalkyl, C(O)NH-aryl, C(O)NH-heteroaryl, SO₂C₁₋₆alkyl, SO₂C₃₋₆cycloalkyl, SO₂C₂₋₅cycloheteroalkyl, SO₂-aryl, or SO₂-heteroaryl.

In one subclass of this class, R¹ is a bond. In one sub-subclass of this subclass, X is a bond. In one sub-subclass of this subclass, X is (C₁₋₂)alkyl.

In one subclass of this class, R¹ is (C₁₋₆)alkyl. In one sub-subclass of this subclass, X is a bond. In one sub-subclass of this subclass, X is (C₁₋₂)alkyl.

In one subclass of this class, R¹ is —O—(C₁₋₆)alkyl-. In one sub-subclass of this subclass, X is a bond. In one sub-subclass of this subclass, X is (C₁₋₂)alkyl, In one subclass of this class, R¹ is (C₃₋₆)cycloalkyl. In one sub-subclass of this subclass, X is a bond. In one sub-subclass of this subclass, X is (C₁₋₂)alkyl.

In one class of this embodiment, R² is C(O)NH₂, C(O)NHC₁₋₆alkyl, C(O)NHcyclopropyl, C(O)NH-cyclobutyl, C(O)NH-cyclopentyl, C(O)NH-cyclohexyl, C(O)NH-oxetane, C(O)NH-tetrahydrofuran, C(O)NH-tetrahydropyran, C(O)NH-pyrrolidine, C(O)NH-piperidine, C(O)NH-phenyl, C(O)NH-thiazole, C(O)NH-oxazole, C(O)NH-imidazole, C(O)NH-furan, C(O)NH-thiophene, C(O)NH-pyridine, C(O)NH-pyrazine, C(O)NH-pyrimidine, SO₂C₁₋₆alkyl, SO₂cyclopropyl, SO₂cyclobutyl, SO₂cyclopentyl, SO₂-oxetane, SO₂-tetrahydrofuran, SO₂-tetrahydropyran, SO₂-pyrrolidine, SO₂-piperidine, SO₂-phenyl, SO₂-thiazole, SO₂-oxazole, SO₂-imidazole, SO₂-furan, SO₂-thiophene, SO₂-pyridine, SO₂-pyrazine or SO₂-pyrimidine.

In one subclass of this class, R¹ is a bond. In one sub-subclass of this subclass, X is a bond. In one sub-subclass of this subclass, X is (C₁₋₂)alkyl.

In one subclass of this class, R¹ is (C₁₋₆)alkyl. In one sub-subclass of this subclass, X is a bond. In one sub-subclass of this subclass, X is (C₁₋₂)alkyl.

In one subclass of this class, R¹ is —O—(C₁₋₆)alkyl-. In one sub-subclass of this subclass, X is a bond. In one sub-subclass of this subclass, X is (C₁₋₂)alkyl.

In one subclass of this class, R¹ is (C₃₋₆)cycloalkyl. In one sub-subclass of this subclass, X is a bond. In one sub-subclass of this subclass, X is (C₁₋₂)alkyl, In one subclass of this class, R¹ is (C₁₋₆)alkyl or —O—(C₁₋₆)alkyl-. In one sub-subclass of this subclass, X is a bond. In one sub-subclass of this subclass, X is (C₁₋₂)alkyl, In one class of this embodiment, R² is hydrogen, hydroxy, COOH or tetrazole. In one subclass of this embodiment, R² is hydroxy, COOH or tetrazole.

In one subclass of this class, R¹ is a bond. In one sub-subclass of this subclass, X is a bond. In one sub-subclass of this subclass, X is (C₁₋₂)alkyl.

In one subclass of this class, R¹ is (C₁₋₆)alkyl. In one sub-subclass of this subclass, X is a bond. In one sub-subclass of this subclass, X is (C₁₋₂)alkyl.

In one subclass of this class, R¹ is —O—(C₁₋₆)alkyl-. In one sub-subclass of this subclass, X is a bond. In one sub-subclass of this subclass, X is (C₁₋₂)alkyl.

In one subclass of this class, R¹ is (C₃₋₆)cycloalkyl. In one sub-subclass of this subclass, X is a bond. In one sub-subclass of this subclass, X is (C₁₋₂)alkyl.

In one subclass of this class, R¹ is (C₁₋₆)alkyl or —O—(C₁₋₆)alkyl-. In one sub-subclass of this subclass, X is a bond. In one sub-subclass of this subclass, X is (C₁₋₂)alkyl.

In one class of this embodiment, R² is COOH or tetrazole.

In one subclass of this class, R¹ is a bond. In one sub-subclass of this subclass, X is a bond. In one sub-subclass of this subclass, X is (C₁₋₂) alkyl.

In one subclass of this class, R¹ is (C₁₋₆)alkyl. In one sub-subclass of this subclass, X is a bond. In one sub-subclass of this subclass, X is (C₁₋₂)alkyl.

In one subclass of this class, R¹ is —O—(C₁₋₆)alkyl-. In one sub-subclass of this subclass, X is a bond. In one sub-subclass of this subclass, X is (C₁₋₂)alkyl.

In one subclass of this class, R¹ is (C₃₋₆)cycloalkyl. In one sub-subclass of this subclass, X is a bond. In one sub-subclass of this subclass, X is (C₁₋₂)alkyl.

In one subclass of this class, R¹ is (C₁₋₆)alkyl or —O—(C₁₋₆)alkyl-. In one sub-subclass of this subclass, X is a bond. In one sub-subclass of this subclass, X is (C₁₋₂)alkyl.

In one embodiment, R¹ is a bond.

In one embodiment, R² is hydrogen. In one class of this embodiment, R¹ is a bond. In one class of this embodiment, R¹ is (C₁₋₆)alkyl. In one class of this embodiment, R¹ is —O—(C₁₋₆)alkyl-. In one class of this embodiment, R¹ is (C₃₋₆)cycloalkyl.

In one embodiment. R² is hydroxy. In one class of this embodiment, R¹ is a bond. In one class of this embodiment, R¹ is (C₁₋₆)alkyl. In one class of this embodiment, R¹ is —O—(C₁₋₆)alkyl-. In one class of this embodiment, R¹ is (C₃₋₆)cycloalkyl.

In one embodiment, R² is COOH. In one class of this embodiment, R¹ is a bond. In one class of this embodiment, R¹ is (C₁₋₆)alkyl. In one class of this embodiment, R¹ is —O—(C₁₋₆)alkyl-. In one class of this embodiment, R¹ is (C₃₋₆)cycloalkyl.

In one class of this embodiment, R² is hydroxyisoxazole or triazole. In one class of this embodiment, R² is hydroxyisoxazole. In one class of this embodiment, R² is triazole, In one class of this embodiment, R² is tetrazolyl. In one subclass of this class, R¹ is a bond. In one subclass of this class, R¹ is (C₁₋₆)alkyl. In one subclass of this class, R¹ is —O—(C₁₋₆)alkyl-. In one subclass of this class, R¹ is (C₃₋₆)cycloalkyl.

In one embodiment, R² is hydrogen, hydroxy, COOH, or tetrazotyl. In one class of this embodiment, R¹ is a bond,

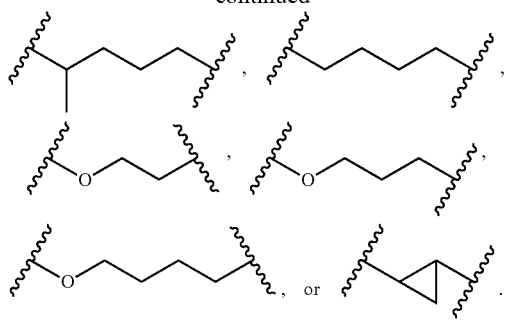

In one embodiment, X is bond, $(C_{1-2})$alkyl, or halo(C1-2)alkyl. In one embodiment, X is bond, or $CH_2$.

In one embodiment, $R^2$ is hydrogen, hydroxy, COOH, or tetrazole. In one embodiment, $R^2$ is hydroxy, COOH, or tetrazole. In one embodiment, $R^2$ is COOK or tetrazole. In one embodiment, $R^2$ is COOH. In one embodiment, $R^2$ is tetrazole.

In one embodiment, $R^3$ is hydrogen, halo, cyano, or $(C_{1-3})$alkyl. In one embodiment, $R^3$ is hydrogen, fluoro, chloro, or methyl. In one class of this embodiment, $R^3$ is hydrogen. In one class of this embodiment, $R^3$ is fluoro. In one class of this embodiment, $R^3$ is chloro. In one class of this embodiment, $R^3$ is fluoro or chloro. In one class of this embodiment, $R^3$ is methyl.

In one embodiment, $R^3$ is hydrogen, F or $CH_3$.

In one embodiment $R^4$ is hydrogen, $(C_{1-3})$alkyl, halo $(C_{1-3})$alkyl, or halo. In one embodiment $R^4$ is hydrogen, or $R^4$ is $(C_{1-3})$alkyl. In one embodiment $R^4$ is hydrogen, or $CH_3$. In one embodiment, $R^4$ is hydrogen. In one embodiment, $R^4$ is $(C_{1-3})$alkyl. In one embodiment, $R^4$ is halo $(C_{1-3})$alkyl. In one embodiment, $R^4$ is halo. In one embodiment, $R^4$ is hydrogen, fluoro, or methyl. In one embodiment $R^4$ is hydrogen.

In one embodiment, $R^5$ is cyano, $(C_{1-3})$alkoxy, halo $(C_{1-3})$alkyl, $(C_{1-3})$alkoxy, halo$(C_{1-3})$alkoxy, or halo. In one embodiment, $R^5$ is —CN, —$CF_3$, —$CHF_2$, —$OCF_3$, Cl, or F. In one embodiment, $R^5$ is methoxy, fluoro, chloro, difluoromethyl, trifluoromethyl, methyl, or cyano. In one embodiment. $R^5$ is cyano, halo$(C_{1-3})$alkyl, $(C_{1-3})$alkoxy, halo$(C_{1-3})$alkoxy, or halo. In one embodiment, $R^5$ is —CN, —$CH_3$, —$OCH_3$, Cl, or F.

In one embodiment, $R^6$ is

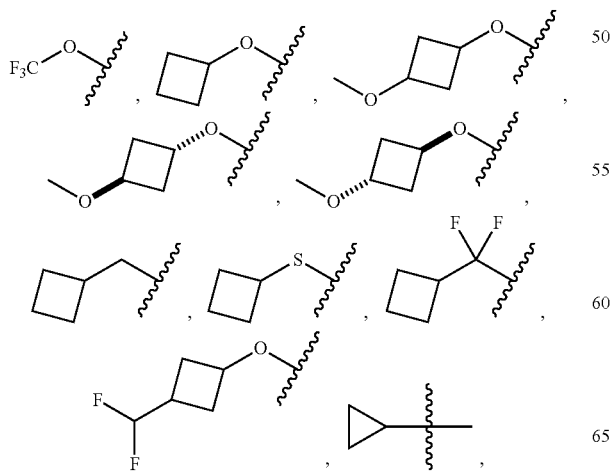

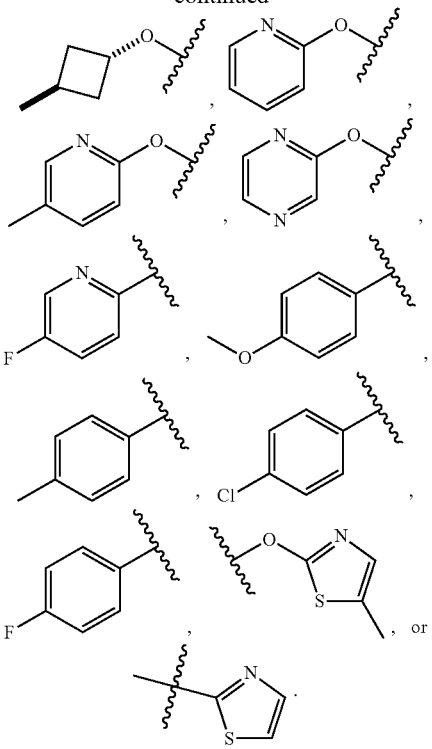

In one embodiment, $R^6$ is

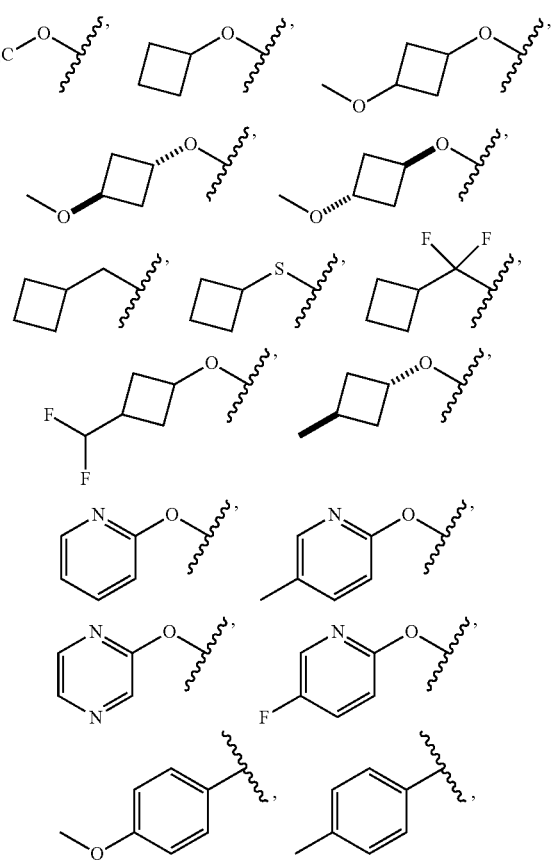

-continued

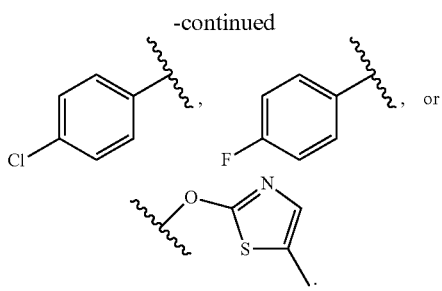

In one embodiment.

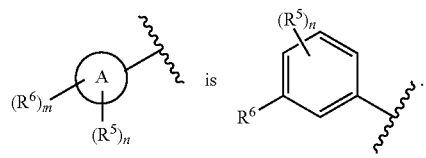

In one embodiment,

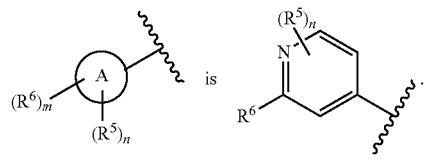

In one embodiment,

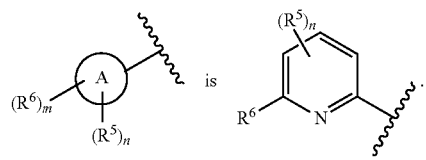

In one embodiment,

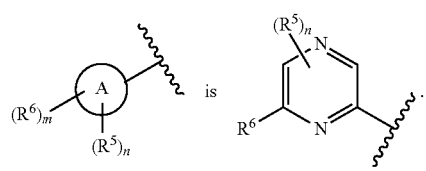

In one embodiment,

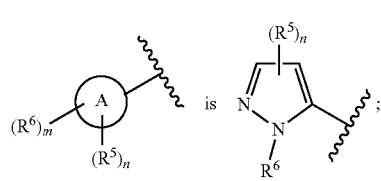

and n is 0, or 2.

In one embodiment,

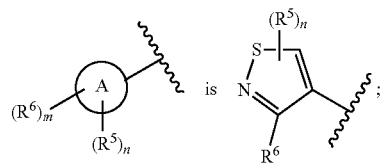

and n is 0, or 1.

In another embodiment of the present invention, the invention relates to compounds of structural formula I:

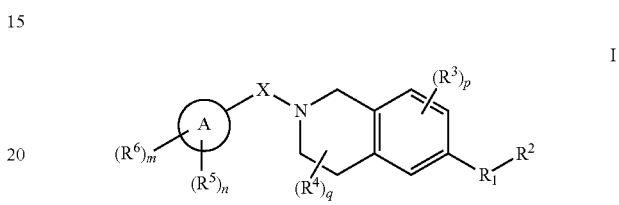

wherein:
X is
 (1) a bond, or
 (2) $(C_{1-2})$alkyl;
ring A is
 (1) aryl,
 (2) 5- or 6-membered heteroaryl containing 1, 2, or 3 heteroatoms independently selected from N, O and S, or
 (3) 9- or 10-membered fused heteroaryl containing 1, 2, or heteroatoms independently selected from N, O, and S;
$R^1$ is
 (1) bond,
 (2) $(C_{1-6})$alkyl,
 (3) —O—$(C_{1-6})$alkyl-, or
 (4) $(C_{3-6})$cycloalkyl;
$R^2$ is
 (1) hydrogen,
 (2) hydroxy,
 (3) COOH, or
 (4) tetrazole;
$R^3$ is
 (1) hydrogen,
 (2) halogen, or
 (3) $(C_{1-3})$alkyl;
$R^4$ is
 (1) hydrogen, or
 (2) $(C_{1-3})$alkyl;
$R^5$ is
 (1) cyano,
 (2) $(C_{1-3})$alkyl,
 (3) halo$(C_{1-3})$alkyl,
 (4) $(C_{1-3})$alkoxy, or
 (5) halogen;
$R^6$ is
 (1) halo$(C_{1-3})$alkoxy,
 (2) halo$(C_{1-3})$alkyl,
 (3) $(C_{3-6})$cycloalkyl,
 (4) $(C_{3-6})$cycloalkyl-O—,
 (5) $(C_{3-6})$cycloalkyl-S—,
 (6) $(C_{3-6})$cycloalkyl-$(C_{1-2})$alkyl-,
 (7) phenyl,
 (8) 5- to 6-membered heteroaryl-O— wherein the heteroaryl contains 1, 2, or 3 heteroatoms independently selected from N, O and S, or (9) 5- to 6-membered heteroaryl- wherein the heteroaryl contains 1, 2, or 3 heteroatoms independently selected from N, O and S.
wherein alkyl, cycloalkyl, phenyl and heteroaryl are unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen;
or a pharmaceutically acceptable salt thereof.

In another embodiment of the present invention, the invention relates to compounds of structural formula I

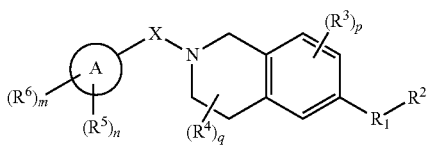

wherein:
X is a bond;
ring A is aryl;
$R^1$ is $(C_{1-6})$alkyl;
$R^2$ is COOH,
$R^3$ is
 (1) hydrogen, or
 (2) halogen;
$R^4$ is hydrogen;
$R^5$ is
 (1) cyano, or
 (2) halogen;
$R^6$ is $(C_{3-6})$cycloalkyl-O—, wherein cycloalkyl is unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen;
or a pharmaceutically acceptable salt thereof.

In one embodiment, the invention relates to compounds of formula I-A:

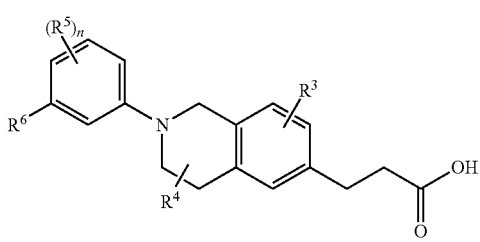

or a pharmaceutically acceptable salt thereof, wherein $R^3$, $R^4$, $R^5$, $R^6$ and n are as previously defined. In one class of this embodiment, $R^3$, and $R^4$ are each hydrogen.

In one embodiment, the invention relates to compounds of formula I-B:

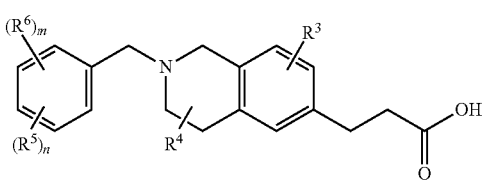

or a pharmaceutically acceptable salt thereof, wherein $R^3$, $R^4$, $R^5$, $R^6$ and n are as previously defined. In one class of this embodiment, $R^3$, and $R^4$ are each hydrogen, In one embodiment, the invention relates to compounds of formula I-C:

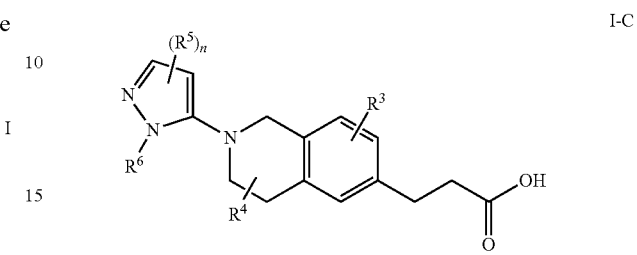

or a pharmaceutically acceptable salt thereof, wherein $R^6$ is phenyl unsubstituted or substituted with $(C_{1-3})$alkyl, $(C_{1-3})$alkoxy, or halo; and n is 0, 1 or 2; and $R^3$, $R^4$, $R^5$ are as previously defined. In one class of this embodiment, $R^3$, and $R^4$ are each hydrogen.

In one embodiment, the invention relates to compounds of formula I-D:

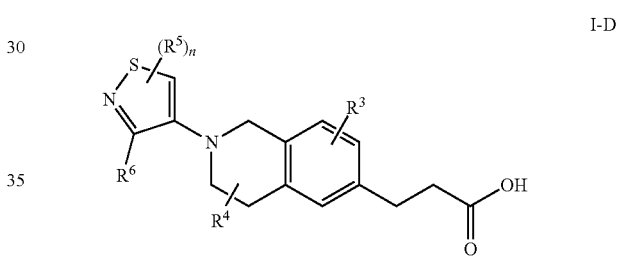

or a pharmaceutically acceptable salt thereof, wherein $R^6$ is phenyl unsubstituted or substituted with $(C_{1-3})$alkyl, $(C_{1-3})$alkoxy, or halo; and n is 0 or 1; and $R^3$, $R^4$, $R^5$ are as previously defined.

In one class of this embodiment, $R^3$, and $R^4$ are each hydrogen.

In one embodiment, the invention relates to compounds of formula I-E:

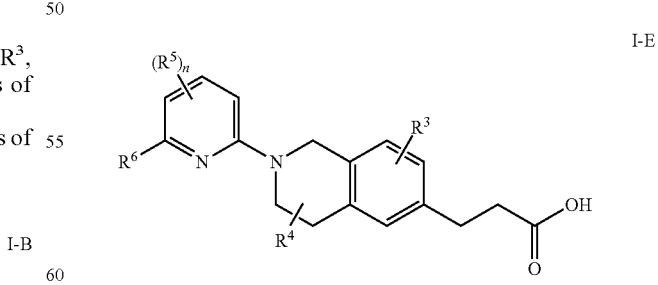

or a pharmaceutically acceptable salt thereof, wherein $R^3$, $R^4$, $R^5$, $R^6$ and n are as previously defined. In one class of this embodiment, $R^3$, and $R^4$ are each hydrogen.

In one embodiment, the invention relates to compounds of formula I-F:

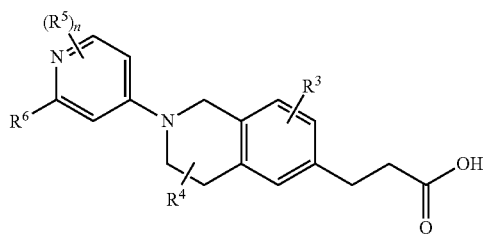

I-F or a pharmaceutically acceptable salt thereof, wherein $R^3$, $R^4$, $R^5$, $R^6$ and n are as previously defined. In one class of this embodiment, $R^3$, and $R^4$ are each hydrogen.

In one embodiment, the invention relates to compounds of formula I-G:

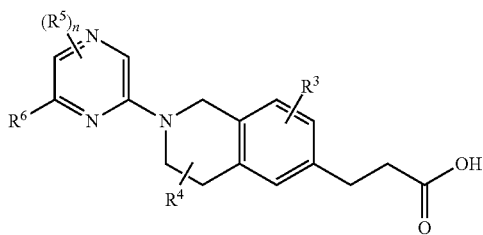

I-G or a pharmaceutically acceptable salt thereof, wherein $R^3$, $R^4$, $R^5$, $R^6$ and n are as previously defined. In one class of this embodiment, $R^3$, and $R^4$ are each hydrogen.

In the compounds of formulas I, I-A, I-B, I-C, I-D, I-E, I-F, and I-G, the $R^4$ substituent is substituted on the piperidine ring of the 1,2,3,4-tetrahydroisoquinoline ring, and the $R^3$ substituent is substituted on the phenyl of the 1,2,3,4-tetrahydroisoquinoline ring, as shown below:

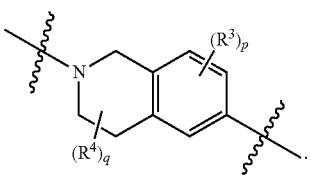

The present invention also relates to a GPR120 function regulating agent containing a compound represented by formulas I to I-G or a pharmaceutically acceptable salt thereof as an active ingredient. Particularly, the present invention relates to a GPR120 agonist containing a compound represented by formulas I to I-G or a pharmaceutically acceptable salt thereof as an active ingredient.

The present invention also relates to an agent for treating and/or preventing diabetes, obesity, hyperlipidemia, NASH, or an inflammation related disorder, containing a compound represented by formulas I to I-G or a pharmaceutically acceptable salt thereof, as an active ingredient.

Furthermore, the present invention relates to a pharmaceutical composition containing the compound represented by formulas I to I-G and a pharmaceutically acceptable carrier.

The present also relates a compound represented by formulas I to I-G for use as a medicament.

The present invention relates to the use of a compound represented by formulas I to I-G or a pharmaceutically acceptable salt thereof, in the manufacture of a medicament for use in treating a condition selected from the group consisting of diabetes, hyperlipidemia, obesity, NASH, and inflammation related disorders.

The present invention relates to the treatment of a condition selected from the group consisting of diabetes, hyperlipidemia, obesity, NASH, and inflammation related disorders comprising administering to an individual in need of such treatment a pharmaceutical composition comprising the compound represented by formulas I to I-G.

A compound according to an embodiment of the present invention or the pharmaceutically acceptable salt thereof has a strong GPR120 function regulating action, particularly an agonist action, and may be useful for treating and/or preventing diabetes, obesity, hyperlipidemia, NASH, or an inflammation related disorder.

The invention is described herein in detail using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkoxy" refers to an alkyl group linked to oxygen.

"Aryl" refers to phenyl or naphthyl.

"Halo" is halogen; halo and halogen include fluorine, chlorine, bromine and iodine.

"Cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Haloalkyl" include mono-substituted as well as multiple halo substituted alkyl groups, up to perhalo substituted alkyl. For example, trifluoromethyl is included.

"Haloalkoxy" and "haloalkyl-O" are used interchangeably and refer to halo substituted alkyl groups linked through the oxygen atom. Haloalkoxy include mono-halo substituted alkoxy groups as well alkoxy groups substituted with multiple halo substituents, up to perhalo substituted alkoxy. For example, trifluoromethoxy is included.

"Heterocyclyl", "heterocycle", "heterocyclic" or "cycloheteroalkyl" refers to nonaromatic cyclic ring structures in which one or more atoms in the ring, the heteroatom(s), is an element other than carbon. Heteroatoms are typically O, S or N atoms. Examples of heterocyclyl groups include: piperidine piperazine, morpholine, pyrrolidine, tetrahydrofuran, azetidine, oxirane, or aziridine, and the like.

"Heteroaryl" refers to aromatic cyclic ring structures in which one or more atoms in the ring, the heteroatoms(s), is an element other than carbon. Heteroatoms are typically O, S, or N atoms. Examples of heteroaryl groups include: pyridine, pyrimidinyl, pyrrole, pyridazine, isoxazole, indole, or imidazole.

"Fused heteroaryl" refers to a heteroaryl group fused to an aryl or heteroaryl group. Examples of fused heteroaryl groups include benzo[d]oxazolyl, or benzo[d]isoxazolyl.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of formulas I to I-G and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of formulas I to I-G may be obtained by stereospecific synthesis using optically pure starting materials or reagents of known configuration.

Furthermore, the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR120 receptor. These compounds and pharmaceutically acceptable salts thereof are modulators of the receptor known as GPR120, and are therefore useful in the treatment of diseases that are modulated by GPR120 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(7) hypercholesterolemia;
(8) hypertriglyceridemia (elevated levels of triglyceride-rich-lipoproteins);
(9) mixed or diabetic dyslipidemia;
(10) low HDL cholesterol;
(11) high LDL cholesterol;
(12) Hyperapobetalipoproteinemia;
(13) atherosclerosis;
(141) inflammation related disorders;
(15) type I diabetes;
(16) insulin resistance;
(17) fatty liver; and
(18) non-alcoholic steatohepatitis (NASH).

Because the compounds are agonists of the GPR120 receptor, the compounds may be useful for lowering glucose, lipids, and insulin resistance and increasing insulin sensitivity in diabetic patients and in non-diabetic patients who have impaired glucose tolerance and/or are in a pre-diabetic condition. The compounds may be useful to ameliorate hyperinsulinemia, which often occurs in diabetic or pre-diabetic patients, by modulating the swings in the level of serum glucose that often occurs in these patients. The compounds may be useful for treating or reducing insulin resistance. The compounds may be useful for increasing insulin sensitivity. The compounds are useful for treating or preventing gestational diabetes.

Additionally, by keeping hyperglycemia under control, the compounds may be useful to delay or for preventing vascular restenosis and diabetic retinopathy.

The compounds of this invention may be useful in improving or restoring β-cell function, so that they may be useful in treating type 1 diabetes or in delaying or preventing a patient with type 2 diabetes from needing insulin therapy.

The compounds of this invention may be useful in treating inflammation related disorders such as obesity, diabetes, NASH, cancer, and cardiovascular disease.

The compounds, compositions, and medicaments as described herein may be further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

One aspect of the invention provides a method for the treatment and control of mixed or diabetic dyslipidemia, hypercholesterolemia, atherosclerosis, low HDL levels, high LDL levels, hyperlipidemia, NASH, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, rosuvastatin and the like). The compound may also be used advantageously in combination with other lipid lowering drugs such as cholesterol absorption inhibitors (e.g., stanol esters, sterol glycosides or azetidinones such as ezetimibe), ACM inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat) or a monoamine neurotransmitter uptake inhibitor (e.g., sibutramine or phentermine). The compound may also be used advantageously in combination with CB-1 inverse agonists or antagonists (e.g., rimonabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension, (22) fatty liver, (23) non-alcoholic steatohepatitis (NASH) and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors (e.g., sitagliptin, alogliptin, omatigliptin linagliptin, vildagliptin, trelagliptin);

(b) insulin sensitizers selected from the group consisting of (i) PPAR agonists and (ii) biguanides;

(c) insulin and insulin mimetics (e.g., insulin degludec, insulin glargine, insulin lispro);

(d) sulfonylureas and other insulin secretagogues;

(e) α-glucosidase inhibitors;

(f) glucagon receptor antagonists;

(g) GLP-1, GLP-1 mimetics, and GLP-1 receptor agonists (e.g., dulaglutide, exenatide, semaglutide, albiglutide, liraglutide, lixisenatide, taspoglutide);

(h) GIP, GIP mimetics, and GIP receptor agonists;

(i) PACAP, PACAP mimetics, and PACAP receptor 3 agonists;

(j) cholesterol lowering agents selected from the group consisting of
 (i) HMG-CoA reductase inhibitors, (ii) sequestrants, (iii) nicotinyl alcohol, nicotinic acid and salts thereof, (iv) PPARα agonists, (v) PPAR α/γdual agonists (e.g., aleglitazar), (vi) inhibitors of cholesterol absorption, (vii) acyl CoA:cholesterol acyltransferase inhibitors, and (viii) anti-oxidants;

(k) PPARδ agonists;

(l) SGLT inhibitors empagliflozin, dapagliflozin, canagliflozin, BI-10773, tofogliflozin, ipragliflozin; LX-4211, PF-4971729, remogloflozin, TS-071, ertugliflozin);

(m) antiobesity compounds;

(n) ileal bile acid transporter inhibitors;

(o) anti-inflammatory agents excluding glucocorticoids;

(p) protein tyrosine phosphatase-1B (PTP-1B) inhibitors;

(q) antihypertensives including those acting on the angiotensin or renin systems, such as angiotensin converting enzyme inhibitors, angiotensin II receptor antagonists or renin inhibitors, (e.g., lisinopril, losartan); and (r) GPR-40 agonists;

said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-di ethylaminoethanol, 2-di methylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds of formulas I to I-G or the other drugs may have utility, where the combination of the drugs together are safer or more effective than either drug alone. Such other drug(s) may be administered, by a route and in an amount commonly used therefore, contemporaneously or sequentially with a compound of formulas I to I-G. When a compound of formulas I to I-G is used contemporaneously with one or more other drugs, a pharmaceutical composition in unit dosage form containing such other drugs and the compound of formulas I to I-G is preferred. However, the combination therapy may also include therapies in which the compound of formulas I to I-G and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formulas I to I-G.

Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, omarigliptin, linagliptin, vildagliptin, trelagliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TFP814);

(3) insulin or insulin analogs (e.g., insulin detemir, insulin glulisine, insulin degludec, insulin insulin lispro and inhalable formulations of each);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, meglitinides, nateglinide and repaglinide);

(7) α-glucosidase inhibitors (e.g., acarbose, voglihose and miglitol);

(8) glucagon receptor antagonists (e.g., MK-3577, MK-0893, LY-2409021 and KT6-971);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof);

(10) LDL cholesterol lowering agents such as (i) HMG-CoA reductase inhibitors (e.g., simvastatin, lovastatin, pravastatin, cerivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors. (e.g., avasimibe);

(11) HDL-raising drugs, (e.g., niacin and nicotinic acid receptor agonists, and extended-release versions thereof);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan; olmesartan medoxomil, valsartan, telmisartan, and eprosartan), renin inhibitors 0-aliskiren), beta blockers, and calcium channel blockers;

(15) glucokinase activators (GKAs) AZD6370);

(16) inhibitors of 11β-hydroxysteroid dehydrogenase type I, (e.g., such as those disclosed in U.S. Pat. No. 6,730,690, and LY-2523199);

(17) CETP inhibitors (e.g., anacetrapib, and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators;

(21) other agonists of the G-protein-coupled receptors: (i) GPR-109, (ii) GPR-9 (e.g., MBX2982 and PSN821), and (iii) GPR-40 (e.g., TAK875);

(22) SSTR3 antagonists (e.g., such as those disclosed in WO 2009/001836);

(23) neuromedin U receptor agonists (e.g., such as those disclosed in WO 2009/042053, including, but not limited to neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canaglitlozin BI-10773, PF-04971729, remogloflozin, TS-071, tofogliflozin, ipragliflozin, ertugliflozin, and LX-4211);

(27) inhibitors of acyl coenzyme A: diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP; PACAP mimetics, and PACAP receptor 3 agonists;

(33) PPAR agonists;

(34) protein tyrosine phosphatase-1B (PTP-1B) inhibitors;

(35) IL-1b antibodies, e.g., XOMA052 and canakinumab); and

(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), omarigliptin, SYR-472, teneligliptin, KRP104, TS021, AMG222, SK0403, LC15-0444, vildagliptin, saxagliptin, alogliptin, melogliptin, linagliptin, and pharmaceutically acceptable salts thereof and fixed-dose combinations of these compounds with metformin hydrochloride, pioglitazone, rosiglitazone, simvastatin, atorvastatin, rosuvastatin, ertugliflozin, ipragliflozin, or a sulfonylurea.

Antiobesity compounds that can be combined with compounds of formulas I to I-G include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$, or $Y_5$ antagonists (such as MK-0557); CB1 receptor inverse agonists and antagonists (such as rimonabant and taranabant); $\beta_3$ adrenergic receptor agonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents,* 11: 1677-1692 (2001); D. Spanswick and K. Lee, "Emerging anti-obesity drugs," *Expert Opin. Emerging Drugs.* 8: 217-237 (2003); J. A. Fernandez-Lopez, et al., "Pharmacological Approaches for the Treatment of Obesity," *Drugs,* 62: 915-944 (2002); and K. M. Gadde, et al., "Combination pharmaceutical therapies for obesity," *Exp. Opin. Pharmacother.,* 10: 921-925 (2009).

In another aspect of the invention, a pharmaceutical composition is disclosed which comprises one or more of the following agents:

(a) a compound of structural formulas I to I-G;

(b) one or more compounds selected from the group consisting of:

(1) dipeptidyl peptidase-IV (DPP-4) inhibitors;

(2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands; including (1) PPARα/γ dual agonists, such as Mil, chiglitazar, GFT505, muraglitazar, aleglitazar, sodelglitazar, and naveglitazar, (2) PPARα; agonists, such as fenofibric acid derivatives e.g.; gemfibrozil, clofibrate, ciprotibrate, fenofibrate and bezafibrate), (3) selective PPARγ modulators (SPPARγM's), and (4) PPARγ partial agonists, (ii) biguanides, such as metformin and its pharmaceutically acceptable salts, in particular; metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP81.4;

(3) sulfonylurea and non-sulfonylurea insulin secretagogues, (e.g., tolbutamide, glyburide, glipizide, glirnepiride mitiglinide, and meglitinides, such as nateglinide and repaglinide);

(4) α-glucosidase inhibitors (e.g., acarbose, voglibose and miglitol), (5) glucagon receptor antagonists;

(6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe);

(7) HDL-raising drugs, such as niacin or a salt thereof and extended-release versions thereof;

(8) antiobesity compounds;

(9) agents intended for use in inflammatory conditions, such as aspirin, non-steroidal anti-inflammatory drugs (NSAIDs), glucocorticoids, and selective cyclooxygenase-2 (COX-2) inhibitors;

(10) antihypertensive agents, such as ACE inhibitors enalapril, lisinopril, ramipril, captopril, quinapril, and tandolapril), A-II receptor blockers (e.g., losartan; candesartan, irbesartan, olmesartan medoxomil, valsartan, telmisartan, and eprosartan), renin inhibitors (e.g., aliskiren), beta blockers (e.g., calcium channel blockers);

(11) glucokinase activators (GKAs) (e.g., AZD6370);

(12) inhibitors of Ilfi-hydroxysteroid dehydrogenase type 1 (e.g., such as those disclosed in U.S. Pat. No. 6,730, 690; WO 03/104207; and WO 04/058741);

(13) inhibitors of cholesteryl ester transfer protein (CETP), (e.g., torcetrapib and anacetripib);

(14) inhibitors of fructose 1,6-bisphosphatase (e.g., such as those disclosed in U.S. Pat. Nos. 6,054,587; 6,110, 903; 6,284,748; 6,399,782; and 6,489,476);

(15) inhibitors of acetyl CoA carboxylase-1 or 2 (ACC1 or ACC2);

(16) AMP-activated Protein Kinase (AMPK) activators;

(17) agonists of the G-protein-coupled receptors: (i) GPR-109, (ii) GPR-119 (e.g., MBX2982, and PSN821), and (iii) GPR-40;

(18) SSTR3 antagonists (e.g., such as those disclosed in WO 2009/011836);

(19) neuromedin U receptor agonists (e.g., such as those disclosed in WO2009/042053, including, but not limited to, neuromedin S (NMS));

(20) inhibitors of stearoyl-coenzyme A delta-9 desaturase (SCD);

(21) GPR-105 antagonists (e.g., such as those disclosed in WO 2009/000087);

(22) inhibitors of glucose uptake, such as sodium-glucose transporter (SGLT) inhibitors and its various isoforms, such as SGLT-1; SGLT-2 (e.g., ASP1941, TS071, B110773, tofogliflozin, LX4211, canagliflozin, dapagliflozin, ertugliflozin, ipragliflozin and remogliflozin; and SGLT-3);

(23) inhibitors of acyl coenzyme A:diacylglycerol acyltransferase 1 and 2 (DGAT-1 and DGAT-2);

(24) inhibitors of fatty acid synthase;

(25) inhibitors of acyl coenzyme A:monoacylglycerol acyltransferase 1 and 2 (MGAT-1 and MGAT-2);

(26) agonists of the TGR5 receptor (also known as GPBAR1, BG37, GPCR19, GPR131, and M-BAR);

(28) bromocriptine mesylate and rapid-release formulations thereof, and

(29) IL-1b antibodies (e.g., XOMA052, and canakinumab); and (c) a pharmaceutically acceptable carrier.

When a compound of the present invention is used contemporaneously with one or more other drugs, a pharmaceutical composition containing such other drugs in addition to the compound of the present invention may be employed. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Abbreviations

The following abbreviations may be used in the synthetic schemes or Examples: ACN is acetonitrile; AcOH is acetic acid; Ac$_2$O is acetic anhydride; arthyd. or anhydr. is anhydrous; aq. is aqueous; Ar is aryl; BINAP is (2,2'-bis(diphenylphosphino)-1,1'-binaphthyl); (BOC)$_2$O is Boc anhydride or di-tert-butyl dicarbonate; n-BuLi is n-butyl lithium; tert-BuOH or t-BuOH is tert-butanol; (t-Bu)$_3$PHBF$_4$ is tri-tert-butylphosphine tetrafluoroborate t-Busphos precatalyst is chloro(2-ditert-butyl-2',6'-dimethoxy-1,1'-biphenyl)[2-(2-aminoethyl-phenyl)]palladium(II)dichloromethane adduct; Bu$_4$NI is tetrabutyl ammonium iodide; $^t$BuOK is potassium tert-butoxide; ° C. is degree Celsius; CataCXium A is di(1-adamantyl)-n-butylphosphine; CDCl$_3$ is deuterated chloroform; CD$_3$OD is deuterated methanol; Celite™ is diatomaceous earth; conc. is concentrated; d is day or days; DAST is diethylaminosulfur trifluoride; DCM is dichloromethane; DEA is N,N-diisopropylethylamine; DEAD is diethyl azodicarboxylate; DIAD is diisopropyl azodicarboxylate; DIBAL is diisobutylaluminum hydride; DIEA is diisopropylethylamine; DMA is N,N-dimethylacetamide; DMF is dimethylformamide; DMP is Dess-Martin periodinane; DMS is dimethyl sulfide; DMSO is dimethylsulfoxide; Et is ethyl; EA or EtOAc is ethyl acetate; EtOH is ethanol; Et$_2$Zn is diethylzinc; g is grams; Et$_3$N is triethylamine; Et$_3$SiH is triethylsilane; iPrOH is isopropyl alcohol; g is gram; G2 Ru Phos is chloro(2-dicyclohexylphosphino-2',6-diisopropoxy-1,1'-biphenyl)[2-(2'-amino-1,1-biphenyl)]palladium(II); G2 X Phos is chloro(2-dicyclohexylphosphino-2',4',6'-triisopropyl-1,1'-biphenyl)[2-(2-amino-1, 1'-biphenyl)]palladium(II); G418 is Geneticin, an aminoglycoside antibiotic; h is hour; HATU is 1-[Bis(dimethylamino)-methylene]-1H-1,2,3-triazolo-[4,5-b]pyridinium 3-oxide-hexa-fluorophosphate); HPLC is high performance liquid chromatography; KHMDS is potassium hexamethyldisilizide; KOTMS is potassium trimethylsiloxide; LAU is lithium aluminum hydride; LDA is lithium diisopropylamide; LHMDS or LiHMDS is lithium bis(trimethylsilamide; LiTMP is lithium tetramethylpiperidide; M is molar; m-CPBA or mCPBA is meta-chloroperoxybenzoic acid; Me is methyl; MeCN is acetonitrile; MeI is methyl iodide; MeOH is methanol; mg is milligram; MHz is megaHertz; min is minute(s); mmol is millimoles; ml or mL is milliliter; mPa is millipascal; N is normal; nBuLi is n-butyllithium; NBS is N-bromosuccinimide; NCS is N-chlorosuccinimide; NMP is N-methylpyrrolidone; NMR is nuclear magnetic resonance; PCC is pyridinium chlorochromate; Pd—C or Pd/C is palladium(0) on carbon; PdCl$_2$(dtbpf) is [1,1'-Bis(di-tert-butylphosphino)-ferrocene]di-chloropalladium(II); PE is petroleum ether; Pd(PPh$_3$)$_4$ is tetrakis(triphenyl-phosphine)palladium(0); Pd(OAc)$_2$ is palladium (II) acetate; Pd$_2$(dba)$_3$ is tris(dibenzylideneacetone)dipalladium (0); Pd(OH)$_2$/C is palladium(II)hydroxide on carbon; PPh$_3$ is triphenyl phosphine; prep is preparative; Prep-HPLC is preparative high performance liquid chromatography; psi is pounds per square inch; PTLC or prep tlc is preparative thin layer chromatography; rac is racemic; rt or Kr or FA, is room temperature; RuPhos precatalyst is 2-dicyclohexylphosphono-2',6'-diisopropoxy-biphenyl; sat. or satd. Is saturated; soln. is solution; SelectFluor is 1-chloromethyl-4-fluoro-1,4-diazoniabicyclo-[2.2.2]-octane bis(tetrafluoroborate); SFC is supercritical fluid chromatography; SPHOS precatalyst is 2-dicyclohexylphosphino-2',6'-dimethoxybiphenyl; TBAB is tetrabutylammonium bromide; TBAF is tetra-n-butylammonium fluoride; TBAI is tetra-n-butylammonium iodide; TEA is triethylamine; $Tf_2O$ is triflic anhydride or tri-fluoromethanesulfonic anhydride; TFA is trifluoroacetic acid; TFAA is trifluoroacetic anhydride: THF is tetrahydrofuran; TIPS-Cl is triisopropyl silylchloride; TLC is thin layer chromatography; TMP is tetramethylpiperidine; TMSCl or TMS-Cl is trimethylsilyl chloride; TRIX-IEPHOS is 2-Di-t-butylphosphino-1,1'-binaphthyl; PTLC or prep-TLC is preparative thin layer chromatography; XantPhos is X; and XPHOS, XPhos or Xphos precatalyst is 2-dicyclohexylphosphino-2'4'6'-triisopropylbiphenyl.

General Schemes

The compounds of the invention can be prepared using the synthetic schemes described herein as well as any of several alternate methods which will be apparent to a chemist skilled in the art.

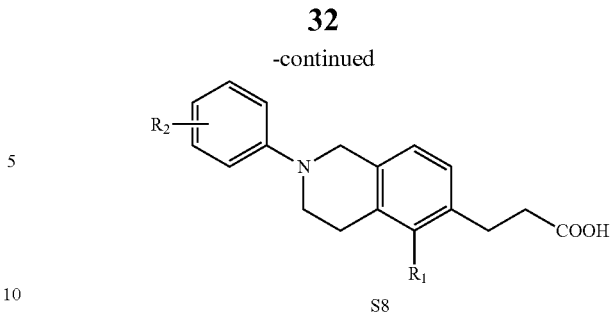

S8 can be obtained by first reacting the 6-halo-isoquinoline derivative S1 with the ethyl acrylate using a palladium catalyst to give S3, which is selectively reduced by hydrogenation with platinum oxide catalysis to yield the ethyl tetrahydroisoquinoline-6-yl-propanoate S5. S5 can be coupled with an aryl halide S6 with a palladium catalyst to give S7. The acid S8 is obtained after treatment of S7 with LiOH or $KOSiMe_3$.

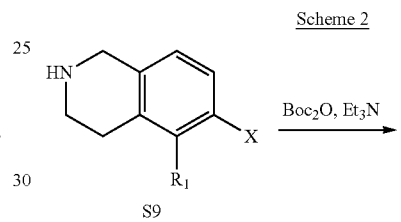

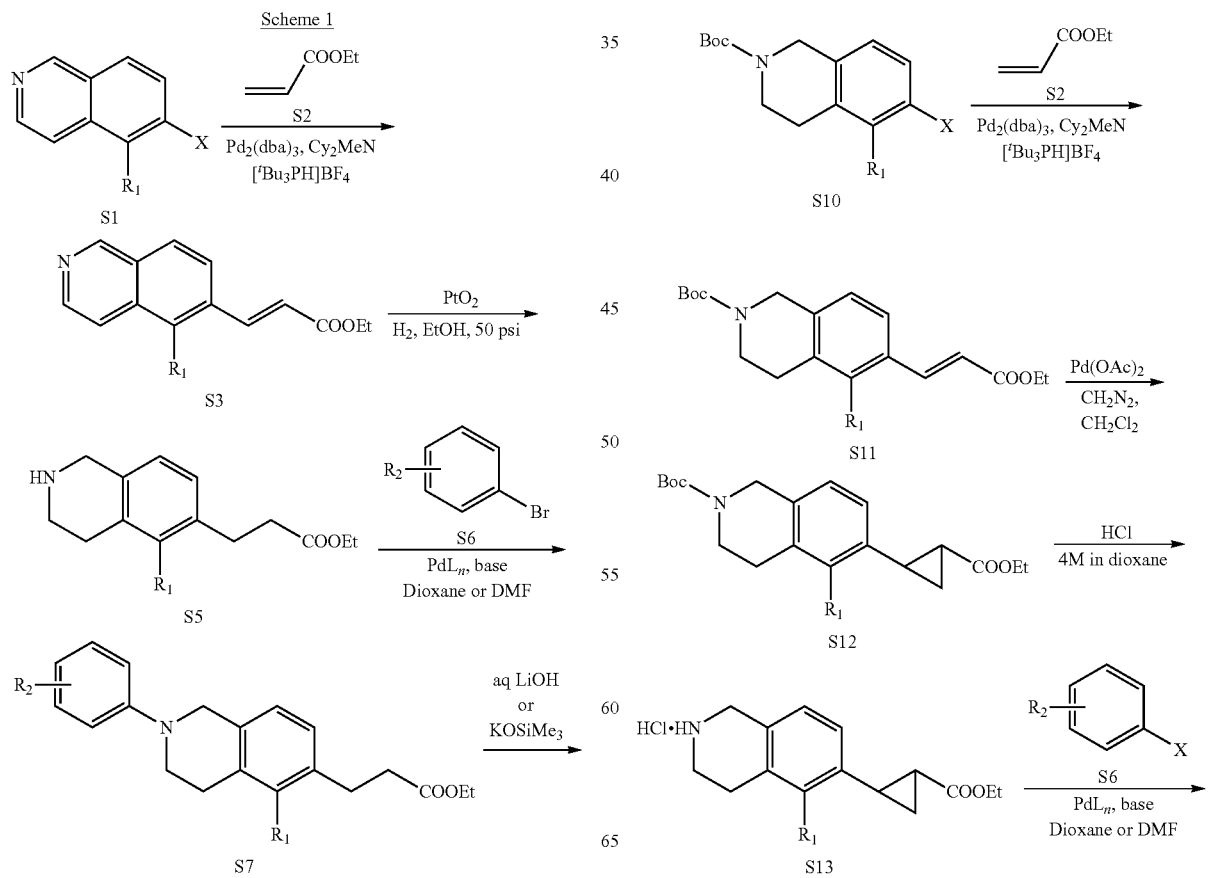

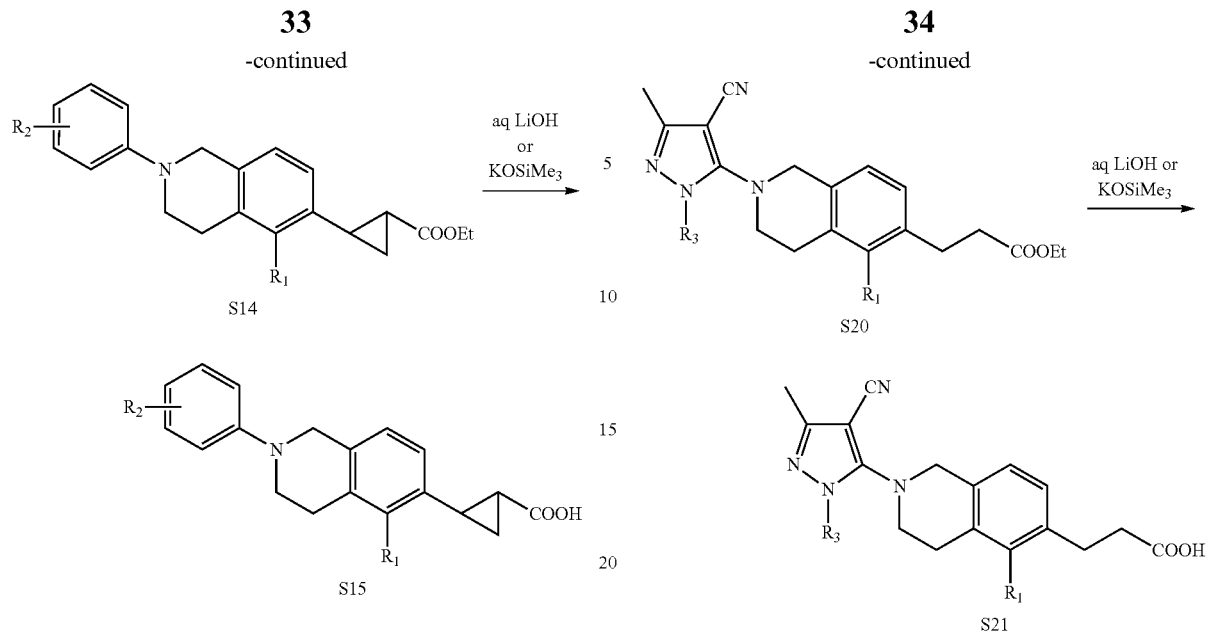

S15 can be obtained by protecting the 6-halo-tetrahydroisoquinoline S9 at the amino group with a Boc group to give S10. The Boc protected compound S10 can further be treated with ethyl acrylate S2 in the presence of a palladium catalyst to give alkene S11. Alkene S11 can be treated under cyclopropanation conditions with diazomethane in the presence of palladium acetate to give the cyclopropyl compound S12. The Boc group is then removed under acidic conditions to give S13 as the hydrochloric acid salt. S13 is then coupled with the aryl halide S6 in the presence of a palladium catalyst to give S14. S14 can be treated with LiOH or KOSiMe$_3$ to give the acid S15.

S21 can be obtained by first reacting the substituted hydrazine S16 with 2-(1-ethoxyethylidene)malononitrile S17 under basic conditions to give amino-pyrazolyl S18. S18 can be treated with an isoamyl nitrite in the presence of a copper (I) halide to give the halo-pyrazolyl compound S19, S19 and S5 can be coupled in the presence of a palladium catalyst to give S20, and S20 can be deprotected with LiOH or KOSiMe$_3$ to give S21.

Scheme 3

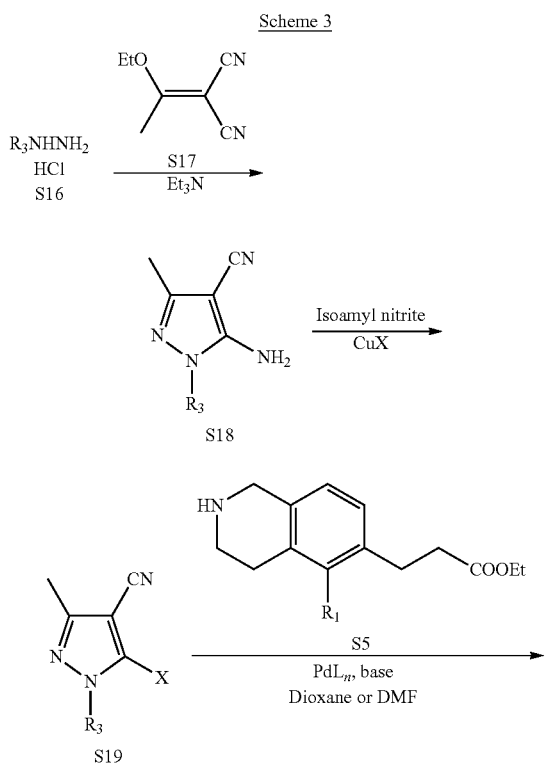

Scheme 4

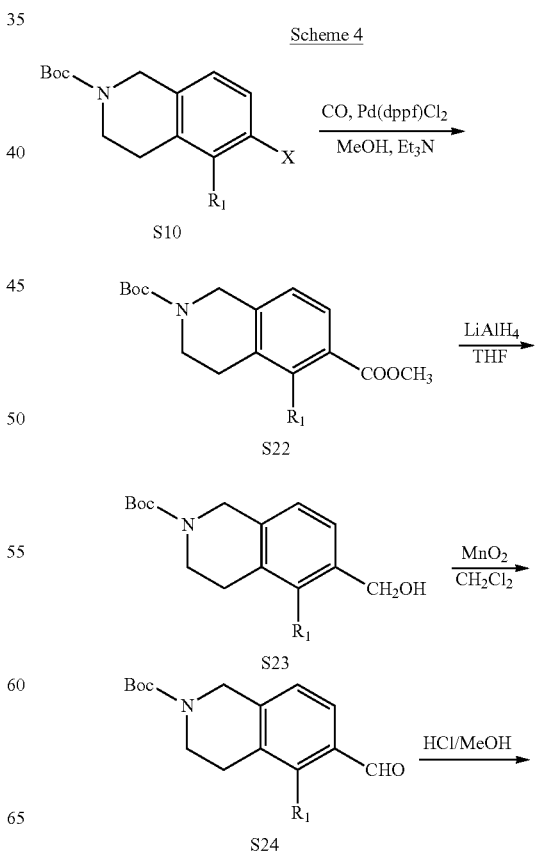

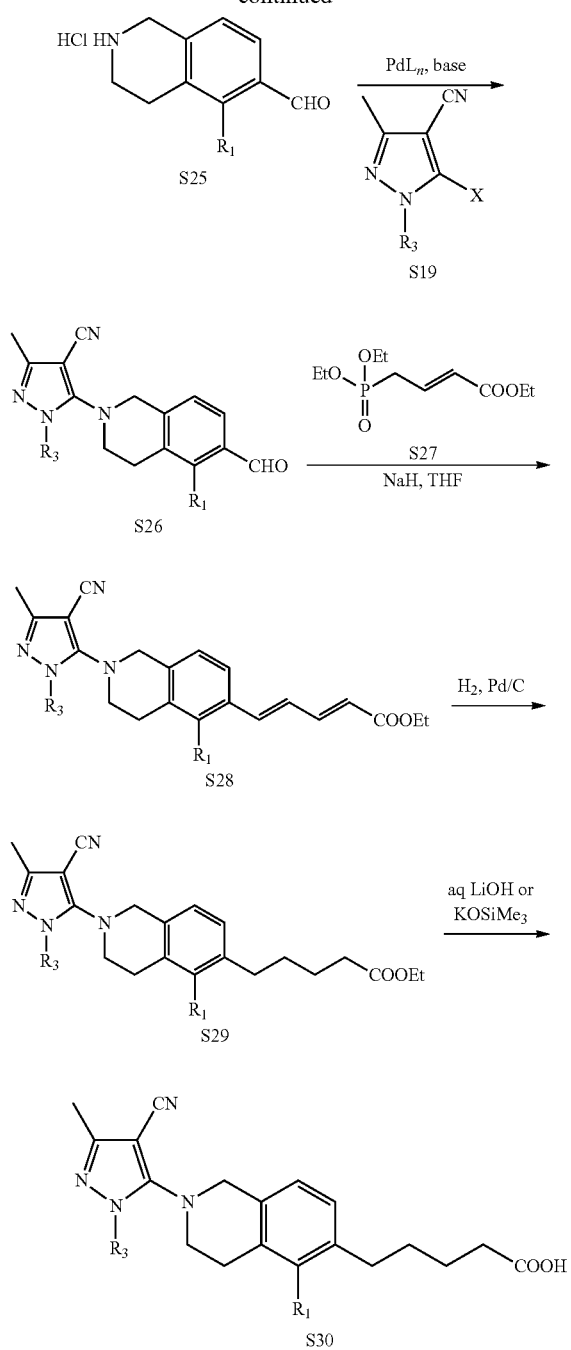

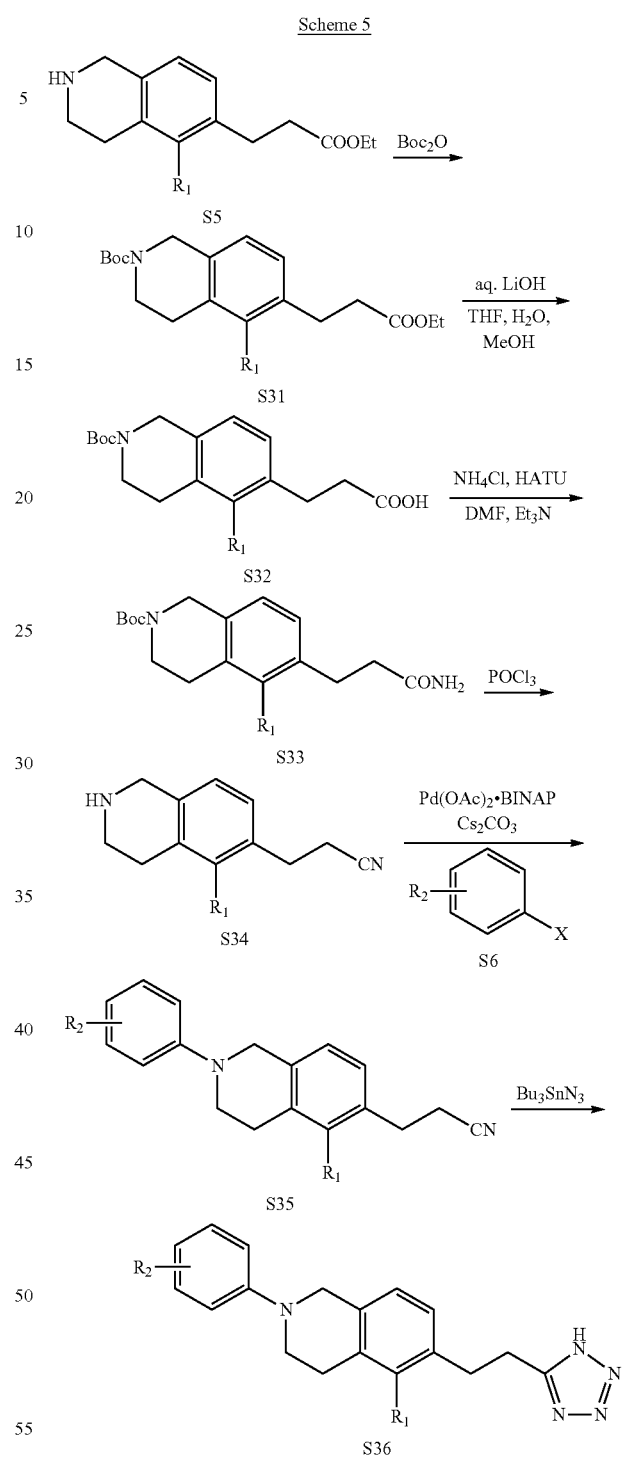

Scheme 5

S30 can be obtained by reacting S10 with carbon monoxide and MeOH in the presence of a palladium catalyst to give S22. The ester S22 can be reduced in the presence of LiAlH₄ to give the alcohol S23, which may be oxided to the aldehyde in the presence of MnO₂ to give S24. The Boc group can be removed using acidic conditions to give the amine S25. Then amine S25 and S19 can be coupled in the presence of a palladium catalyst to give S26. S27 after treatment with NaH can be activated to react with S26 to give the diene S28. The diene S28 can be reduced in the presence of hydrogen and palladium on carbon to give the alkane S29. S30 can be obtained after treatment of S29 with either LiOH or KOSiMe₃.

S36 can be obtained by first treating S5 with Boc₂O to give the Boc protected compound S31. S31 can be treated with LiOH to give acid S32. S32 can be treated in peptide coupling conditions in the presence of NH₄Cl to give amide S33. The amide S33 can be reduced in the presence of POCl₃ to give the deprotected cyano compound S34. S34 and S6 can be coupled in the presenced of a palladium catalyst to give S35, S35 can be treated with Bm SnN₃ to give the tetrazolyl compound S36.

Intermediate 1

2-(3-Bromo-5-chloro-4-fluorophenoxy)-5-methylthiazole

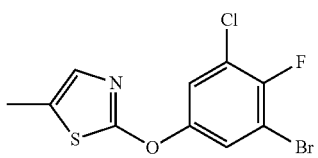 [SMILES: Cc1cnc(Oc2cc(Cl)c(F)c(Br)c2)s1]

Step A.
(3-Chloro-4-fluorophenoxy)triisopropylsilane

To a solution of 3-chloro-4-fluorophenol (20.0 g, 136 mmol) in DMF (100 mL) was added 1H-imidazole (9.29 g, 136 mmol) and chlorotriisopropylsilane (26.3 g, 136 mmol), and the mixture was stirred at 10° C. for 18 h. The mixture was diluted with water (500 mL) and extracted with EtOAc (3×150 mL). The separated organic layer was dried (MgSO$_4$), filtered and concentrated in vacuo. The resulting residue was purified via silica gel chromatography (PE) to afford the the title compound.

Step B. (3-Bromo-5-chloro-4-fluorophenoxy)triisopropylsilane

To a soln. of 2,2,6,6-tetramethylpiperidine (5.60 g, 39.6 mmol) in THF (80 mL) was added 2.5 M n-BuLi (16 mL, 40.0 mmol) dropwise at −78° C. wider N$_2$. The reaction mixture was stirred for 1 h, then the mixture was allowed to warm to 0° C. and stirred for 10 min. The reaction was cooled back to −78° C., and (3-chloro-4-fluorophenoxy)triisopropylsilane (10.0 g, 33.0 mmol) in THF (40 mL) was added dropwise at −78° C., and the mixture was stirred at −78° C. for 2 h. Br$_2$ (7.91 g, 49.5 mmol) was added, then the mixture was stirred at −78° C. for another 2 h. The mixture was quenched by addition of satd. aq. NH$_4$Cl (50 mL), diluted with water (100 mL), and extracted with EtOAc (3×150 mL). The organic layer was dried (Na$_2$SO$_4$) and concentrated in vacuo. The residue was purified via silica gel chromatography (PE) to afford the title compound.

Step C. 3-Bromo-5-chloro-4-fluorophenol

To a soln. of (3-bromo-5-chloro-4-fluorophenoxy)triisopropylsilane (10.40 g, 27.2 mmol) in THF (120 mL) was added TBAF (33 mL, 33.0 mmol), and the mixture was stirred at 20° C. for 1 h. Then the mixture was diluted with water (150 mL) and extracted with EtOAc (150 mL×3). The organic layer was seperated, dried (Na$_2$SO$_4$) and concentrated in vacuo. The residue was purified via silica gel chromatography (PE:EtOAc=50:1) to afford the title compound.

Step D. 2-(3-Bromo-5-chloro-4-fluorophenoxy)-5-methylthiazole

A mixture of 3-bromo-5-chloro-4-fluorophenol (500 mg, 2.218 mmol), 2-bromo-5-methylthiazole (434 mg, 2.440 mmol) and Cs$_2$CO$_3$ (1.08 g, 3.33 mmol) in NMP (6 mL) was stirred under microwave irradiation at 150° C. for 30 min. The mixture was extracted with EtOAc (20 mL×3), and the organic layer was washed with water (15 mL). The organic layer was dried (Na$_2$SO$_4$) and concentrated in vacuo. The residue was purified by reverse phase HPLC on a GILSON 281 instrument fitted with a Phenomenex Synergi C18 (250*21.2 mm*4 μm) column using water (0.2% TFA) and ACN as eluents (Mobile phase A: water (0.2% TFA). Mobile phase B: ACN, Detector wavelength: 220 nm) followed by concentration in vacuo to obtain the title compound. $^1$H NMR (400 MHz, CDCl$_3$) δ 7.43 (dd, J=4.89, 2.93 Hz, 1H) 7.34 (dd, J=5.48, 2.74 Hz, 1H) 6.91 (s, 1H) 2.38 (s, 3H).

Intermediate 2

2-Bromo-6-cyclobutoxy-3-fluoropyridine

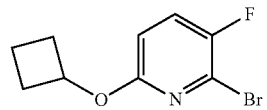 [SMILES: Fc1ccc(OC2CCC2)nc1Br]

Step A. 2-Cyclobutoxy-5-fluoropyridine

To a suspension of NaH (1.25 g. 31.30 mmol) in THF (30 mL) was added cyclobutanol (2.25 g, 31.30 mmol) at rt in one portion, and the mixture was stirred at ~25° C. for 10 min, followed by the dropwise addition of 2,5-difluoropyridine (3.00 g, 26.10 mmol). The above suspension was stirred at rt for 1 h. The mixture was diluted with water (30 mL) and extracted with EtOAc (20 mL). The organic layer was collected, washed with brine (10 mL), dried over anhyd. Na$_2$SO$_4$, filtered, and then concentrated in vacuo to afford the title compound. m/z 168.2 [M+H]$^+$

Step B. 2-Cyclobutoxy-5-fluoropyridine 1-oxide

To a soln. of 2-cyclobutoxy-5-fluoropyridine (1.20 g, 7.18 mmol) in DCM (20 mL) was added m-CPBA (2.47 g, 14.36 mmol) at rt in one portion, and the mixture was stirred at ~25° C. for 36 h. The solvent was removed in vacuo, and the residue was purified by silica gel column chromatography (PE:EtOAc from 2:1 to DCM:EtOAc 5:1) to afford the title compound. m/z 184.1 [M+H]$^+$

Step C. 2-Bromo-6-cyclobutoxy-3-fluoropyridine

To a soln. of 2-cyclobutoxy-5-fluoropyridine-1-oxide (400 mg, 2.18 mmol) in toluene (5 mL) was added phosphoryl tribromide (689 mg, 2.40 mmol) in one portion, and the mixture was stirred at 100° C. for 1 h. The mixture was added to a satd. aq. NaHCO$_3$ soln. (10 mL), and then extracted with EtOAc (10 mL). The organic layer was concentrated in vacuo, and the remaining residue was purified by silica gel PTLC (PE) to afford the title compound. m/z=245.8 [M+H]$^+$

Intermediate 3

1-Bromo-5-cyclobutoxy-2,3-difluorobenzene

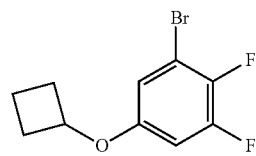 [SMILES: Fc1cc(OC2CCC2)cc(Br)c1F]

Step A. 4,5-Difluoro-2-nitrophenol

To a soln. of 3,4-difluorophenol (40.00 g, 307 mmol) in AcOH (100 mL) was added dropwise a soln. of fuming nitric acid (18.0 ml, 431 mmol) in AcOH (60 mL) maintaining the temperature below 50° C. Then the reaction mixture was stirred at 16° C. for 2 h. The reaction mixture was poured into water (200 mL) and the solid separating out was filtered. The solid was dissolved in dichloromethane (200 mL). The organic layer was dried (Na$_2$SO$_4$) and concentrated in vacuo to give the title compound which was used directly in the next step.

Step B. Cyclobutoxy-4,5-difluoro-2-nitrobenzene

To a soln. of 4,5-difluoro-2-nitrophenol (45.00 g, 257 mmol) in DMF (200 mL) was added bromocyclobutane (69.4 g, 514 mmol), mono(4-(tributylammonio)butan-1-ylium) monoiodide (95 g, 257 mmol) and Cs$_2$CO$_3$ (84 g, 257 mmol). Then the reaction mixture was stirred at 90° C. for 16 h. Water (1.5 L) was added, and the mixture was extracted with EtOAc (300 mL×3). The resulting organic layer was concentrated in vacuo. The crude product was purified by silica gel chromatography (PE to PE/EtOAc=50:1 to 40:1) to give the title compound.

Step C. 2-Cyclobutoxy-4,5-difluoroaniline

To a soln. of 1-cyclobutoxy-4,5-difluoro-2-nitrobenzene (5.00 g, 21.82 mmol) in MeOH (60 mL) and water (6 mL) was added NH$_4$Cl (11.67 g, 218 mmol) and iron (6.09 g, 109 mmol). Then the reaction mixture was stirred at 90° C. for 16 h. The reaction mixture was filtered, and water (50 mL) was added to the filtrate. The filtrate was extracted with EtOAc (30 mL×2), and the organic layer was concentrated in vacuo to give the crude product which was used without further purification.

Step D. 2-Bromo-6-cyclobutoxy-3,4-difluoroaniline

To a soln. of 2-cyclobutoxy-4,5-difluoroaniline (2.30 g, 11.55 mmol) in AcOH (50 mL) was added Br$_2$ (0.68 mL, 13.28 mmol). Then the reaction mixture was stirred at 14° C. for 16 h. A satd. aq. solution of Na$_2$S$_2$O$_3$ (30 mL) was added, and the mixture was extracted with EtOAc (50 mL). The organic layer was seperated and concentrated in vacuo. The crude product was purified by PTLC (PE/EtOAc=10:1) to give the title compound.

Step E. 1-Bromo-5-cyclobutoxy-2,3-difluorobenzene

To a soln. of 2-bromo-6-cyclobutoxy-3,4-difluoroaniline (450 mg, 1.618 mmol) in THF (3 mL) was added isopentyl nitrite (380 mg, 3.24 mmol). Then the reaction mixture was stirred at 70° C. for 16 h. The mixture was concentrated in vacuo. Water (30 mL) was added, and the mixture was extracted with EtOAc (30 mL×2). The organic layer was concentrated in vacuo, and the resulting crude product purified by silica gel TLC (PE/EtOAc=10:1) to give title compound. $^1$H NMR (400 MHz, CDCl$_3$) δ 6.74 (d, J=2.0 Hz, 1H), 6.58-6.61 (m, 1H), 4.53-4.58 (m, 1H), 2.43-2.45 (m, 2 H), 2.12-2.17 (m, 2H), 1.84-1.87 (m, 2H), 1.65-1.71 (m, 2H).

Intermediate 4

2,3-Difluoro-5-((1R,3R)-3-methoxycyclobutoxy) phenyl trifluoromethanesulfonate

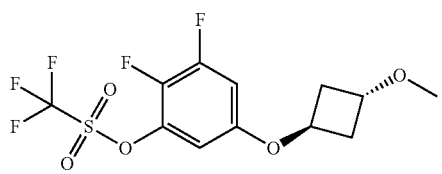 [SMILES: CO[C@H]1C[C@H](Oc2cc(F)c(F)c(OS(=O)(=O)C(F)(F)F)c2)C1]

Step A: 1-(Benzyloxy)-5-((1r,3r)3-(benzyloxy)cyclobutoxy)-2,3-difluorobenzene To a solution of 3-(benzyloxy)-4,5-difluorophenol (2.50 g, 10.58 mmol), 3-(benzyloxy) cyclobutanol (2.07 g, 11.64 mmol) and PPh$_3$ (4.16 g, 15.88 mmol) in THF (50 mL) was added DIAD (2.9 mL, 14.82 mmol) dropwise with stirring at 0° C. under N$_2$. After the addition was complete, the reaction mixture was stirred at 70° C. for an additional 18 h under N$_2$. The solvent was removed in vacuo, and the residue was purified via silica gel chromatography (PE: EtOAc=50:1 to 20:1) to afford the title compound.

Step B. 2,3-Difluoro-5-(3-hydroxycyclobutoxy)phenol

To a solution of 1-(benzyloxy)-5-(1r,3r)-3-(benzyloxy) cyclobutoxy)-2,3-difluorobenzene (1.50 g, 3.78 mmol) in MeOH (50 mL) was added 10% Pd—C (600 mg, 2.82 mmol). Then the mixture was stirred at rt for 18 h under H$_2$ (50 Psi). The mixture was filtered, and the filtrate was concentrated in vacuo. The residue was purified via silica gel chromatography (PE:EtOAc=1:1) to afford the title compound.

Step C: 3-(3-(Benzyloxy)-4,5-difluorophenoxy)cyclobutanol

To a suspension of 2,3-difluoro-5-((1r,3r)-3-hydroxycyclobutoxy) phenol (1.00 g, 4.63 mmol) and K$_2$CO$_3$ (1.279 g, 9.25 mmol) in acetone (30 mL) was added (bromomethyl) benzene (0.87 g, 5.09 mmol) dropwise with stirring at rt. Then the mixture was stirred at rt for 48 h. After removing the solvent in vacuo, the residue was diluted with water (30 mL), extracted with EtOAc (30 mL×3). The organic layer was dried over anhyd. Na$_2$SO$_4$, filtered and concentrated in vacuo. The residue was purified by silica gel chromatography (PE:EtOAc=2:1) to afford title compound.

Step D. 1-(Benzyloxy)-2,3-difluoro-5-((1R,3R)-3-methoxycyclobutoxy)benzene

To a soln. of (1R,3R)-3-(3-(benzyloxy)-4,5-difluorophenoxy)cyclobutan-1-ol from step C (380 mg, 1.241 mmol) in dry DMF (10 mL) was added NaH. (60 mg, 1.5 mmol) (60% in oil) in portions at 0° C. After 1 h, MeI (528 mg, 3.72 mmol) was added dropwise at 0° C. Then the mixture was stirred for 18 h with gradual warming to it Water (~10 mL) was added to quench the reaction, and the mixture was diluted with water (100 mL) and extracted with EtOAc (2×20 mL). The organic layer was dried over Na$_2$SO$_4$, filtered and concentrated in vacuo. The residue was purified by silica gel chromatography (PE:EtOAc=10:1) to afford the title compound.

Step E. Cis 2,3-Difluoro-5-((1R,3R)-3-methoxycyclobutoxy)phenol

To a soln. of 1-(benzyloxy)-2,3-difluoro-5-((1R,3R)-3-methoxycyclobutoxy)benzene (310 mg, 0.968 mmol) in MeOH (30 mL) was added 10% Pd—C (50 mg, 0.235 mmol). Then the mixture was stirred at rt for 2 h under $H_2$ (40 PSI). The mixture was filtered, and the filtrate was concentrated in vacuo to give the title compound.

Step F. 2,3-Difluoro-5-((1r,3r)-3-methoxycyclobutoxy)phenyl trifluoromethane sulfonate To a soln. of 2,3-difluoro-5-((1r,3r)-3-methoxycyclobutoxy)phenol (200 mg, 0.869 mmol) in DCM (5 was added pyridine (89 mg 1.129 mmol) and trifluoromethanesulfonic anhydride (319 mg, 1.129 mmol) dropwise with stirring at 0° C. Then the mixture was stirred at rt for 3 h. Water (10 mL) was added, and the mixture was extracted with DCM (20 mL×2). The organic layer was dried over $Na_2SO_4$, filtered and concentrated in vacuo. The residue was purified by silica gel chromatography (PE:EtOAc=2.0:1) to afford the title compound. $^1$H NMR (400 MHz, $CDCl_3$) 6.65 (ddd, J=11.05, 5.77, 2.74 Hz. 1H) 6.52-6.56 (m, 1H) 4.73-4.79 (m, 1H) 4.10-4.16 (m 1H) 3.28 (s, 3H) 2.37-2.50 (m, 4H).

Intermediate 5

1-Bromo-3-chloro-2-fluoro-5-(trifluoromethoxy)benzene

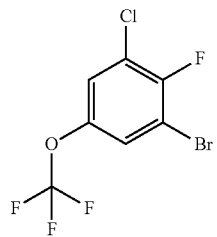 [SMILES: Fc1c(Cl)cc(OC(F)(F)F)cc1Br]

Step A. 1-Bromo-2-fluoro-4-nitro-5-(trifluoromethoxy)benzene

To a soln. of 2-bromo-1-fluoro-4-(trifluoromethoxy)benzene (10.0 g, 38.6 mmol) in ACN (150 mL) was added nitronium tetrafluoroborate (5.38 g, 40.5 mmol) at 0° C., and the mixture was stirred at 0-18° C. for 16 h. The reaction mixture was extracted with EtOAc (3×200 mL), and washed with water (2×150 mL) and brine (2×150 mL). The organic layer was dried over anhyd. $Na_2SO_4$, filtered, and the filtrate was concentrated in vacuo. The resulting residue was purified by silica gel chromatography (PE:EtOAc=20:1 to 5:1) to give the title compound.

Step B. 4-Bromo-5-fluoro-2-(trifluoromethoxy)aniline

To a stirred soln, of 1-bromo-2-fluoro-4-nitro-5-(trifluoromethoxy)benzene (4.0 g. 13.16 mmol) in MeOH (20 mL) and water (2 mL) was added $NH_4Cl$ (7.04 g, 132 mmol) and iron (2.204 g, 39.5 mmol). The mixture was stirred at 50° C. for 18 h. The mixture was washed with water (2×30 mL) and extracted with EtOAc (2×50 mL). The extract was dried over by $Na_2SO_4$, filtered and concentrated in vacuo. The residue was purified by silica gel column chromatography (PE:EtOAc=10:1) to give the title compound.

Step C. 4-Bromo-2-chloro-3-fluoro-6-(trifluoromethoxy)aniline

To a stirred soln. of 4-bromo-5-fluoro-2-(trifluoromethoxy)aniline (750 mg, 2.74 mmol) in ACN (30 mL) was added 1-chloropyrrolidine-2,5-dione (365 mg, 2.74 mmol) and the mixture was stirred at 50° C. for overnight (18 h). The mixture was washed with water (2×10 mL) and extracted with EtOAc (2×30 mL). The organic layer was dried over anhyd. $Na_2SO_4$ and concentrated in vacuo. The residue was purified by silica gel column chromatography (PE:EtOAc=50:1 to 30:1) to give the title compound.

Step D. 1-Bromo-3-chloro-2-fluoro-5-(trifluoromethoxy)benzene

To a stirred soln. of 4-bromo-2-chloro-3-fluoro-6-(trifluoromethoxy)aniline (300 mg, 0.973 mmol) in THF (5 mL) was added isopentyl nitrite (228 mg, 1.945 mmol), and the mixture was stirred at 50° C. for 4 h. The mixture was washed with water (2×10 mL) and extracted with EtOAc (2×30 mL). The combined organic layer was dried over anhyd. $Na_2SO_4$, filtered and concentrated in vacuo. The residue was purified by TLC (PE:EtOAc=10:1) to give the title compound.

Intermediate 6

4-Bromo-3-(4-Chlorophenyl)-5-(trifluoromethyl)isothiazole

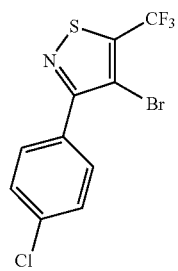 [SMILES: FC(F)(F)c1snc(-c2ccc(Cl)cc2)c1Br]

Step A. 5-(4-chlorophenyl)-1,3,4-oxathiazol-2-one

To a solution of 4-chlorobenzamide (3.0 g, 17.35 mmol) in toluene (10 ml) was added carbonochloridic hypochlorous thioanhydride (4.55 g, 34.7 mmol) at ~20° C. Then the mixture was stirred overnight (~18 h) at 100° C. The resulting mixture was concentrated in vacuo. The resulting residue was purified by column chromatography on silica gel (EtOAc/PE=1:20) to give the title compound.

Step B—ethyl 3-(4-chlorophenyl)-5-(trifluoromethyl)isothiazole-4-carboxylate Into a 100 mL sealed tube was placed 5-(4-chlorophenyl)-1,3,4-oxathiazol-2-one (2.2 g, 9.78 mmol), ethyl 4,4,4- trifluorobut-2-ynoate (2.437 g, 14.67 mmol) and 1,3-dichlorobenzene (20 ml). The resulting solution was stirred for 18 h at 130° C. The mixture was stirred at 150° C. for 5 h. The resulting mixture was concentrated in vacuo. The resulting residue was purified by silica gel column chromatography (PE) to give the title compound.

Step C. 3-(4-chlorophenyl)-5-(trifluoromethyl)isothiazole-4-carboxylic acid

To a solution of ethyl 3-(4-chlorophenyl)-5-(trifluoromethyl)isothiazole-4-carboxylate (2.6 g, 6.58 mmol) in THF (10 mL) and water (5 mL) was added LiOH hydrate (0.829 g, 19.75 mmol). Then the mixture was stirred at rt for 18 h. After acidification with 1N HCl to pH=2, the solvent was removed in vacuo. The residue was purified by silica gel column chromatography (EtOAc/PE=10:1 to 1:1) to give the title compound.

Step D. tert-butyl (3-(4-chlorophenyl)-5-(trifluoromethyl)isothiazol-4-yl) carbamates To a mixture of 3-(4-chlorophenyl)-5-(trifluoromethyl) isothiazole-4-carboxylic acid (600 mg, 1.755 mmol) and Et₃N (195 mg, 19931 mmol) in t-BuOH (20 ml) was added diphenylphosphoryl azide (531 mg, 1.931 mmol) at rt. Then the mixture was refluxed for 3 h. The reaction mixture was concentrated in vacuo, and the residue was partitioned between EtOAc (30 mL) and H₂O (30 mL). The organic layer was washed with brine (30 mL), dried over MgSO₄, filtered and concentrated in vacuo. The residue was purified by silica gel chromatography (EtOAc/PE 1:20) to give the title compound.

Step E. 3-(4-chlorophenyl)-5-(trifluoromethyl)isothiazol-4-amine

To a solution of tert-butyl (3-(4-chlorophenyl)-5-(trifluoromethyl)isothiazol-4-yl)carbamate (590 mg, 1.246 mmol) in EtOAc (10 ml) was added HCl/EtOAc (3 ml, 4 M in dioxane) at rt. Then the mixture was stirred rt (under an N₂ atmosphere) for 18 h. The mixture was concentrated in vacuo to give crude product. To the crude product was added EtOAc (20 mL) and water (20 mL) basified with saturated Na₂CO₃ to pH=7~8. Then the mixture extracted with EtOAc (2×10 mL). The organic layer was washed with brine (20 mL), dried over anhydrous MgSO₄, filtered and concentrated in vacuo. The residue was purified by silica gel column chromatography (EtOAc/PE=20:1) to give the title compound.

Step F. 4-bromo-3-(4-chlorophenyl)-5-(trifluoromethyl)isothiazole

To a solution of 3-(4-chlorophenyl)-5-(trifluoromethyl) isothiazol-4-amine (50 mg, 0.161 mmol) in MeCN (2 mL) was added CuBr₂ (72 mg, 0.322 mmol) and tert-butyl nitrite (37 mg, 0.359 mmol) at 0° C. and the mixture was stirred at 0° C. for 30 min. The mixture was concentrated in vacuo and washed with water (10 mL), and extracted with EtOAc (2×10 mL). The combined organic layer was washed with brine (2×10 mL) and concentrated in vacuo to give the crude product, which was purified by silica gel chromatography (PE:EtOAc=50:1) to give the title compound. ¹H NMR (400 MHz, CDCl₃) δ ppm 7.78 (d, J=8.41 Hz, 2H) 7.49 (d J=8.41 Hz, 2H).

Intermediate 7

Ethyl 3-(1,2,3,4-tetrahydroisoquinolin-6-yl)propanoate

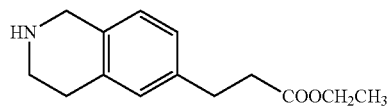

Step A. (E)-ethyl 3-(isoquinolin-6-yl)acrylate

To a solution of 6-bromoisoquinoline (10.0 g, 48.06 mmol) in dry 1,4-dioxane (100 ml) was added tri-tert-butylphosphonium tetrafluoroborate (1.4 g, 4.8 mmol), ethyl acrylate (7.22 g, 72.10 mmol) and N-cyclohexyl-N-methyl-cyclo-hexanamine (28.17 g, 144.19 mmol). Then the mixture was degassed for 5 min with N₂, and Pd₂(dba)₃ (3.5 g, 4.8 mmol) was added. The mixture was stirred at 100° C. for 18 h under a N₂ atmosphere. The mixture was extracted with EtOAc (2×200 mL), washed with brine (500 mL), dried (Na₂SO₄), and then purified by chromatography (PE:EtOAc=20:1 to 10:1) to give the title compound.

Step B. ethyl 3-(1,2,3,4-tetrahydroisoquinolin-6-yl)propanoate

To a solution of (E)-ethyl 3-(isoquinolin-6-yl)acrylate (9.0 g, 39.60 mmol) in EtOH (150 ml) was added platinum (IV) oxide (0.899 g, 3.96 mmol). The reaction mixture was stirred under hydrogen (50 PSI) at 60° C. for 5 h. The reaction mixture was cooled to rt, the mixture was filtered, and the filtrate was concentrated in vacuo to give the title compound. m/z 234.3 [M+H]⁺.

Intermediate 8

2-Bromo-4-(cyclobutyldifluoromethyl)-1-fluorobenzene

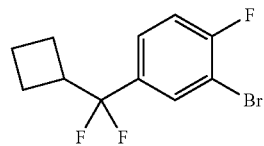 [SMILES: Fc1ccc(C(F)(F)C2CCC2)cc1Br]

Step A:
3-Bromo-4-fluoro-N-methoxy-N-methylbenzamide

To a soln, of DIEA (4.78 ml, 27.4 mmol), 3-bromo-4-fluorobenzoic acid (2.0 g, 9.13 mmol) and N,O-dimethylhydroxylamine hydrochloride (0.891 g, 9.13 mmol) in DMF (25 ml) was added HATU (3.47 g, 9.13 mmol) at 0° C., and the mixture was stirred 18 h (0° C.→rt). The mixture was poured into water (100 mL), extracted with EtOAc (3×200 mL), washed with water (5×50 mL) and brine (2×50 mL). The organic soln. was dried over Na₂SO₄, the salt was filtered off, and the filtrate was concentrated in vacuo. The residue was purified by silica gel chromatography (PE: EtOAc=20:1 to 5:1) to give the title compound. m/z 264.0 [M+H]⁺.

Step B. (3-Bromo-4-fluorophenyl)(cyclobutyl)methanone

To a suspension of magnesium (0.538 g, 22.13 mmol) in THF (20 ml) was added $I_2$ (0.028 g, 0.111 mmol) at 40° C., the mixture was stirred at 40° C. for 10 min, and then bromocyclobutane (2.99 g, 22.13 mmol) was added dropwise with stirring at 10° C. ($N_2$ atmosphere). After the addition was complete, the reaction mixture was stirred at 40° C. for additional 2 h. The above soln. was added dropwise to a soln. of 3-bromo-4-fluoro-N-methoxy-N-methylbenzamide (2.9 g, 11.07 mmol) in THF (30 mL) at 0° C. (under $N_2$ atmosphere). The mixture was stirred for 16 h (0° C.-rt). The reaction mixture was poured into ice water (20 mL), and the mixture was extracted with EtOAc (2×30 mL). The combined organic layer was washed with brine (2×20 mL) and then dried over anhyd. $Na_2SO_4$. The organic layer was filtered and concentrated in vacuo to give crude product. The crude product was purified by silica gel column chromatography (PE/DCM=100:1 to 5:1) to give compound the title compound.

Step C. 2-bromo-4-(cyclobutyldifluoromethyl)-1-fluorobenzene

To a soln. of (3-bromo-4-fluorophenyl)(cyclobutyl) methanone (300 mg, 1.167 mmol) in DAST (3.0 ml, 16.27 mmol) was added dropwise MeOH (7.58 µl, 0.187 mmol) with stirring at 0° C. (under $N_2$ atmosphere). After the addition was complete, the reaction mixture was stirred at 80° C. for additional 3 days. The reaction mixture was cooled to rt, and poured into sat. $Na_2CO_3$ (10 mL). Then the mixture was extracted with PE (~20 mL×2). The combined organic layers were washed with brine (~10 mL×2), dried over $Na_2SO_4$, filtered, and concentrated in vacuo to give crude product. The crude product was purified by PTLC (PE) to give the title compound. ¹H NMR (400 MHz, $CDCl_3$) δ 7.66 (d, J=5.5 Hz, 1H), 7.37 (br. s., 1H), 7.15 (t, J=8.4 Hz, 1H), 3.03-2.85 (m, 1H), 2.27-2.11 (m, 2H), 2.05-1.77 (m, 4H).

Intermediate 9

2,3-Difluoro-5-(3-methylcyclobutoxy)phenyl trifluormethanesulfonate

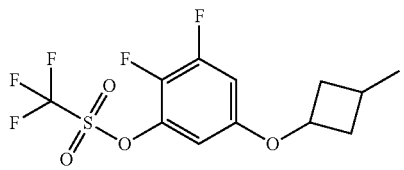 [SMILES: CC1CC(Oc2cc(F)c(F)c(OS(=O)(=O)C(F)(F)F)c2)C1]

Step A. 1-(benzyloxy)-5-(3-(bromomethyl)cyclobutoxy)-2,3-difluoro-benzene

To a stirred soln. of (3-(3-(benzyloxy)-4,5-difluorophenoxy)cyclobutyl)methanol (800 mg, 2.498 mmol) and $CBr_4$ (1.24 g, 3.75 mmol) in DMF (8 mL) was added $PPh_3$ (982 mg, 3.75 mmol) portionwise at 0° C. Then the reaction mixture was stirred at rt for 2 h. The mixture was diluted with water (50 mL) and extracted with EtOAc (2×30 mL). The organic layer was concentrated in vacuo, and the crude product was purified by silica gel chromatography (PE/EtOAc=40:1) to give the title compound.

Step B. 1-(benzyloxy)-2,3-difluoro-5-(3-methylcyclobutoxy)benzene

To a stirred soln. of 1-(benzyloxy)-5-(3-(bromomethyl) cyclobutoxy)-2,3-difluorobenzene (580 mg, 1.51 mmol) in DMF (8 mL) was added $NaBH_4$ (115 mg, 3.03 mmol). Then the reaction mixture was placed under $N_2$ and stirred at rt for 18 h. The reaction was quenched with satd. aq. of $NH_4Cl$ (20 mL), extracted with EtOAc (20 mL×2), washed with water (100 mL), and the organic layer was concentrated in vacuo. The crude product was purified by silica gel chromatography (PE/EtOAc=5:1) to give the title compound.

Step C. 2,3-difluoro-5-(3-methylcyclobutoxy)phenol

A mixture of 1-(benzyloxy)-2,3-difluoro-5-(3-methylcyclobutoxy)benzene (390 mg, 1.28 mmol) and 10% Pd—C (100 mg, 0.094 mmol) in MeOH (50 mL) was stirred under hydrogen (40 PSI) at rt for 2 h. The mixture was filtered and concentrated in vacuo to give the crude title compound.

Step D. 2,3-difluoro-5-(3-methylcyclobutoxy)phenyl trifluormethanesulfonate

To a stirred soln. of 2,3-difluoro-5-(3-methylcyclobutoxy) phenol (200 mg, 0.934 mmol) in DCM (5 mL) was added pyridine (96 mg, 1.214 mmol) and trifluoromethanesulfonic anhydride (342 mg, 1.214 mmol) dropwise at 0° C. Then the reaction mixture was warmed to rt for 5 h. The solvent was evaporated in vacuo, and the resulting mixture was diluted with water (20 mL) and extracted with EtOAc (20 mL×2). The organic layer was concentrated in vacuo, and the crude product was purified by silica gel chromatography (PE/EtOAc=10:1) to give the title compound.

Intermediate 10

2-(5-Bromo-4-fluoro-2-methoxyphenoxy)-5-methyl-thiazole

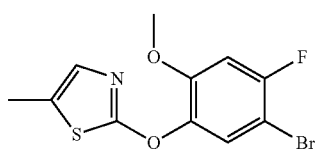 [SMILES: COc1cc(F)c(Br)cc1Oc1ncc(C)s1]

Step A. 5-Bromo-4-fluoro-2-methoxyphenol

To a soln. of 4-fluoro-2-methoxyphenol (2.0 g, 14.07 mmol) in MeCN (40 mL) was added NHS (2.63 g, 14.78 mmol) at 0° C., and the mixture was stirred at rt for 18 h. After removing the solvent in vacuo, the residue was extracted with EtOAc (60 mL) and water (60 mL). The organic layer was separated, dried and concentrated in vacuo. The residue was purified via silica gel chromatography (PE:EtOAc=100:1) to afford the title compound.

Step B. 2-(5-Bromo-4-fluoro-2-methoxyphenoxy)-5-methylthiazole

A mixture of 2-bromo-5-methylthiazole (300 mg, 1.68 mmol). 5-bromo-4-fluoro-2-methoxyphenol (410 mg, 1.85 mmol) and K$_2$CO$_3$ (466 mg, 3.37 mmol) in DMF (10 mL) was stirred at 120° C. for 18 h. The mixture was diluted with water (200 mL) and extracted with EtOAc 3×20 mL). The organic layer was dried and concentrated in vacuo. The residue was purified via prep-HPLC to afford the title compound. m/z 319 [M+H]$^+$.

Intermediate 11

5-Bromo-3-methyl-1-(p-tolyl)-1H-pyrazole-4-carbonitrile

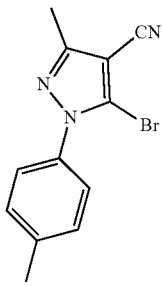 [SMILES: Cc1ccc(-n2nc(C)c(C#N)c2Br)cc1]

Step A. 5-Amino-3-methyl-1-(p-tolyl)-1H-pyrazole-4-carbonitrile

To a soln. of p-tolylhydrazine hydrochloride (50 g, 315 mmol) in EtOH (400 ml) was added TEA (132 ml, 946 mmol), and the reaction mixture was stirred at rt for 40 min. Then 2-(1-ethoxyethylidene)-malononitrile (38.6 g, 284 mmol) was added slowly at 0° C. and the reaction mixture was stirred at 25° C. for 12 h. The reaction mixture was partitioned between EtOAc (200 mL) and water (200 mL), and the separated organic layer was washed with brine (200 mL). The organic layer was dried (Na$_2$SO$_4$) and concentrated in vacuo, and the resulting residue was purified by silica gel chromatography (PE/EtOAc 5:1 to 1:1) to give the title compound. m/z 213.2 [M+H]$^+$.

Step B. 5-Bromo-3-methyl-1-(p-tolyl)-1H-pyrazole-4-carbonitrile

To a soln. of 5-amino-3-methyl-1-(p-tolyl)-1H-pyrazole-4-carbonitrile (10 g, 47.1 mmol) and CuBr (10.14 g, 70.7 mmol) in MeCN (100 mL) was added isopentyl nitrite (11.04 g, 94 mmol) dropwise. The reaction mixture was stirred at 25° C. under a N$_2$ atmosphere for 2 h. The reaction mixture was partitioned between EtOAc (60 mL) and water (60 mL), and the separated organic layer was washed with brine (60 mL). The organic layer was concentrated in vacuo, and the residue was purified by silica gel chromatography (PE/EtOAc 15:1-10:1) to give the title compound. m/z 276.1 [M+H]$^+$.

Intermediate 12

2-(5-bromo-4-fluoro-2-methoxyphenoxy)-5-methylpyridine

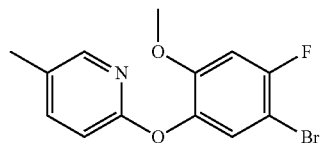 [SMILES: COc1cc(F)c(Br)cc1Oc1ccc(C)cn1]

Step A. 2-(5-bromo-4-fluoro-2-methoxyphenoxy)-5-methyl-3-nitropyridine

A mixture of 2-chloro-5-methyl-3-nitropyridine (2 g, 10.5 mmol), 5-bronco-4-fluoro-2-methoxyphenol (2.56 g, 10.5 mmol) and K$_2$CO$_3$ (4.8 g, 34.8 mmol) in DMF (20 mL) was stirred at rt overnight. The mixture was poured into cold water (100 mL) and extracted with EtOAc (3×50 mL). The combined organic layers were washed with brine, and the organic layer was concentrated in vacuo. The resulting residue was stirred with PE (10 mL) for 30 min., and the solid that separated was filtered off to give the title compound.

Step B. 2-(5-bromo-4-fluoro-2-methoxyphenoxy)-5-methylpyridin-3-amine

To a mixture of 2-(5-bromo-4-fluoro-2-methoxyphenoxy)-5-methyl-3-nitropyridine (2.7 g, 7.56 mmol) and iron powder (1.7 g, 30.4 mmol) in EtOH (25 mL) was added a soln. of NH$_4$Cl (1.0 g, 18.9 mmol) in water (3 mL) dropwise at 55-60° C. After addition, the mixture was heated to reflux for 3 h. The reaction mixture was filtered through Celite™, and the filtrate was concentrated in vacuo. The residue was dissolved in EtOAc (20 mL), and the organic layer was washed with water (10 mL) and brine (10 mL). The organic layer was concentrated in vacuo to give the title compound.

Step C: 2-(5-bromo-4-fluoro-2-methoxyphenoxy)-5-methylpyridine

To the soln. of 2-(5-bromo-4-fluoro-2-methoxyphenoxy)-5-methylpyridin-3-amine (2.0 g, 6.1 mmol) in THF (20 mL) was added dropwise a soln. of isopentyl nitrite (1.4 g, 12.2 mmol) in THF (3 mL) at rt under N$_2$. Then the reaction mixture was heated to reflux for 3 h. The reaction mixture was concentrated in vacuo, and the resulting residue was purified by silica gel chromatography (PE:EA=20:1) to give the title compound. $^1$H NMR (400 MHz, CDCl$_3$) δ ppm 7.93 (s, 1H) 7.48-7.56 (m, 1H) 7.30 (d, 1=7.04 Hz, 1H) 6.77-6.92 (m, 2H) 3.71-3.81 (m, 3H) 2.28 (s, 3H).

Intermediate 13

(2-(Cyclobutylthio)-5-fluoropyridin-4-yl)boronic acid

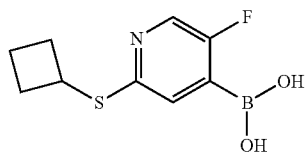 [SMILES: OB(O)c1cc(SC2CCC2)ncc1F]

Step A. 5-Fluoropyridine-2-thiol

Prepared from 5-fluoropyridin-2-ol according to the procedure described in US 2012/0309796.

Step B. 2-(Cyclobutylthio)-5-fluoropyridine

A reaction vial was charged with $Cs_2CO_3$ (652 mg, 2.00 mmol) and 5-fluoro-2-thiopyridone (129 mg, 1 mmol). The vial was sealed and flushed with $N_2$. Dry DMF (5 mL) and bromocyclobutane (113 μl, 1.200 mmol) were added via syringe. The tube was heated (50° C.) for 2 h. The mixture was diluted with EtOAc (20 mL) and washed with water (2×10 mL). The organic layer was washed with brine (5 mL), dried over $MgSO_4$, filtered and concentrated in vacuo. The residue was purified by silica gel chromatography (0 to 30% EtOAc/hexanes) to give the title compound. m/z 184.50 [M+H]$^+$

Step C. (2-(Cyclobutylthio)-5-fluoropyridin-4-yl)boronic acid

A three-necked round-bottom flask was charged with a soln. of diisopropylamine (0.097 ml, 0.682 mmol) in dry THF (2 ml). The solution was cooled to −20° C. and 2.5 M n-BuLi (0.262 ml, 0.655 mmol) as added. The soln was stirred for 10 min and then warmed to 0° C. for 10 min. The soln. was cooled to −78° C. and a soln. of 2-(cyclobutylthio)-5-fluoropyridine (100 mg, 0.546 mmol) from step B in dry THF (3 ml) was added dropwise. The mixture was stirred for 1 h, followed by the addition of trimethyl borate (0.305 ml, 2.73 mmol). The mixture was gradually warmed to rt and stirred for 4 h. The reaction was quenched by addition of aq. 1 M HCl (10 mL), and the mixture was stirred for 10 min. The product was extracted with EtOAc (2×15 mL). The combined organic layers were washed with brine (5 mL), dried over $MgSO_4$, filtered and concentrated in vacuo. The crude product was used for next step without further purification. m/z 228.17 [M+H]$^+$

Intermediate 14

1-Bromo-3-chloro-5-cyclobutoxy-2-fluorobenzene

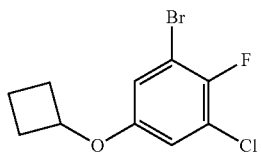 [SMILES: Fc1c(Cl)cc(OC2CCC2)cc1Br]

Step A. 2-chloro-4-cyclobutoxy-1-fluorobenzene

To a soln. of 3-chloro-4-fluorophenol (5 g, 34.12 mmol) in DMF (50 mL) was added bromocyclobutane (9.21 g, 68.24 mmol), $Bu_4NI$ (12.60 g, 34.12 mmol) and $Cs_2CO_3$ (11.12 g, 34.12 mmol). Then the mixture was stirred at 90° C. for 18 h. The mixture was extracted with EtOAc (3×100 mL) and water (600 mL), and the organic layer was separated, dried and concentrated in vacuo. The residue was purified by silica gel chromatography (PE) to afford the title compound.

Step B. 1-bromo-3-chloro-5-cyclobutoxy-2-fluorobenzene

To a soln. of 2,2,6,6-tetramethyl-piperidine (0.845 g, 5.98 mmol) in THF (20 mL) was added dropwise n-BuLi. (2.5 M, 2.4 mL, 6.00 mmol) at −78° C. under $N_2$. After 20 min, the mixture was allowed to warm to 0° C. and stirred for 10 min. Then 2-Chloro-4-cyclobutoxy-1-fluorobenzene (1.0 g, 4.98 mmol) in THF (5 mL) was added dropwise to the mixture at −78° C. The mixture was stirred at −78° C. for 40 min. Then bromine (1,195 g, 7.48 mmol) was added, and the mixture was stirred at −78° C. for 40 min. The mixture was quenched with satd. aq. $NH_4Cl$ (10 mL), and extracted with EtOAc (3×30 mL) and water (20 mL). The organic layer was separated, dried and concentrated in vacuo. The residue was purified by silica gel chromatography (PE) to afford the title compound. $^1$H NMR (400 MHz, $CDCl_3$, ppm): δ 1.63-1.72 (m, 1H) 1.85 (q, J=10.30 Hz, 1H) 2.07-2.17 (m, 2H) 2.37-2.47 (m, 2H) 4.53 (quin, J=6.95 Hz, 1H) 6.77 (dd, J=5.28, 2.93 Hz, 1H) 6.87 (dd, J=4.89, 2.93 Hz, 1H).

Intermediate 15

4-Fluoro-1-(4-fluorophenyl)-5-iodo-3-methyl-1H-pyrazole

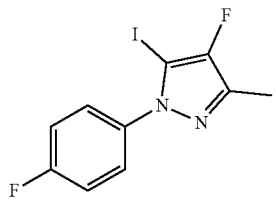

Step A. 1-(4-Fluorophenyl)-3-methyl-1H-pyrazol-5-amine

To a soln. of (4-fluorophenyl)-hydrazine hydrochloride (30.0 g, 185 mmol) in EtOH (100 mL) was added $Et_3N$ (56.0 g, 554 mmol) and 2-(ethoxymethylene)malononitrile (23.66 g, 194 mmol). After the addition was complete, the reaction mixture was stirred 70° C. for 15 h. The reaction mixture was cooled to rt and concentrated in vacuo. Then the mixture was extracted with EtOAc (2×100 mL). The combined organic layer was washed with brine, and then dried over $Na_2SO_4$, filtered and concentrated in vacuo to give crude product. The crude product was purified by silica gel column chromatography (PE/EtOAc 10:1 to 5:1) to give the title compound.

Step B. 4-fluoro-1-(4-fluorophenyl)-3-methyl-1H-pyrazol-5-amine

To a soln. of 1-(4-fluoro-(10.0 g, 52.3 mmol) in THF (50 mL) was added Selectfluor® (18.53 g, 52.3 mmol). After the addition was complete, the mixture was stirred at rt for 15 h. The reaction was concentrated in vacuo, and the mixture was extracted with EtOAc (2×50 mL). The organic layer was washed with brine, then dried over $Na_2SO_4$, filtered and concentrated in vacuo to give the crude product. The crude product was purified by silica gel column chromatography (PE/EtOAc 30:1 to 10:1) to give the title compound.

Step C. 4-fluoro-1-(4-fluorophenyl)-5-iodo-3-methyl-1H-pyrazole

To a soln. of 4-fluoro-1-(4-fluorophenyl)-3-methyl-1H-pyrazol-5-amine (2.0 g, 9.56 mmol) in MeCN (30 mL) was added isobutyl nitrite (2.465 g, 23.90 mmol) and CuI (3.64 g, 19.12 mmol). After the addition was complete, the mixture was stirred at 60° C. for 1 h. The reaction mixture was cooled to rt, filtered, and concentrated in vacuo. Then the mixture was extracted with EtOAc (50 mL×2). The combined organic layer was washed with brine, and then dried over Na$_2$SO$_4$, filtered and concentrated in vacuo to give the crude product. The crude product was purified by silica gel column chromatography (PE'EtOAc 30:1 to 10:1) to give the title compound, m/z 321.0 [M+H]$^+$

Intermediate 16

2-Chloro-6-(cyclobutylthio)pyridine

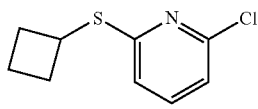 [SMILES: Clc1cccc(SC2CCC2)n1]

Step A: 6-chloropyridine-2-thiol

To a mixture of 6-chloropyridin-2-ol (2.00 g, 15.44 mmol) and Lawesson's reagent (6.56 g, 16.21 mmol) was added THF (50 mL), and the soln. was stirred at about 80° C. overnight under a N$_2$ atmosphere. The soln. was concentrated in vacuo to give the crude product which was purified by silica gel chromatography (PE:EtOAc=6:1) to afford the title compound.

Step B: 2-chloro-6-(cyclobutylthio)pyridine

To a mixture of 6-chloropyridine-2-thiol (270 mg, 1.85 mmol) in DMF (3 mL) was added bromocyclobutane (250 mg, 1.85 mmol) and Cs$_2$CO$_3$ (725 mg, 2.23 mmol). Then the soln. was stirred at 100° C. about 2 h. The soln. was treated with H$_2$O (20 mL) and extracted with EtOAc (10 mL×3). The combined organic layer was washed with brine (10 mL), and then dried over anhyd. Na$_2$SO$_4$, filtered and concentrated in vacuo. The crude product was purified by silica gel chromatography (PE:EtOAc=20:1) to afford the title compound. $^1$H NMR (400 MHz, CDCl$_3$) ppm 7.40 (t, J=7.83 Hz, 1H), 6.96 (dd, J=7.83, 2.74 Hz, 1H), 4.30 (quin, J=7.92 Hz, 1H), 2.49-2.62 (m, 2H), 2.00-2.19 (m, 4H).

Intermediate 17

2-Chloro-6-cyclobutoxypyrazine

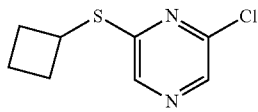

To a suspension of NaH (322 mg, 8.05 mmol) in THF (10 ml) was added cyclobutanol (581 mg, 8.05 mmol), and the mixture was stirred at rt for 15 min. To this soln, was added 2,6-dichloropyrazine (1 g, 6.71 mmol), and the mixture was stirred at 50° C. for 18 h. The soln. was diluted with H$_2$O (20 mL), and the mixture was extracted with EtOAc (3×20 mL). The combined organic layer was washed with brine (10 mL), dried over Na$_2$SO$_4$, filtered and concentrated in vacuo to afford crude product. The residue was purified by silica gel chromatography (PE) to give the title compound. $^1$H NMR (400 MHz, CDCl$_3$) ppm 8.09 (d, J=16.82 Hz, 2H), 5.17 (q, J=7.34 Hz, 1H), 2.43-2.52 (m, 2H), 2.10-2.20 (m, 2H), 1.86 (q, J=10.30 Hz, 1H), 1.62-1.75 (m, 1H).

Intermediate 18

4-Chloro-5-iodo-3-methyl-1-(p-tolyl)-1H-pyrazole

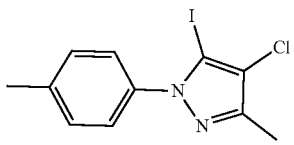

Step A: 4-Chloro-3-methyl-1-(p-tolyl)-1H-pyrazol-5-amine

To a soln. of 3-methyl-1-(p-tolyl)-1H-pyrazol-5-amine (3.0 g, 16.02 mmol, synthesized using similar conditions as described for the fluoro intermediate 15) in MeCN (50 mL) was added NCS (2.35 g, 17.62 mmol), and the mixture was stirred at rt (~25° C.) for 18 h. Then the solvent evaporated in vacuo, and the resulting residue was desolved in EtOAc (100 mL), washed with H$_2$O (60 mL×3 and brine (60 mL). The organic layer was concentrated in vacuo and purified by silica gel chromatography (PE:EtOAc=10:1) to give the title compound. m/z 221.6 [M+H]$^+$.

Step B: 4-Chloro-5-iodo-3-methyl-1-(p-tolyl)-1H-pyrazole

To a soln. of 4-chloro-3-methyl-1-(p-tolyl)-1H-pyrazol-5-amine (2.5 g, 11.28 mmol) in MeCN (50 mL) was added CuI (6.44 g, 33.84 mmol) and isopentyl nitrite (3.30 g, 28.19 mmol) at 0° C. Then the reaction mixture was stirred under reflux for 3 h. The solvent was evaporated in vacuo, and the residue was dissolved in EtOAc (100 mL). The organic layer was washed with H$_2$O (60 mL×3) and brine (60 mL). Then the organic layer was concentrated in vacuo, and the residue was purified by silica gel chromatography (PE:EtOAc=50:1) to give the title compound. m/z 332.9 [M+H]$^+$. $^1$H NMR (400 MHz, CDCl$_3$) δ ppm 2.34 (s, 3H), 2.40 (s, 3H), 7.23-7.28 (m 3H), 7.29-7.37 (m, 2H),

Intermediate 19

2-Bromo-4-cyclobutoxy-6-fluorobenzonitrile

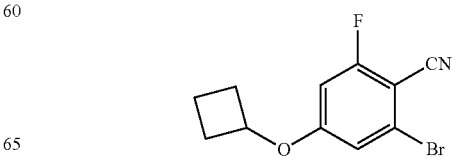

Step A. 1-Bromo-3-cyclobutoxy-5-fluorobenzene

To a soln. of 3-bromo-5-fluorophenol (3.0 g, 15.71 mmol) in DMF (15 mL) was added bromocyclobutane (4.24 g, 31.41 mmol), Bu$_4$NI (5.80 g, 15.71 mmol) and Cs$_2$CO$_3$ (5.12 g, 15.71 mmol). Then the mixture was stirred at 90° C. overnight. The mixture was extracted with EtOAc (90 mL) and water (300 mL). The organic layer was dried (Na$_2$SO$_4$) and concentrated in vacuo. The residue was purified via silica gel chromatography (PE) to afford the title compound.

Step B. 2-Bromo-4-cyclobutoxy-6-fluorobenzaldehyde

To a soln. of 2,2,6,6-tetramethyl-piperidine (692 mg, 4.90 mmol) in THF (10 mL) was added n-BuLi (2.5 M, 1.96 mL, 4.90 mmol) at −78° C. under N$_2$. After 30 min, 1-bromo-3-cyclobutoxy-5-fluorobenzene (1 g, 4.08 mmol) in THF (5 mL) was added dropwise at −78° C. under N$_2$. Then the mixture was stirred at −78° C. for 40 min. DMF (447 mg, 6.12 mmol) was added, and the mixture was stirred at −78° C. for 1 h. The reaction was quenched with saturated NH$_4$Cl soln., acidified to pH 1-2 with 6 N HCl, then partitioned with EtOAc (30 mL) and water (20 mL). The organic layer was dried (Na$_2$SO$_4$) and concentrated in vacuo. The residue was purified via silica gel (PE:EtOAC=400:1) to afford the title compound.

Step C. (E)-2-Bromo-4-cyclobutoxy-6-fluorobenzaldehyde oxime

To a soln. of 2-bromo-4-cyclobutoxy-6-fluorobenzaldehyde (700 mg, 2.56 mmol) in EtOH (10 mL). was added NH$_2$OH (aq., 50% w/w, 340 mg, 5.13 mmol). Then the mixture was stirred at 100° C. for 2 h. After cooling to rt, the mixture was poured onto ice and stirred for 30 min. The resulting suspension was filtered, and the cake was dried to afford the title compound. m/z 288 [M+H]$^+$.

Step D: 2-Bromo-4-cyclobutoxy-6-fluorobenzonitrile

To a soln. of (E)-2-bromo-4-cyclobutoxy-6-fluorobenzaldehyde oxime (650 mg, 2.26 mmol) in DMF (5 mL) was added POCl$_3$ (865 mg, 5.64 mmol) dropwise at 0° C. Then the mixture was allowed to warm to rt and stirred for 4 h. The mixture was poured into water, and the mixture was stirred for 1 h. The mixture was extracted with EtOAc (30 mL) and water (100 mL). The organic layer was dried (Na$_2$SO$_4$) and concentrated in vacuo. The residue was purified via silica gel chromatography (PE:EtOAc=50:1) to afford the title compound. $^1$H NMR (400 MHz, CDCl$_3$, ppm): a 1.70-1.78 (m, 1H) 1.89-1.97 (m, 1H) 2:15-2.25 (m, 2H) 2.48 (d, J=7.43 Hz, 2H) 4.61-4:68 (m, 1H) 6.57 (d, J=10.56 Hz, 1H) 6.92 (br. s., 1H).

Intermediate 20

1-Bromo-2-chloro-5-cyclobutoxy-4-methoxybenzene

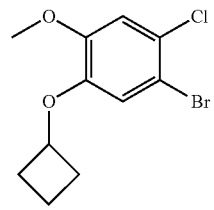

Step A. 4-chloro-1-cyclobutoxy-2-methoxybenzene

To a soln. of 4-chloro-2-methoxyphenol (5.0 g, 31.5 mmol) in 50 mL of DMF was slowly added bromocyclobutane (8.50 g, 63.0 mmol), Cs$_2$CO$_3$ (20.52 g, 63.0 mmol) and Bu$_4$NI (11.64a, 31.6 mmol). The mixture was stirred at 90° C. overnight. The mixture was diluted with water (400 mL), extracted with EtOAc (100 mL), and concentrated in vacuo. The resulting residue was purified by silica gel flash column chromatography (Petroleum ether:ethyl acetate=100:1) to give the title compound.

Step B: 1-bromo-2-chloro-5-cyclobutoxy-4-methoxybenzene

To a soln. of 4-chloro-1-cyclobutoxy-2-methoxybenzene (2 g, 9.49 mmol) in MeCN (20 mL) was slowly added NBS (1.832 g, 10.44 mmol). The mixture was stirred at rt for overnight. The mixture was extracted with EtOAc (100 mL), and the organic layer was washed with H$_2$O (50 mL×3), and concentrated in vacuo. The residue was purified by silica gel flash column chromatography (Petroleum ether:ethyl acetate=100:1) to afford the title compound. $^1$H NMR (400 MHz, CDCl$_3$) ppm 6.91 (d, J=8.78 Hz, 2H) 4.61 (quin, J=7.15 Hz, 1H) 3.84 (s, 3H) 2.42-2.52 (m, 2H) 2.17-2.29 (m, 2H) 1.87 (q, J=10.29 Hz, 1H) 1.64-1.75 (m, 1H).

Intermediate 21

2-(3-bromo-5-(difluoromethyl)-4-fluorophenoxy)pyridine

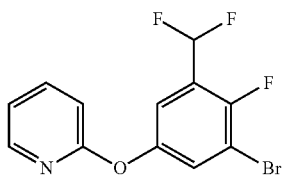 [SMILES: Fc1c(Br)cc(Oc2ccccn2)cc1C(F)F]

Step A. 3-bromo-2-fluoro-5-((triisopropylsilyl)oxy)benzaldehyde

To a stirred soln. of 2,2,6,6-tetramethylpiperidine (18.06 g, 0.13 mol) in THF (250 mL) in a three necked round bottom flask was added n-BuLi (2.5 M, 51.1 mL, 0.13 mmol) dropwise at −78° C. over 0.5 h. Then the mixture was stirred at 0° C. for 0.5 h. A solution of (3-bromo-4-fluorophenoxy)-triisopropylsilane (37.0 g, 0.11 mmol) in THF (300 mL) was added to the above mixture dropwise at −78° C. over 0.5 h. The mixture was stirred for 1 h, and then DMF (15.57 g, 213 mmol) was added. The mixture was diluted with water (300 mL) and extracted with EtOAc (2×100 mL). The organic layer was collected, washed with brine, dried over anhydrous $Na_2SO_4$, filtered, and concentrated in vacuo. The crude product was purified by silica gel column chromatography (PE:EtOAc from 20:1 to 1:1) to afford 3-bromo-2-fluoro-5-((triisopropylsilyl)oxy) benzaldehyde and 3-bromo-2-fluoro-5-hydroxybenzaldehyde.

Step B-3-bromo-5-(difluoromethyl)-4-fluorophenol

To a stirred solution of 3-bromo-2-fluoro-5-((triisopropylsilyl)oxy)benzaldehyde (22.00 g, 58.60 mmol) in DCM (200 mL) was added DAST (11.62 ml, 88.00 mmol) dropwise at 0° C., and the resulting mixture was allowed to warm to rt for 2 h with stirring. The mixture was poured into a diluted $NaHCO_3$ solution to adjust the of the mixture to about pH 5, then diluted with water (100 mL), extracted with DCM (100 mL). The organic layer was collected, washed with brine, dried over anhydrous $Na_2SO_4$, and filtered. The organic layer was concentrated in vacuo. The resulting residue was purified by silica gel column chromatography (PE:EtOAc from 20:1 to 5:1) to give the title compound.

Step C-3-bromo-5-(difluoromethyl)-4-fluorophenol

A mixture of (3-bromo-5-(difluoromethyl)-4-fluorophenoxy)triisopropylsilane (10.0 g, 25.2 mmol) and TBAF (7.90 g, 30.2 mmol) in THF (50 ml) was stirred at 15° C. for 2 h. The mixture was diluted with water (50 mL) and extracted with EtOAc (50 mL). The organic layer was collected, washed with brine, dried over anhydrous $Na_2SO_1$, and filtered, and the concentrated in vacuo. The crude product was purified by silica gel column chromatography (PE:EtOAc from 10:1 to 3:1) to afford the title compound.

Step D-2-(3-bromo-5-(difluoromethyl)-4-fluorophenoxy)pyridine

A mixture of 2-fluoropyridine (200 mg, 2.06 mmol) and 3-bromo-5-(difluoromethyl)-4-fluorophenol (596 mg, 2.47 mmol), $Cs_2CO_3$ (1.34 g, 4.12 mmol) in NMP (5 mL) was heated at 140° C. under microwave irradiation for 1 h. The mixture was diluted with water (20 mL), and extracted with EtOAc mL). The organic layer was collected, washed with brine, dried over anhydrous $Na_2SO_4$, filtered, and concentrated in vacuo. The crude product was further purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$. Detector wavelength: 220 nm), followed by concentration (below 50° C.) to afford the title compound.

Intermediate 22

2-Bromo-4-cyclobutoxy-1-fluorobenzene

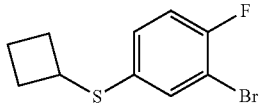 [SMILES: Fc1ccc(SC2CCC2)cc1Br]

To a soln. of 3-bromo-4-fluorophenol (50.0 g, 262 mmol) in DMF (400 mL) was added bromocyclobutane (38.9 g, 288 mmol), TBAI (48.3 g, 131 mmol) and $Cs_2CO_3$ (102 g, 314 mmol). The mixture was stirred at 90° C. for 12 h. The reaction mixture was diluted with water (1 L) and extracted with the mixture of PE:EtOAc=4:1 (3×1 L). The organic layer was concentrated in vacuo to give the crude product, which was purified by silica gel column chromatography (PE) to give the title compound. $^1$H-NMR (400 MHz, $CDCl_3$) ppm 6.97-7.03 (m, 2H) 6.70-6.73 (m, 1H) 4.53-4.60 (m, 1H) 2.43-2.46 (m, 2H) 2.14-2.17 (m, 2H) 1.80-1.91 (m, 1H) 1.60-1.73 (n, 1H).

Intermediate 23

1-Bromo-5-cyclobutoxy-3-(difluoromethyl)-2-fluorobenzene

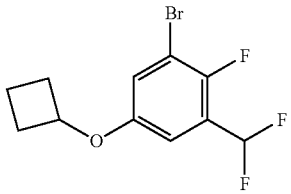 [SMILES: Fc1c(Br)cc(OC2CCC2)cc1C(F)F]

Step A.
3-Bromo-5-cyclobutoxy-2-fluorobenzaldehyde

To a soln. of 2,2,6,6-tetramethyl-piperidine (3.46 g, 24.48 mmol) in THF (50 mL) was added 2.5 M nBuLi (9.8 mL, 24.48 mmol) dropwise at −78° C. under $N_2$. After 30 min, 2-bromo-4-cyclobutoxy-1-fluorobenzene (5.0 g, 20.4 mmol) in THF (15 mL) was added dropwise at −78° C. Then the mixture was stirred at −78° C. for 1 h. DMF (2.237 g, 30.6 mmol) was added dropwise at −78° C., and the mixture was stirred for another 1 h. The reaction was quenched with satd. aq. $NH_4Cl$ soln. (10 mL), and the mixture was extracted with EtOAc (3×50 mL) and water (30 mL). The organic layer was dried with anhyd. $Na_2SO_4$ and concentrated in vacuo. The residue was purified via silica gel chromatography (PE) to afford the title compound.

Step B. 1-Bromo-5-cyclobutoxy-3-(difluoromethyl)-2-fluorobenzene

To a soln. of 3-bromo-5-cyclobutoxy-2-fluorobenzaldehyde (1.00 g, 3.66 mmol) in DCM (20 mL), was added DAST (2.4 mL, 18.16 mmol) dropwise at 0° C. Then the mixture was stirred at 19° C. for 2 h. The mixture was quenched with water (5 mL) and extracted with DCM (20 mL×2) and water (15 mL). The organic layer was dried over $Na_2SO_4$ and concentrated to vacuo. The residue was purified via silica gel chromatography (PE) to afford the title compound. $^1$H-NMR (400 MHz, $CDCl_3$) δ 1.66-1.77 (m, 1H) 1.83-1.95 (m, 1H) 2.09-2.24 (m, 2H) 2.39-2.53 (m, 2H) 4.55-4.66 (m, 1H) 6.67-7.01 (m, 2H) 7.10 (br. s., 1H).

Intermediate 24

1-Bromo-2-fluoro-3-methoxy-5-(trifluoromethoxy)benzene

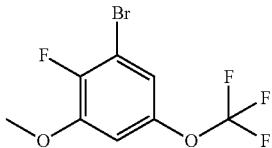

Step A. 2-fluoro-5-(trifluoromethoxy)phenol

To a stirred soln. of (2-fluoro-5-(trifluoro-methoxy)phenyl)boronic acid (13.40 g, 60 mmol) in anhyd. EtOH (20 mL) was added dropwise 30% $H_2O_2$ (10.2 mL, 90 mmol) at 0-5° C., and the reaction mixture was stirred for 3 h. The reaction was quenched with a satd. soln. of $Na_2S_2O_3$, and concentrated in vacuo. The resulting residue was dissolved in DCM (30 mL), and the soln. was washed with brine (10 mL×2). The organic layer was concentrated in vacuo to give the title compound.

Step B. 1-Fluoro-2-methoxy-4-(trifluoromethoxy)benzene

To a stirred suspension of 2-fluoro-5-(trifluoromethoxy)phenol (5.00 g, 25 mmol) and $K_2CO_3$ (5.20 g, 38 mmol) in DMF (10 mL) was added MeI dropwise at rt. The reaction mixture was stirred for 18 h at rt, then poured into water (100 mL), and extracted with DCM (20 mL×3). The organic layer was washed with brine (20 mL) and concentrated in vacuo. The resulting residue was purified by silica gel chromatography (PE:EtOAc=10:1) to give the title compound.

Step C. 1-Bromo-2-fluoro-3-methoxy-5-(trifluoromethoxy)benzene

To a soln. of 2,2,6,6-tetramethylpiperidine (3.40 g, 24 mmol) in anhyd. THF (30 mL) was added dropwise 2.5 M n-BuLi (9.0 mL, 23 mmol) at −78° C. under $N_7$. After the addition, the reaction mixture was stirred at −75° C. for 30 minutes. Then a soln. of 1-fluoro-2-methoxy-4-(trifluoromethoxy)-benzene (4.0 g, 19 mmol) in THF (10 mL) was added dropwise to the reaction mixture at −78° C. After the addition, the reaction mixture was stirred for 2 h at −78° C., and $Br_2$ (3.70 g, 23 mmol) was added dropwise to the reaction mixture while maintaining at −78° C. The reaction mixture was allowed to stir for 1 h at −75° C., and the reaction was quenched with satd. aq. $NH_4Cl$ (5 mL). The mixture was washed with with brine (20 mL), and the organic layer was concentrated in vacuo. The resulting residue was purified by reverse phase HPLC on a GILSON 281 instrument fitted with a Phenomenex Synergi C18 (250×21.2 mm×4 μm) using water (0.2% Formic acid) and ACN as eluents (Mobile phase A: water (0.2% Formic acid), Mobile phase B: ACN, Detective wavelength: 220 nm) followed by concentration in vacuo to obtain the title compound. $^1H$ NMR (400 MHz, $CDCl_3$) ppm: 7.04 (br. s., 1H) 6.79 (d, J=4.30 Hz, 1H) 3.91 (s, 3H).

Intermediate 25

2-(3-Bromo-5-(difluoromethyl)-4-fluorophenoxy)-5-methylpyridine

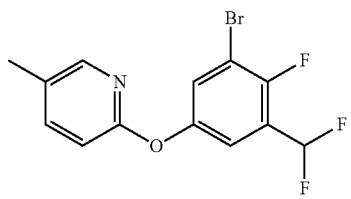 [SMILES: Cc1ccc(Oc2cc(Br)c(F)c(C(F)F)c2)nc1]

Step A. 2-(3-Bromo-5-(difluoromethyl)-4-fluorophenoxy)-5-methyl-3-nitropyridine A mixture of 2-chloro-5-methyl-3-nitropyridine (300 mg, 1.74 mmol) and 3-bromo-5-(difluoromethyl)-4-fluorophenol (503 mg, 2.09 mmol) and $Cs_2CO_3$ (850 mg, 2.61 mmol) in DMF (10 mL) was stirred at 15° C. for 2 h. The mixture was diluted with water (20 mL), and extracted with PE:EtOAc (1:1, 2×10 mL). The organic layer was collected, washed with brine, dried over anhyd. $Na_2SO_4$, filtered, and concentrated in vacuo. The crude product was purified by silica gel column chromatography (PE:EtOAc from 100:1 to 1:1) to afford the title compound. m/z 377.1 $[M+H]^+$

Step B. 2-(3-bromo-5-(difluoromethyl)-4-fluorophenoxy)-5-methylpyridin-3-amine A mixture of 2-(3-bromo-5-(difluoromethyl)-4-fluorophenoxy)-5-methyl-3-nitropyridine (550 mg, 1.46 mmol), zinc (286 mg, 4.38 mmol), and $NH_4Cl$ (390 mg, 7.29 mmol) in a mixture of MeOH (10 nil) and water (1 mL) was heated at 60° C. for 3 h. The suspension was diluted with DCM (20 ml) and filtered through silica gel. The filtrate was concentrated in vacuo, and the mixture was diluted with water (10 mL) and extracted with DCM (20 The organic layer was collected, washed with brine, dried over anhyd. $Na_2SO_4$, filtered, then concentrated under in vacuo to afford the title compound. m/z=348.1 $[M+H]^+$.

Step C. 2-(3-Bromo-5-(difluoromethyl)-4-fluorophenoxy)-5-methylpyridine

A mixture of 2-(3-bromo-5-(difluoromethyl)-4-fluorophenoxy)-5-methylpyridin-3-amine (500 mg, 1.44 mmol) and isopentyl nitrate (384 mg, 2.88 mmol) in THF (10 mL) was heated under reflux for 2 h. After cooling to rt, the mixture was diluted with water (20 mL), and extracted with EtOAc (15 mL×2). The organic layer was collected, washed with brine, dried over anhyd. $Na_2SO_4$, filtered, then concentrated in vacuo. The crude product was purified by silica gel column chromatography (PE:EtOAc from 20:1 to 10:1) to afford the title compound. m/z 333.1 $[M+H]^+$.

Intermediate 26

2-(3-Bromo-4-fluoro-5-methoxyphenoxy)-5-methyl-thiazole

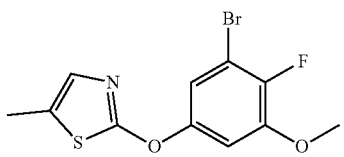

Step A. 3-Bromo-2-fluoro-5-((triisopropylsilyl)oxy)phenol

To a stirred soln. of 2,2,6,6-tetramethylpiperidine (2.5 g, 17.2 mmol) in anhyd. THF (30 mL) was added dropwise n-BuLi (7.0 mL, 17.2 mmol) below −75° C. under $N_2$. The reaction mixture was stirred for 30 min. Then a soln. of (3-bromo-4-fluorophenoxy) triisopropylsilane (5.0 g. 14.4 mmol) in THF (5 mL) was added dropwise to the reaction mixture below −75° C. After the addition, the reaction mixture was stirred for 2 h maintaining at −75° C. Trimethyl borate (1.80 g, 17.2 mmol) was added dropwise to the reaction mixture below −75° C. Then the reaction mixture was stirred for 1 h. The reaction mixture was warmed to rt to give a soln. of crude dimethyl (3-bromo-2-fluoro-5-((triisopropylsilyloxy)phenyl)boronate. Then, 30% NaOH (4 mL, 28.8 mmol)) was added to the soln. with stirring at rt. The reaction mixture was cooled in an ice-bath, and 30% $H_2O_2$ (3.3 mL, 28.8 mmol) was added dropwise to the mixture. After the addition, the reaction was warmed to rt and stirred for 10 h. The reaction mixture was acidified to pH-4 with 3 N HCl and extracted with EtOAc (3×30 mL). The combined organic layers were washed with brine and concentrated in vacuo. The residue was purified by silica gel chromatography (PE/EtOAc 20:1) to give the title compound.

Step B. (3-Bromo-4-fluoro-5-methoxyphenoxy) triisopropylsilane

To a stirred suspension of 3-bromo-2-fluoro-5-((triisopropylsilyl)oxy)phenol (3.3 g. 9 mmol) and $K_2CO_3$ (1.50 g, 11 mmol) in DMF (10 mL), cooled by an ice water bath, was added dropwise MeI (2.60 g, 18 mmol). After the addition, the reaction mixture was stirred for 3 h at ~16° C. The reaction mixture was poured into water (100 mL) and extracted with PE (2×10 mL). The combined organic layers were washed with brine, concentrated in vacuo to give crude product.

Step C. 3-Bromo-4-fluoro-5-methoxyphenol

To a stirred soln. of (3-bromo-4-fluoro-5-methoxyphenoxy) triisopropylsilane (3.10 g, 8.2 mmol) in THF (10 mL) was added dropwise 1 M TBAF (9.8 mL, 9.8 mmol) ~16° C. The reaction mixture was stirred at ~16° C. for 3 h and concentrated in vacuo. The resulting residue was dissolved in DCM (20 mL), and the organic layer was separated and washed with brine. The organic layer was then concentrated in vacuo. The resulting residue was purified by silica gel chromatography (PE:EtOAc=10:1) to give the title compound.

Step D. 2-(3-Bromo-4-fluoro-5-methoxyphenoxy)-5-methylthiazole

To a soln. of 3-bromo-4-fluoro-5-methoxyphenol (663 mg, 3 mmol) and 2-promo- 5-methylthiazole (587 mg, 3.3 mmol) in NMP (5 mL) was added $Cs_2CO_3$ (1.20 g, 3.6 mmol) in one portion. The reaction vessel was sealed and heated by microwave irradiation at 150° C. for 3 h. The reaction mixture was poured into cold water (50 mL) and extracted with DCM (3×10 mL). The combined layers were combined and washed with brine, dried ($Na_2SO_4$) and concentrated in vacuo. The residue was purified by silica gel chromatography (PE:EtOAc=10:1) to afford the title compound. $^1$H NMR (400 MHz. $CDCl_3$) δ ppm 7.06 (dd, J=4.70, 2.74 Hz, 1H) 6.82-6.92 (m, 2H) 3.89 (s, 3H) 2.38 (s, 3H).

Intermediate 27

2-Bromo-4-cyclobutoxybenzonitrile

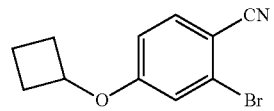 [SMILES: N#Cc1ccc(OC2CCC2)cc1Br]

Step A. 2-Bromo-4-hydroxybenzonitrile

To a soln. of 2-bromo-4-methoxybenzonitrile (1 g, 4.72 mmol) in MeCN (40 mL) was added NaI (2.12 g, 14.15 mmol) and TMSCl (1.54 g, 14.15 mmol). Then the mixture was stirred at 80° C. overnight. Then the mixture was concentrated in vacuo and poured into water basified with $Na_2CO_3$. The mixture was extracted with EtOAc. The aq. layer was acidified with HCl and extracted with EtOAc. The organic layer was washed with brine, dried ($Na_2SO_4$), and concentrated in vacuo to give the title compound.

Step B. 2-Bromo-4-cyclobutoxybenzonitrile

To a soln. of 2-bromo-4-hydroxybenzonitrile (110 mg, 0.56) in DMF (40 mL) was added bromocyclobutane (150 mg, 1.11 mmol), $Bu_4NI$ (205 mg, 0.56 mmol) and $Cs_2CO_3$ (181 mg, 0.56 mmol). The reaction mixture was stirred at 90° C. overnight. The mixture was washed with water, extracted with EtOAc, and the separated organic layer was washed with brine, dried ($Na_2SO_4$) and concentrated in vacuo. The crude product was purified by silica gel chromatography (PE:EA=20:1) to give the title compound. $^1$H NMR (400 MHz, $CDCl_3$) δ: 7.54 (d, 1=8.61 Hz, 1H), 7.08 (d, J=1.96 Hz, 1H), 681 (dd, J=8.80, 2.15 Hz, 1H), 4.67 (t, J=7.24 Hz, 1H), 2.40-2.54 (m, 2H), 2.19 (ddd, J=9.88, 7.53, 2.54 Hz, 2H), 1.91 (d, 1=10.56 Hz, 1H), 1.66-1.81 (m, 1H).

Intermediate 28

1-bromo-5-cyclobutoxy-2-fluoro-4-methoxybenzene

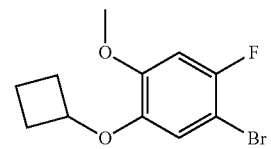

Step A. 1-cyclobutoxy-4-fluoro-2-methoxybenzene

To a solution of compound 4-fluoro-2-methoxyphenol (1 g, 7 mmol) and bromocyclobutane (1.13 g, 8.4 mmol) in DMF (5 mL) was added $Cs_2CO_3$ (3.4 g, 10.6 mmol) at rt. The mixture was stirred at 80° C. for 12 h. The mixture was concentrated in vacuo and extracted with EtOAc (40 mL). The organic layer was concentrated in vacuo, and the crude product was purified by silica gel column (PE:EA=100:1) to give the title compound.

Step B. 1-bromo-5-cyclobutoxy-2-fluoro-4-methoxybenzene

To a solution of compound 1-cyclobutoxy-4-fluoro-2-methoxybenzene (1 g, 5.2 mmol) in MeCN (10 mL) was added NBS (1.02 g, 5.8 mmol) at 0° C. The mixture was stirred at rt for 12 h. Water (50 mL) was added to the mixture, and the mixture was extracted with EtOAc (40 mL). The organic layer was concentrated in vacuo, and the crude product was purified by silica gel chromatography (PE:EA=100:1) to give the title compound.

Intermediate 29

2-(3-bromo-5-(difluoromethyl)-4-fluorophenoxy)-5-me thiazole

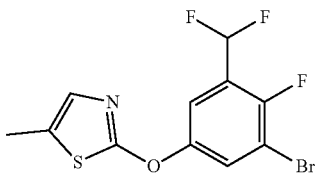 [SMILES: Cc1cnc(Oc2cc(Br)c(F)c(C(F)F)c2)s1]

Step A. 3-bromo-2-fluoro-5-((triisopropylsilyloxy) benzaldehyde

To a stirred solution of 2,2,6,6-tetramethylpiperidine (18.06 g, 0.13 mol) in THF (250 mL) was added n-BuLi (2.5 M, 51.1 mL, 0.13 mol) dropwise at −78° C. over 0.5 h. The mixture was stirred at 0° C. for 0.5 h. Then a solution of 3-bromo-4-fluorophenoxy)triisopropylsilane (37.0 g, 0.11 mmol) in THF (300 mL) was added to the above mixture dropwise at −78° C. over 0.5 h. The mixture was stirred for 1 h, and DMF (15.57 g, 213 mmol) was added. The mixture was diluted with water (300 mL), and extracted with EtOAc (2×100 mL). The organic layer was separated, washed with brine, dried over anhydrous $Na_2SO_4$, filtered and concentrated in vacuo. The crude product was purified by silica gel column chromatography (PE:EtOAc from 20:1 to 1:1) to afford 3-bromo-2-fluoro-5-((triisopropylsilyl)oxy)benzaldehyde and 3-bromo-2-fluoro-5-hydroxybenzaldehyde.

Step B. 3-bromo-5-(difluoromethyl)-4-fluorophenoxy)triisopropylsilane

To a stirred solution of 3-bromo-2-fluoro-5-((triisopropylsilyl)oxy)benzaldehyde (22.00 g, 58.60 mmol) in DCM (200 mL) was added dropwise DAST (11.62 ml, 88.00 mmol) at 0° C. The resulting mixture was warmed to rt for 2 h. The mixture was pouring into diluted $NaHCO_3$ solution until the pH was 5. Water (100 mL) was added and the mixture was extracted with DCM (100 ml). The organic layer was separated, washed with brine (50 mL), dried over anhydrous $Na_2SO_4$, filtered, and concentrated in vacuo. The residue was purified by silica gel chromatography (PE: EtOAc 20:1 to 5:1) to afford the title compound.

Step C: 3-bromo-5-(difluoromethyl)-4-fluorophenol

A mixture of (3-bromo-5-(difluoromethyl)-4-fluorophenoxy)triisopropylsilane (10.0 g, 25.2 mmol) and TBAF (7.90 g, 30.2 mmol) in THF (50 mL) was stirred at 15° C. for 2 h. The mixture was diluted with water (50 mL), and extracted with EtOAc (50 mL). The organic layer was collected, washed with brine, dried over anhydrous $Na_3SO_4$, filtered, and concentrated in vacuo. The crude product was purified by silica gel chromatography (PE:EtOAc from 10:1 to 3:1) to afford the title compound.

Step D. 2-(3-bromo-5-(difluoromethyl)-4-fluorophenoxy)-5-methylthiazole

A mixture of 2-bromo-5-methylthiazole (300 mg, 1.68 mmol), 3-bromo-5-(difluoromethyl)-4-fluorophenol (487 mg, 2.02 mmol) and $Cs_2CO_3$ (1.09 g, 3.37 mmol) in DMF (5 mL) was irradiated by microwave at 160° C. for 0.5 h. The mixture was diluted with water (20 mL), and extracted with EtOAc (2×10 mL). The organic layer was collected, washed with brine, dried over anhydrous $Na_2SO_4$, filtered and concentrated in vacuo. The residue was further purified by reverse phase HPLC on a GILSON 281 instrument fitted with a Phenomenex Synergi C18 (250×21.2 mm×4 um) using water (0.2% Formic acid) and MeCN as eluents (Mobile phase A: water (0.2% Formic acid), Mobile phase B: $CH_3CN$, Detective wavelength: 220 nm), followed by concentration (below 50° C.) to afford the title compound.

Intermediate 30

1-Bronco-5-cyclobutoxy-2-fluoro-3-methoxybenzene

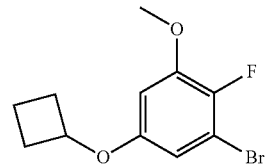

Step A. 3-bromo-5-cyclobutoxy-2-fluorophenol

To a solution of TMP (5.9 g, 41.6 mmol) in anhydrous THF (5 mL) was added dropwise 2.5 M n-BuLi (17 mL, 41.6 mmol) at between −78 and −75° C. under nitrogen. After the addition the reaction mixture was stirred at −75° C. for 30 min. Then a solution of 2-bromo-4-cyclobutoxy-1-fluorobenzene (8.5 g, 34.6 mmol) in THF (10 mL) was added dropwise to the reaction mixture at −75° C. The reaction mixture was stirred for 1 h at −75° C. Then a solution of trimethyl borate (4.3 g, 41.6 mmol) in THF (5 mL) was added dropwise to the reaction mixture while maintaining at −75° C. After the addition, the reaction mixture was allowed to stir for 1 h at −75° C. Then reaction mixture was allowed to warm to rt. Then 30% aq. NaOH (11 mL, 68.7 mmol)) was added to the solution with stirring at rt. The reaction mixture cooled by ice-bath, and 30% hydrogen peroxide (8 mL, 68.7 mmol) was slowly added dropwise. After addition, the reaction mixture was warmed to the rt and stirred for 10 h. The reaction mixture was acidified to pH~4 with 3 N HO and extracted with EtOAc (30 mL×3). The organic layer was washed with brine and concentrated in vacuo. The residue was purified by silica gel chromatography (PE:EtOAc 20:1) to give the title compound.

Step B.
1-bromo-5-cyclobutoxy-2-fluoro-3-methoxybenzene

To a suspension of 3-bromo-5-cyclobutoxy-2-fluorophenol (8.0 g, 30.6 mmol) and $K_2CO_3$ (8.5 g, 61.2 mmol) in DMF (25 mL), cooled by an ice bath, was added dropwise MeI (20.0 g, 141.0 mmol). After the addition, the reaction mixture was stirred for 12 h at rt. The reaction mixture was poured into cold water (100 mL) and extracted with DCM (30 mL×3). The organic layer was rinsed with brine and concentrated in vacuo. The residue was purified by reverse phase HPLC on a OLSON 281 instrument fitted with a Phenomenex Synergi C18 (250×21.2 mm×4 μm) using water (0.2% Formic acid) and MeCN as eluents (Mobile phase A: water (0.2% Formic acid), Mobile phase B: MeCN, Detective wavelength: 220 nm) followed by concentration (below 50° C.) to obtain the title compound. $^1$H NMR (400 MHz, CDCl$_3$) δ ppm 6.47 (d, J=4.02 Hz, 1H) 6.39-6.45 (m, 1H) 4.56 (quin, J=7.15 Hz, 1H) 3.85 (s, 3H) 2.39-2.51 (m, 2H) 2.07-2.21 (m, 2H) 1.87 (q, J=10.21 Hz, 1H) 1.64-1.77 (m, 1H).

Intermediate 31

Ethyl-2-(5-fluoro-1,2,3,4-tetrahydroisoquinolin-6-yl) cyclopropanecarboxylate

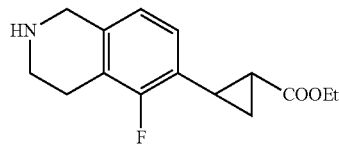 [SMILES: CCOC(=O)C1CC1c1ccc2c(c1F)CCNC2]

Step A. Tert-butyl-6-bromo-5-fluoro-3,4-dihydroisoquinoline-2(1H)-carboxylate

To a solution of 6-bromo-5-fluoro-1,2,3,4-tetrahydroisoquinoline (1.8 g, 7.82 mmol) in DCM (30 mL) was added Boc$_2$O (2.0 mL, 8.61 mmol) in one portion with stirring at −26° C. Then the reaction mixture was stirred at 26° C. for an additional 18 h. The reaction mixture was concentrated in vacuo to give the crude product which was purified by silica gel column chromatography (PE/EtOAc 40:1-20:1) to give the title compound.

Step B. (E)-tert-butyl-6-(3-ethoxy-3-oxoprop-1-en-1-yl)-5-fluoro-3,4-dihydroisoquinoline-2(1H)-carboxylate To a solution of tert-butyl 6-bromo-5-fluoro-3,4-dihydroisoquinoline-2(1H)-carboxylate (2.2 g, 6.66 mmol) in dry 1,4-dioxane (20 mL) was added tri-tert-butyl phosphonium tetrafluoroborate (0.387 g, 1.333 mmol), N-cyclohexyl-N-methylcyclo-hexanamine (1.952 g, 9.99 mmol), and ethyl acrylate (0.800 g, 8.00 mmol) with stirring at ~26° C. The mixture was degassed for 5 min with N$_2$, and Pd$_2$(dba)$_3$ (203 mg, 0.221 mmol) was added. The mixture was stirred at 100° C. for 18 h under a N$_2$ atmosphere. The mixture was cooled to rt and diluted with EtOAc (20 mL). The organic layer was filtered, and the filtrate was concentrated in vacuo to give the residue which was purified by silica gel chromatography (PE:EtOAc=20:1 to 10:1) to afford the title compound.

Step C. Tert-butyl 6-(2-(ethoxycarbonyl)cyclopropyl)-5-fluoro-3,4-dihydroiso-quinoline-2(1H)-carboxylate To a solution of (E)-tert-butyl-6-(3-ethoxy-3-oxoprop-1-en-1-yl)-5-fluoro-3,4-dihydroisoquinoline-2(1H)-carboxylate (5.1 g, 14.60 mmol) and palladium acetate (0.328 g, 1.460 mmol) in dry DCM/ether (1:2, 450 mL) was added CH$_2$N$_2$ (117 mL, 58.4 mmol) in diethyl ether at 0° C. over a period of 2 h. Then the reaction mixture was slowly warmed to rt and stirred for 18 h. The reaction was quenched by addition of AcOH (10 mL). The resulting mixture was washed with water (200 mL) and brine (100 mL). The organic layer was dried (Na$_2$SO$_4$) and concentrated in vacuo to give the crude product. The crude product was purified by silica gel column chromatography (PE/EtOAc 30:1-10:1) to give tort-butyl 6-(2-(ethoxycarbonyl)cyclopropyl)-5-fluoro-3,4-dihydroisoquinoline-2(1H)-carboxylate. $^1$H NMR (400 MHz, CDCl$_3$) δ 6.82-6.73 (m, 2H), 4.51 (br. s., 2H), 4.16 (q, J=7.0 Hz, 2H), 3.61 (br. s., 2H), 2.77 (br. s., 2H), 2.63-2.58 (m, 1H), 1.89-1.84 (m, 1H), 1.58-1.53 (m, 1H), 1.33-1.28 (m, III), 1.28-1.23 (m, 3H). The two enantiomers were seperated by SFC using the following conditions: Instrument: MG-II, Column: Chiralpak AD 250×30 mm I.D., 5 um, Mobile phase: Supercritical CO$_2$/A (0.1% NH$_3$/H$_2$O) =85/15 at 60 mL/min, A=MeOH+HEP (1:1), Column Temp: 38° C. Nozzle Pressure: 100 Bar, Nozzle Temp: 60° C. Evaporator Temp: 20° C., Trimmer Temp: 25° C. Wavelength: 220 nm Peak 1 (ee 97.0% fast eluting) and Peak 2 (ee 97.7% slow eluting) were obtained from the racemate. (Peak1)$^1$H NMR (400 MHz, CDCl$_3$) δ 6.82-6.75 (m, 2H), 4.53 (br.s., 2H), 4.17 (d, J=7.0 Hz, 2H), 3.63 (br. s., 2H), 2.79 (br. s., 2H), 2.65-2.59 (m, 1H), 1.91-1.85 (m, 1H), 1.60-1.56 (m, 1H), 1.48 (s, 9H), 1.36-1.30 (m, 1H), 1.30-1.26 (m, 3H); Peak2) $^1$H NMR (400 MHz, CDCl$_3$) δ 6.83-6.74 (m, 2H), 4.53 (br, s., 2H), 4.18 (q, J=7.2 Hz, 2H), 3.63 (br. s., 2H), 2.79 (br. s., 2H), 2.62 (t, J=9.8 Hz, 1H), 1.91-1.86 (m, 1H), 1.58 (d, J=4.3 Hz, 1H), 1.48 (s, 9H), 1.35-1.31 (m, 1H), 1.30-1.26 (m, 3H)

Step E. Ethyl 2-(5-fluoro-1,2,3,4-tetrahydroisoquinolin-6-yl)cyclopropane-carboxylate To a solution of tert-butyl 6-(2-(ethoxycarbonyl)cyclopropyl)-5-fluoro-3,4-dihydroisoquinoline-2(1H)-carboxylate (500 mg, 1.376 mmol) in DCM (6 mL) was added TFA (3 mL, 38.9 mmol) dropwise with stirring at ~26° C. The solvent was removed in vacuo. The residue was purified by cation ion exchange column chromatography (1 M NH$_3$-MeOH) to afford the title compound.

Intermediate 32

2-(3-promo-4-fluorophenoxy)pyrazine

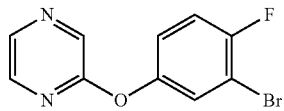 [SMILES: Fc1ccc(Oc2cnccn2)cc1Br]

To a stirred solution of 2-fluoropyrazine 10.20 mmol) in DMSO (12 mL) was added 3-bromo-4-fluorophenol (1.95 g, 10.21 mmol), and K$_2$CO$_3$ (2.82 g, 20.39 mmol). The reaction mixture was stirred at 75° C. for 15 h. The mixture was filtered, and the filtrate was diluted with brine (50 mL). The filtrate was extracted with EtOAc (2×100 mL). The organic layer was dried over Na$_2$SO$_4$, filtered and concentrated in vacuo to give the title compound. m/z 270.9 (M+2+H)$^+$.

Intermediate 33

5-((1R,3R)-3-(benzyloxy)cyclobutoxy)-3-bromo-2-fluorobenzonitrile

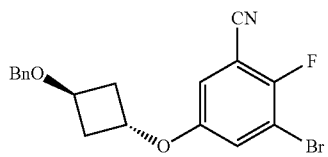 [SMILES: N#Cc1cc(O[C@H]2C[C@H](OCc3ccccc3)C2)cc(Br)c1F]

Step A. (3-bromo-4-fluorophenoxy)triisopropylsilane

TIPS-Cl (33.3 mL, 157 mmol) was added to a stirred mixture of 3-bronco-4-fluorophenol (30 g, 157 mmol) and imidazole (10.69 g, 157 mmol) in DMF (150 mL) at rt, and the mixture was stirred at rt for 12 h. The mixture was diluted with EtOAc (300 mL), washed with water (2×800 mL), dried (Na$_2$SO$_4$), and filtered, and the filtrate was concentrated in vacuo. The residue was purified by silica gel chromatography (PE) to give the title compound.

Step B. 3-bromo-2-fluoro-5-((triisopropylsilyl)oxy) benzaldehyde

To a solution of 2,2,6,6-tetramethylpiperidine (4.64 g, 32.8 mmol) in THF (50 mL) was added n-BuLi (13 mL, 32.5 mmol, 2.5 M in hexane) dropwise at −78° C. under N$_2$. After 30 min, the mixture was allowed to warm to 0° C. and stirred for 10 min. Then (3-bromo-4-fluorophenoxy) triisopropylsilane (10 g, 27.4 mmol) in THF (30 mL) was added dropwise at −78° C., and the mixture was stirred at −78° C. for 1.5 h. DMF (3.00 g, 41.0 mmol) was added, and the mixture was stirred at −78° C. for 40 min. The reaction was quenched by the addition of said. NH$_4$Cl solution (50 mL). Then the mixture was extracted with EtOAc (150 mL×2). The organic layer was washed with brine (50 mL), dried over Na$_2$SO$_4$, filtered and concentrated in vacuo. The resulting residue was purified by silica gel chromatography (EtOAc: petroleum ether 1:100 to 1:50) to give the title compound.

Step C: 3-bromo-2-fluoro-5-((triisopropylsilyl)oxy) benzaldehyde oxime

To a solution of 3-bromo-2-fluoro-5-((triisopropylsilyl) oxy)benzaldehyde (7.60 g, 19.24 mmol) in EtOH (80 mL) was added hydroxylamine (2.54 g. 38.5 mmol) (50% in water). The mixture was stirred at 80° C. for 5 h and cooled to it. The mixture was poured onto water (100 mL), and the mixture was stirred for 30 min. The mixture was concentrated in vacuo, and the residue was extracted with DCM (3×50 mL) and water (30 mL). The organic layer was dried over Na$_2$SO$_4$, filtered and concentrated in vacuo. The residue was purified by silica gel chromatography (PE: EtOAc=50:1) to afford the title compound. m/z 390.0 [M+H]$^+$.

Step D. 3-bromo-2-fluoro-5-((triisopropylsilyl)oxy) benzonitrile

To a solution of 3-bromo-2-fluoro-5-((triisopropylsilyl) oxy)benzaldehyde oxime (7.30 g, 18.35 mmol) in DMF (80 mL) was added POCl$_3$ (7.03 g, 4.27 mL, 45.9 mmol) dropwise at 0° C. The mixture was stirred at rt for 15 h. The mixture was poured into water (800 mL), and the mixture was stirred for 1 h. The mixture was extracted with EtOAc (2×150 mL), dried over Na$_2$SO$_4$, filtered and concentrated in vacuo. The residue was purified by silica gel chromatography (PE) to afford the title compound.

Step E: 3-bromo-2-fluoro-5-hydroxybenzonitrile

TBAF (10 mL, 10.00 mmol) (1 M in THF) was added to a stirred mixture of 3-bromo-2-fluoro-5-((triisopropylsilyl) oxy) benzonitrile (4.0 g, 9.67 mmol) in THF (20 mL) at rt. The mixture was stirred at rt 20° C. for 2 h. The mixture was concentrated in vacuo, and the residue was diluted with EtOAc (30 mL) and washed with water (20 mL). The organic layer was dried over Na$_2$SO$_4$, filtered and concentrated in vacuo. The residue was purified by silica gel chromatography (EtOAc: PE 1:2) to give the title compound.

Step F. 5-(1r,3r)-3-(benzyloxy)cyclobutoxy)-3-bromo-2-fluorobenzonitrile

To a solution of 3-bromo-2-fluoro-5-hydroxybenzonitrile (1.00 g, 4.40 mmol), (1S,3S)-3-(benzyloxy)cyclobutanol (0.862 g, 4.84 mmol) and PPh$_3$ (1.730 g, 6.60 mmol) in THF (15 mL) was added DIAD (1.197 ml, 6.16 mmol) dropwise with stirring at 0° C. under a N$_2$ atmosphere: After the addition was complete, the reaction mixture was stirred at ~70° C. for additional 15 h under a N$_2$ atmosphere. The solvent was removed in vacuo. The resulting residue was purified via silica gel chromatography (PE:EtOAc=100:1 to 50:1) to afford the title compound. $^1$HNMR δ (CDCl$_3$, 400 MHz, ppm): 7.29-7.41 (m, 5H) 7.22 (dd, J=5.40, 2.98 Hz, 1H) 6.88-6.95 (m, 1H) 4.76-4.85 (m, 1H) 4.43-4.49 (m, 2H) 4.29-4.37 (m, 1H) 2.49-2.60 (m, 2H) 2.36-2.46 (m, 2H).

Intermediate 34

2-(3-bromo-5-(difluoromethyl)-4-fluorophenoxy)-5-fluoropyridine

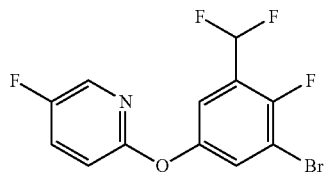 [SMILES: Fc1ccc(Oc2cc(Br)c(F)c(C(F)F)c2)nc1]

Step A. 2-(3-bromo-5-(difluoromethyl)-4-fluorophenoxy)-5-fluoro-3-nitropyridine A mixture of 2-chloro-5-fluoro-3-nitropyridine (300 mg, 1.69 mmol) and 3-bromo-5-(difluoromethyl)-4-fluorophenol (491 mg, 2.03 mmol), Cs$_2$CO$_3$ (554 mg, 1.69 mmol) in DMF (10 mL) was stirred at 15° C. for 2 h. The mixture was diluted with water (20 mL), extracted with PE:EtOAc (1:1, 2×10 mL). The organic layer was separated and washed with brine, dried over anhydrous Na$_2$SO$_4$, filtered, and concentrated in vacuo. The crude product was purified by silica gel chromatography (DCM) to yield the title compound.

Step B: 2-(3-bromo-5-(difluoromethyl)-4-fluorophenoxy)-5-fluoropyridin-3-amine A mixture of 2-(3-bromo-5-(difluoromethyl)-4-fluorophenoxy)-5-fluoro-3-nitro pyridine (600 mg, 1.574 mmol), zinc (309 mg, 4.72 mmol) and NH$_4$Cl (421 mg, 7.87 mmol) in water (1 mL) and MeOH (10 mL) was heated at 60° C. for 6 h. The mixture was diluted with DCM (20 mL) and filtered through silica gel. The filtrate was concentrated in vacuo. Water (10 mL) was added to the residue, and the mixture was extracted with DCM (20 mL). The organic layer was separated, washed with brine, dried over anhydrous Na$_2$SO$_4$, filtered, and concentrated in vacuo to afford the title compound.

Step C: 2-(3-bromo-5-(difluoromethyl)-4-fluorophenoxy)-5-fluoropyridine

A mixture of 2-(3-bromo-5-(difluoromethyl)-4-fluorophenoxy)-5-fluoro pyridin-3-amine (500 mg, 1.42 mmol) and isopentyl nitrate (379 mg, 2.85 mmol) in THF (10 mL) was heated at 66° C. for 2 h. After cooling the mixture to rt, the mixture was diluted with water (20 mL), and extracted with EtOAc (2×15 mL). The organic layer was collected, washed with brine, dried over anhydrous Na$_2$SO$_4$, filtered, and concentrated in vacuo. The crude product was purified by silica gel chromatography (PE:EtOAc from 20:1 to 10:1) to afford the title compound.

Intermediate 35

5-Iodo-1-(4-methoxyphenyl)-3-methyl-1H-pyrazole-4-carbonitrile

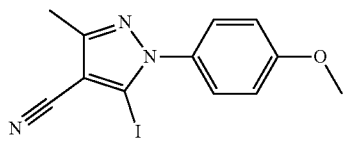 [SMILES: COc1ccc(-n2nc(C)c(C#N)c2I)cc1]

Step A: 5-amino-1-(4-methoxyphenyl)-3-methyl-1H-pyrazole-4-carbonitrile

To a solution of (4-methoxyphenyl)hydrazine hydrochloride (50 g, 286.32 mmol) in EtOH (400 mL) was added Et$_3$N (31.87 g, 314.96 mmol), and the mixture was stirred for 10 min. Then 2-(1-ethoxy-ethylidene)malononitrile (38.98 g, 286.32 mmol) was added portionwise. The reaction mixture was stirred at rt overnight. Then the reaction mixture was filtered, and the filtrate was extracted with EtOAc (3×200 mL). The organic layer was dried (Na$_2$SO$_4$), filtered and concentrated in vacuo. The residue was purified by silica gel chromatography (DCM to MeOH:DCM=1:20) to give the title compound.

Step B. 5-Iodo-1-(4-methoxyphenyl)-3-methyl-1H-pyrazole-4-carbonitrile

To a solution of 5-amino-1-(4-methoxyphenyl)-3-methyl-1H-pyrazole-4-carbonitrile (30 g, 131.6 mmol) in CH$_2$I$_2$ (105.78 g, 394.74 mmol) was added isopentyl nitrite (46.18 g, 394.74 mmol) dropwise at 0° C. The reaction mixture was stirred at 90'C for 2 h. The precipitate was filtered off, washed with water and extracted with DCM (3×100 mL). The extract was dried over Na$_2$SO$_4$ and concentrated in vacuo. The residue was purified by silica gel column chromatography (PE:EA=4:1) to give the title compound.

Intermediate 36

2-bromo-6-fluoro-4-(trifluoromethoxy)benzonitrile

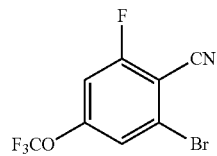

Step A. 1-bromo-2-fluoro-5-nitro-4-(trifluoromethoxy)benzene

To a solution of 1-bromo-2-fluoro-4-(trifluoromethoxy) benzene (5.00 g, 19.31 mmol) in MeCN (20 mL) was added NO$_2$BF$_4$ (2.69 g, 20.27 mmol) in portions keeping the temperature between −40 to −30° C., The mixture was stirred at between −40° C. to −30° C. for 2 h. Then the mixture was allowed to warm to rt and stirred for 18 h. The mixture was poured into ice, and extracted with EtOAc (3×30 mL). The combined organic layers were dried over Na₂SO₄, filtrated and concentrated in vacuo. The residue was purified on silica gel (PE:EtOAc=80:1 to 50:1) to afford the title compound.

Step B.
5-bromo-4-fluoro-2-(trifluoromethoxy)aniline

To a solution of 1-bromo-2-fluoro-5-nitro-4-(trifluoromethoxy)benzene (2.00 g, 6.58 mmol) in MeOH (30 mL) and water (3 mL) was added Fe (1.837 g, 32.9 mmol) and NH₄Cl (1.760 g, 32.9 mmol). The mixture was stirred at 75° C. for 4 h. The mixture was filtered, and the solvent was removed in vacuo. The residue was extracted with DCM (3×30 mL) and water (3×30 mL). The organic layer was dried over Na₂SO₄, filtrated and concentrated in vacuo. The residue was purified via silica gel chromatography (PE: EtOAc) to afford the title compound.

Step C: 3-bromo-5-(difluoromethyl)-4-fluorophenol

To a solution of 5-bromo-4-fluoro-2-(trifluoromethoxy) aniline (520 mg, 1.898 mmol) in DMA (5 mL) was added dicyanozinc (134 mg, 1.139 mmol), zinc (10 mg, 0.153 mmol), dppf (105 mg, 0.190 mmol) and Pd₂(dba)₃ (87 mg, 0.095 mmol). Then the reaction mixture was stirred and irradiated by microwave at 160° C. for 30 min. Water (50 mL) was added to the mixture, and the mixture was extracted with EtOAc (20 mL×3). The organic layer was concentrated in vacuo, and the crude product was purified by silica gel chromatography (PE/EtOAc=10:1 to 5:1) to give the title compound.

Step D. 3-amino-2-bromo-6-fluoro-4-(trifluoromethoxy)benzonitrile

To a solution of 5-amino-2-fluoro-4-(trifluoromethoxy) benzonitrile (370 mg, 1.681 mmol) in DMF (10 mL), was added 1-bromopyrrolidine-2,5-dione (299 mg, 1.681 mmol). The mixture was stirred at rt for 2 h. The reaction mixture was extracted with EtOAc (3×30 mL) and water (80 mL), and the organic layer was dried over Na₂SO₄, filtered and concentrated in vacuo. The residue was purified via silica gel chromatography (PE:EtOAc=10:1) to afford the title compound.

Step E. 3-amino-2-bromo-6-fluoro-4-(trifluoromethoxy)benzonitrile

To a solution of 3-amino-2-bromo-6-fluoro-4-(trifluoromethoxy)benzonitrile (220 mg, 0.736 mmol) in THF (5 mL) was added isopentyl nitrite (172 mg, 1.471 mmol). Then the mixture was stirred at 70° C. for 18 h. The mixture was concentrated in vacuo, and the resulting residue was extracted with EtOAc (3×20 mL) and water (20 mL). The organic layer was dried over Na₂SO₄, filtrated and concentrated. The residue was purified by silica gel PTLC (PE: EtOAC=10:1) to afford the title compound. ¹H NMR (CD₃OD, 400 MHz, ppm) δ: 7.68 (s, 1H) 7.51 (d, J=9.39 Hz, 1H).

Intermediate 37

1-bromo-2-chloro-5-cyclobutoxy-3-fluorobenzene

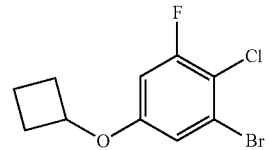 [SMILES: Fc1cc(OC2CCC2)cc(Br)c1Cl]

Step A. 1-bromo-3-cyclobutoxy-5-fluorobenzene

To a solution of 3-bromo-5-fluorophenol (10.00 g, 52.4 mmol) in DMF (50 mL) was added bromocyclobutane (14.14 g, 105 mmol), Bu₄NI (19.34 g, 52.4 mmol) and Cs₂CO₃ (17.06 g, 52.4 mmol). Then the mixture was stirred at 90° C. for 18 h. The mixture was diluted with water (400 mL) and extracted with EtOAc (3×80 mL). The organic layer was dried and concentrated in vacuo. The residue was purified via silica gel chromatography (PE) to afford the title compound.

Step B.
1-bromo-2-chloro-5-cyclobutoxy-3-fluorobenzene

To a solution of 1-bromo-3-cyclobutoxy-5-fluorobenzene (2.00 g, 8.16 mmol) in DMF (15 mL) was added 1,3,5-trichloro-1,3,5-triazinane-2,4,6-trione (0626 g, 2.69 mmol). Then the mixture was stirred at 50° C. for 3 h. The mixture was poured into water (30 mL) and extracted with EtOAc (3×30 mL). The organic layer was dried (Na₇SO₄), filtered and concentrated in vacuo. The residue was purified by reverse phase HPLC on a Shimadzu pump LC-8A instrument fitted with a SYNERGI (250×50×10 μm) using water (0.1% TFA) and MeCN as eluents (Mobile phase A: water (0.1% TFA), Mobile phase B: MeCN, Detective wavelength: 220 nm), followed by concentration (below 50° C.) to afford the title compound. ¹H NMR (CDCl₃, 400 MHz, ppm) δ, 1.66-1.76 (m, 1H) 1.89 (q, J=10.30 Hz, 1H) 2.10-2.22 (m, 2H) 2.40-2.51 (m, 2H) 4.58 (quin, J=7.04 Hz, 1H) 6.60 (dd, J=10.17, 2.35 Hz, 1H) 6.90 (hr. s, 1H).

Intermediate 38

3-bromo-5-cyclobutoxy-2-fluorobenzonitrile

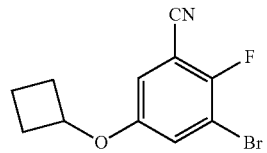 [SMILES: N#Cc1cc(OC2CCC2)cc(Br)c1F]

Step A. 3-bromo-2-fluoro-5-((triisopropylsilyl)oxy)benzaldehyde

To a solution of 3-bromo-5-cyclobutoxy-2-fluorobenzaldehyde (Intermediate 23, step A, 1.00 g, 3.66 mmol) in EtOH (20 mL) was added NH₂OH (0.484 g, 7.32 mmol), and the mixture was stirred at reflux for 5 h. After cooling to rt, the mixture was poured onto ice, and the mixture was stirred for 30 min. The mixture was concentrated in vacuo, and the residue was extracted with DCM (3×30 mL) and water (30 mL). The organic layer was dried (Na₂SO₄) and concentrated in vacuo to afford the title compound. m/z 289.0 m/z [M+H]⁺.

Step B. 3-bromo-5-(difluoromethyl)-4-fluorophenoxy)triisopropylsilane

To a solution of (Z)-3-bromo-5-cyclobutoxy-2-fluorobenzaldehyde oxime (950 mg, 3.30 mmol) in DMF (5 mL) was added POCl₃ (1.77 g, 11.54 mmol) dropwise at 0° C. Then the mixture was stirred at 20° C. for 18 h. The mixture was poured into water and stirred for 1 h, and the solid that formed was filtered. The solid was dissolved in DCM (30 mL), dried (Na₂SO₄) and concentrated in vacuo to afford the title compound. ¹HNMR (CDCl₃ 400 MHz, ppm), δ: 1.68-1.79 (m, 1H) 1.91 (q, J=10.30 Hz, 1H) 2.09-2.23 (m, 2H) 2.39-2.52 (m, 2H) 4.58 (quin, J=6.95 Hz, 1H) 6.90-6.96 (m, 1H) 7.24 (dd, J=5.09, 2.74 Hz, 1H).

Intermediate 39

2-bromo-4-((1r,3r)-3-methoxycyclobutoxy)benzonitrile

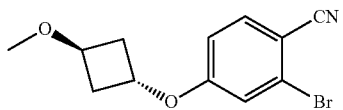

Step A. (1S,3S)-3-((tert-butyldimethylsilyl) oxy) cyclobutanol

To a stirred solution of 3-((tert-butyldimethylsilyl)oxy) cyclobutanone (5.0 g, 0.025 mol) in MeOH (60 mL) was added sodium tetrahydridoborate (1.5 g, 0.040 mol) at 0° C. The resulting mixture was allowed to warm to rt and stirred for an additional 2 h. Then the mixture was cooled to rt, and the reaction was quenched with ice-water and saturated sodium sulfate solution (10 mL). The mixture was filtered, and the filtrate was concentrated in vacuo to afford crude product. Water (100 mL) added to the crude product and the mixture was extracted with EtOAc (3×50 mL). The organic layer was dried (Na₂SO₄) and concentrated in vacuo to afford the title compound.

Step B. 2-bromo-4-((1R,3R)-3-((tert-butyldimethylsilyl)oxy) cyclobutoxy) benzonitrile To a stirred solution of (1S,3S)-3-((tert-butyldimethylsilyl)oxy)cyclobutanol (0.14 g, 0.69 mmol) in THF (8 mL) was added PPh₃ (0.25 g, 0.95 mmol), 2-bromo-4-hydroxybenzonitrile (0.15 g, 0.76 mmol) at 0° C. DEAD (0.15 g, 0.86 mmol) was added dropwise to the reaction mixture under a N₂ atmosphere. The resulting mixture was stirred at 60° C. for 16 h. The mixture was cooled to rt and water (20 mL) was added. The mixture was extracted with EtOAc (3×15 mL), and the organic layer was dried (Na₂SO₄), filtered, and concentrated in vacuo. The resulting residue was purified by silica gel chromatography (PE/EtOAc=50:1) to give the title compound.

Step C. 2-bromo-4-((1R,3R)-3-hydroxycyclobutoxy) benzonitrile

To a stirred solution of 2-bromo-4-((1R,3R)-3-((tert-butyldimethylsilyl)oxy)cyclobutoxy)benzonitrile (120 mg, 0.31 mmol) in THF (5 mL) was added TBAF (110 mg, 0.42 mmol) at rt, and the mixture was stirred for 3 h under a N₂ atmosphere. Water (15 mL) was added to the mixture, and the mixture was extracted with EtOAc (3×8 mL). The organic layer was dried (Na₂SO₄), and concentrated in vacuo to afford crude product. The crude product was purified by silica gel chromatography (MeOH/DCM=1:50) to give the title compound.

Step D. 2-bromo-4-((1R,3R)-3-methoxycyclobutoxy)benzonitrile

To a stirred solution of 2-bromo-4-((1R,3R)-3-hydroxycyclobutoxy)benzonitrile (65 mg, 0.24 mmol) in THF was added NaH (60% in mineral oil, 12 mg, 0.30 mmol) at rt, and the mixture was stirred for 30 min. Then MeI (37 mg, 0.26 mmol) as added, and the mixture was stirred for 16 h. Water (15 mL) was added, and the mixture was extracted with EtOAc (3×10 mL). The organic layer was dried (Na₂SO₄) and concentrated in vacuo to afford crude product. The crude product was purified by silica gel chromatography (PE/EtOAc=18:1 to 10:1 as eluent) to give the title compound. ¹H-NMR, (400 MHz, CDCl₃) δ ppm: 2.29-2.46 (m, 4H), 3.21 (s, 3H), 4.00-4.13 (m, 1H), 4.71-4.82 (m, 1H), 6.68-6.80 (m, 1H), 6.95-7.02 (m, 1H), 7.48 (d, J=8.60 Hz, 1H).

Intermediate 40

2-chloro-1-fluoro-3-iodo-5-(trifluoromethoxy)benzene

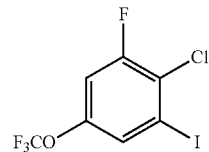

Step A. 2-fluoro-6-iodo-4-(trifluoromethoxy)aniline

To a solution of 2-fluoro-4-(trifluoromethoxy)aniline (1.00 g, 5.13 mmol) in EtOH (20 mL) was added Ag₂SO₄ (1598 g, 5.13 mmol) and I₂ (1.301 g, 5.13 mmol). The mixture was stirred at rt for 1 h, and the mixture was filtered, and concentrated in vacuo. The residue was purified via silica gel chromatography (PE:EtOAc=80:1 to 40:1) to afford the title compound.

Step B. 2-chloro-1-fluoro-3-iodo-5-(trifluoromethoxy)benzene

To a solution of 2-fluoro-6-iodo-4-(trifluoromethoxy)aniline (300 mg, 0.935 mmol) and CuCl₂ (251 mg, 1.869 mmol) in MeCN (20 mL) was added tert-butyl nitrite (193 mg, 1.869 mmol) at 0° C. The mixture was stirred at rt for 2 h, and the mixture was concentrated in vacuo. Water (30 mL) was added, and the mixture was extracted with EtOAc (3×30 mL). The organic layer was dried (Na₂SO₄), filtered and concentrated in vacuo. The residue was purified via silica gel chromatography (PE:EtOAc=50:1) to afford the title compound. NMR (CD₃OD, 400 MHz, ppm): 7.73 (br. s., 1H) 7.40 (dd, J=9.16, 1.88 Hz, 1H).

Intermediate 41

2-promo-4-(cyclobutylmethyl)-1-fluorobenzene

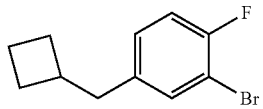

Step A.
3-promo-4-fluoro-N-methoxy-N-methylbenzamide

To a solution of DIEA (4.78 ml, 27.4 mmol), 3-promo-4-fluorobenzoic acid (2.0 g, 9.13 mmol) and N,O-dimethylhydroxylamine hydrochloride (0.891 g, 9.13 mmol) in DMF (25 ml) was added HATU (3.47 g, 9.13 mmol) at 0° C., and the mixture while stirring was allowed to gradually warm to rt. The mixture was stirred at rt for 18 h. Water (100 mL) was added, and the mixture was extracted with EtOAc (3×200 mL) and washed with brine (2×50 mL). The organic layer was dried (Na₂SO₄), filtered, and concentrated in vacuo. The resulting residue was purified by silica gel chromatography (PE:EtOAc=20:1-5:1) to give the title compound. m/z 264.0 [M+H]⁺.

Step B: (3-bromo-4-fluorophenyl)(cyclobutyl)methanone

To a suspension of magnesium (0.538 g, 22.13 mmol) in THF (20 nil) was added I₂ (0.028 g, 0.111 mmol) at 40° C., and the mixture was stirred at 40° C. for 10 min. Then bromocyclobutane (2.99 g, 22.13 mmol) was added dropwise with stirring at 10° C. (under a N₂ atmosphere). After the addition was complete, the reaction mixture was stirred at 40° C. for 2 h. The above solution was added dropwise to a solution of 3-bromo-4-fluoro-N-methoxy-N-methylbenzamide (2.9 g, 11.07 mmol) in THF (30 mL) at 0° C. (under a N₂ atmosphere). The mixture was stirred at rt for 16 h. The reaction mixture was poured into ice water (20 mL), and the mixture was extracted with EtOAc (30 mL×2). The combined organic layer was washed with brine (20 mL×2), dried (Na₂SO₄), filtered and concentrated in vacuo to give crude product. The crude product was purified by silica gel column chromatography using (PE/DCM=100:1-5:1) to give the title compound.

Step C.
2-bromo-4-(cyclobutylmethyl)-1-fluorobenzene

To a solution of (3-bromo-4-fluorophenyl)(cyclobutyl)methanone (125 mg, 0.486 mmol) in TEA (2 mL) was added triethylsilane (170 mg, 1.459 mmol) dropwise at 0° C. The mixture was stirred at 0° C., and gradually allowed to warm to it, and the mixture was stirred for 16 h. The mixture was poured into aq. NaOH (30%, 50 mL), and the mixture was extracted with DCM (3×300 mL), washed with water (2×150 mL), and brine (2×150 mL). The organic layer was dried (Na₂SO₄), filtered, and the filtrate was concentrated in vacuo. The residue was purified by silica gel chromatography (PE:EtOAc=200:1-50:1) to give the crude product. H NMR (400 MHz, CDCl₃) δ 8.12 (dd, J=2.0, 6.7 Hz, 1H), 7.84 (ddd, J=1.8, 4.7, 8.4 Hz, 1H), 7.19 (t, J=8.2 Hz, 1H), 3.94 (quin, J=8.4 Hz, 1H), 2.47-2.25 (m, 4H), 2.18-2.03 (m, 1H), 1.98-1.86 (m, 1H).

Intermediate 42

Ethyl 3-(5-fluoro-1,2,3,4-tetrahydroisoquinolin-6-yl)propanoate

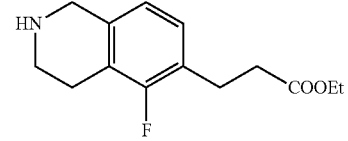 [SMILES: CCOC(=O)CCc1ccc2c(c1F)CCNC2]

Step A. (E)-ethyl 3-(6-chloroquinolin-2-yl)acrylate

To a solution of 6-bromo-5-fluoroisoquinoline (210 mg, 0.929 mmol) in dry 1,4-dioxane (10 mL) was added tri-tert-butylphosphonium tetrafluoroborate (51 mg, 0.176 mmol), dicyclohexylamine (253 mg, 1.394 mmol), and ethyl acrylate (112 mg, 1.115 mmol). The mixture was degassed for 5 min with N₂. Then Pd₂(dba)₃ (85 mg, 0.093 mmol) was added to the mixture, and the mixture was stirred at 100° C. for 18 h under a N₂ atmosphere. The mixture was diluted with EtOAc (20 mL), and the mixture was filtered. The filtrate was concentrated in vacuo, and the resulting residue was purified by silica gel chromatography (PE:EtOAc=20:1 to 3:1) to afford the title compound.

Step B. Ethyl 3-(5-fluoro-1,2,3,4-tetrahydroisoquinolin-6-yl)propanoate

To a solution of (E)-ethyl 3-(5-fluoroisoquinolin-6-yl)acrylate (220 mg, 0.897 mmol) in MeOH (20 mL) was added platinum(IV) oxide (40 mg, 0.176 mmol). The reaction mixture was stirred under a hydrogen atmosphere (50 psi) at 30° C. for 5 h. The reaction mixture was cooled to rt and filtered. The filtrate was concentrated in vacuo to give the title compound, which was used in the next step without further purification. ¹HNMR (400 MHz, CDCl₃) δ 7.02-6.91 (m, 1H), 6.73 (d, J=7.4 Hz, 1H), 4.12 (q, J=7.0 Hz, 2H), 3.97 (s, 2H), 3.13 (t, J=6.1 Hz, 2H), 2.92 (t, J=7.6 Hz, 2H), 2.73 (t, J=5.7 Hz, 2H), 2.60 (t, J=7.6 Hz, 2H), 1.24 (t, J=7.0 Hz, 3H).

Intermediate 43

5-((1r,3r)-3-benzyloxy cyclobutoxy)-1-bromo-2-fluoro-3-methoxybenzene

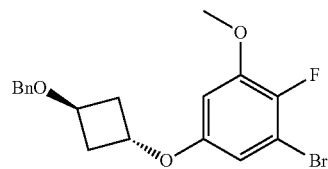 [SMILES: COc1cc(O[C@H]2C[C@H](OCc3ccccc3)C2)cc(Br)c1F]

Step A. (3-bromo-2-fluoro-5-((triisopropylsilyl)oxy)phenyl)boronic acid

To a solution of 2,2,6,6-tetramethylpiperidine (6.10 g, 43.2 mmol) in THF (150 ml) was added n-BuLi 17.27 ml, 43.2 mmol) at −78° C. The mixture was stirred at −78° C. for 0.5 h, and then warmed to rt and stirred for 1 h. The mixture was extracted with EtOAc (100 mL×2), washed with water (1 L), and dried (Na$_2$SO$_4$). The organic layer was concentrated in vacuo to give the crude product, which was used in the next step without further purification.

Step B. 3-bromo-2-fluoro-5-((triisopropylsilyl)oxy)phenol

To a solution of (3-bromo-2-fluoro-5-((triisopropylsilyl)oxy)phenyl)boronic acid (17.15 g, 43.8 mmol) in THF (150 ml) was added NaH (11.69 g, 88 mmol) (30%). Then H$_2$O$_2$ (9.94 g, 88 mmol) (30%) was added at 0° C. The mixture was stirred at 15° C. for 16 h, then diluted with aqueous saturated Na$_2$SO$_3$ (100 mL) and stirred for 0.5 h. The mixture was extracted with EtOAc (2×100 mL), washed with water (500 mL), dried (Na$_2$SO$_4$), filtered, concentrated in vacuo. The residue was purified by silica gel column chromatography (PE:EtOAc=50:1 to 20:1) to give the title compound.

Step C. (3-bromo-4-fluoro-5-methoxyphenoxy)triisopropylsilane

To a solution of 3-bromo-2-fluoro-5-((triisopropylsilyl)oxy)phenol (8.0 g, 22.02 mmol) and K$_2$CO$_3$ (6.09 g, 44.0 mmol) in DMF (50 ml) was added MeI (11.834 g, 83 mmol) at 0° C. The mixture was stirred at 15° C. for 16 h. Aq. saturated Na$_2$S$_2$O$_3$ (100 mL) was added, and the mixture was extracted with EtOAc (50 mL×2), washed with water (500 mL), dried (Na$_2$SO$_4$), filtered, concentrated in vacuo. The residue was purified by silica gel column chromatography (PE:EtOAc=50:1 to 20:1) to give the title compound.

Step D. 3-bromo-4-fluoro-5-methoxyphenol

To a solution of (3-bromo-4-fluoro-5-methoxyphenoxy)triisopropylsilane (5.0 g, 13.25 mmol) in THF (50 ml) was added TBAF (13.25 ml, 13.25 mmol. 1 M in THF). The mixture was stirred at 25° C. for 2 h. Water (100 mL) was added, and the mixture was extracted with EtOAc (2×50 mL). The organic layer was washed with water (200 mL), dried (Na$_2$SO$_4$), and concentrated in vacuo. The residue was purified by silica gel column chromatography (PE:EtOAc=10:1 to 5:1) to give the title compound.

Step E. 5-((1R,3R)-3-(benzyloxy)cyclobutoxy)-1-bromo-2-fluoro-3-methoxy benzene To a stirred solution of 3-bromo-4-fluoro-5-methoxyphenol (0.546 g, 2.469 mmol), (1S,3S)-3-(benzyl-oxy)cyclobutanol (0.4 g, 2.244 mmol) and PPh$_3$ (0.883 g, 3.37 mmol) in THF (15 mL) was added DEAD (0.569 nit 3.59 mmol) dropwise at 0° C. Then the reaction mixture was placed under a nitrogen atmosphere and stirred at 80° C. for 15 h. The solvent was removed in vacuo, and the resulting residue was purified by silica gel chromatography (PE/EtOAc=20:1 to 10:1) to give the title compound. $^1$H NMR (400 MHz, CDCl$_3$) ppm δ 2.38-2.48 (m, 2H) 2.48-2.59 (m, 2H) 3.87 (s, 3H) 4.30-4.40 (m, 1H) 4.75-4.88 (m, 1H) 6.42 (dd, J=6.65, 2.64 Hz, 1H) 6.44-6.47 (m, 1H) 7.30-7.42 (m, 5H).

Intermediate 44

3-bromo-2-fluoro-5-(trifluoromethoxy)benzonitrile

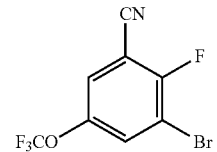

Step A. 1-bromo-2-fluoro-4-nitro-5-(trifluoromethoxy)benzene

To a solution of 2-bronco-1-fluoro-4-(trifluoromethoxy)benzene (10.0 g, 38.6 mmol) in CH$_3$CN (150 mL) was added nitronium tetrafluorborate (5.38 g, 40.5 mmol) at 0° C., and the mixture was stirred at 0-18° C. for 16 h. The mixture was poured into water (50 mL) and extracted with EtOAc. (200 mL×3). The organic layer was washed with water (150 mL×2) and brine (150 mL×2), dried (Na$_2$SO$_4$), and filtered. The filtrate was concentrated in vacuo, and the resulting residue was purified by silica gel chromatography (PE:EtOAc=20:1-5:1) to give the title compound.

Step B. 4-bromo-5-fluoro-2-(trifluoromethoxy)aniline

To a stirred solution of 1-bromo-2-fluoro-4-nitro-5-(trifluoromethoxy)benzene (4.0 g, 13.16 mmol) in MeOH (20 mL) and water (2 mL) was added NH$_4$Cl (7.04 g, 132 mmol) and iron (2.204 g, 39.5 mmol). The mixture was stirred at 50° C. for 18 h. The mixture was extracted with EtOAc (2×50 mL) and water (2×30 mL), and the organic layer was dried (NaSO$_4$), filtered and concentrated in vacuo. The residue was purified by silia gel chromatography (PE:EtOAc=10:1) to give the title compound.

Step C. 4-amino-3-bromo-2-fluoro-5-(trifluoromethoxy)benzonitrile

To a stirred solution of 4-amino-2-fluoro-5-(trifluoromethoxy)benzonitrile (0.76 g, 3.45 mmol) in CH$_3$CN (30 mL) was added NHS (0.615 g, 3.45 mmol), and the mixture was stirred at rt for 2 h. The mixture was diluted with water (60 mL) and extracted with EtOAc (2×50 mL). The organic layer was dried (Na$_2$SO$_4$) and concentrated in vacuo. The residue was purified by silia gel chromatography (PE:EtOAc=30:1) to give the title compound.

Step D. 3-bromo-2-fluoro-5-(trifluoromethoxy)benzonitrile

To a stirred solution of 2-amino-5-bromo-6-fluoro-3-(trifluoromethoxy)benzonitrile (330 mg, 1.104 mmol) in THF (10 mL) was added isopentyl nitrite (388 mg, 3.31 mmol), and the mixture was stirred at 50° C. for 24 h. The mixture was washed with water (2×10 mL) and extracted with EtOAc (2×30 mL). The organic layer was dried (Na$_2$SO$_4$),

Intermediate 45 methyl 3-(1-methyl-1,2,3,4-tetrahydroisoquinolin-6-yl)propanoate

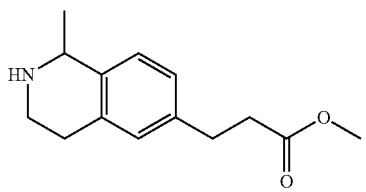 [SMILES: COC(=O)CCc1ccc2c(c1)CCNC2C]

Step A—6-bromo-3,4-dihydroisoquinoline

To a solution of 6-bromo-1,2,3,4-tetrahydro-isoquinoline (15.00 g, 71.1 mmol) in DCM (160 mL) was added activated MnO$_2$ (77.84 g, 859.7 mmol). The mixture was stirred for 18 h at rt and filtered. The filtrate was concentrated in vacuo, and the residue was purified by silica gel chromatography (PE:EtOAc=20:1 to 5:1) to afford the title compound.

Step B—6-bromo-1-methyl-1,2,3,4-tetrahydroisoquinoline

To a solution of 6-bromo-3,4-dihydroisoquinoline (2.50 g, 11.9 mmol) in dry THF (50 ml) was added BF$_3$.Et$_2$O (9.0 ml, 71.0 mmol) at −78° C. in a N$_2$ atmosphere. After stirring for 5 min at −78° C., MeMgBr (426 g, 35.7 mmol) was added. The mixture was warmed to rt and stirred 18 h. The mixture was cooled to 0° C., and water was added to quench the reaction. The mixture was extracted with EtOAc (100 mL×2). The organic layer was washed with brine, dried (Na$_2$SO$_4$), and concentrated in vacuo to afford the title compound, which was used in the next step without further purification.

Step C. tert-butyl 6-bromo-1-methyl-3,4-dihydroisoquinoline-2(1H)-carboxylate To a solution of 6-bromo-1-methyl-1,2,3,4-tetrahydroisoquinoline (1.50 g, 6.63 mmol) in DCM (15 ml) was added TEA (1.8 ml, 13.2 mmol), followed by (Boc)$_2$O (2.2 g, 9.95 mmol). The mixture was stirred for 1 h at rt, and the mixture was concentrated in vacuo. The residue was purified by silica gel chromatography (PE:EtOAc=30:1) to afford the title compound.

Step D. (E)-tert-butyl. 6-(3-methoxy-3-oxoprop-1-en-1-yl)-1-methyl-3,4-dihydro-isoquinoline-2(1H)-carboxylate To a solution of tert-butyl 6-bromo-1-methyl-3,4-dihydroisoquinoline-2(1H)-carboxylate (1.50 g, 4.60 mmol) in dioxane (15 mL) was added N,N-dicyclohexylmethylamine (1.34 g, 6.86 mmol), tri-tort-butylphosphonium tetrafluoroborate (0.13 g, 0.45 mmol). The final mixture was degassed for 5 min with N$_2$. Then Pd$_2$(dba)$_3$ (0.21 g, 0.229 mmol) and methyl acrylate (1.98 g, 23.00 mmol) were added. The final mixture was heated to 110° C. and stirred overnight in a N$_2$ atmosphere. The mixture was diluted with EtOAc (20 mL), filtered, and the filtrate was concentrated in vacuo. The residue was purified by silica gel chromatography (PE:EA=40:1 to 20:1) to afford the title compound. m/z 317.0 [M−16]$^+$.

Step E tert-butyl 6-(3-methoxy-3-oxopropyl)-1-methyl-3,4-dihydroisoquinoline-2(1H)-carboxylate To a solution of (E)-tert-butyl 6-(3-methoxy-3-oxoprop-1-en-1-yl)-1-methyl-3,4-dihydroisoquinoline-2(1H)-carboxylate (700 mg, 2.112 mmol) in MeOH (15 ml) was added Pd—C (70 mg, 0.66 mmol). The mixture was stirred overnight at 22° C. in a H$_2$ atmosphere (45 PSI). The mixture was filtered, and the filtrate was concentrated in vacuo to afford the title compound.

Step F. methyl 3-(1-methyl-1,2,3,4-tetrahydroisoquinolin-6-yl)propanoate

To a solution of tert-butyl-6-(3-methoxy-3-oxopropyl)-1-methyl-3,4-dihydro-iso-quinoline-2(1H)-carboxylate (350 mg, 1.05 mmol) in DCM (10 mL) was added HCl (4.0 M dioxane solution, 3 mL). The mixture was stirred for 1 h at rt, and concentrated in vacuo. The residue was dissolved in MeOH (10 mL), and Cs$_2$CO$_3$ was added to adjust the pH to pH 8-9. Then the mixture was concentrated in vacuo to afford the title compound, which was used in the next step without further purification.

Intermediate 46 tert-butyl 6-(4-ethoxy-4-oxobutan-2-yl)-3,4-dihydroisoquinoline-2(1H)-carboxylate

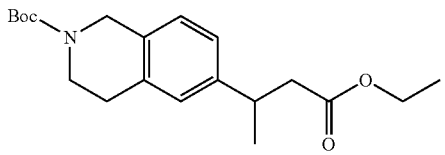 [SMILES: CCOC(=O)CC(C)c1ccc2c(c1)CCN(C(=O)OC(C)(C)C)C2]

Step A. (E)-tert-butyl 6-(4-ethoxy-4-oxobut-2-en-2-yl)-3,4-dihydroisoquinoline-2(1H)-Carboxylate To a solution of tert-butyl 6-bromo-3,4-dihydroisoquinoline-2(1H)-carboxylate (2.0 g, 6.41 mmol) and (E)-ethyl but-2-enoate (1.462 g, 12.81 mmol) in dioxane (20 ml) was added tri-terbutylphosphonium tetrafluoroborate (0.186 g, 0,641 mmol) and Pd$_2$(dba)$_3$ (0.117 g, 0.128 mmol) followed by the addition of N-cyclohexyl-N-methylcyclohexanamine (1.502 g, 7.69 mmol). The reaction was stirred at 100° C. under a 1N) atmosphere for 12 h. The reaction mixture was partitioned between EtOAc (50 mL) and water (50 mL), and the organic layer was washed with brine (50 mL), dried (Na$_2$SO$_4$), filtered and concentrated in vacuo. The crude product was purified by silica gel chromatography (PE/EtOAc 30:1 to 10:1) to give the title compound.

Step B. tert-butyl 6-(4-ethoxy-4-oxobutan-2-yl)-3,4-dihydroisoquinoline-2(1H)-carboxylate To a mixture of (E)-tert-butyl 6-(4-ethoxy-4-oxobut-2-en-2-yl)-3,4-dihydroisoquinoline-)-carboxylate (400 mg, 1.158 mmol) in MeOH (10 ml) was added Pd—C (40 mg, 0.038 mmol), and the mixture was stirred at rt under a H₂ atmosphere (30 psi) for 50 min. The mixture was filtered and concentrated in vacuo to afford the title compound. m/z 348.2 [M+H]⁺. ¹HNMR (400 MHz, CDCl₃) δ 7.05 (s, 1H) 7.00 (s, 1H) 4.54 (s, 2H) 4.09 (q, J=7.04 Hz, 2H) 3.64 (br. s., 2H) 3.24 (dq, J=14.38, 7.08 Hz, 1H) 2.81 (hr. s., 2H) 2.49-2.63 (m, 2H) 1.49 (s, 9H) 1.29 (d, J=7.04 Hz, 3H) 1.20 (t, J=7.24 Hz, 3H), Step C. tert-butyl 6-(4-ethoxy-4-oxobutan-2-yl)-3,4-dihydroisoquinoline-2(1H)-carboxylate Tert-butyl 6-(4-ethoxy-4-oxobutan-2-yl)-3,4-dihydroisoquinoline-2(1H)-carboxylate (350 mg) was purified by SFC (Column: Chiral Pak WHELK-O1, 5 um, Daicel Chemical Industries, Ltd 250×30 mm I.D. Mobile phase A: Supercritical CO₂, Mobile phase B: EtOH (contained 0.1% ETOA), A:B=75:25 at 60 mL/min, Column Temp: 38° C., Wavelength: 220 nm, Nozzle Pressure: 100 Bar Nozzle Temp: 60° C.) to afford tert-butyl 6-(4-ethoxy-4-oxobutan-2-yl)-3,4-dihydro-isoquinoline-2(1H)-carboxylate and tert-butyl 6-(4-ethoxy-4-oxobutan-2-yl)-3,4-di-hydroisoquinoline-2(1H)-carboxylate. m/z 348.2 [M+H]⁺.

Intermediate 47 ethyl 3-(5-fluoro-1,2,3,4-tetrahydroisoquinolin-6-yl)-2-methylpropanoate hydrochloride

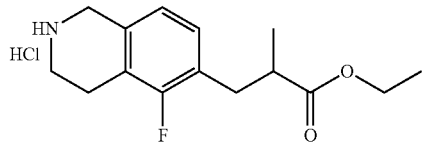 [SMILES: Cl ; CCOC(=O)C(C)Cc1ccc2c(c1F)CCNC2]

Step A. tert-butyl 6-(3-ethoxy-3-oxopropyl)-5-fluoro-3,4-dihydroisoquinoline-2(1H)-carboxylate To a solution of ethyl 3-(5-fluoro-1,2,3,4-tetrahydroisoquinolin-6-yl)propanoate (Intermediate 7, 1.0 g, 3.98 mmol) in DCM (20 mL) were added Et₃N (0.6 mL, 4.30 mmol) and BOC₂O (1.1 mL, 4.74 mmol) with stirring at 0° C. (under a N₂ atmosphere). The mixture was stirred at ~26° C. overnight (~18 h). The solvent was evaporated in vacuo, and the residue was purified by silica gel column chromatography (PE/EtOAc=20:1~5:1) to give the title compound.

Step B. tert-but 6-(3-ethoxy-2-methyl-3-oxopropyl)-5-fluoro-3,4-dihydro-isoquinoline-2(1H)-carboxylate To a solution of tert-butyl 6-(3-ethoxy-3-oxopropyl)-5-fluoro-3,4-dihydro isoquinoline-2(1H)-carboxylate (0.3 g, 0,854 mmol) in anhydrous THF (10 mL) with stirring at −78° C. was added KHMDS (1.3 mL, 1.300 mmol) in THF dropwise. The mixture was stirred at −78° C. for 30 min, and MeI (0.182 g, 1,281 mmol) was added. The mixture was stirred for an additional 30 min at −78° C., and the mixture was gradually warmed to rt for 18 h. The reaction was quenched with water (10 mL), and the mixture was extracted with EtOAc (2×20 mL). The organic phase was concentrated in vacuo to give crude product, which was purified by silica gel column chromatography (EtOAc/PE 1:20~1:10) to give the title compound.

Step C. tert-butyl ethyl 3-(5-fluoro-1,2,3,4-tetrahydroisoquinolin-6-yl)-2-methyl-propanoate To a solution of tert-butyl 6-(3-ethoxy-2-methyl-3-oxopropyl)-5-fluoro-3,4-dihydroisoquinoline-2(1H)-carboxylate (500 mg, 1.368 mmol) in dioxane (10 mL) was added a solution of 4 M FICA in dioxane (5 mL), and the mixture was stirred at 24° C. for 18 h. The Mixture was concentrated in vacuo to give the title compound. ¹H NMR (400 MHz, CDCl₃) δ ppm 6.92 (t, J=7.63 Hz, 1H) 6.71 (d, J=8.22 Hz, 1H) 4.06-4.12 (m, 2H) 3.96 (s, 2H) 3.12 (t, J=6.06 Hz, 2H) 2.96 (d, J=6.65 Hz, 1H) 2.72 (br. s., 4H) 1.16-1.23 (m, 6H).

Intermediate 48 ethyl 3-(5-fluoro-7-methyl-1,2,3,4-tetrahydroisoquinolin-6-yl)propanoate

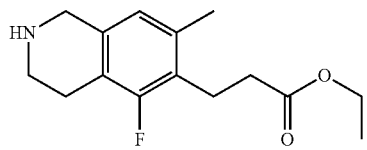 [SMILES: CCOC(=O)CCc1c(C)cc2c(c1F)CCNC2]

Step A. 3-bromo-2-fluoro-4-methylbenzaldehyde

To a stirred solution of 2-bromo-1-fluoro-3-methylbenzene (9.0 g, 47.6 mmol) in THF (150 mL) was added LDA (26.2 ml, 52.4 mmol) at −70° C. under a nitrogen atmosphere. The mixture was stirred for 1 h at −70° C., then DMF (4.5 g, 61.6 mmol) was added to the mixture. The mixture was allowed to warm to rt and stirred for 2 h. The reaction was quenched by addition of NH₄Cl solution (10 mL) and extracted with EtOAc (2×30 mL). The organic layer was dried (Na₂SO₄), filtered and concentrated in vacuo to give a residue. The residue was purified by silica gel column chromatography (PE:EtOAc=20:1) to give the title compound.

Step B. (E)-methyl 3-(3-bromo-2-fluoro-4-methylphenyl)acrylate

To stirred solution of ethyl 2-(diethoxyphosphoryl)acetate (5.34 g, 23.82 mmol) in THF (80 mL) was added NaH (1.0 g, 25.00 mmol). The resulting solution was stirred at rt for 30 min. Then 3-bromo-2-fluoro-4-methylbenzaldehyde (4.7 g, 21.66 mmol)) in THF (20 mL) was added dropwise, and the mixture was stirred at rt for 2 h. The reaction was quenched with NH₄Cl solution (5 mL), the resulting mixture was extracted with EtOAc (100 mL×2). The organic layer was dried over Na₂SO₄, filtered and concentrated in vacuo to give a residue. The residue was purified by silica gel column chromatography (EtOAc:PE=1:15) to give the title compound.

Step C. (E)-3-(3-bromo-2-fluoro-4-methylphenyl)acrylic acid

To a solution of (E)-methyl 3-(3-bromo-2-fluoro-4-methylphenyl)acrylate (12.0 g, 43.9 mmol) in THF (20 ml), MeOH (20 ml) and water (10 ml) was added LiOH hydrate (3.69 g, 88 mmol). The mixture was stirred at 15° C. for 16 h. The mixture was diluted with water (200 mL) and aqueous HCl (6N, 15 mL) to adjust the pH to 4. The mixture was then extracted with EtOAc (2×100 mL), and the organic layer was washed with water (200 mL), dried over anhydrous $Na_7SO_4$, and concentrated in vacuo to give the crude title compound, which was used in next step without further purification.

Step D (E)-3-(3-bromo-2-fluoro-4-methylphenyl) acryloyl chloride

To a solution of (E)-3-(3-bromo-2-fluoro-4-methylphenyl)acrylic acid (4.5 g, 16.50 mmol) in THF (30 mL) was added oxalyl chloride (2.304 g, 18.15 mmol) and DMF (0.005 mL). The mixture was stirred at 18° C. for 2 h. The mixture was concentrated in vacuo to give the crude title compound, which was used in next step without further purification.

Step E. (E)-3-(3-bromo-2-fluoro-4-methylphenyl) acryloyl azide

To a solution of sodium azide (1.44 g, 22.15 mmol) in dioxane (8 mL) and water (5 mL) was added (E)-3-(3-bromo-2-fluoro-4-methylphenyl)acryloyl chloride (4.58 g, 16.50 mmol) in dioxane (10 mL) dropwise at 0° C. The mixture was stirred at 0° C. for 1 h, and water MO mL) was added. The mixture was extracted with diethyl ether (3×30 mL), and organic layer was washed with sat. aqueous of $NaHCO_3$ (2×30 ml) and brine (50 mL), dried over $Na_2SO_4$, and filtered. The organic layer was concentrated in vacuo at a temperature of less than 40° C. behind a protective screen to afford the title compound.

Step F.
6-bromo-5-fluoro-7-methylisoquinolin-1(2H)-one

A solution of (E)-3-(3-bromo-2-fluoro-4-methylphenyl) acryloyl azide (4.69 g, 16.51 mmol) in diphenyl ether (20 ml) was stirred at 250° C. for 3 h. The mixture was cooled to 20° C. and diluted with cyclohexane (40 mL). The precipitate was filtered and dried to give the title compound. m/z 255.9 $(M+H)^+$, Step G.
6-bromo-1-chloro-5-fluoro-7-methylisoquinoline 6-bromo-5-fluoro-7-methyl-isoquinolin-1(2H)-one (0.65 g, 2.54 mmol) was dissolved in $POCl_3$ (10.29 ml, 110 mmol), and the mixture was stirred at 110° C. for 2 h. The reaction mixture was concentrated in vacuo, and the concentrate was poured into water (20 mL). The water layer was extracted with EtOAc×30 mL), and the organic layer was washed with aqueous saturated $NaHCO_3$ solution. The organic layer was washed with brine (20 mL×2), dried over $Na_2SO_4$, filtered and concentrated in vacuo to give crude product. The crude product was purified by silica gel column chromatography (PE/EtOAc 10:1) to give the title compound. m/z 276.0 $(M+H)^+$.

Step H. 6-bromo-5-fluoro-7-methylisoquinoline

To a solution of 6-bromo-1-chloro-5-fluoro-7-methylisoquinoline (350 mg, 1.275 mmol) in AcOH (5 ml) and hydrochloric acid, 37% (1 ml) was added tin (454 mg, 3.82 mmol). The mixture was stirred at 60° C. for 0.5 h. The mixture was diluted with water (100 mL), and the mixture was extracted with EtOAc (2×50 mL). The organic layer was washed with water (200 mL), dried over anhydrous $Na_2SO_4$, filtered, concentrated in vacuo, and the residue was purified by silica column chromatography (PE:EtOAc=50:1 to 20:1) to give the title compound. m/z 240.1 $[M+H]^+$.

Step I. (E)-ethyl 3-(5-fluoro-7-methylisoquinolin-6-yl)acrylate

To a solution of 6-bromo-5-fluoro-7-methylisoquinoline (180 mg, 0.750 mmol) in dry 1,4-dioxane (10 ml) was added tri-tert-butylphosphonium tetrafluoroborate (22 mg, 0.076 mmol), ethyl acrylate (120 mg, 1.2 mmol) and N-cyclohexyl-N-methylcyclohexanamine (439 mg, 2.249 mmol). Then the mixture was degassed for 5 min with $N_2$, and $Pd_2(dba)_3$ (137 mg, 0,150 mmol) was added to the mixture. The mixture was heated to 100° C. and stirred for 18 h in a $N_2$ atmosphere. The mixture was diluted with water (100 mL) and extracted with EtOAc (2×50 mL). The organic layer was washed with water (200 mL), dried over anhydrous $Na_2SO_4$, and concentrated in vacuo. The residue was purified by silica gel column chromatography (PE:EtOAc=50:1 to 20:1) to give the title compound. m/z 260.3 $[M+H]^+$.

Step J. ethyl 3-(5-fluoro-7-methyl-1,2,3,4-tetrahydroisoquinolin-6-yl)propanoate To a solution of (E)-ethyl 3-(5-fluoro-7-methylisoquinolin-6-yl)acrylate (0.2 g, 0.771 mmol) in EtOH (15 ml) was added platinum(IV) oxide (0,035 g, 0.154 mmol). The reaction mixture was stirred under a hydrogen atomosphere (50 PSI) at 50° C. for 5 h. The mixture was filtered, and the filtrate was concentrated in vacuo to give the title compound. m/z 266.1 $[M+H]^+$.

Intermediate 49 ethyl 3-(7-fluoro-1,2,3,4-tetrahydroisoquinolin-6-yl) propanoate

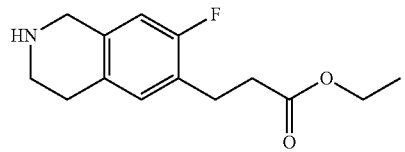 [SMILES: CCOC(=O)CCc1cc2c(cc1F)CNCC2]

Step A. 2-(3-bromo-4-fluorophenyl)acetamide

To a solution of 2-(3-bromo-4-fluorophenyl)-acetic acid (5.0 g, 21.46 mmol), $NH_4Cl$ (1.262 g, 23.60 mmol) and DIPEA (11.3 ml, 64.7 mmol) in DMF (50 ml) was stirred at 15° C. for 15 min. Then HATU (8.16 g, 21.46 mmol) was added at 15° C., and the mixture was stirred at 15° C. for 5 h. The reaction was quenched with water (100 mL), and the mixture was extracted with DCM (3×80 mL). The organic layer was washed with water (3×30 mL) and brine (3×30 mL), dried ($Na_2SO_4$), and filtered. The filtrate was concentrated in vacuo, and the resulting residue was purified by silica gel chromatography (PE:EtOAc=5:1 to 1:1) to give the title compound.

Step B. 2-(3-bromo-4-fluorophenyl)ethanamine

To a solution of 2-(3-bromo-4-fluoro-phenyl)acetamide (3.0 g, 12.93 mmol) in THF (25 mL) was added dropwise BH$_3$.THF (24 mL, 24.00 mmol) at 0° C. The mixture was stirred at 70° C. for 16 h. The mixture was cooled to 0° C., and water (2 mL) and conc. HO solution (8 mL) were added to the mixture. The reaction mixture was stirred at 70° C. for 10 min, then cooled to rt. Then the mixture was poured into NaOH aqueous solution (4 N, 25 mL). The mixture was extracted with EtOAc (3×50 mL), and the organic layer was washed with water (5×20 mL) and brine (2×20 mL), dried over Na$_2$SO$_4$, filtered, and the filtrate was concentrated in vacuo to give crude title compound, which was used in the next step without further purification.

Step C. N-(3-bromo-4-fluorophenethyl)-2,2,2-trifluoroacetamide

To a solution of 2-(3-bromo-4-fluorophenyl)ethanamine (1.5 g, 6.88 mmol) and TEA (1.4 ml, 10.04 mmol) in THF (20 ml) was added TFAA (1.1 mL, 7.79 mmol) at 0° C., and the mixture was stirred at 0~19° C. for 3 h. The mixture was poured into aq. NaHCO$_3$ (2 M, 10 mL), and the mixture was extracted with EtOAc (3×30 mL), washed with water (2×10 mL), and brine (2×10 mL). The organic layer was dried over Na$_2$SO$_4$, and filtered, and the filtrate was concentrated in vacuo. The residue was purified by silica gel chromatography (PE:EtOAc=20:1~5:1) to give the title compound.

Step D. 1-(6-bromo-7-fluoro-3,4-dihydroisoquinolin-2(1H)-yl)-2,2,2-trifluoroethanone To a solution of concentrated sulfuric acid (2.5 ml, 46.9 mmol) in AcOH (10 ml) was added N-(3-bromo-4-fluorophenethyl)-2,2,2-trifluoroacetamide (1.2 g, 3.82 mmol) and formaldehyde (0.229 g, 7.64 mmol), and the mixture was stirred at 20° C. for 24 h. The mixture was poured into ice water (100 mL), and the mixture was extracted with EtOAc (3×30 mL). The organic layer was washed with water (2×20 mL) and brine (2×20 mL), dried over Na$_2$SO$_4$, filtered, and the filtrate was concentrated in vacuo. The resulting residue was purified by silica gel chromatography (PE:EtOAc=20:1-5:1) to give 1-(6-bromo-7-fluoro-3,4-dihydroisoquinolin-2(1H)-yl)-2,2,2-trifluoroethanone and 1-(8-bromo-7-fluoro-3,4-dihydroisoquinolin-2(1H)-yl)-2,2,2-trifluoroethanone.

Step E. (E)-ethyl 3-(7-fluoro-2-(2,2,2-trifluoroacetyl)-1,2,3,4-tetrahydroisoquinolin-6-yl)acrylate To a solution of 1-(8-bromo-7-fluoro-3,4-dihydroisoquinolin-2(1H)-yl)-2,2,2-trifluoroethanone (250 mg, 0,767 mmol), and 1-(6-bromo-7-fluoro-3,4-dihydro-isoquinolin-2(1H)-yl)-2,2,2-trifluoroethanone (500 mg, 1.533 mmol) in dry 1,4-dioxane (10 ml) was added tri-tert-butylphosphonium tetrafluoroborate (45 mg, 0,155 mmol), ethyl acrylate (246 mg, 2.453 mmol), and N-cyclohexyl-N-methylcyclohexanamine (899 mg, 4.60 mmol). Then the mixture was degassed for 5 min with N$_2$, and Pd$_2$(dba)$_3$ (281 mg, 0307 mmol) was added. The mixture was then heated to 100° C. and stirred for 18 h in a N$_2$ atmosphere. EtOAc (100 mL) was added, and the mixture was filtered. The filtrate was concentrated in vacuo, and the residue was purified by silica gel chromatography (PE:EtOAc=20:1 to 10:1) to afford the crude title compound. The mixture was purified by SFC to give title compound.

Step F: ethyl 3-(7-fluoro-2-(2,2,2-trifluoroacetyl)-1,2,3,4-tetrahydroisoquinolin-6-yl)propanoate To a solution of (E)-ethyl-3-(7-fluoro-2-(2,2,2-trifluoroacetyl)-1,2,3,4-tetrahydroisoquinolin-6-yl)acrylate (500 mg, 1.448 mmol) in EtOH (20 mL) was added Pd—C (15 mg, 0.141 mmol). The mixture was stirred at 45° C. under H$_7$ (30 psi) for 2 h. The mixture was filtered, washed with EtOH (10 mL), and the filtrate was concentrated in vacuo to give the crude title compound.

Step G. ethyl 3-(7-fluoro-1,2,3,4-tetrahydroisoquinolin-6-yl)propanoate

To a solution of ethyl 3-(7-fluoro-2-(2,2,2-trifluoroacetyl)-1,2,3,4-tetrahydroisoquinolin-6-yl)propanoate (200 mg, 0.576 mmol) in EtOH (10 mL) was added K$_2$CO$_3$ (239 mg, 1,728 mmol). The mixture was stirred at 15° C. for 12 h, and the mixture was cooled to rt and dilited with EtOAc (20 mL). The organic layer was washed with water (2×20 mL), dried with Na$_2$SO$_4$, and concentrated in vacuo to give the crude title compound.

Intermediate 50

Ethyl 2-(1,2,3,4-tetrahydroisoquinolin-6-yl)cyclopropanecarboxylate

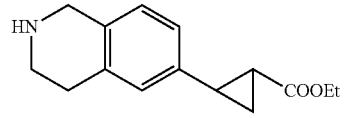 [SMILES: CCOC(=O)C1CC1c1ccc2c(c1)CCNC2]

Step A. Tert-butyl 6-bromo-3,4-dihydroisoquinoline-2(1H)-carboxylate

To a solution of 6-bromo-1,2,3,4-tetrahydroisoquinoline (19.17 g, 90.39 mmol) in DCM (200 mL) was added TEA (18.29 g, 180.77 mmol) and Boc$_2$O (23.67 g, 108.46 mmol) at 0° C. After the completion of the addition, the mixture was stirred at 25° C. for 15 h. Water (300 mL) was added, and the mixture was extracted with EtOAc (3×100 mL). The organic layer was dried over Na$_2$SO$_4$ and concentrated in vacuo. The resulting residue was purified by silica gel column chromatography (PE:EtOAc=50:1 to 10:1) to give the title compound.

Step B. 6-(3-ethoxy-3-oxoprop-1-en-1-yl)-3,4-dihydroisoquinoline-2(1H)-carboxylate To a solution of tert-butyl 6-bromo-3,4-dihydroisoquinoline-2(11)-carboxylate (11.30 g, 36.20 mmol) in dioxane (100 mL) was added ethyl acrylate (7.25 g, 72.39 mmol), (t-Bu)$_3$PHBF$_4$ (2.10 g, 72.40 mmol), CH$_3$N(C$_6$H$_4$)$_2$ and Pd$_2$(dba)$_3$ (3.3 g, 3.62 mmol). Then the mixture was stirred at 100° C. under N$_2$ for 15 h. After the reaction mixture was cooled to rt, and water (200 mL) was added. The mixture was extracted with EtOAc (3×100 mL), and the organic layer was washed with brine, dried (Na$_2$SO$_4$), filtered, concentrated in vacuo. The resulting residue was purified by silica gel column chromatography (PE:EtOAc=50:1 to 10:1) to give the title compound.

Step C. Tert-butyl 6-(2-(ethoxycarbonyl)cyclopropyl)-3,4-dihydro-isoquino-line-2(1H)-carboxylate To a solution of tert-butyl 6-(3-ethoxy-3-oxoprop-1-en-1-yl)-3,4-dihydro-isoquinoline-2(1H)-carboxylate (6.3 g, 19.01 mmol) and Pd(OAc)$_2$ (043 g, 1.90 mmol) in DCM (200 mL) and diethyl ether (400 mL) was added diazomethane in diethyl ether (250 mL, 125 mmol) at 0° C. under a N$_2$ atmosphere. Then the reaction mixture was slowly warmed to rt and stirred for 15 h. The reaction mixture was quenched with AcOH (20 mL), washed with brine (100 mL), and the organic layer was concentrated in vacuo. The crude product was purified by silica gel column chromatography to give the title compound.

Step D. Ethyl 2-(1,2,3,4-tetrahydroisoquinolin-6-yl)cyclopropanecarboxylate

To a solution of tert-butyl 6-(2-(ethoxycarbonyl)cyclopropyl)-3,4-dihydroisoquinoline-2(1H)-carboxylate (2.00 g, 5.79 mmol) in dioxane (5 mL) was added HCl-dioxane (4 M, 5 mL). Then the mixture was stirred at 25° C. for 2 h, and then concentrated in vacuo. The residue was purified by cation ion exchange column chromatography (1 M NH$_3$-MeOH) to afford the title compound. $^1$H NMR (400 MHz, CD$_3$OD) δ 6.90-6.97 (m, 1H), 6.81-6.90 (m, 2H), 4.14 (q, J=7.30 Hz, 2H), 3.89 (s, 2H), 3.00-3.07 (m, 2H), 2.78 (t, J=5.87 Hz, 2H), 2.35-2.43 (m, 1H), 1.80-1.88 (m, 1H), 1.48 (s, 1H), 1.31-1.35 (m, 1H), 1.21-1.29 (m, 3H).

Intermediate 51

2-bromo-6-Chloro-4-cyclobutoxybenzonitrile

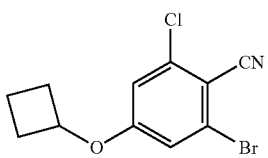 [SMILES: N#Cc1c(Cl)cc(OC2CCC2)cc1Br]

Step A 2-Chloro-4-cyclobutoxy-1-nitrobenzene

To a stirred solution of NaH (3.42 g, 85 mmol) in DMF (50 mL) was added dropwise cyclobutanol (6.16 g, 85 mmol), and the solution was stirred at 20° C. for about 5 minutes. Then 2-chloro-4-fluoro-1-nitrobenzene (10.00 g, 57.0 mmol) was added to the reaction, and the reaction was stirred for 18 h at room temperature. Saturated NH$_4$Cl aqueous solution (100 mL) and EtOAc (100 mL) were added to the reaction. The organic layer was separated and washed with saturated NH$_4$Cl aqueous solution (100 mL×4), dried over sodium sulfate and concentrated to give the title compound.

Step B 2-Chloro-4-cyclobutoxyaniline

To a solution of 2-chloro-4-cyclobutoxy-1-nitrobenzene (11.20 g, 49.2 mmol) in MeOH (100 mL) was added Raney Ni (0.42 g, 4.92 mmol) at 20° C. under an argon atmosphere. Then the reaction mixture was stirred at 20° C. for 1 h under 50 psi of H$_2$ atmosphere. The mixture was filtered and the filtrate was concentrated and purified on silica gel (PE/EtOAc=10:1-2:1) to afford the title compound.

Step C 2-Bromo-6-chloro-4-cyclobutoxyaniline

To a stirred solution of 2-chloro-4-cyclobutoxyaniline (8.95 g, 45.3 mmol) in DCM (150 mL) was added bromine (2.449 mL, 47.5 mmol) by syringe at 0° C. The solution was stirred at 0° C. for about 4 h, then aqueous saturated Na$_2$S$_2$O$_3$ (20 mL) and water (100 mL) were added dropwise. The resulting mixture was further stirred at room temperature for 5 min. Then the organic layer was separated, washed with brine (100 mL×2), dried over sodium sulfate and concentrated. The resulting residue was purified by flash chromatography (PE:EA=100:1) to give the title compound.

Step D
1-Bromo-3-chloro-5-cyclobutoxy-2-iodobenzene

To a stirred solution of 2-bromo-6-chloro-4-cyclobutoxyaniline (5.50 g, 19.89 mmol) and copper(I) iodide (5.68 g, 29.8 mmol) in acetonitrile (40 mL) at 65° C. was added dropwise isopentyl nitrite (4.66 g, 39.8 mmol). The reaction was stirred at 65° C. for about 20 min, then cooled to room temperature. Then water (50 ml) and EtOAc (50 mL) were added to the reaction mixture. The organic layer was separated, washed with water (50 mL×2) and brine (50 mL×2), dried over sodium sulfate and filtered. The filtrate was concentrated and purified by flash chromatography (petroleum ether) to afford the title compound.

Step E 2-Bromo-6-chloro-4-cyclobutoxybenzonitrile

To a stirred solution of 1-bromo-3-chloro-5-cyclobutoxy-2-iodobenzene (4.30 g, 11.10 mmol) in DMF (25 mL) was added cyanocopper (1.988 g, 22.20 mmol). The reaction was stirred at 110° C. overnight (18 h). then cooled to room temperature and poured into 30 mL of saturated aqueous NH$_4$Cl. The resulting mixture was stirred for about 5 min, then 30 mL of EtOAc were added, and the mixture was stirred 5 min. Then the organic layer was separated, washed with brine (60 mL×2), dried over sodium sulfate and filtered. The filtrate was concentrated and purified by flash chromatography (PE:EtOAc=40:1) to give partially purified crude product. The crude product was further purified by reverse phase HPLC on a GILSON 281 instrument fitted with a Phenomenex Synergi C18 (250*21.2 mm*4 μm) using water (0.2% Formic acid) and acetonitrile as eluents (Mobile phase A water (0.2% Formic acid), Mobile phase B acetonitrile, Detective wavelength: 220 nm) to give the title compound.

Intermediate 52 methyl 3-(5-chloro-1,2,3,4-tetrahydroisoquinolin-6-yl)propanoate

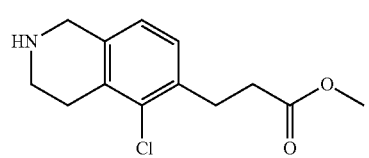 [SMILES: COC(=O)CCc1ccc2c(c1Cl)CCNC2]

Step A 1,2,3,4-tetrahydroisoquinolin-6-ol hydrobromide 6-methoxy-1,2,3,4-tetrahydroisoquinoline (10.0 g, 61.3 mmol) was dissolved in 48% HBr (40 mL, 354 mmol). The reaction was stirred at 100° C. for 15 h, then evaporated in vacuo to give the title compound, which was used directly in the next step without further purification.

Step B tert-butyl 6-hydroxy-3,4-dihydroisoquinoline-2(1H)-carboxylate

To a solution of 1,2,3,4-tetrahydroisoquinolin-6-ol hydrobromide (10 g) in H$_2$O (100 mL) was added a solution of triethylamine (20 mL, 143 mmol) and di-tert-butyl dicarbonate (10.43 g, 47.8 mmol) in THF (30 mL) dropwise. The reaction mixture was stirred at 25° C. for 15 h. Then the reaction mixture was evaporated in vacuo to give the crude product, which was purified by silica gel (SiO$_2$, PE:EtOAc from 100:1 to 10:1) to afford the title compound.

Step C tert-butyl-5-chloro-6-hydroxy-3,4-dihydroisoquinoline-2(H)-carboxylate Sulfuryl dichloride (3.28 g, 24.27 mmol) was added dropwise to a stirred mixture of tert-butyl 6-hydroxy-3,4-dihydroisoquinoline-2(H)-carboxylate (5.5 g, 22.06 mmol) in acetic acid (50 mL) at room temperature (~25° C.), and the mixture was stirred at room temperature (~25° C.) for 1.5 h. Then the mixture was concentrated. The resulting residue was dissolved in anhydrous DMF (50.0 mL), and Et$_3$N (9.22 mL, 66.2 mmol) and BOC-Anhydride (6.15 mL, 26.5 mmol) were added. Then the mixture was stirred at room temperature (25° C.) for 3 h, then concentrated in vacuo. Water (50 mL) was added to the residue and the mixture was extracted with ethyl acetate (50 mL×3). The combined organic layers were washed with aqueous ammonium chloride (30 mL), dried over Na$_2$SO$_4$, and filtered. The filtrate was evaporated under reduced pressure to give a residue, which was purified by column chromatography on silica gel (SiO$_2$), eluting with EA/PE=1:20-1:5 to to give the title compound.

Step D tert-butyl-5-chloro-6-(((trifluoromethyl)sulfonyl)oxy)-3,4-dihydroisoquinoline-2(1H)-carboxylate To a stirred solution of tert-butyl 5-chloro-6-hydroxy-3,4-dihydroisoquinoline-2(1H) carboxylate (1.4 g, 4.93 mmol) in CH$_2$Cl$_2$(20 mL) was added pyridine (1.171 g, 14.8 mmol) and trifluoromethanesulfonic anhydride (2.09 g, 7.40 mmol) dropwise at 0° C. The reaction mixture was warmed to room temperature (20° C.) and stirred for 30 min. Then the solvent was removed by rotary evaporation, and the resulting mixture was diluted with water (20 mL) and extracted with DCM (20 mL×3). The combined organic layers were evaporated, and the resulting crude product was purified on silica gel (SiO$_2$, PE/EtOAc=20:1-10:1) to give the title compound.

Step E tert-butyl-6-(3-(tert-butoxy)-3-oxopropyl)-5-chloro-3,4-dihydroisoquinoline-2(1H)-carboxylate To a solution of tert-butyl 5-chloro-6-(((trifluoromethyl)sulfonyl)oxy)-3,4-dihydroisoquinoline-2(1H)-carboxylate (0.92 g, 2.1 mmol) in toluene (20 ml) and H$_2$O (2 ml) was added potassium 3-trifluoroboratopropionate tert-butyl ester (0.49 g, 2.1 mmol) and sodium carbonate (0.66 g, 6.3 mmol), followed by the addition of G2Ruphos (75 mg, 0.1 mmol) under a N$_2$ atmosphere. The reaction mixture was stirred at 90° C. for 12 h, then poured into water (10 mL) and extracted with EA (30 mL×3). The combined organic layers were washed with water (10 mL×3), and dried over Na$_2$SO$_4$. After filtration and concentration, the resulting residue was purified by prep-HPLC (acid) to give the title compound.

Step F methyl 3-(5-chloro-1,2,3,4-tetrahydroisoquinolin-6-yl)propanoate

To a solution of tert-butyl 6-(3-(tert-butoxy)-3-oxopropyl)-5-chloro-3,4-dihydroisoquinoline-2(1H)-carboxylate (395 mg, 1 mmol) in MeOH (10 mL) was added HCl-MeOH (5 mL, 3M). The mixture was stirred at 70° C. for 4 h, then the reaction mixture was cooled to room temperature and concentrated to give the title compound. MS (ESI) m/z: 254 [M+H$^+$]

Intermediate 53

1-bromo-2,3-dichloro-5-(trifluoromethoxy)benzene

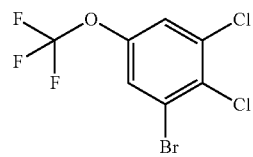 [SMILES: FC(F)(F)Oc1cc(Cl)c(Cl)c(Br)c1]

1-bromo-2,3-dichloro-5-(trifluoromethoxy)benzene. A suspension of copper(II) chloride (403 mg, 3.00 mmol) and tert-butyl nitrite (309 mg, 3.00 mmol) in anhydrous MeCN (15 mL) was warmed to 65° C. Then a solution of 2-bromo-6-chloro-4-(trifluoromethoxy)aniline (870 mg, 3.00 mmol) in anhydrous MeCN (5 mL) was added dropwise. The reaction mixture was stirred for 1 h at 65° C., then allowed to cool to 25° C. and poured into 1 M HCl (15 mL). The acidic mixture was neutralized with saturated NaHCO$_3$ and aqueous ammonia (35%. 5 mL). The mixture was extracted with DCM (25 mL) and then washed with aqueous ammonia (17.5%, 20 mL) and brine (2×20 mL). The resulting crude product was purified by column (SiO$_2$, eluting with PE) to give the title compound.

Intermediate 54 methyl 3-(5-methyl-1,2,3,4-tetrahydroisoquinolin-6-yl)propanoate

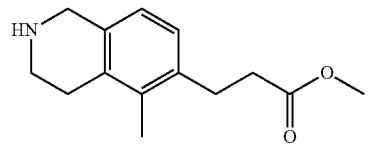 [SMILES: COC(=O)CCc1ccc2c(c1C)CCNC2]

Step A tert-butyl 5-methyl-6-oxo-3,4,6,7,8,8a-hexahydroisoquinoline-2(1H)-carboxylate To a solution of N-Boc-4-piperidone (19.8 g, 9.92 mol) in toluene (400 ml) was added pyrrolidine (10.9 g, 1.55 equiv).

The reaction was heated to reflux for 2 h and the water was removed by azeotropic distillation. The reaction was then concentrated in vacuo and cooled to 20° C. Toluene (100 mL) was added to the residue, followed by a slurry of hydroquinone (64 mg, 0.5 mol %) in toluene (3 mL). The reaction was cooled to 10° C., and ethyl vinyl ketone (8.30 g, 0.99 eq) was added. The solution was heated to 40° C. for 1 h and then heated to 105° C. for 18 h, before being cooled to 26-28° C. The organic layer was washed with saturated NH$_4$C solution, followed by water (100 mL). The organic phase was concentrated to give a toluene solution, which was used directly in the next reaction.

Step B tert-butyl 5-methyl-6-((triethylsilyl)oxy)-3,4,8,8a-tetrahydroisoquinoline-2(1H)-carboxylate To a solution of tert-butyl 5-methyl-6-oxo-3,4,6,7,8,8a-hexahydro-isoquinoline-2 (1H)-carboxylate (700 mg, 2.64 mmol) in THF (10 mL) was added LiHMDS (2 mL, 4 mmol) at 0° C. for 0.2 h. The reaction mixture was stirred at 0° C. for 5 h, then poured into ice water (30 mL) and extracted with EA (40 mL). The organic layer was washed with brine (20 mL), and dried over Na$_2$SO$_4$. After filtration, the solvent was concentrated to afford the title compound, which used in the next step without further purification

Step C tert-butyl 6-hydroxy-5-methyl-3,4-dihydroisoquinoline-2(1H)-carboxylate To a solution of tert-butyl 5-methyl-6-((triethylsilyl)oxy)-3,4,8,8a-tetrahydroisoquinoline-2-(1H)-carboxylate (750 mg, 1.581 mmol) in THF (10 mL) was added Pd(OAc)$_2$ (426 mg, 1.897 mmol) at 10° C. The reaction mixture was stirred at 20° C. for 10 h. Then potassium formate (199 mg, 2.371 mmol) in water (0.5 mL) was added, and the mixture was stirred at 20° C. for 2 h. TBAF (0.790 ml, 0.790 mmol) was added to the reaction and the reaction was stirred at 20° C. for 2 h, then poured into ice water (30 mL) and extracted with EA (40 mL*2). The combined organic layers were washed with brine (20 mL) and dried over anhydrous NaSO$_4$. After filtration and concentration, the resulting residue was purified by flash chromatography (SiO$_2$), eluting with 0-20% EA in PE to give the title compound.

Step D tert-butyl 5-methyl-6-((((trifluoromethyl)sulfonyl)oxy)-3,4-dihydroisoquinoline-2(1H)-carboxylate To a solution of tert-butyl-6-hydroxy-5-methyl-3,4-dihydro-isoquinoline-2(1H)-carboxylate (230 mg, 0.873 mmol), pyridine (0.21 mL, 2.6 mmol) in DCM (5 mL) was added Tf$_2$O (0.18 mL, 1 mmol) at −35° C. for 0.2 h. The mixture was stirred at −35° C. for 1 h, then poured into ice HCl (0.5N, 10 mL) and extracted with EA (20 mL*2). The combined organic layers were washed with NaHCO$_3$ (10 mL) and brine (20 mL). After filtration, the filtrate was concentrated to give the title compound, which was used in the next step without further purification.

Step E tert-butyl-6-(3-(tert-butoxy)-3-oxopropyl)-5-methyl-3,4-dihydroisoquinoline-2(1H)-carboxylate To a solution of tert-butyl 5-methyl-6-((((trifluoromethyl)sulfonyl)oxy)-3,4-dihydroisoquinoline-2(1H)-carboxylate (1.8 g, 4.55 mmol), potassium 3-trifluoroboratopropionate tert-butyl ester (3.22 g, 13.66 mmol), Na$_2$CO$_3$ (1.45 g, 13.66 mmol) in water (2 mL) and toluene (20 mL) was added G2-Ru-Phos (0.354 g, 0.455 mmol). The mixture was stirred at 100° C. for 10 h, then the solvent was removed under reduced pressure. The resulting mixture was purified by prep-HPLC (TFA) to afford the title compound.

Step F methyl 3-(5-methyl-1,2,3,4-tetrahydroisoquinolin-6-yl)propanoate

The mixture of tert-butyl 6-(3-(tert-butoxy)-3-oxopropyl)-5-methyl-3,4-dihydroisoquinoline-2(1H)-carboxylate (1.2 g, 3.2 mmol) in HCl-MeOH (4M, 15 mL, 60 mmol) was stirred at 65° C. for 10 h, then the solvent was removed under reduced pressure to give the title compound, which was used in the next step without further purification. MS (EST) m/z: 254.1 [M+H+]

Example 1

3-(2-(2-chloro-5-cyclobutoxy-4-methoxyphenyl)-1,2,3,4-tetrahydroisoquinolin-6-yl)-propanoic acid

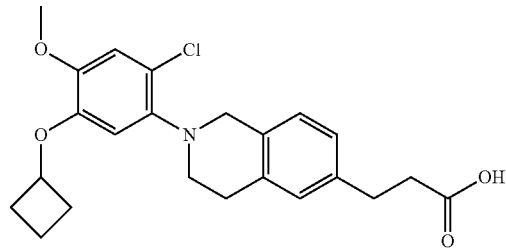 [SMILES: COc1cc(Cl)c(N2CCc3cc(CCC(=O)O)ccc3C2)cc1OC1CCC1]

Step A. Methyl-3-(2-(2-chloro-5-cyclobutoxy-4-methoxyphenyl)-1,2,3,4-tetra-hydro-isoquinolin-6-yl)propanoate Methyl-3-(1,2,3,4-tetrahydro-isoquinolin-6-yl)-propanoate (100 mg, 0.456 mmol), 1-bromo-2-chloro-5-cyclo-butoxy-4-methoxybenzene (Intermediate 20,146 mg, 0.502 mmol), Cs$_2$CO$_3$ (297 mg, 0.912 mmol), Xantphos (53 mg, 0.092 mmol) and Pd$_2$(dba)$_3$ (42 mg, 0.046 mmol) in 1,4-dioxane (5 mL) were stirred at 90° C. for 18 h under a N$_2$ atmosphere. The mixture was diluted with water (15 mL), extracted with EtOAc (3×20 mL). The organic layer was dried over Na$_2$SO$_4$, filtered and concentrated in vacuo. The residue was purified via silica gel PTLC (PE:EtOAc=5:1) to afford the title compound. m/z 430.1 [M+1]$^+$.

Step-B. 3-(2-(2-chloro-5-cyclobutoxy-4-methoxyphenyl)-1,2,3,4-tetrahydro-isoquinolin-6-yl)propanoic acid To a solution of methyl 3-(2-(2-chloro-5-cyclobutoxy-4-methoxyphenyl)-1,2,3,4-tetrahydroisoquinolin-6-yl)propanoate (60 mg, 0.140 mmol) in THF (4 mL) and water (2 mL), was added LiOH hydrate (12 mg, 0.286 mmol). Then the mixture was stirred at ~17° C. for 2 h. After acidification to pH 2-3, the solvent was removed in vacuo. The residue was purified by reverse phase HPLC on a GILSON 281 instrument fitted with a Phenomenex Synergi C18 column (250×21.2 mm×4 μm) using water (0.2% Formic acid) and CH$_3$CN as eluents (Mobile phase A: water (0.2% Formic acid), Mobile phase B: CH$_3$CN. Detector wavelength: 220 nm) followed by concentration (below 50° C.) in vacuo to give the title compound. $^1$H NMR (400 MHz, CDCl$_3$) δ 6.98-7.08 (m, 3H), 6.91 (s, 1H), 6.56 (s, 1H), 4.55 (q, J=7.14 Hz, 1H), 4.18 (s, 2H), 3.94 (s, 3H). 3.33 (t, J=7.48 Hz. 2H), 2.90-2.99 m, 4H), 2.68 (t, J=7.63 Hz, 2H), 2.28-2.38 (m, 2H), 2.18-2.26 (m, 2H), 1.82-1.84 (m, 1H), 1.60-1.68 (m, 1H); m/z=416.1 [M+1]$^+$.

Example 2

3-(2-(3-(difluoromethyl)-2-fluoro-5-(pyridin-2-yloxy)phenyl)-1,2,3,4-tetrahydro-isoquinolin-6-yl)propanoic acid

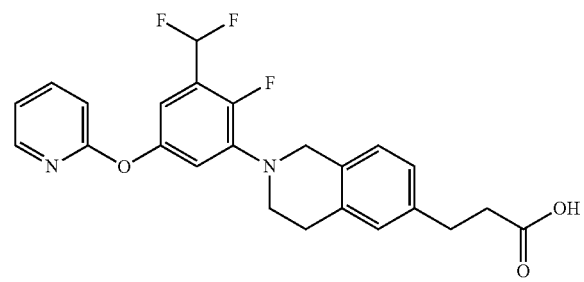 [SMILES: O=C(O)CCc1ccc2c(c1)CCN(c1cc(Oc3ccccn3)cc(C(F)F)c1F)C2]

Step A. Methyl 3-(2-(3-(difluoromethyl)-2-fluoro-5-(pyridin-2-yloxy)phenyl)-1,2,3,4-tetrahydroisoquinolin-6-yl)propanoate To a stirred solution of methyl 3-(1,2,3,4-tetrahydroisoquinolin-6-yl)propanoate (100 mg, 0.456 mmol) in 1,4-dioxane (3 mL) was added 2-(3-bromo-5-(difluoromethyl)-4-fluorophenoxy)pyridine (Intermediate 21, 160 mg, 0.502 mmol), 2-di-tert-butylphosphino-2',4',6'-triisopropylbiphenyl (39 mg, 0.092 mmol) and Cs$_2$CO$_3$ (223 mg, 0.684 mmol). The mixture was degassed with N$_2$, and Pd$_2$(dba)$_3$ (42 mg, 0.046 mmol) was added. The mixture was heated to 100° C. and stirred for 18 h. The reaction mixture was diluted with EtOAc (5 mL) and filtered. The filtrate was concentrated in vacuo to afford the crude title compound, which was used in the next step without further purification.

Step B. 3-(2-(3-(difluoromethyl)-2-fluoro-5-(pyridin-2-yloxy)phenyl)-1,2,3,4-tetrahydroisoquinolin-6-yl)propanoic acid To a stirred solution of methyl 3-(2-(3-(difluoromethyl)-2-fluoro-5-(pyridin-2-yloxy)phenyl)-1,2,3,4-tetrahydroisoquinolin-6-yl) propanoate (80 mg, crude) in THF (5 ml) was added LiOH H$_2$O (40 mg, 0.953 mmol) and water (2.5 mL). The mixture was stirred for 5 h rt, and HCl (3N) was added to adjust the mixture to pH=2-3. Then the mixture was diluted with EtOAc (20 mL). The organic layer was separated, dried over Na$_2$SO$_4$ and concentrated in vacuo. The residue was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN. Detector wavelength: 220 nm) followed by concentration (below 50° C.) in vacuo to afford the title compound. $^1$H-NMR (400 MHz, CDCl$_3$) δ 8.19 (d, J=7.6 Hz, 1H), 7.72 (t, J=6.8 Hz, 1H), 7.02-6.91 (m, 4H), 6.89-6.76 (m, 1H), 4.28 (m, 2H), 3.46 (t, J=5.6 Hz, 2H), 2.97-2.90 (m, 2H), 2.69-2.65 (m, 2H): m/z=443.0 [M+1]$^+$.

Example 3

3-(2-(2,3-difluoro-5-(3-methoxycyclobutoxy)phenyl)-1,2,3,4-tetrahydroisoquinolin-6-yl)-propanoic acid (trans)

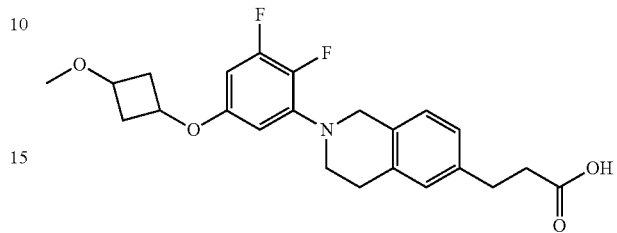

Step A. Ethyl 3-(2-(2,3-difluoro-5-(3-methoxycyclobutoxy)phenyl)-1,2,3,4-tetrahydroisoquinolin-6-yl)propanoate (trans)

To a solution of ethyl 3-(1,2,3,4-tetra-hydroisoquinolin-6-yl)propanoate (84 mg, 0.359 mmol) in 1,4-dioxane (5 mL) was added 2,3-difluoro-5-(3-methoxycyclobutoxy)phenyl trifluoromethanesulfonate (Intermediate 4, 130 mg, 0.359 mmol), Cs$_2$CO$_3$ (351 mg, 1.077 mmol), XPhos (35 mg, 0.073 mmol) and Pd$_2$(dba)$_3$ (33 mg, 0.036 mmol). The mixture was stirred at 90° C. for 15 h under a N$_2$ atmosphere. The reaction mixture was concentrated in vacuo, and the residue was diluted with water (20 mL) and extracted with EtOAc (3×30 mL). The organic layer was dried over Na$_2$SO$_4$, filtered and concentrated in vacuo. The residue was purified by silica gel chromatography (PE:EtOAc=20:1 to 5:1) to afford the title compound. m/z 446.2[M+1]$^+$.

Step-B—3-(2-(2,3-difluoro-5-(3-methoxycyclobutoxy)phenyl)-1,2,3,4-tetrahydro-isoquinolin-6-yl) propanoic acid (trans)

To a solution of ethyl 3-(2-(2,3-difluoro-5-(3-methoxycyclobutoxy)phenyl)-1,2,3,4-tetrahydroisoquinolin-6-yl)propanoate (20 mg, 0.045 mmol) in THF (2 mL), MeOH (2 mL) and Water (1 mL) was added LiOH hydrate (4 mg, 0.095 mmol). The mixture was stirred at rt for 2 h. After acidification with 1N HCl to pH=2, the solvent was removed in vacuo. The residue was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN. Detector wavelength: 220 nm) followed by concentration (below 50° C.) in vacuo to give the title compound. $^1$H NMR (400 MHz, CDCl$_3$) δ7.05 (s, 2H), 7.00 (s, 1H), 6.12-6.22 (m, 2H), 4.63-4.70 (m, 1H). 4.29 (s, 2H), 4.08-4.14 (m, 1H), 3.48 (t, J=5.67 Hz, 2H). 3.28 (s, 3H), 2.87-2.97 (m, 4H), 2.64-2.72 (m, 2H), 2.32-2.39 (m, 4H): m/z=418.1 [M+1]$^+$.

Example 4

3-(2-(2-fluoro-4-methoxy-5-((5-methylthiazol-2-yl)oxy)phenyl)-1,2,3,4-tetrahydroisoquinolin-6-yl)propanoic acid

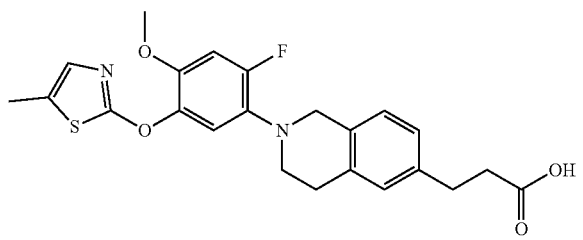 [SMILES: COc1cc(F)c(N2CCc3cc(CCC(=O)O)ccc3C2)cc1Oc1ncc(C)s1]

Step A. Methyl 3-(2-(2-fluoro-4-methoxy-5-((5-methylthiazol-2-yl)oxy)phenyl)-1,2,3,4-tetrahydroisoquinolin-6-yl)propanoate To a solution of methyl 3-(1,2,3,4-tetrahydroisoquinolin-6-yl)propanoate (100 mg, 0.456 mmol) in dioxane (4.00 mL) was added 2-(5-bromo-4-fluoro-2-methoxyphenoxy)-5-methylthiazole (Intermediate 10, 214 mg, 0.673 mmol), $Cs_2CO_3$ (446 mg, 1.368 mmol), 2-di-tert-butylphosphino-2′,4′,6′-triisopropylbiphenyl (40 mg, 0.094 mmol) and $Pd_2(dba)_3$ (42 mg. 0.046 mmol). Ten the reaction mixture was placed under nitrogen and stirred at 100° C. for 24 h. the mixture was concentrated in vacuo, and water (30 mL) was added to the residue. The mixture was extracted with EtOAc (30 mL×2), and the organic layer was concentrated in vacuo. The resulting crude product was purified by silica gel PTLC (PE/EtOAc=5:1) to give the title compound.

Step B. 3-(2-(2-fluoro-4-methoxy-5-((5-methylthiazol-2-yl)oxy)phenyl)-1,2,3,4-tetrahydroisoquinolin-6-yl)propanoic acid To a solution of methyl 3-(2-(2-fluoro-4-methoxy-5-((5-methylthiazol-2-yl)oxy)phenyl)-1,2,3,4-tetrahydroisoquinolin-6-yl) propanoate (30 mg, 0.066 mmol) in THF (1 mL), MeOH (1 mL) and water (0.5 mL) was added LiOH hydrate (14 mg, 0.334 mmol). Then the reaction mixture was stirred at rt for 2 h. The mixture was acidified with HCl (0.25 mL, 6 N) and concentrated in vacuo. The crude product as purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid). Mobile phase B: $CH_3CN$, Detector wavelength: 220 nm) followed by concentration in vacuo to give the title compound. $^1H$ NMR (400 MHz, $CDCl_3$) δ 6.94-7.04 (m, 4H), 6.78-6.86 (m, 2H), 4.19 (s, 2H) 3.79 (s, 3H), 3.35 (t, J=5.48 Hz, 2H), 2.88-3.00 (m, 4H), 2.62-2.70 (m, 2H), 2.33 (s, 3H); m/z=443.1 $[M+1]^+$

Example 5

3-(2-(6-cyclobutoxy-3-fluoropyridin-2-yl)-1,2,3,4-tetrahydro-isoquinolin-6-yl)-propanoic acid

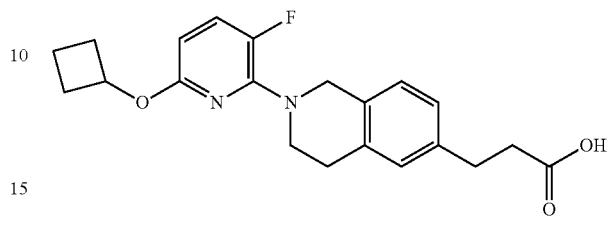

Step A. (methyl 3-(2-(6-cyclobutoxy-3-fluoropyridin-2-yl)-1,2,3,4-tetrahydroiso-quinolin-6-yl)propanoate To a solution of 2-bromo-6-cyclobutoxy-3-fluoropyridine (Intermediate 2, 150 mg, 0.61 mmol) and ethyl 3-(1,2,3,4-tetrahydroisoquinolin-6-yl)propanoate (Intermediate 7, 142 mg, 0.61 mmol) in 1,4-dioxane (10 ml) was added $Cs_2CO_3$ (397 mg, 1.22 mmol) and XPhos precatalyst (45.0 mg, 0.06 mmol), and the mixture was stirred at 90° C. for 18 h under a $N_2$ atmosphere. The mixture was diluted with water (10 mL) and extracted with EtOAc (10 mL). The organic layer was collected, washed with brine (10 mL), dried over anhydrous $Na_2SO_4$. filtered, and concentrated under in vacuo. The residue was purified by silica gel column chromatography (PE:EtOAc from 10:1 to 1:1) to afford the title compound.

Step B. 3-(2-(6-cyclobutoxy-3-fluoropyridin-2-yl)-1,2,3,4-tetrahydroisoquinolin-6-yl)propanoic acid A mixture of ethyl 3-(2-(6-cyclobutoxy-3-fluoropyridin-2-yl)-1,2,3,4-tetrahydroisoquinolin-6-yl)propanoate (80 mg, 0.20 mmol) and LiOH hydrate (20 mg, 0.47 mmol) in THF (4 mL) and water (2 mL) was stirred at rt for 1 h. The mixture was acidified with 1N HCl (10 mL) to pH=~6, and extracted with EtOAc (20 mL). The organic layer was separated, washed with brine (10 mL), dried over anhydrous $Na_2SO_4$, filtered, and concentrated in vacuo. The crude product was further purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm), followed by concentration (below 50° C.) in vacuo to afford the title compound. $^1H$ NMR (400 MHz, $CD_3OD$) δ 7.16 (d, J=3.6 Hz, 1H), 7.13 (s, 1H), 7.08 (d, J=8.0 Hz, 1H), 7.03 (d, J=8.0 Hz, 1H), 6.01 (dd, J=1.6, 8.4 Hz, 1H), 5.02-4.95 (m, 1H), 4.61 (s, 2H), 3.78 (t, J=6.0 hZ, 2H), 2.96-2.92 (m, 4H), 2.69-2.66 (m, 2H), 2.42-2.40 (m, 2H), 2.18-2.14 (m, 2H), 1.82-1.81 (m, 1H), 1.70-1.69 (m, 1H): m/z=371.0 $[M+1]^+$.

Example 6

3-(2-(5-cyclobutoxy-2-fluorophenyl)-1-methyl-1,2,3,4-tetrahydroisoquinolin-6-yl)-propanoic acid

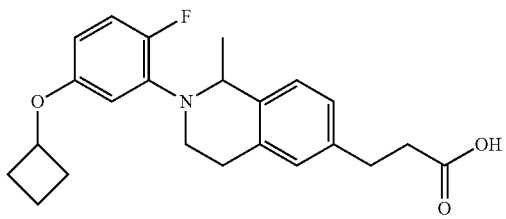 [SMILES: CC1c2ccc(CCC(=O)O)cc2CCN1c1cc(OC2CCC2)ccc1F]

Step A. methyl 3-(2-(5-cyclobutoxy-2-fluoro-4-nitrophenyl)-1-methyl-1,2,3,4-tetra-hydroisoquinolin-6-yl)propanoate To a solution of methyl 3-(1-methyl-1,2,3,4-tetrahydroisoquinolin-6-yl)propanoate (Intermediate 45, 250 mg, 1.07 mmol) was added 1-cyclobutoxy-4,5-difluoro-2-nitrobenzene (Intermediate 3 Step B, 319 mg, 1.39 mmol) and $Cs_2CO_3$ (698 mg, 2.14 mmol). The mixture was heated at 150° C. and stirred for 3 h. Then the reaction mixture was cooled to rt and EtOAc (20 mL) was added. The mixture was washed with brine, dried over $Na_2SO_4$ and evaporated in vacuo. The residue was purified by silica gel PTLC (PE: EtOAc=4:1) to afford the title compound.

Step B. Methyl 3-(2-(4-amino-5-cyclobutoxy-2-fluorophenyl)-1-methyl-1,2,3,4-tetrahydroiso-quinolin-6-yl)propanoate To a solution of methyl 3-(2-(5-cyclobutoxy-2-fluoro-4-nitrophenyl)-1-methyl-1,2,3,4-tetrahydroisoquinolin-6-yl)propanoate (180 mg, 0.41 mmol) in MeOH (10 ml) was added Fe powder (114 mg, 2.03 mmol), $NH_4Cl$ (109 mg, 2.03 mmol) and water (1 mL). The mixture was heated to reflux and stirred overnight. The mixture was filtered, and the filtrate was concentrated in vacuo to afford the title compound, which was taken to next step without further purification.

Step C. methyl 3-(2-(5-cyclobutoxy-2-fluorophenyl)-1-methyl-1,2,3,4-tetrahydroiso-quinolin-6-yl)propanoate To a solution of methyl 3-(2-(4-amino-5-cyclobutoxy-2-fluorophenyl)-1-methyl-1,2,3,4-tetrahydroisoquinolin-6-yl)propanoate (150 mg, 0.36 mmol) in dry THF (5 ml) was added isopentyl nitrite (128 mg, 1.09 mmol). The mixture was heated to reflux for 3 h. The reaction mixture was concentrated in vacuo to give the crude title compound, which was taken to next step without further purification.

Step D. 3-(2-(5-cyclobutoxy-2-fluorophenyl)-1-methyl-1,2,3,4-tetrahydroisoquino-lin-6-yl)propanoic acid To a solution of methyl 3-(2-(5-cyclobutoxy-2-fluorophenyl)-1-methyl-1,2,3,4-tetrahydroisoquinolin-6-yl)propanoate (150 mg, 0.38 mmol) in THF (3 ml) was added $LiOH \cdot H_2O$ (38 mg, 0.91 mmol) and water (1.5 ml). The final mixture was stirred overnight at rt. Then HCl (3 N aqueous solution) was added to adjust the pH to 2-3. The organic layer was separated, dried over $Na_2SO_4$ and concentrated in vacuo. The residue was purified by reverse phase HPLC on a GILSON 281 instrument fitted with a Phenomenex Synergi C18 (250×21.2 mm×4 µm) using water (0.2% Formic acid) and $CH_3CN$ as eluents (Mobile phase A: water (0.2% Formic acid), Mobile phase B: $CH_3CN$, Detector wavelength: 220 nm) to afford the title compound. m/z 384.1 $[M+H]^+$. $^1$H-NMR (400 MHz, $CDCl_3$) δ: 7.06 (m, 2H), 6.96 (s, 1H), 6.89 (m, 1H), 4.75 (m, 1H), 4.52 (m, 1H), 3.47 (m, 1H), 2.92-3.12 (m, 3H), 2.66-2.75 (m, 3H), 2.33 (m, 2H), 2.17-2.25 (m, 2H), 1.84 (m, 1H), 1.81 (m, 1H), 1.34 (d, J=6.8 Hz, 3H).

Example 7

3-(2-(2-fluoro-5-(trifluoromethoxy)phenyl)-1,2,3,4-tetrahydroisoquinolin-6-yl)butanoic acid

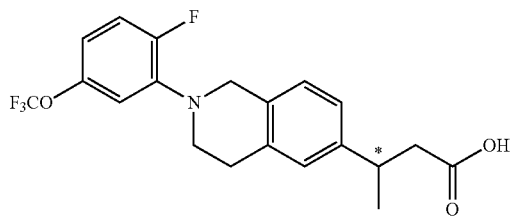 [SMILES: CC(CC(=O)O)c1ccc2c(c1)CCN(c1cc(OC(F)(F)F)ccc1F)C2]

Step A. ethyl 3-(1,2,3,4-tetrahydroisoquinolin-6-yl)butanoate hydrochloride (slow eluting)

To a solution of tert-butyl 6-(4-ethoxy-4-oxobutan-2-yl)-3,4-dihydroisoquinoline-2(H)-carboxylate (92 mg, 0.265 mmol) in MeOH (3 ml) was added 4 M HCl (1 mL, 4.0 mmol) and stirred 15° C. for 1 h. The mixture was concentrated in vacuo, to give the crude product which was used directly in the next step without further purification. m/z 247.1 $[M+H]^+$.

Step B. ethyl 3-(2-(2-fluoro-5-(trifluoromethoxy)phenyl)-1,2,3,4-tetrahydroisoquinolin-6-yl)-Butanoate To a solution of ethyl 3-(1,2,3,4-tetrahydroisoquinolin-6-yl)butanoate hydrochloride from the previous step (65 mg, 0.255 mmol) and 2-bromo-1-fluoro-4-(trifluoromethoxy)benzene (66 mg, 0.255 mmol) in dioxane (3 mL) was added XANTPHOS (25 mg, 0.043 mmol) and $Pd_2(dba)_3$ (49 mg, 0.054 mmol), followed by the addition of $Cs_2CO_3$ (138 mg, 0.423 mmol). The reaction mixture was stirred at 100° C. under a $N_2$ atmosphere for 12 h. The reaction mixture was partitioned between EtOAc (50 mL) and water (50 mL), and the organic layer was washed with brine (50 mL), dried over $Na_2SO_4$, filtered and concentrated in vacuo. The crude title compound was used in the next step without further purification. m/z 426.1 $[M+H]^+$.

Step C. 3-(2-(2-fluoro-5-(trifluoromethoxy)phenyl)-1,2,3,4-tetrahydroisoquinolin-6-yl)butanoic acid To a solution of ethyl 3-(2-(2-fluoro-5-(trifluoromethoxy)phenyl)-1,2,3,4-tetrahydroisoquinolin-6-yl)butanoate (20 mg, 0.047 mmol) in THF-MeOH—$H_2O$ (2:2:1 2.5 mL) was added LiOH hydrate (2 mg, 0.048 mmol) at 25° C. The reaction mixture was stirred at 25° C. for 2 h. The reaction mixture was concentrated in vacuo. and the residue was acidified with diluted 1 M HCl until pH <5. The reaction mixture was partitioned between EtOAc (20 mL) and water (20 mL), and the separated organic layer was washed with brine (20 mL). The organic layer was concentrated in vacuo. The crude product was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm), followed by concentration (below 50° C.) in vacuo to give the title compound. $^1HNMR$ (400 MHz, $CDCl_3$) δ:7.00-7.09 (m, 4H) 6.83 (d, J=6.65 Hz, 1H) 6.77 (d, J=8.22 Hz, 1H) 4.28 (s, 2H) 3.46 (t, J=5.67 Hz, 2H) 3.21-3.30 (m, 1H) 3.00 (t, J=5.48 Hz, 2H) 2.56-2.72 (m, 2H) 1.32 (d, J=6.65 Hz, 3H). MS m/z 397.1 $[M+H]^+$.

Example 8

3-(2-(2-fluoro-5-(trifluoromethoxy)phenyl)-1,2,3,4-tetrahydro-isoquinolin-6-yl)-butanoic acid

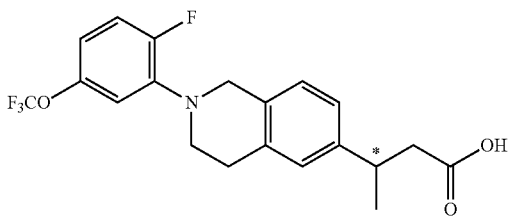 [SMILES: CC(CC(=O)O)c1ccc2c(c1)CCN(c1cc(OC(F)(F)F)ccc1F)C2]

Step A-ethyl 3-(1,2,3,4-tetrahydroisoquinolin-6-yl)butanoate hydrochloride (slow eluting)

To a solution of tert-butyl 6-(4-ethoxy-4-oxobutan-2-yl)-3,4-dihydro isoquinoline-2(1H)-carboxylate (92 mg, 0.265 mmol, slower eluting) in MeOH (3 mL) was added 4M HCl (1 mL, 4.00 mmol) and stirred 15° C. for 1 h. The mixture was evaporated in vacuo, to give the crude title compound which was used in the next step without further purification. m/z 247.1 $[M+H]^+$.

Step B. Ethyl-3-(2-(2-fluoro-5-(trifluoromethoxy)phenyl)-1,2,3,4-tetrahydro-isoquino-lin-6-yl)butanoate To a solution of ethyl 3-(1,2,3,4-tetrahydroisoquinolin-6-yl)butanoate hydrochloride (65 mg, 0.229 mmol) and 2-bromo-1-fluoro-4-(trifluoro-methoxy)benzene (71 mg, 0.274 mmol) in dioxane (3 ml) was added XANTPHOS (3 mg, 0.005 mmol), $Pd_2(dba)_3$ (49 mg, 0.054 mmol) and $Cs_2CO_3$ (149 mg, 0.458 mmol). The the mixture stirred at 100° C. under $N_2$ atmosphere for 12 h. The reaction mixture was partitioned between EtOAc (50 mL) and water (50 mL), and the organic layer was washed with brine (50 mL), dried over $Na_2SO_4$, filtered and concentrated in vacuo. The crude title compound was used in the next step without further purification. m/z 426.1 $[M+H]^+$.

Step C. 3-(2-(2-fluoro-5-(trifluoromethoxy)phenyl)-1,2,3,4-tetrahydroisoquinolin-6-yl)butanoic acid (Peak 2)

To a solution of crude ethyl 3-(2-(2-fluoro-romethoxy)-phenyl)-1,2,3,4-tetrahydroisoquinolin-6-yl)butanoate (20 mg, 0.047 mmol) in THF-MeOH—$H_2O$ (2:2:1, 2.5 mL) was added LiOH hydrate (2 mg, 0.048 mmol) at 25° C., and the mixture was stirred at 25° C. for 2 h. The mixture was concentrated in vacuo. and the resulting residue was acidified with diluted 1 M HCl until pH <5. The reaction mixture was partitioned between EtOAc (20 mL) and water (20 mL), and the organic layer was washed with brine (20 mL). The organic layer was concentrated in vacuo, and the crude product was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm) followed by concentration (below 50° C.) in vacuo to obtain the title compound. $^1HNMR$ (400 MHz, ppm) δ: 7.06 (s, 2H) 7.00-7.05 (m, 2H) 6.83 (d, J=7.04 Hz, 1H) 6.77 (d, J=8.61 Hz, 1H) 4.27 (s, 2H) 3.45 (t, J=5.67 Hz, 2H) 3.25 (br. s., 1H) 2.99 (t, J=5.28 Hz, 2H) 2.67 (br. s., 2H) 1.32 (d, J=5.87 Hz, 3H); m-z 397.1 $[M+H]^+$.

The examples in Table 1 were prepared from the appropriate starting materials described previously or commercially available starting materials available using procedures described in Examples 1-8.

TABLE 1

| Example | Structure | Name | [M + H]+ |
|---|---|---|---|
| 9 | 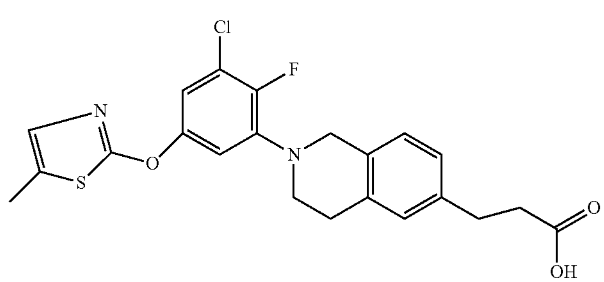 [SMILES: Cc1cnc(Oc2cc(Cl)c(F)c(N3CCc4cc(CCC(=O)O)ccc4C3)c2)s1] | 3-(2-{3-chloro-2-fluoro-5-[(5-ethyl-1,3-thiazol-2-yl)oxy]phenyl}-1,2,3,4-tetrahydroisoquinolin-6-yl)propanoic acid | 447.0 |

TABLE 1-continued

| Example | Structure | Name | [M + H]+ |
| --- | --- | --- | --- |
| 10 | 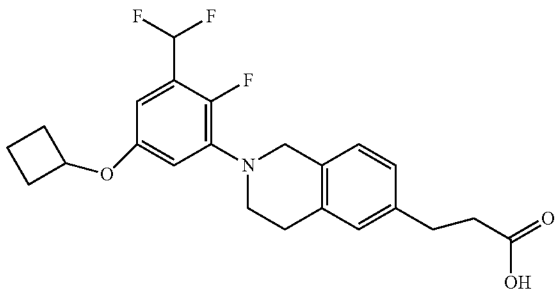 [SMILES: O=C(O)CCc1ccc2c(c1)CCN(c1cc(OC3CCC3)cc(C(F)F)c1F)C2] | 3-{2-[5-(cyclobutyloxy)-3-(difluoromethyl)-2-fluorophenyl]-1,2,3,4-tetrahydroisoquinolin-6-yl}-propanoic acid | 420.1 |
| 11 | 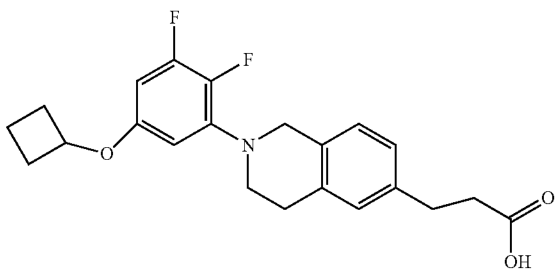 [SMILES: O=C(O)CCc1ccc2c(c1)CCN(c1cc(OC3CCC3)cc(F)c1F)C2] | 3-{2-[5-(cyclobutyloxy)-2,3-difluorophenyl]-1,2,3,4-tetrahydro-isoquinolin-6-yl}propanoic acid | 388.1 |
| 12 | 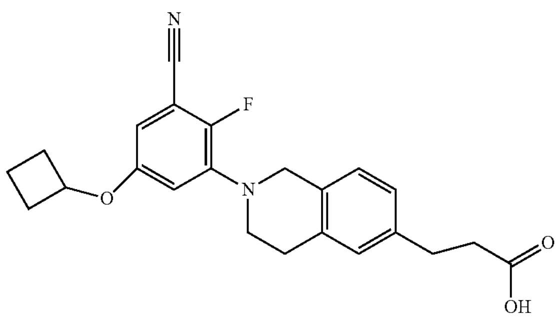 [SMILES: N#Cc1cc(OC2CCC2)cc(N2CCc3cc(CCC(=O)O)ccc3C2)c1F] | 3-{2-[3-cyano-5-(cyclobutyloxy)-2-fluorophenyl]-1,2,3,4-tetra-hydroisoquinolin-6-yl}propanoic acid | 395.1 |
| 13 | 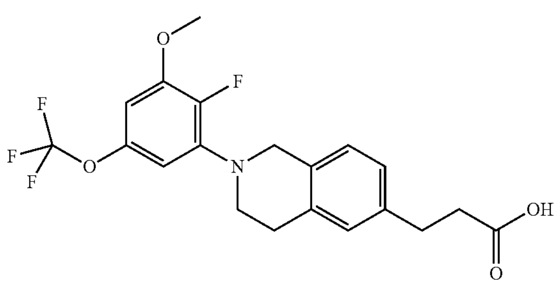 [SMILES: COc1cc(OC(F)(F)F)cc(N2CCc3cc(CCC(=O)O)ccc3C2)c1F] | 3-{2-[2-fluoro-3-methoxy-5-(trifluoromethoxy)phenyl]-1,2,3,4-tetrahydroisoquinolin-6-yl}-propanoic acid | 413.1 |
| 14 | 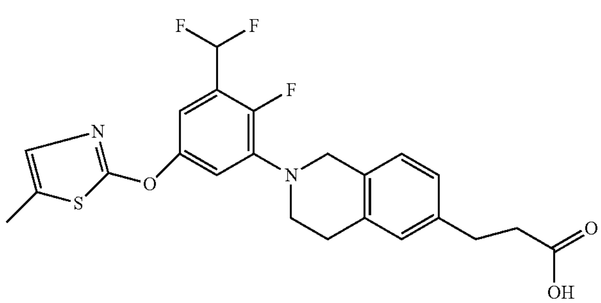 [SMILES: Cc1cnc(Oc2cc(C(F)F)c(F)c(N3CCc4cc(CCC(=O)O)ccc4C3)c2)s1] | 3-(2-{3-(difluoromethyl)-2-fluoro-5-[(5-methyl-1,3-thiazol-2-yl)oxy]phenyl}-1,2,3,4-tetrahydro-isoquinolin-6-yl)propanoic acid | 463.1 |

TABLE 1-continued

| Example | Structure | Name | [M + H]+ |
|---|---|---|---|
| 15 | 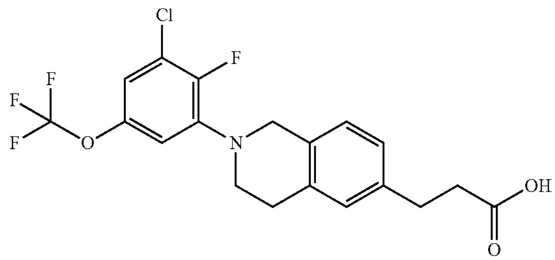 [SMILES: O=C(O)CCc1ccc2c(c1)CCN(c1cc(OC(F)(F)F)cc(Cl)c1F)C2] | 3-{2-[3-chloro-2-fluoro-5-(trifluoromethoxy)phenyl]-1,2,3,4-tetrahydroisoquinolin-6-yl}-propanoic acid | 418.0 |
| 16 | 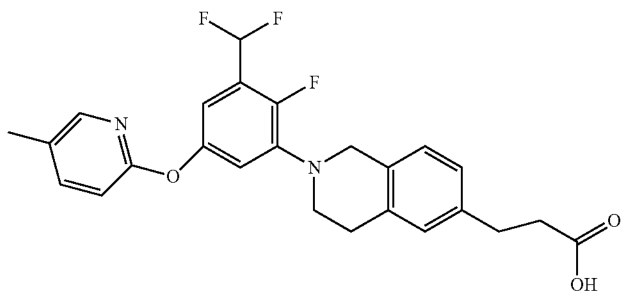 [SMILES: Cc1ccc(Oc2cc(C(F)F)c(F)c(N3CCc4cc(CCC(=O)O)ccc4C3)c2)nc1] | 3-(2-{3-(difluoromethyl)-2-fluoro-5-[(5-methylpyridin-2-yl)oxy]phenyl}-1,2,3,4-tetrahydroisoquinolin-6-yl)propanoic acid | 457.1 |
| 17 | 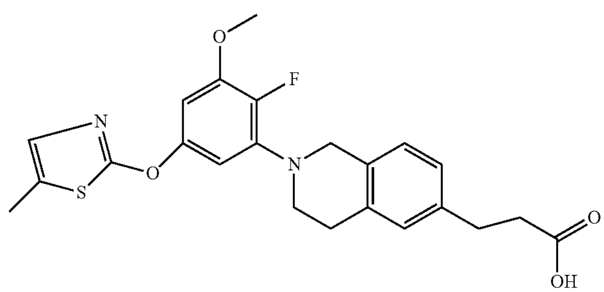 [SMILES: COc1cc(Oc2ncc(C)s2)cc(N2CCc3cc(CCC(=O)O)ccc3C2)c1F] | 3-(2-{2-fluoro-3-methoxy-5-[(5-methyl-1,3-thiazol-2-yl)oxy]phenyl}-1,2,3,4-tetrahydroisoquinolin-6-yl)propanoic acid | 443.2 |
| 18 | 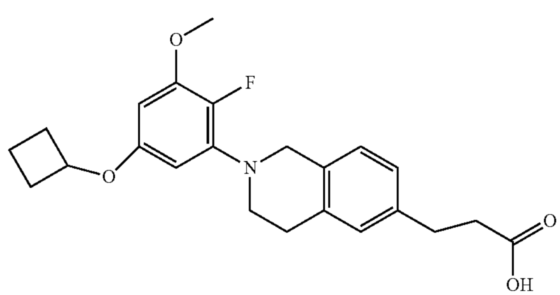 [SMILES: COc1cc(OC2CCC2)cc(N2CCc3cc(CCC(=O)O)ccc3C2)c1F] | 3-{2-[5-(cyclobutyloxy)-2-fluoro-3-methoxyphenyl]-1,2,3,4-tetrahydroisoquinolin-6-yl}propanoic acid | 400.1 |
| 19 | 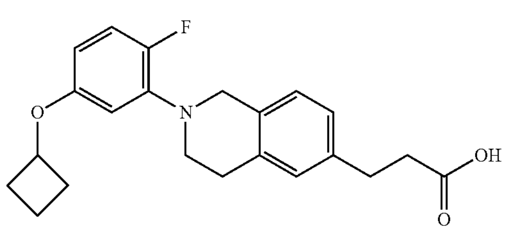 [SMILES: O=C(O)CCc1ccc2c(c1)CCN(c1cc(OC3CCC3)ccc1F)C2] | 3-{2-[5-(cyclobutyloxy)-2-fluoro phenyl]-1,2,3,4-tetrahydroisoquinolin-6-yl}propanoic acid | 370.1 |

TABLE 1-continued

| Example | Name | [M + H]+ |
|---|---|---|
| 20 | 3-(2-{2,3-difluoro-5-[(trans-3-methoxycyclobutyl)oxy]phenyl}-1,2,3,4-tetrahydroisoquinolin-6-yl)propanoic acid | 418.1 |
| 21 | 3-(2-{2-fluoro-4-methoxy-5-[(5-methyl-1,3-thiazol-2-yl)oxy]phenyl}-1,2,3,4-tetrahydroiso-quinolin-6-yl)propanoic acid | 443.1 |
| 22 | 3-{2-[4-chloro-3-methyl-1-(4-methylphenyl)-1H-pyrazol-5-yl]-1,2,3,4-tetrahydroisoquinolin-6-yl}propanoic acid | 410.1 |
| 23 | 3-{2-[5-(cyclobutylmethyl)-2-fluorophenyl]-5-fluoro-1,2,3,4-tetrahydroisoquinolin-6-yl}propanoic acid | 386.2 |
| 24 | 3-{2-[2-chloro-5-(cyclobutyloxy)-4-methoxyphenyl]-1,2,3,4-tetrahydroisoquinolin-6-yl}propanoic acid | 416.1 |
| 25 | 3-{2-[6-(cyclobutyloxy)-3-fluoro pyridin-2-yl]-1,2,3,4-tetrahydroiso-quinolin-6-yl}propanoic acid | 371.0 |

TABLE 1-continued

| Example | Structure | Name | [M + H]+ |
|---|---|---|---|
| 26 | 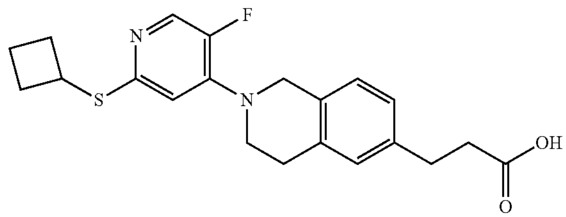 [SMILES: O=C(O)CCc1ccc2c(c1)CCN(c1cc(SC3CCC3)ncc1F)C2] | 3-{2-[2-(cyclobutylsulfanyl)-5-fluoropyridin-4-yl]-1,2,3,4-tetrahydro-isoquinolin-6-yl}propanoic acid | 387.1 |
| 27 | 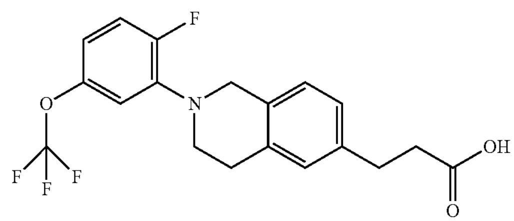 [SMILES: O=C(O)CCc1ccc2c(c1)CCN(c1cc(OC(F)(F)F)ccc1F)C2] | 3-{2-[2-fluoro-5-(trifluoro-methoxy)phenyl]-1,2,3,4-tetrahydro-isoquinolin-6-yl}propanoic acid | 384.3 |
| 28 | 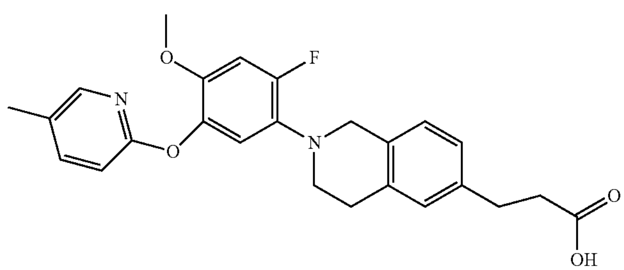 [SMILES: COc1cc(F)c(N2CCc3cc(CCC(=O)O)ccc3C2)cc1Oc1ccc(C)cn1] | 3-(2-{2-fluoro-4-methoxy-5-[(5-methylpyridin-2-yl)oxy]phenyl}-1,2,3,4-tetrahydroisoquinolin-6-yl)propanoic acid | 437.1 |
| 29 | 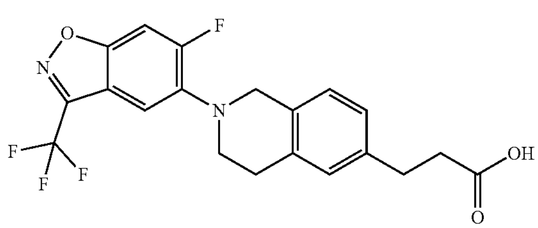 [SMILES: O=C(O)CCc1ccc2c(c1)CCN(c1cc3c(C(F)(F)F)noc3cc1F)C2] | 3-{2-[6-fluoro-3-(trifluoromethyl)-1,2-benzisoxazol-5-yl]-1,2,3,4-tetrahydroisoquinolin-6-yl}-propanoic acid | 409.0 |
| 30 | 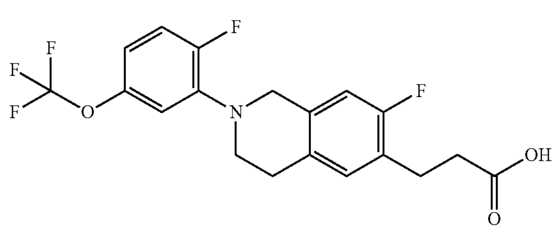 [SMILES: O=C(O)CCc1cc2c(cc1F)CN(c1cc(OC(F)(F)F)ccc1F)CC2] | 3-{7-fluoro-2-[2-fluoro-5-(trifluoromethoxy)phenyl]-1,2,3,4-tetrahydroisoquinolin-6-yl}-propanoic acid | 402.1 |
| 31 | 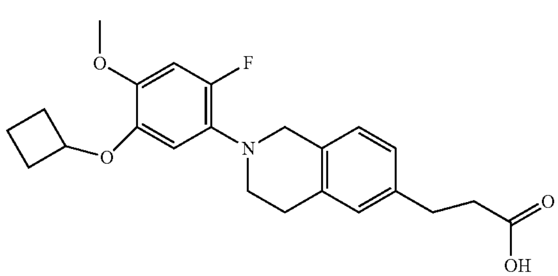 [SMILES: COc1cc(F)c(N2CCc3cc(CCC(=O)O)ccc3C2)cc1OC1CCC1] | 3-{2-[5-(cyclobutyloxy)-2-fluoro-4-methoxyphenyl]-1,2,3,4-tetrahydroisoquinolin-6-yl}-propanoic acid | 400.1 |

TABLE 1-continued

| Example | Structure | Name | [M + H]+ |
|---|---|---|---|
| 32 | 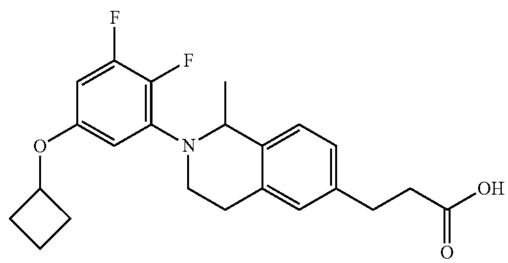 [SMILES: CC1c2ccc(CCC(=O)O)cc2CCN1c1cc(OC2CCC2)cc(F)c1F] | 3-{2-[5-(cyclobutyloxy)-2,3-difluorophenyl]-1-methyl-1,2,3,4-tetrahydroisoquinolin-6-yl}-propanoic acid | 402.1 |
| 33 | 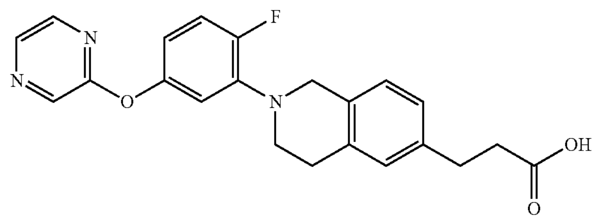 [SMILES: O=C(O)CCc1ccc2c(c1)CCN(c1cc(Oc3cnccn3)ccc1F)C2] | 3-{2-[2-fluoro-5-(pyrazin-2-yloxy)phenyl]-1,2,3,4-tetrahydroiso-quinolin-6-yl}propanoic acid | 394.1 |
| 34 | 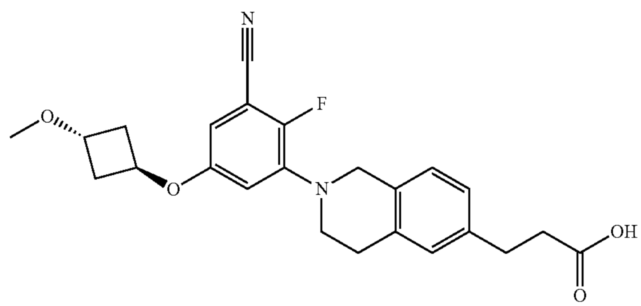 [SMILES: CO[C@H]1C[C@H](Oc2cc(C#N)c(F)c(N3CCc4cc(CCC(=O)O)ccc4C3)c2)C1] | 3-(2-{3-cyano-2-fluoro-5-[(trans-3-methoxycyclobutyl)oxy]phenyl}-1,2,3,4-tetrahydroisoquinolin-6-yl)propanoic acid | 425.4 |
| 35 | 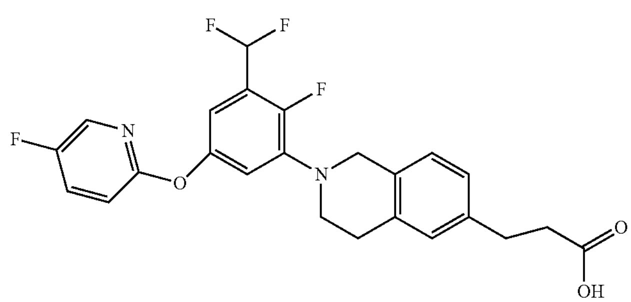 [SMILES: O=C(O)CCc1ccc2c(c1)CCN(c1cc(Oc3ccc(F)cn3)cc(C(F)F)c1F)C2] | 3-(2-{3-(difluoromethyl)-2-fluoro-5-[(5-fluoropyridin-2-yl)oxy]phenyl}-1,2,3,4-tetrahydroisoquinolin-6-yl)propanoic acid | 461.1 |
| 36 | 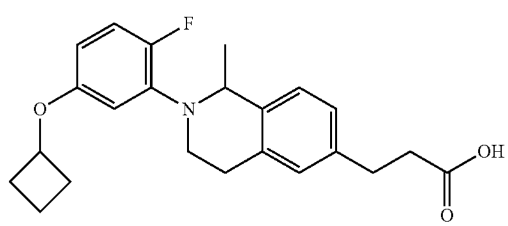 [SMILES: CC1c2ccc(CCC(=O)O)cc2CCN1c1cc(OC2CCC2)ccc1F] | 3-{2-[5-(cyclobutyloxy)-2-fluoro phenyl]-1-methyl-1,2,3,4-tetrahydroisoquinolin-6-yl}propanoic acid | 384.2 |
| 37 | 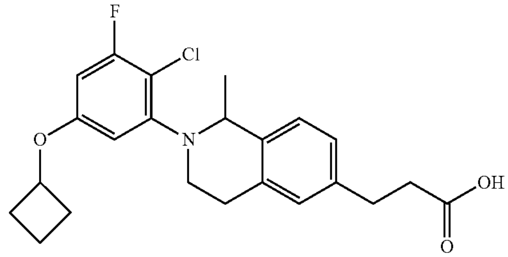 [SMILES: CC1c2ccc(CCC(=O)O)cc2CCN1c1cc(OC2CCC2)cc(F)c1Cl] | 3-{2-[2-chloro-5-(cyclobutyloxy)-3-fluorophenyl]-1-methyl-1,2,3,4-tetrahydroisoquinolin-6-yl}-propanoic acid | 418.1 |

TABLE 1-continued

| Example | Structure | Name | [M + H]+ |
| --- | --- | --- | --- |
| 38 | 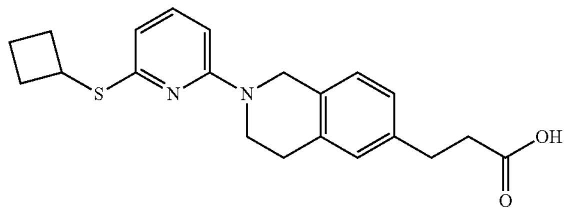 [SMILES: O=C(O)CCc1ccc2c(c1)CCN(c1cccc(SC3CCC3)n1)C2] | 3-{2-[6-(cyclobutylsulfanyl)pyridin-2-yl]-1,2,3,4-tetrahydroisoquinolin-6-yl}propanoic acid | 369.1 |
| 39 | 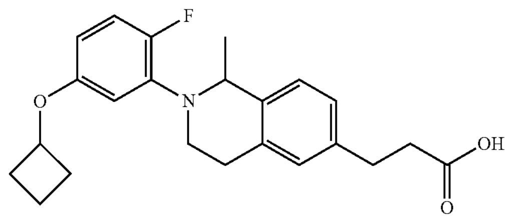 [SMILES: CC1c2ccc(CCC(=O)O)cc2CCN1c1cc(OC2CCC2)ccc1F] | 3-{2-[5-(cyclobutyloxy)-2-fluorophenyl]-1-methyl-1,2,3,4-tetrahydroisoquinolin-6-yl}propanoic acid | 384.1 |
| 40 | 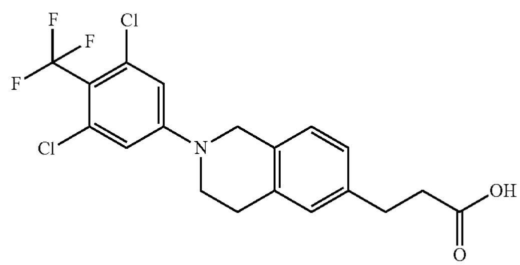 [SMILES: O=C(O)CCc1ccc2c(c1)CCN(c1cc(Cl)c(C(F)(F)F)c(Cl)c1)C2] | 3-{2-[3,5-dichloro-4-(trifluoromethyl)phenyl]-1,2,3,4-tetrahydroisoquinolin-6-yl}propanoic acid | |
| 41 | 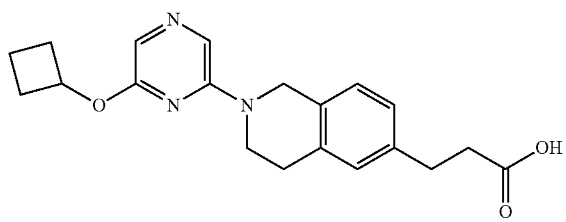 [SMILES: O=C(O)CCc1ccc2c(c1)CCN(c1cncc(OC3CCC3)n1)C2] | 3-{2-[6-(cyclobutyloxy)pyrazin-2-yl]-1,2,3,4-tetrahydroisoquinolin-6-yl}propanoic acid | 354.1 |
| 42 | 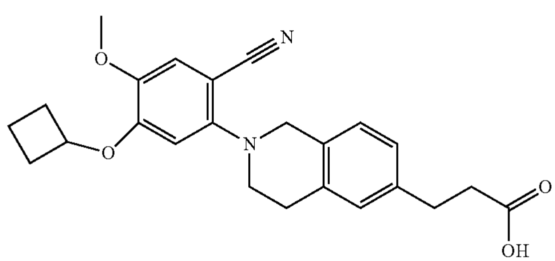 [SMILES: COc1cc(C#N)c(N2CCc3cc(CCC(=O)O)ccc3C2)cc1OC1CCC1] | 3-{2-[2-cyano-5-(cyclobutyloxy)-4-methoxyphenyl]-1,2,3,4-tetrahydroisoquinolin-6-yl}propanoic acid | 407.2 |
| 43 | 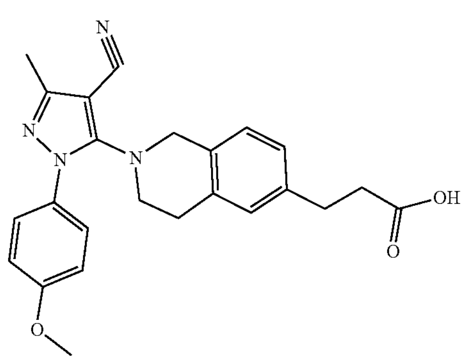 [SMILES: COc1ccc(-n2nc(C)c(C#N)c2N2CCc3cc(CCC(=O)O)ccc3C2)cc1] | 3-{2-[4-cyano-1-(4-methoxyphenyl)-3-methyl-1H-pyrazol-5-yl]-1,2,3,4-tetrahydroisoquinolin-6-yl}propanoic acid | 417.3 |

TABLE 1-continued

| Example | Structure | Name | [M + H]+ |
|---|---|---|---|
| 44 | 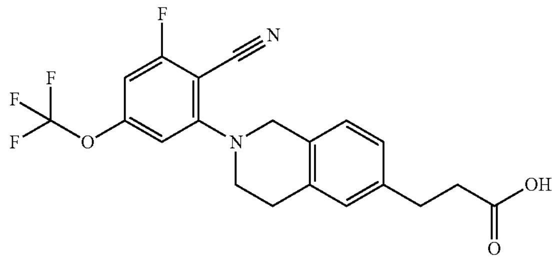 [SMILES: N#Cc1c(F)cc(OC(F)(F)F)cc1N1CCc2cc(CCC(=O)O)ccc2C1] | 3-{2-[2-cyano-3-fluoro-5-(trifluoromethoxy)phenyl]-1,2,3,4-tetrahydroisoquinolin-6-yl}propanoic acid | 409.1 |
| 45 | 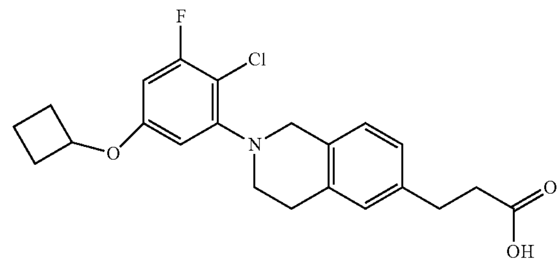 [SMILES: O=C(O)CCc1ccc2c(c1)CCN(c1cc(OC3CCC3)cc(F)c1Cl)C2] | 3-{2-[2-chloro-5-(cyclobutyloxy)-3-fluorophenyl]-1,2,3,4-tetrahydroisoquinolin-6-yl}propanoic acid | 404.1 |
| 46 | 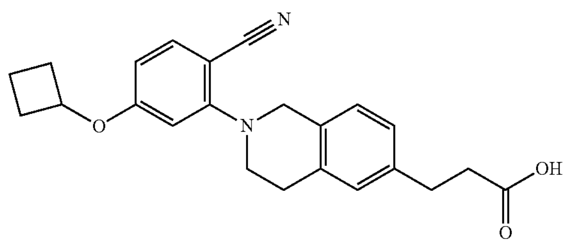 [SMILES: N#Cc1ccc(OC2CCC2)cc1N1CCc2cc(CCC(=O)O)ccc2C1] | 3-{2-[2-cyano-5-(cyclobutyloxy)phenyl]-1,2,3,4-tetrahydroisoquinolin-6-yl}propanoic acid | 395.1 |
| 47 | 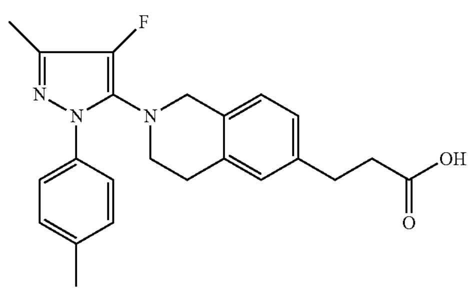 [SMILES: Cc1ccc(-n2nc(C)c(F)c2N2CCc3cc(CCC(=O)O)ccc3C2)cc1] | 3-{2-[4-fluoro-3-methyl-1-(4-methylphenyl)-1H-pyrazol-5-yl]-1,2,3,4-tetrahydroisoquinolin-6-yl}propanoic acid | 394.2 |
| 48 | 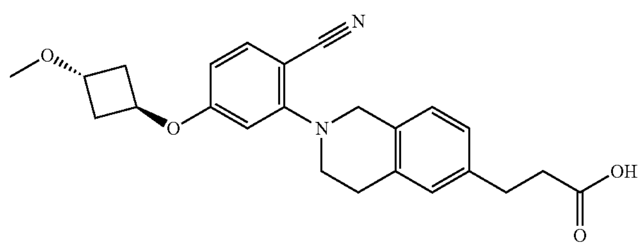 [SMILES: CO[C@H]1C[C@H](Oc2ccc(C#N)c(N3CCc4cc(CCC(=O)O)ccc4C3)c2)C1] | 3-(2-{2-cyano-5-[(trans-3-methoxycyclobutyl)oxy]phenyl}-1,2,3,4-tetrahydroisoquinolin-6-yl)propanoic acid | 407.2 |
| 49 | 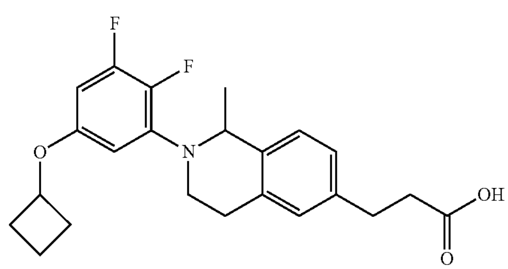 [SMILES: CC1c2ccc(CCC(=O)O)cc2CCN1c1cc(OC2CCC2)cc(F)c1F] | 3-{2-[5-(cyclobutyloxy)-2,3-difluorophenyl]-1-methyl-1,2,3,4-tetrahydroisoquinolin-6-yl}propanoic acid | 402.1 |

TABLE 1-continued

| Example | Structure | Name | [M + H]+ |
| --- | --- | --- | --- |
| 50 | 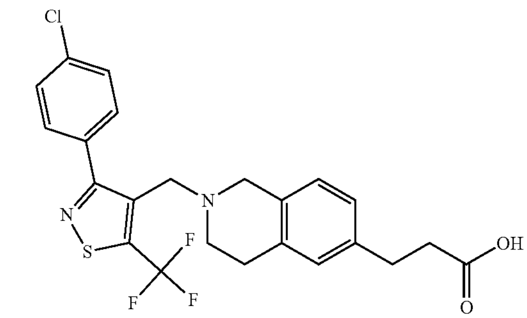 [SMILES: O=C(O)CCc1ccc2c(c1)CCN(Cc1c(-c3ccc(Cl)cc3)nsc1C(F)(F)F)C2] | 3-(2-{[3-(4-chlorophenyl)-5-(trifluoromethyl)isothiazol-4-yl]methyl}-1,2,3,4-tetrahydroiso-quinolin-6-yl)propanoic acid | 481.1 |
| 51 | 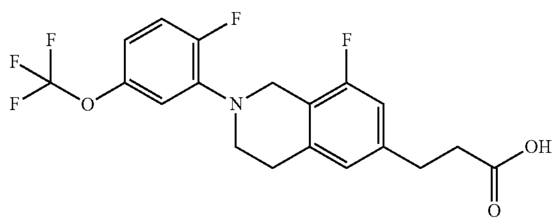 [SMILES: O=C(O)CCc1cc(F)c2c(c1)CCN(c1cc(OC(F)(F)F)ccc1F)C2] | 3-{8-fluoro-2-[2-fluoro-5-(trifluoromethoxy)phenyl]-1,2,3,4-tetrahydroisoquinolin-6-yl}-propanoic acid | 402.1 |
| 52 | 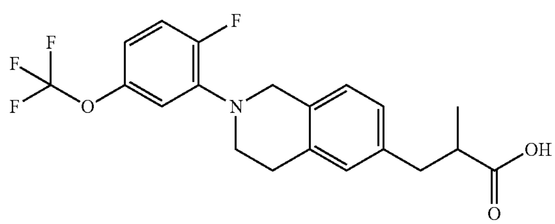 [SMILES: CC(Cc1ccc2c(c1)CCN(c1cc(OC(F)(F)F)ccc1F)C2)C(=O)O] | 3-{2-[2-fluoro-5-(trifluoromethoxyphenyl]-1,2,3,4-tetrahydroiso-quinolin-6-yl}-2-methyl-propanoic acid | 398.1 |
| 53 | 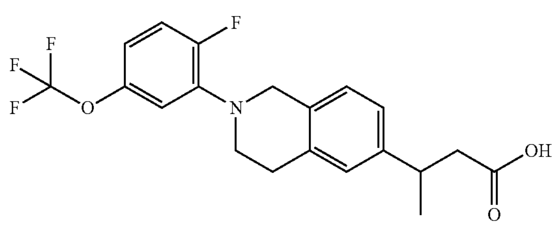 [SMILES: CC(CC(=O)O)c1ccc2c(c1)CCN(c1cc(OC(F)(F)F)ccc1F)C2] | 3-{2-[2-fluoro-5-(trifluoromethoxy)phenyl]-1,2,3,4-tetrahydroiso-quinolin-6-yl}butanoic acid | 398.1 |
| 54 | 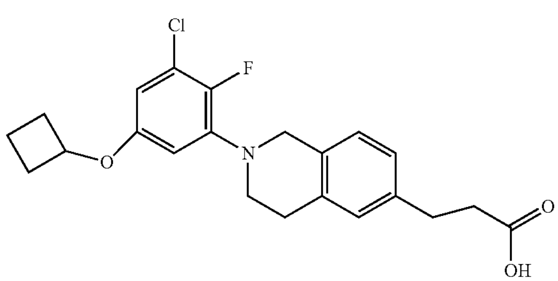 | 3-{2-[3-chloro-5-(cyclobutyloxy)-2-fluorophenyl]-1,2,3,4-tetrahydro-isoquinolin-6-yl}propanoic acid | 404.1 |
| 55 | 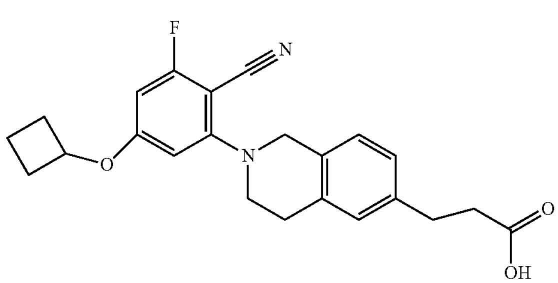 [SMILES: N#Cc1c(F)cc(OC2CCC2)cc1N1CCc2cc(CCC(=O)O)ccc2C1] | 3-{2-[2-cyano-5-(cyclobutyloxy)-3-fluorophenyl]-1,2,3,4-tetrahydro-isoquinolin-6-yl}propanoic acid | 395.0 |

Example 56

3-(2-(5-(cyclobutyldifluoromethyl)-2-fluorophenyl)-5-fluoro-1,2,3,4-tetrahydro-isoquinolin-6-yl)propanoic acid

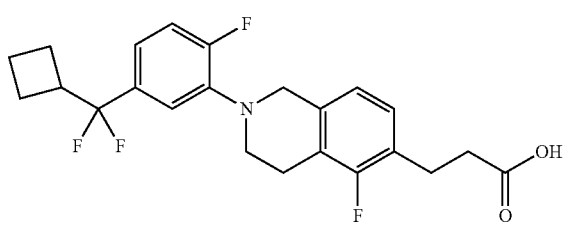 [SMILES: O=C(O)CCc1ccc2c(c1F)CCN(c1cc(C(F)(F)C3CCC3)ccc1F)C2]

Step A. Ethyl-3-(2-(5-(cyclobutyldifluoromethyl)-2-fluorophenyl)-5-fluoro-1,2,3,4-tetrahydroisoquinolin-6-yl)propanoate To a solution of ethyl 3-(5-fluoro-1,2,3,4-tetrahydroisoquinolin-6-yl)propanoate (Intermediate 42, 100 mg, 0.398 mmol) in 1,4-dioxane (5 mL), were added 2-bromo-4-(cyclobutyldifluoromethyl)-1-fluorobenzene (111 mg. 0.398 mmol), Cs$_2$CO$_3$ (389 mg, 1.194 mmol) and X-Phos precatalyst (30 mg, 0.041 mmol), then the mixture was stirred at 90° C. for 18 h under N$_2$. After completion of the reaction according to TLC (PE:EtOAc=10:1), the solvent was removed under reduced pressure. The residue was diluted with water (20 mL), and extracted with EtOAc (2×30 mL). The organic layer was dried over Na$_2$SO$_4$, filtrated and concentrated. The residue was purified by silica gel chromatography (PE:EtOAc=30:1) to afford the title compound. m/z=450.2 [M+1]$^+$.

Step-B. 3-(2-(5-(cyclobutyldifluoromethyl)-2-fluorophenyl)-5-fluoro-1,2,3,4-tetrahydroisoquinolin-6-yl)propanoic acid To a solution of ethyl 3-(2-(5-(cyclobutyl-difluoromethyl)-2-fluorophenyl)-5-fluoro-1,2,3,4-tetrahydroisoquinolin-6-yl)propanoate (60 mg, 0.133 mmol) in THF (2 mL), MeOH (2 mL) and water (1 mL), was added LiOH hydrate (12 mg, 0.286 mmol), then the mixture was stirred at r.t. (ca. 27° C.) for 2 h. After acidification with 1N HCl to pH=0.02, the solvent was removed under reduced pressure. The residue was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) followed by concentration (below 50° C.) to obtain the title compound. $^1$H NMR (400 MHz, CDCl$_3$) δ6.98-7.12 (m, 4H), 6.86 (d, J=7.83 Hz, 1H), 4.27 (s, 2H). 3.44 (t, J=5.87 Hz, 2H), 2.87-3.03 (m, 5H), 2.69 (t, J=7.63 Hz, 2H), 2.15-2.25 (m, 2H), 1.85-1.99 (m, 4H); m/z=422.1 [M+1]$^+$.

Example 57

3-(2-(3-chloro-2-fluoro-5-(trifluoromethoxy)phenyl)-5-fluoro-1,2,3,4-tetrahydro-isoquinolin-6-yl)-2-methylpropanoic acid

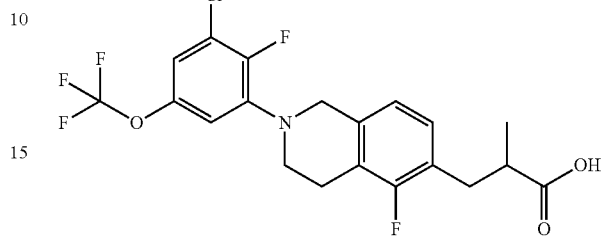

Step A. ethyl 3-(2-(3-chloro-2-fluoro-5-(trifluoromethoxy)phenyl)-5-fluoro-1,2,3,4-tetrahydroisoquinolin-6-yl)-2-methylpropanoate To a solution of ethyl 3-(5-fluoro-1,2,3,4-tetrahydroisoquinolin-6-yl)-2-methyl propanoate (Intermediate 47, 300 mg, 1.131 mmol) in THF (10 mL) were added 1-bromo-3-chloro-2-fluoro-5-(trifluoromethoxy)-benzene (Intermediate 5, 398 mg, 1.357 mmol), sodium 2-methylpropan-2-olate (1.1 mL, 2.200 mmol, 2 M, THF solution) and t-Buxphos-precatalyst (116 mg, 0.170 mmol)) at rt. Then the reaction mixture was placed under nitrogen atmosphere and stirred at 40° C. for 15 h. The mixture was diluted with water (25 mL), extracted with EtOAc (40 mL×2), and the organic layer was evaporated. The crude product was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) followed by concentration (below 50° C.) to obtain the title compound.

Step B. tert-butyl ethyl 3-(5-fluoro-1,2,3,4-tetrahydroisoquinolin-6-yl)-2-methyl-propanoate To a solution of ethyl 3-(2-(3-chloro-2-fluoro-5-(trifluoromethoxy)-phenyl)-5-fluoro-1,2,3,4-tetrahydroisoquinolin-6-yl)-2-methylpropanoate (300 mg, 0.565 mmol) in THF (6 mL) and water (3 mL) was added LiOH hydrate (119 mg, 2.83 mmol). The reaction mixture was stirred at rt for 4 h. The mixture was acidified to pH-2 with HCl (2 mL. 1 N), extracted with EtOAc (20 mL×2), and the organic layer was evaporated to give the title compound, which was used directly in next step without further purification.

Step C. 3-(2-(3-chloro-2-fluoro-5-(trifluoromethoxy)phenyl)-5-fluoro-1,2,3,4-tetrahydro-isoquinolin-6-yl)-2-methylpropanoyl chloride To a solution of 3-(2-(3-chloro-2-fluoro-5-(trifluoromethoxy)phenyl)-5-fluoro-1,2,3,4-tetrahydroisoquinolin-6-yl)-2-methylpropanoic acid (250 mg, 0.365 mmol) in DCM (10 mL) was added SOCl$_2$(0.5 ml, 6.85 mmol) with stirring at −78° C. The mixture was placed under a N$_2$ atmosphere and stirred at rt overnight (~18 h). The reaction mixture was concentrated in vacuo to give the title compound, which was directly used in the next step without further purification.

Step D. (4R)-4-benzyl-3-(3-(2-(3-chloro-2-fluoro-5-(trifluoromethoxy)phenyl)-5-fluoro-1,2,3,4-tetrahydroisoquinolin-6-yl)-2-methylpropanoyl)oxazolidin-2-one To a solution of (R)-4-benzyloxazolidin-2-one (91 mg, 0.513 mmol) in THF (10 mL) was added NaH (28 mg, 0.700 mmol) (60% in NaH) with stirring at 0° C. The mixture was placed under $N_2$ atmosphere and stirred at rt for about 30 min. Then a solution of 3-(2-(3-chloro-2-fluoro-5-(trifluoromethoxy)phenyl)-5-fluoro-1,2,3,4-tetrahydro-isoquinolin-6-yl)-2-methylpropanoyl chloride (160 mg, 0.342 mmol) in THF (2 mL) was added dropwise at rt. The mixture was stirred at rt for about 2 h. The reaction mixture was diluted with water (10 mL) and EtOAc (15 mL), and was stirred for about 10 min at rt (15° C.). Then the organic layer was separated and washed with water (2×10 m), brine (2×10 m), dried ($Na_2SO_4$) and filtered. The filtrate was concentrated to give crude product, which was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm) followed by concentration (below 50° C.) to obtain the title compound.

Step E. (4R)-4-benzyl-3-(3-(2-(3-chloro-2-fluoro-5-(trifluoromethoxy)phenyl)-5-fluoro-1,2,3,4-tetrahydroisoquinolin-6-yl)-2-methylpropanoyl)oxazolidin-2-one (4R)-4-benzyl-3-(3-(2-(3-chloro-2-fluoro-5-(trifluoromethoxy)phenyl)-5-fluoro-1,2,3,4-tetrahydroisoquinolin-6-yl)-2-methylpropanoyl)oxazolidin-2-one (90 mg, 0.145 mmol) was separated by SFC-HPLC on Chiralpak AD-3 150×4.6 mm I.D., 3 um Mobile phase: A: $CO_2$ B:methanol (0.05% DEA) Gradient: from 5% to 40% of B in 5.0 min and hold 40% for 2.5 min, then 5% of B for 2.5 min Flow rate: 2.5 mL/min Column temperature: 35° C. Wavelength: 220 nm to give (4R)-4-benzyl-3-(3-(2-(3-chloro-2-fluoro-5-(trifluoro-methoxy)phenyl)5-fluoro-1,2,3,4-tetra-hydroisoquinolin-6-yl)-2-methylpropanoyl)oxazolidin-2-one and (4R)-4-benzyl-3-(3-(2-(3-chloro-2-fluoro-5-(trifluoromethoxy)phenyl)-5-fluoro-1,2,3,4-tetrahydroisoquinolin-6-yl)-2-methylpropanoyl)oxazolidin-2-one.

Step F. 3-(2-(3-chloro-2-fluoro-5-(trifluoromethoxy)phenyl)-5-fluoro-1,2,3,4-tetra-hydroisoquinolin-6-yl)-2-methylpropanoic acid To a solution of (4R)-4-benzyl-3-(3-(2-(3-chloro-2-fluoro-5-(trifluoromethoxy)phenyl)-5-fluoro-1,2,3,4-tetrahydroiso-quinolin-6-yl)-2-methylpropanoyl)oxazolidin-2-one (30 mg, 0.046 mmol) in THF (4 mL) and water (2 ml) at 0° C. was added dropwise a solution of lithium peroxide prepared by adding $H_2O_2$ (0.065 ml, 0.741 mmol) to LiOH hydrate (6 mg, 0.143 mmol) in water (0.2 mL). The reaction mixture was stirred for 0° C. for 1 h and then quenched with saturated aqueous $Na_2SO_3$ (0.5 mL). The mixture was diluted with water (10 mL) and acidified with 1 N HCl to pH=2, and extracted with EtOAc (2×10 mL). The EtOAc extracts were combined, washed with brine (5 mL), dried over anhydrous $MgSO_4$, and concentrated. The residue was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm), followed by concentration (below 50° C.) to obtain the title compound. m/z 450.2 $[M+H]^+$, $^1H$ NMR (400 MHz, $CD_3OD$) δ ppm 7.05 (t, J=7.63 Hz, 1H) 7.00 (br. s., 1H) 6.87-6.94 (m, 2H) 4.26 (s, 2H) 3.46 (t, J=5.67 Hz, 2H) 2.95 (d, J=6.06 Hz, 1H) 2.87-2.93 (m, 2H) 2.66-2.74 (m, 2H) 1.12 (d, J=6.26 Hz, 3H).

Example 58

3-(5-fluoro-2-(2-fluoro-5-(trifluoromethoxy)phenyl)-7-methyl-1,2,3,4-tetra-hydroisoquinolin-6-yl)propanoic acid

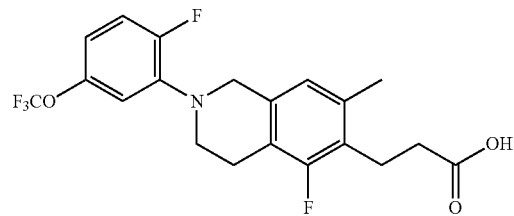 [SMILES: Cc1cc2c(c(F)c1CCC(=O)O)CCN(c1cc(OC(F)(F)F)ccc1F)C2]

Step A. ethyl 3-(5-fluoro-2-(2-fluoro-5-(trifluoromethoxy)phenyl)-7-methyl-1,2,3,4-tetrahydroisoquinolin-6-yl)propanoate To a solution of ethyl 3-(5-fluoro-7-methyl-1,2,3,4-tetrahydro-isoquinolin-6-yl)propanoate (Intermediate 48, 100 mg, 0.377 mmol) and 2-bromo-1-fluoro-4-(trifluoromethoxy)benzene (117 mg, 0.452 mmol) in dioxane (3 mL) were added Xphos-precatalyst (32 mg, 0.039 mmol) and $Cs_2CO_3$ (368 mg, 1.131 mmol). The mixture was stirred at 90° C. for 16 h. Then water (100 mL) was added. The mixture was extracted with EtOAc (2×50 mL), washed with water (200 mL), dried over anhydrous $Na_2SO_4$ filtered, concentrated in vacuo and purified by silica gel column chromatography (PE/EtOAc=50:1 to 20:1) to give the title compound. ESI MS m/z 444.1 $[M+H]^+$.

Step B. 3-(5-fluoro-2-(2-fluoro-5-(trifluoromethoxy)phenyl)-7-methyl-1,2,3,4-tetra-hydroisoquinolin-6-yl)propanoic acid To a solution of ethyl 3-(5-fluoro-2-(2-fluoro-5-(trifluoromethoxy)-phenyl)-7-methyl-1,2,3,4-tetrahydroisoquinolin-6-yl)propanoate (127 mg, 0.286 mmol) in THF (6 ml) and water (3 ml) was added LiOH hydrate (12 mg, 0.286 mmol). The mixture was stirred at 20° C. for 2 h, then acidified with HCl (6 N, about 3 mL). The mixture was extracted with EtOAc (2×20 mL), washed with water (20 mL), dried over anhydrous $Na_2SO_4$, and evaporated. The crude product was purified with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm) followed by concentration to obtain the title compound. $^1H$ NMR (400 MHz, $CDCl_3$) ppm δ 2.33 (s, 3H) 2.55-2.64 (m, 2H) 2.91 (t, J=5.51 Hz, 2H) 2.98 (t, J=7.83 Hz, 2H) 3.44

(t, J=5.84 Hz, 2H) 4.22 (s, 2H) 6.74 (s, 1H) 6.76-6.85 (m, 2H) 7.04 (dd, J=11.80, 8.71 Hz, 1H); ESI MS m/z 416.1 [M+H]$^+$

Example 59

3-(2-(3-(4-chlorophenyl)-5-(trifluoromethyl)isothiazol-4-yl)-5-fluoro-1,2,3,4-tetrahydroisoquinolin-6-yl)propanoic acid

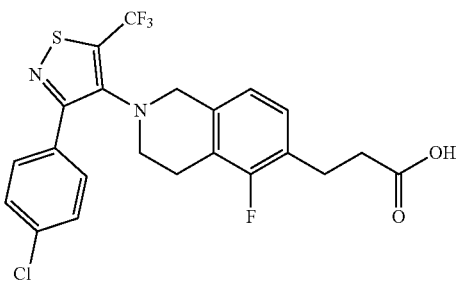 [SMILES: O=C(O)CCc1ccc2c(c1F)CCN(c1c(-c3ccc(Cl)cc3)nsc1C(F)(F)F)C2]

Step A. Ethyl 3-(2-(3-(4-chlorophenyl)-5-(trifluoromethyl)isothiazol-4-yl)-5-fluoro-1,2,3,4-tetrahydroisoquinolin-6-yl)propanoate A solution of ethyl 3-(5-fluoro-1,2,3,4-tetrahydroisoquinolin-6-yl)propanoate (53 mg, 0.211 mmol), 4-bromo-3-(4-chlorophenyl)-5-(trifluoromethyl)isothiazole (60 mg, 0.175 mmol) in dioxane (1.00 mL) was treated with Xantphos (30 mg, 0.035 mmol) and Cs$_2$CO$_3$ (170 mg, 0.525 mmol), and then heated at 100° C. for 16 h. The mixture was concentrated under reduced pressure to give a residue, which was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) followed by concentration (below 50° C.) to obtain to the title compound.

Step B. 3-(2-(3-(4-chlorophenyl)-5-(trifluoromethyl) isothiazol-4-yl)-5-fluoro-1,2,3,4-tetrahydroisoquinolin-6-yl)propanoic acid To a solution of ethyl 3-(2-(3-(4-chlorophenyl)-5-(trifluoromethyl)isothiazol-4-yl)-5-fluoro-1,2,3,4-tetrahydroisoquinolin-6-yl)propanoate (1 mg, 1.950 μmol) in THF (1 ml), EtOH (1 ml) and water (0.5 ml), was added LiOH hydrate (1 mg, 0.024 mmol). The mixture was stirred at 30° C. for 15 h. After acidification with 1N HCl to pH=2, the solvent was removed under reduced pressure. The residue was purified by reverse phase HPLC on a GILSON 281 instrument fitted with a Phenomenex Synergi C18 (250*21.2 mm*4 μm) using water (0.2% Formic acid) and CH$_3$CN as eluents (Mobile phase A: water (0.2% Formic acid), Mobile phase B: CH$_3$CN, Detector wavelength: 220 nm) followed by concentration (below 50° C.) to obtain the title compound. m/z 485.1 [M+H]$^+$; $^1$H NMR (400 MHz, CDCl$_1$) S ppm 7.80 (d, J=8.60 Hz, 2H) 7.25 (d, J=8.38 Hz, 2H) 6.90-6.98 (m, 1H) 6.58 (d, J=7.94 Hz, 1H) 4.05 (s, 2H) 3.30 (t, J=5.51 Hz, 2H) 2.88-2.95 (m, 2H) 2.75-2.83 (m, 2H) 2.61-2.68 (m, 2H).

Example 60

3-(2-(5-(cyclobutylmethyl)-2-fluorophenyl)-5-fluoro-1,2,3,4-tetrahydroisoquinolin-6-yl)-propanoic acid

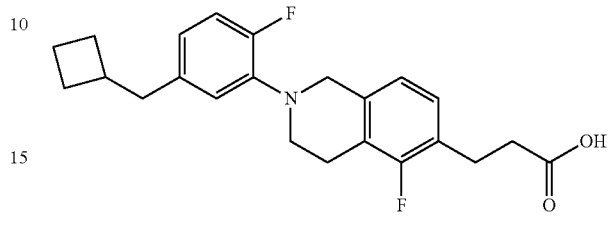

Step A-ethyl 3-(2-(5-(cyclobutylmethyl)-2-fluorophenyl)-5-fluoro-1,2,3,4-tetra-hydroisoquinolin-6-yl) propanoate To a solution of ethyl 3-(5-fluoro-1,2,3,4-tetrahydro-isoquinolin-6-yl)propanoate (100 mg, 0.398 mmol) in dioxane (6 mL) was added 2-bromo-4-(cyclobutylmethyl)-1-fluorobenzene (Intermediate 41, 97 mg, 0.398 mmol), Cs$_2$CO$_3$ (389 mg, 1.194 mmol) and XPHOS-precatalyst (32 mg, 0.041 mmol). The reaction mixture was placed under a N$_2$ atmosphere and heated to 90° C. for 18 h. The solvent was removed in vacuo and the resulting mixture was diluted with water (20 mL) and extracted with EtOAc (2×20 mL), dried, filtered and the concentrated in vacuo. The crude product was purified by silica gel chromatography (PE/EtOAc=40:1) to give the title compound. m/z 414.1[M+H]$^+$.

Step-B. 3-(2-(5-(cyclobutylmethyl)-2-fluorophenyl)-5-fluoro-1,2,3,4-tetrahydro-isoquinolin-6-yl)propanoic acid To a solution of ethyl 3-(2-(5-(cyclobutymethyl)-2-fluorophenyl)-5-fluoro-1,2,3,4-tetrahydroisoquinolin-6-yl)propanoate (80 mg, 0.193 mmol) in THF (4 mL) and water (2 mL) was added LiOH hydrate (40 mg, 0.953 mmol). Then the reaction mixture was stirred at rt for 18 h. The mixture was acidified to pH-2 with HCl (0.7 mL, 1 N) and concentrated in vacuo. The crude product was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) followed by concentration to give the title compound. $^1$HNMR (400 MHz, ppm) δ 7.04 (t, J=7.65 Hz. 1H), 6.97 (dd, J=12.05, 8.28 Hz, 1H), 6.80-6.91 (m, 3H), 4.25 (s, 2H), 3.42 (t, J=5.90 Hz, 2H), 2.89-3.00 (m, 5H), 2.69 (t, J=7.78 Hz, 2H), 2.02-2.09 (m, 2H), 1.76-1.84 (m, 2H), 1.66-1.73 (m, 2H), 1.50-1.60 (m, 2H). m/z 386.2 [M+H]$^+$.

Example 61

3-(2-(5-cyclobutoxy-2-fluorophenyl)-5-fluoro-1,2,3,4-tetrahydro-isoquinolin-6-yl)-propanoic acid

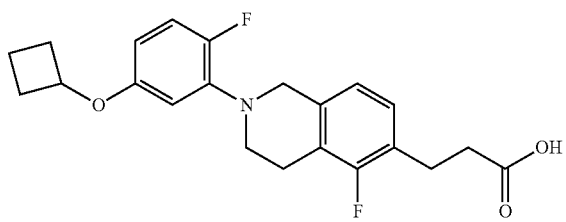 [SMILES: O=C(O)CCc1ccc2c(c1F)CCN(c1cc(OC3CCC3)ccc1F)C2]

Step A—(E)-ethyl 3-(6-chloroquinolin-2-yl)acrylate

To a solution of 6-bromo-5-fluoroisoquinoline (210 mg, 0.929 mmol) in dry 1,4-dioxane (10 ml) was added tri-tert-butylphosphonium tetrafluoroborate (51 mg, 0.176 mmol), dicyclohexylamine (253 mg, 1.394 mmol), and ethyl acrylate (112 mg, 1.115 mmol). Then the mixture was degassed for 5 min with $N_2$. Then $Pd_2(dba)_1$ (85 mg, 0.093 mmol) was added. The final mixture was heated to 100° C. and stirred for 18 h in a $N_2$ atmosphere. The reaction mixture was diluted with EtOAc (20 mL). The solid was filtered off, and the filtrate was concentrated in vacuo. The residue was purified by silica gel chromatography (PE/EtOAc=20:1 to 3:1) to afford the title compound.

Step B. ethyl 3-(5-fluoro-1,2,3,4-tetrahydroisoquinolin-6-yl)propanoate

To a solution of (E)-ethyl 3-(5-fluoroisoquinolin-6-yl)acrylate (220 mg, 0.897 mmol) in MeOH (20 ml) was added platinum (IV) oxide (40 mg, 0.176 mmol). The reaction mixture was stirred under 50 psi of hydrogen atmosphere at 30° C. for 5 hours. The mixture was filtered, and the filtrate was concentrated in vacuo to give the title compound.

Step C. Ethyl 3-(2-(5-cyclobutoxy-2-fluorophenyl)-5-fluoro-1,2,3,4-tetrahydro-isoquinolin-6-yl) propanoate To a solution of ethyl 3-(5-fluoro-1,2,3,4-tetrahydro-isoquinolin-6-yl)propanoate (100 mg, 0.398 mmol) in 1,4-dioxane (5 ml) was added 2-bromo-4-cyclobutoxy-1-fluoro benzene (117 mg, 0.478 mmol), $Cs_2CO_3$ (194 mg, 0.597 mmol), XANTPHOS (46 mg, 0.080 mmol) and $Pd_2(dba)_3$ (36 mg. 0.039 mmol). Then the reaction mixture was placed under nitrogen and stirred for 20 min at 100° C. under microwave. The mixture was concentrated in vacuo, then water (10 mL) was added and extracted with EtOAc (2×10 mL). The combined organic layers were concentrated in vacuo, and the crude product was purified by silica gel preparative TLC (PE/EtOAc=2:1) to give the title compound.

Step D. 3-(2-(5-cyclobutoxy-2-fluorophenyl)-5-fluoro-1,2,3,4-tetrahydro-isoquinolin-6-yl)propanoic acid To a solution of ethyl 3-(2-(5-cyclobutoxy-2-fluoro-phenyl)-5-fluoro-1,2,3,4-tetrahydroisoquinolin-6-yl)propanoate (20 mg, 0.048 mmol) in THF (2.00 mL), MeOH (2.00 mL) and water (1.00 mL) was added LiOH (6 mg, 0.251 mmol). Then the mixture was stirred at rt for 3 h. The mixture was acidified with HCl (0.5 mL, 6 N) and concentrated in vacuo. The crude product was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm) followed by concentration to give the title compound. $^1$H NMR (400 MHz, $CDCl_3$) δ 6.97 (t, J=7.4 Hz, 1H), 6.86 (dd, J=8.8, 11.9 Hz, 1H), 6.76 (d, J=7.8 Hz, 1H), 6.45-6.38 (m, 1H), 6.28-6.21 (m, 1H), 4.52-4.44 (m, 1H), 4.16 (s, 2H), 3.35 (t, J=5.7 Hz, 2H), 2.94-2.80 (m, 4H), 2.61 (t, J=7.0 Hz, 2H), 2.37-2.28 (m, 2H), 2.11-2.01 (m, 2H), 1.77 (d, J=10.2 Hz, 1H), 1.64-1.56 (m, 1H). m/z=388.1 [M+H]$^+$.

The examples in Table 2 were prepared from the appropriate starting materials described previously or commercially available starting materials available using procedures described in Examples 56-61.

TABLE 2

| Example | Structure | Name | [M + H]$^+$ |
|---|---|---|---|
| 62 | 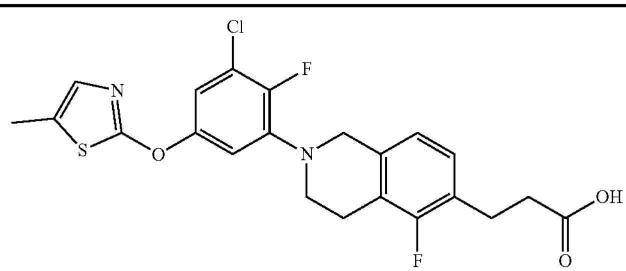 | 3-(2-{3-chloro-2-fluoro-5-[(5-methyl-1,3-thiazol-2-yl)oxy]phenyl}-5-fluoro-1,2,3,4-tetrahydroisoquinolin-6-yl)propanoic acid | 465.0 |
| 63 | 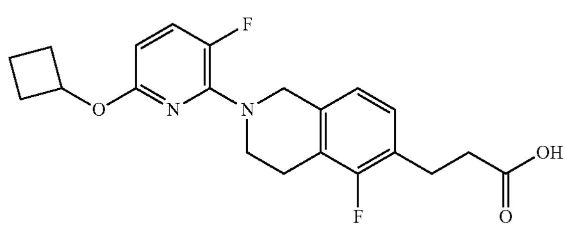 [SMILES: O=C(O)CCc1ccc2c(c1F)CCN(c1nc(OC3CCC3)ccc1F)C2] | 3-{2-[6-(cyclobutyloxy)-3-fluoro-pyridin-2-yl]-5-fluoro-1,2,3,4-tetrahydro-isoquinolin-6-yl} propanoic acid | 389.1 |

TABLE 2-continued

| Example | Structure | Name | [M + H]+ |
|---|---|---|---|
| 64 | 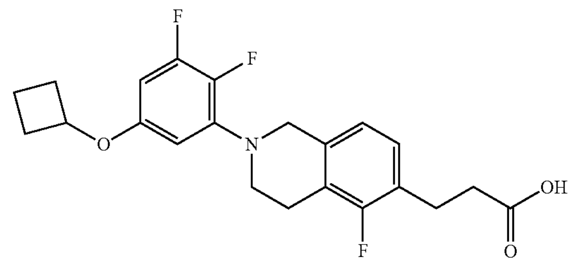 [SMILES: O=C(O)CCc1ccc2c(c1F)CCN(c1cc(OC3CCC3)cc(F)c1F)C2] | 3-{2-[5-(cyclobutyloxy)-2,3-difluorophenyl]-5-fluoro-1,2,3,4-tetra-hydroisoquinolin-6-yl}propanoic acid | 406.1 |
| 65 | 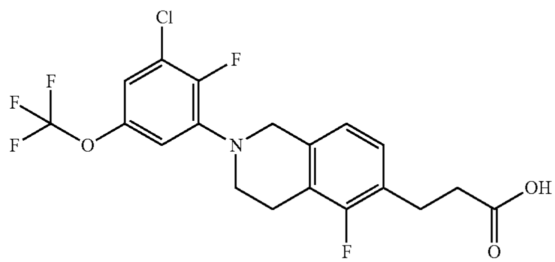 [SMILES: O=C(O)CCc1ccc2c(c1F)CCN(c1cc(OC(F)(F)F)cc(Cl)c1F)C2] | 3-{2-[3-chloro-2-fluoro-5-(trifluoromethoxy)phenyl]-5-fluoro-1,2,3,4-tetra-hydroisoquinolin-6-yl}propanoic acid | 436.0 |
| 66 | 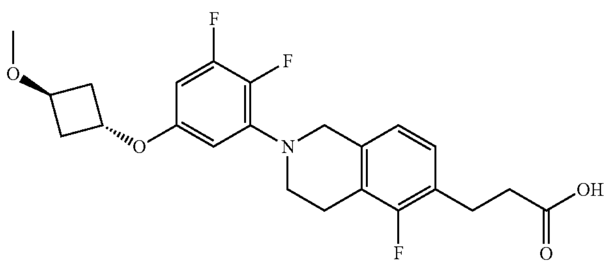 [SMILES: CO[C@H]1C[C@H](Oc2cc(F)c(F)c(N3CCc4c(ccc(CCC(=O)O)c4F)C3)c2)C1] | 3-(2-{2,3-difluoro-5-[(trans-3-methoxycyclobutyl)oxy]phenyl}-5-fluoro-1,2,3,4-tetrahydroisoquinolin-6-yl)-propanoic acid | 436.1 |
| 67 | 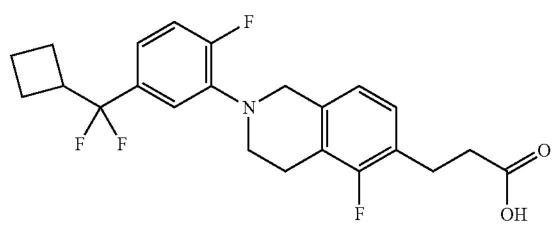 [SMILES: O=C(O)CCc1ccc2c(c1F)CCN(c1cc(C(F)(F)C3CCC3)ccc1F)C2] | 3-(2-{5-[cyclobutyl(difluoro)methyl]-2-fluorophenyl}-5-fluoro-1,2,3,4-tetrahydroisoquinolin-6-yl)-propanoic acid | 422.1 |
| 68 | 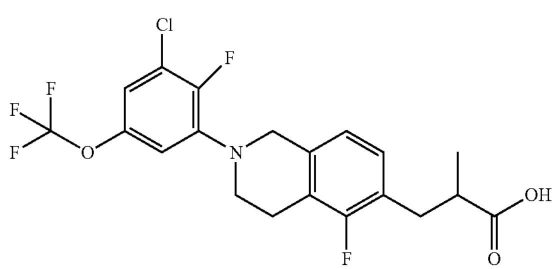 [SMILES: CC(Cc1ccc2c(c1F)CCN(c1cc(OC(F)(F)F)cc(Cl)c1F)C2)C(=O)O] | 3-{2-[3-chloro-2-fluoro-5-(trifluoromethoxy)phenyl]-5-fluoro-1,2,3,4-tetrahydroisoquinolin-6-yl}-2-methyl-propanoic acid | 450.0 |
| 69 | 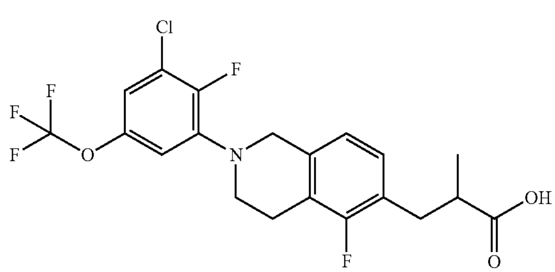 [SMILES: CC(Cc1ccc2c(c1F)CCN(c1cc(OC(F)(F)F)cc(Cl)c1F)C2)C(=O)O] | 3-{2-[3-chloro-2-fluoro-5-(trifluoromethoxy)phenyl]-5-fluoro-1,2,3,4-tetrahydroisoquinolin-6-yl}-2-methyl-propanoic acid | 450.1 |

TABLE 2-continued

| Example | Structure | Name | [M + H]+ |
|---|---|---|---|
| 70 | 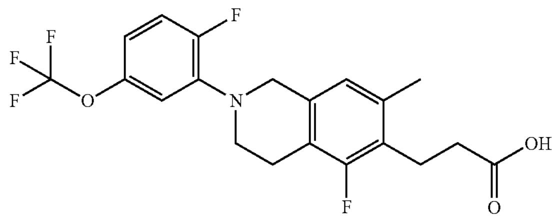 [SMILES: Cc1cc2c(c(F)c1CCC(=O)O)CCN(c1cc(OC(F)(F)F)ccc1F)C2] | 3-{5-fluoro-2-[2-fluoro-5-(trifluoromethoxy)phenyl]-7-methyl-1,2,3,4-tetrahydroisoquinolin-6-yl}-propanoic acid | 416.1 |
| 71 | 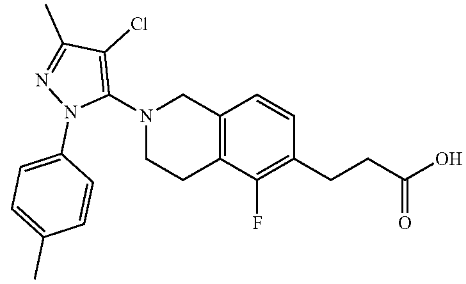 [SMILES: Cc1ccc(-n2nc(C)c(Cl)c2N2CCc3c(ccc(CCC(=O)O)c3F)C2)cc1] | 3-{2-[4-chloro-3-methyl-1-(4-methylphenyl)-1H-pyrazol-5-yl]-5-fluoro-1,2,3,4-tetrahydroisoquinolin-6-yl}-propanoic acid | 428.1 |
| 72 | 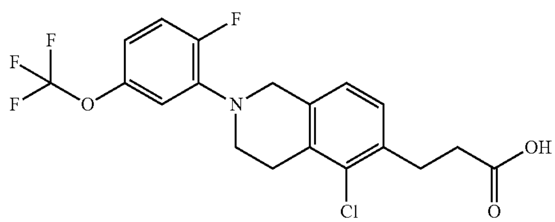 [SMILES: O=C(O)CCc1ccc2c(c1Cl)CCN(c1cc(OC(F)(F)F)ccc1F)C2] | 3-{5-chloro-2-[2-fluoro-5-(trifluoromethoxy)phenyl]-1,2,3,4-tetrahydroiso-quinolin-6-yl}propanoic acid | 418.1 |
| 73 | 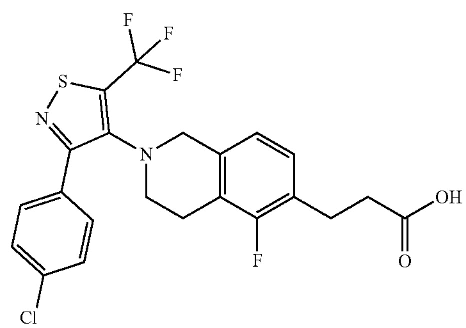 [SMILES: O=C(O)CCc1ccc2c(c1F)CCN(c1c(-c3ccc(Cl)cc3)nsc1C(F)(F)F)C2] | 3-{2-[3-(4-chlorophenyl)-5-(trifluoromethyl)isothiazol-4-yl]-5-fluoro-1,2,3,4-tetrahydroisoquinolin-6-yl}-propanoic acid | 485.1 |
| 74 | 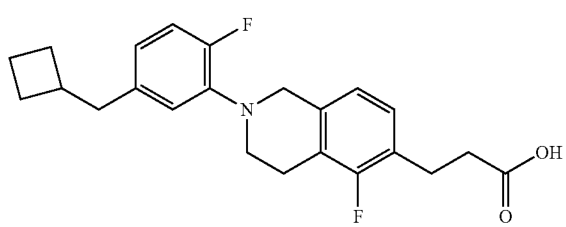 | 3-{2-[5-(cyclobutylmethyl)-2-fluorophenyl]-5-fluoro-1,2,3,4-tetrahydroisoquinolin-6-yl}propanoic acid | 386.2 |
| 75 | 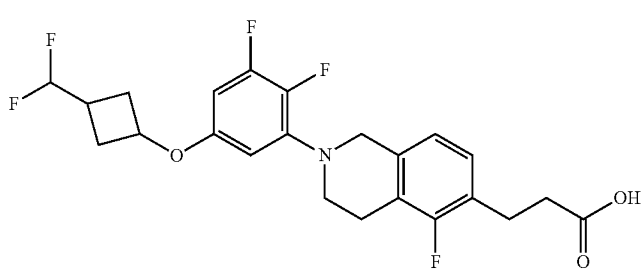 [SMILES: O=C(O)CCc1ccc2c(c1F)CCN(c1cc(OC3CC(C(F)F)C3)cc(F)c1F)C2] | 3-[2-(5-{[3-(difluoromethyl)cyclobutyl]oxy}-2,3-difluorophenyl)-5-fluoro-1,2,3,4-tetrahydroisoquinolin-6-yl]-propanoic acid | 456.1 |

TABLE 2-continued

| Example | Structure | Name | [M + H]+ |
|---|---|---|---|
| 76 | 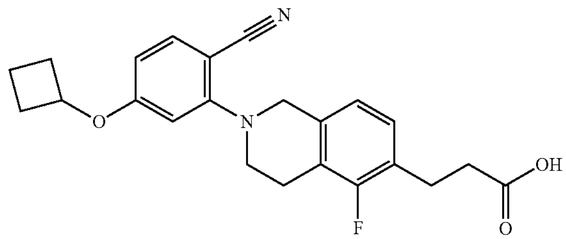 | 3-{2-[2-cyano-5-(cyclobutyloxy)-phenyl]-5-fluoro-1,2,3,4-tetrahydro-isoquinolin-6-yl}propanoic acid | 395.1 |
| 77 | 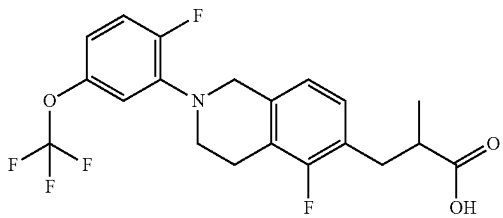 [SMILES: CC(Cc1ccc2c(c1F)CCN(c1cc(OC(F)(F)F)ccc1F)C2)C(=O)O] | 3-{5-fluoro-2-[2-fluoro-5-(trifluoromethoxy)phenyl]-1,2,3,4-tetrahydro-isoquinolin-6-yl}-2-methyl-propanoic acid | 416.1 |
| 78 | 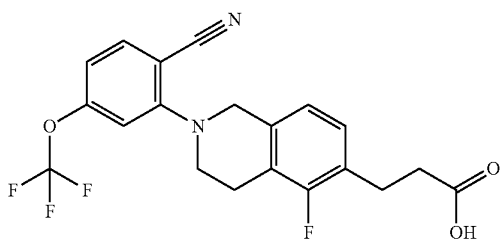 [SMILES: N#Cc1ccc(OC(F)(F)F)cc1N1CCc2c(ccc(CCC(=O)O)c2F)C1] | 3-{2-[2-cyano-5-(trifluoromethoxy)phenyl]-5-fluoro-1,2,3,4-tetrahydro-isoquinolin-6-yl}propanoic acid | 409.1 |
| 79 | 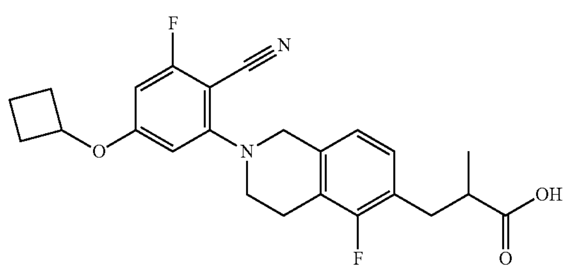 [SMILES: CC(Cc1ccc2c(c1F)CCN(c1cc(OC3CCC3)cc(F)c1C#N)C2)C(=O)O] | 3-(2-(2-cyano-5-cyclobutyloxy-3-fluorophenyl)-5-fluoro-1,2,3,4-tetrahydroisoquinolin-6-yl)-2-methyl-propanoic acid | 425.1 |
| 80 | 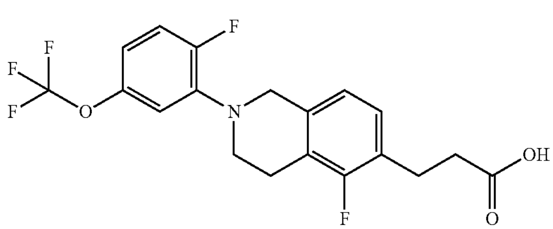 [SMILES: O=C(O)CCc1ccc2c(c1F)CCN(c1cc(OC(F)(F)F)ccc1F)C2] | 3-{5-fluoro-2-[2-fluoro-5-(trifluoromethoxy)phenyl]-1,2,3,4-tetrahydro-isoquinolin-6-yl}propanoic acid | 402.0 |
| 81 | 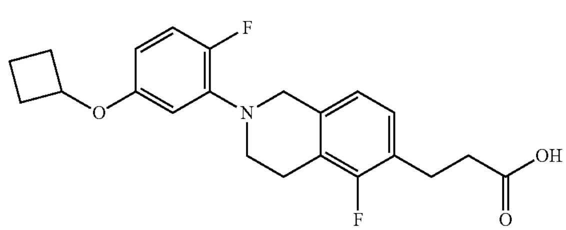 [SMILES: O=C(O)CCc1ccc2c(c1F)CCN(c1cc(OC3CCC3)ccc1F)C2] | 3-{2-[5-(cyclobutyloxy)-2-fluorophenyl]-5-fluoro-1,2,3,4-tetrahydro-isoquinolin-6-yl}propanoic acid | 388.1 |

TABLE 2-continued

| Example | Structure | Name | [M + H]+ |
|---|---|---|---|
| 82 | 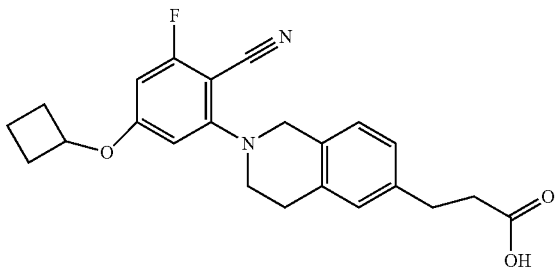 [SMILES: N#Cc1c(F)cc(OC2CCC2)cc1N1CCc2cc(CCC(=O)O)ccc2C1] | 3-{2-[2-cyano-5-(cyclobutyloxy)-3-fluorophenyl]-1,2,3,4-tetrahydro-isoquinolin-6-yl}propanoic acid | 395.0 |

Example 83

(1S,2S)-2-(2-(2,3-difluoro-5-((1R,3S)-3-methylcyclobutoxy)phenyl)-1,2,3,4-tetrahydroisoquinolin-6-yl)cyclopropanecarboxylic acid

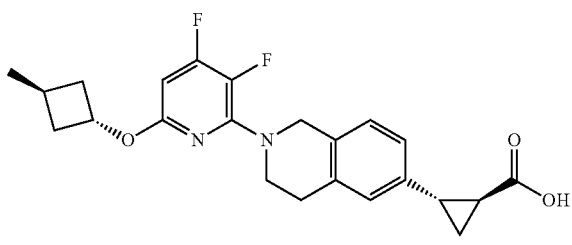 [SMILES: C[C@H]1C[C@H](Oc2cc(F)c(F)c(N3CCc4cc([C@H]5C[C@@H]5C(=O)O)ccc4C3)n2)C1]

Step A. (1S,2S)-ethyl 2-(2-(2,3-difluoro-5(1r,3r)-3-metylcyclobutoxy)phenyl)-1,2,3,4-tetrahydroisoquinolin-6-yl)cyclopropanecarboxylate To a solution of 2,3-difluoro-5-((1R,3R)-3-methylcyclobutoxy)phenyl trifluoromethanesulfonate (200 mg, 0.578 mmol) in dioxane (4 mL) were added (1S,2S)-ethyl 2-(1,2,3,4-tetrahydro-isoquinolin-6-yl)-cyclopropanecarboxylate (156 mg, 0.635 mmol), Cs$_2$CO$_3$ (565 mg, 1.733 mmol) and RUPHOS precatalyst (94 mg, 0.116 mmol). After the addition was complete, the mixture was stirred under argon at 90° C. for 15 h. The reaction mixture was filtered, washed with water (2×20 mL), extracted with EtOAc (3×20 mL). The combined organic layers were evaporated in vacuo to give crude product, which was further purified by silica gel preparative TLC (PE:EtOAc=10:1 as elute) to give the title compound. ESI MS m/z=442.1 [M+1]+.

Step B. (1S,2S)-2-(2-(2,3-difluoro-5-((1r,3S)-3-methylcyclobutoxy)phenyl)-1,2,3,4-tetrahydroisoquinolin-6-yl)cyclopropanecarboxylic acid To a solution of (1S,2S)-ethyl 2-(2-(2,3-difluoro-5-((1r,3S)-3-methylcyclobutoxy)phenyl)-1,2,3,4-tetrahydroisoquinolin-6-yl)-cyclopropanecarboxylate (20 mg, 0.045 mmol) in MeOH (2 mL), THF (2 mL) and water (1 mL) was added LiOH hydrate (10 mg, 0.238 mmol) and stirred at rt for 15 h. The mixture was acidified by the diluted hydrochloride acid (1N) to pH-2. The mixture was concentrated in vacuo to give crude product. The crude product was further purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid). Mobile phase B: CH$_3$CN, Detector wavelength: 220 nm), then concentrated on a lyophilizer to afford the title compound. $^1$H NMR (400 MHz, CDCl$_3$) δ 7.04 (d, J=7.78 Hz, 1H), 6.88-6.98 (m, 2H), 6.12-6.24 (m, 2H), 4.66 (t, J=6.15 Hz, 1H), 4.27 (s, 2H), 3.45 (t, J=5.77 Hz, 2H), 2.94 (t, J=5.52 Hz, 2H); 2.53-2.63 (m, 1H), 2.40-2.52 (m, 1H), 2.25-2.34 (m, 2H), 2.02-2.10 (m, 2H), 1.89 (dt, J=8.34, 4.49 Hz, 1H), 1.65 (dt, J=9.54, 4.77 Hz, 1H), 1.36-1.45 (m. 1H), 1.19 (d, J=7.03 Hz, 3H); ESI MS m/z=414.1.

Example 84

2-(2-(2-fluoro-5-(trifluoromethoxy)phenyl)-1,2,3,4-tetrahydroisoquinolin-6-yl)-cyclopropanecarboxylic acid

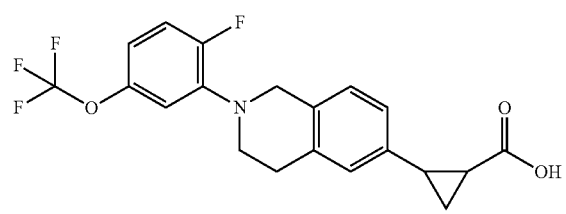 [SMILES: O=C(O)C1CC1c1ccc2c(c1)CCN(c1cc(OC(F)(F)F)ccc1F)C2]

Step A. tert-butyl 6-vinyl-3,4-dihydroisoquinoline-2(H)-carboxylate

To a stirred solution of tert-butyl 6-bromo-3,4-dihydroisoquinoline-2(1H)-carboxylate (1.5 g, 4.80 mmol) in THF (30 mL) was added 4,4,6-trimethyl-2-vinyl-1,3,2-dioxaborinane (0.740 g, 4.80 mmol), triphenylphosphine (1.260 g. 4.80 mmol) and potassium 2-methyl-propan-2-olate (0.027 g, 0.240 mmol). The mixture was stirred at 67° C. for 24 h. The mixture was washed with water (2×10 mL) and extracted with EtOAc (2×30 mL). The extract was dried over by Na$_2$SO$_4$ filtered, and concentrated in vacuo. The residue was purified by silica gel column chromatography (PE:EtOAc=20:1) to give the title compound.

Step B. 6-vinyl-1,2,3,4-tetrahydroisoquinoline hydrochloride

A solution of tert-butyl 6-vinyl-3,4-dihydroisoquinoline-2(1H)-carboxylate (970 mg, 3.74 mmol) in HCl-EtOAc (10 mL) was stirred at rt for 1 h. The mixture was then evaporated under reduce pressure to give the crude title compound.

Step C. 2-(2-fluoro-5-(trifluoromethoxy)phenyl)-6-vinyl-1,2,3,4-tetrahydro-isoquinoline To a stirred solution of 6-vinyl-1,2,3,4-tetrahydroisoquinoline hydrochloride (732 mg, 3.74 mmol) in 1,4-dioxane (30 mL) was added 2-bromo-1-fluoro-4-(trifluoromethoxy) benzene (969 mg, 3.74 mmol), $Cs_2CO_3$ (2438 mg, 7.48 mmol), XANTPHOS (433 mg, 0.748 mmol) and $Pd_2(dba)_3$ (343 mg, 0.374 mmol). The mixture was stirred at 90° C. for 18 h. The mixture was washed with water (10 mL×2) and extracted with EtOAc (30 mL×2). The extract was dried over by $Na_2SO_4$ and concentrated in vacuo. The residue was purified by silica gel column chromatography (PE:EtOAc=40:1) to give the title compound.

Step D. ethyl 2-(2-(2-fluoro-5-(trifluoromethoxy)phenyl)-1,2,3,4-tetrahydro-isoquinolin-6-yl)cyclopropanecarboxylate To a solution of 2-(2-fluoro-5-(trifluoro-methoxy)phenyl)-6-vinyl-1,2,3,4-tetrahydroisoquinoline (60 mg, 0.178 mmol) in DCM (10 mL) was added CuI (7 mg, 0.037 mmol) and the mixture was stirred for 5 min. Then ethyl 2-diazoacetate (61 mg, 0.535 mmol) in DCM (10 mL) was added dropwise slowly and the reaction was stirred at rt for overnight (18 h). The mixture was washed with water (10 mL×2) and extracted with DCM (30 mL×2). The extract was dried over by $Na_2SO_4$ and concentrated in vacuo. The residue was purified by silica gel PTLC (PE:EtOAc=10:1) to give the title compound.

Step E. 2-(2-(2-fluoro-5-(trifluoromethoxy)phenyl)-1,2,3,4-tetrahydroisoquinolin-6-yl)cyclopropanecarboxylic acid To a stirred solution of ethyl 2-(2-(2-fluoro-5-(trifluoromethoxy)phenyl)-1,2,3,4-tetrahydroisoquinolin-6-yl)cyclopropanecarboxylate (30 mg, 0.071 mmol) in THF (4 mL) and water (2 mL) was added $LiOH \cdot H_2O$ (6 mg, 0.143 mmol) and the mixture was stirred at rt for 2 h. The mixture was diluted with water and extracted with EtOAc (2+30 mL). The extract was dried ($Na_2SO_4$) filtered, and concentrated in vacuo. The residue was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm) followed by concentration (below 50° C.) to give the title compound. $^1$HNMR (400 MHz, $CDCl_3$) δ (400 MHz, ppm): 7.00-7.10 (m, 2H) 6.90-6.98 (m, 2H) 6.83 (d, J=6.65 Hz, 1H) 6.78 (d, J=8.61 Hz, 1H) 4.28 (s, 2H) 3.46 (t, J=5.67 Hz, 2H) 2.98 (t, J=5.09 Hz, 2H) 2.59 (br. s., 1H) 1.91 (br. s., 1H) 1.62-1.71 (m, 1H) 1.41 (d, J=3.52 Hz, 1H). m/z 369.1 [M+H]$^+$.

The examples in Table 3 were prepared from the appropriate starting materials described previously or commercially available starting materials available using procedures described in Examples 83-81.

TABLE 3

| Example | Structure | IUPAC Name | [M + H]+ |
|---|---|---|---|
| 85 | 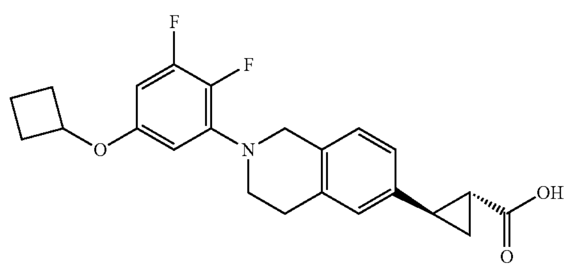 [SMILES: O=C(O)[C@@H]1C[C@H]1c1ccc2c(c1)CCN(c1cc(OC3CCC3)cc(F)c1F)C2] | (1R,2R)-2-{2-[5-(cyclobutyloxy)-2,3-difluorophenyl]-1,2,3,4-tetrahydroisoquinolin-6-yl}cyclopropane-carboxylic acid | 400.1 |
| 86 | 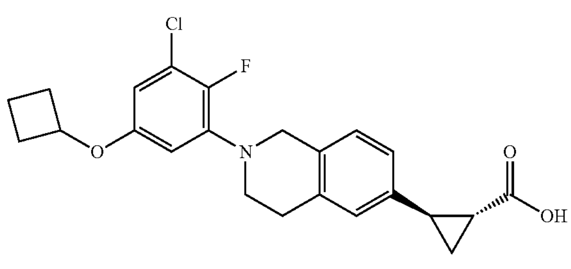 [SMILES: O=C(O)[C@@H]1C[C@H]1c1ccc2c(c1)CCN(c1cc(OC3CCC3)cc(Cl)c1F)C2] | (1R,2R)-2-{2-[3-chloro-5-(cyclobutyloxy)-2-fluorophenyl]-1,2,3,4-tetrahydroisoquinolin-6-yl}cyclopropanecarboxylic acid | 416.1 |
| 87 | 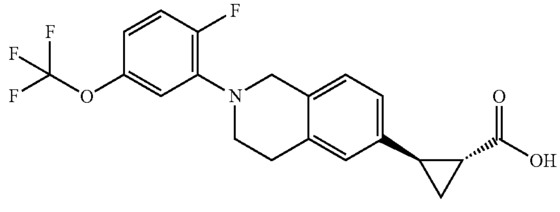 [SMILES: O=C(O)[C@@H]1C[C@H]1c1ccc2c(c1)CCN(c1cc(OC(F)(F)F)ccc1F)C2] | (1R,2R)-2-{2-[2-fluoro-5-(trifluoromethoxy)phenyl]-1,2,3,4-tetrahydroisoquinolin-6-yl}cyclopropane carboxylic acid | 396.1 |

TABLE 3-continued

| Example | Structure | IUPAC Name | [M + H]+ |
|---|---|---|---|
| 88 | 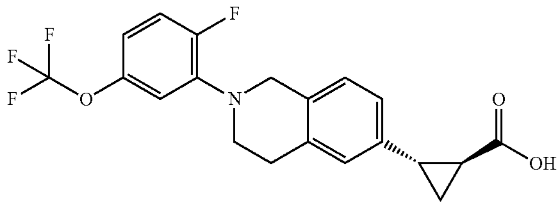 [SMILES: O=C(O)[C@H]1C[C@@H]1c1ccc2c(c1)CCN(c1cc(OC(F)(F)F)ccc1F)C2] | (1S,2S)-2-{2-[2-fluoro-5-(trifluoromethoxy)phenyl]-1,2,3,4-tetrahydroisoquinolin-6-yl}cyclopropane carboxylic acid | 396.1 |
| 89 | 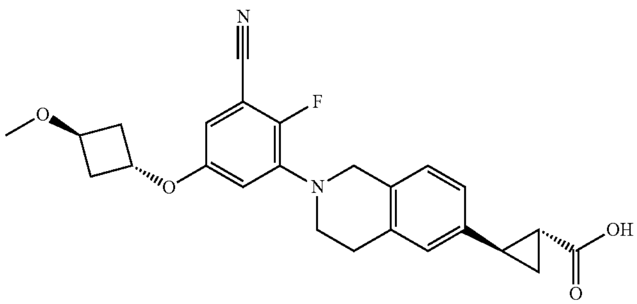 [SMILES: CO[C@H]1C[C@H](Oc2cc(C#N)c(F)c(N3CCc4cc([C@@H]5C[C@H]5C(=O)O)ccc4C3)c2)C1] | (1R,2R)-2-(2-{3-cyano-2-fluoro-5-[(trans-3-methoxycyclobutyl)oxy]phenyl}-1,2,3,4-tetrahydroisoquinolin-6-yl)cyclopropanecarboxylic acid | 437.2 |
| 90 | 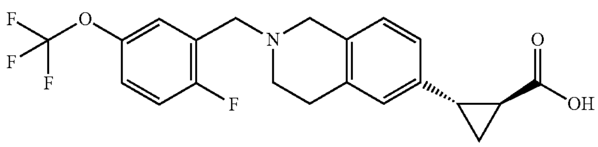 [SMILES: O=C(O)[C@H]1C[C@@H]1c1ccc2c(c1)CCN(Cc1cc(OC(F)(F)F)ccc1F)C2] | (1S,2S)-2-{2-[2-fluoro-5-(trifluoromethoxy)benzyl]-1,2,3,4-tetrahydroisoquinolin-6-yl}cyclopropane carboxylic acid | 410.4 |
| 91 | 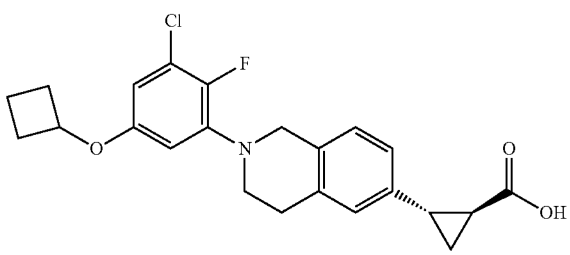 [SMILES: O=C(O)[C@H]1C[C@@H]1c1ccc2c(c1)CCN(c1cc(OC3CCC3)cc(Cl)c1F)C2] | (1S,2S)-2-{2-[3-chloro-5-(cyclobutyloxy)-2-fluorophenyl]-1,2,3,4-tetrahydroisoquinolin-6-yl}cyclopropane carboxylic acid | 416.1 |
| 92 | 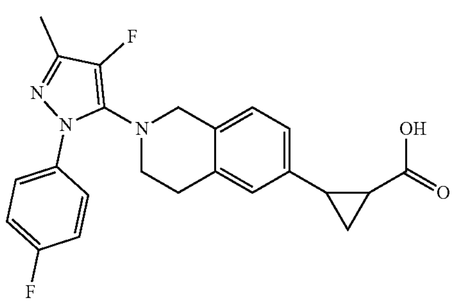 [SMILES: Cc1nn(-c2ccc(F)cc2)c(N2CCc3cc(C4CC4C(=O)O)ccc3C2)c1F] | 2-{2-[4-fluoro-1-(4-fluorophenyl)-3-methyl-1H-pyrazol-5-yl]-1,2,3,4-tetrahydroisoquinolin-6-yl}cyclo-propanecarboxylic acid | 410.1 |
| 93 | 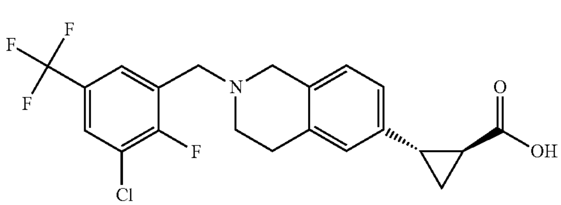 [SMILES: O=C(O)[C@H]1C[C@@H]1c1ccc2c(c1)CCN(Cc1cc(C(F)(F)F)cc(Cl)c1F)C2] | (1S,2S)-2-{2-[3-chloro-2-fluoro-5-(trifluoromethyl)benzyl]-1,2,3,4-tetrahydroisoquinolin-6-yl}cyclopropanecarboxylic acid | 428.1 |

TABLE 3-continued

| Example | Structure | IUPAC Name | [M + H]+ |
|---|---|---|---|
| 94 | 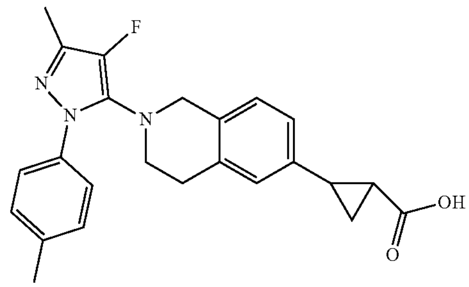 [SMILES: Cc1ccc(-n2nc(C)c(F)c2N2CCc3cc(C4CC4C(=O)O)ccc3C2)cc1] | 2-{2-[4-fluoro-3-methyl-1-(4-methylphenyl)-1H-pyrazol-5-yl]-1,2,3,4-tetrahydroisoquinolin-6-yl}cyclo-propanecarboxylic acid | 406.2 |
| 95 | 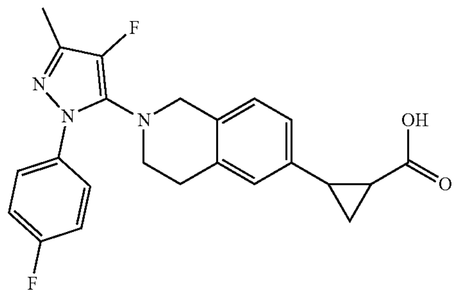 [SMILES: Cc1nn(-c2ccc(F)cc2)c(N2CCc3cc(C4CC4C(=O)O)ccc3C2)c1F] | 2-{2-[4-fluoro-1-(4-fluorophenyl)-3-methyl-1H-pyrazol-5-yl]-1,2,3,4-tetrahydroisoquinolin-6-yl}cyclo-propanecarboxylic acid | 410.1 |
| 96 | 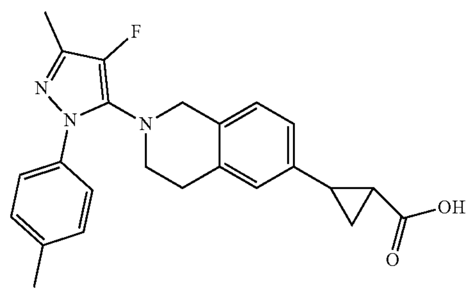 [SMILES: Cc1ccc(-n2nc(C)c(F)c2N2CCc3cc(C4CC4C(=O)O)ccc3C2)cc1] | 2-{2-[4-fluoro-3-methyl-1-(4-methylphenyl)-1H-pyrazol-5-yl]-1,2,3,4-tetrahydroisoquinolin-6-yl}cyclopropanecarboxylic acid | 406.2 |
| 97 | 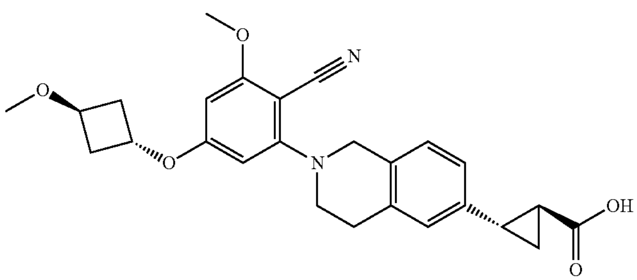 [SMILES: COc1cc(O[C@H]2C[C@H](OC)C2)cc(N2CCc3cc([C@H]4C[C@@H]4C(=O)O)ccc3C2)c1C#N] | (1S,2S)-2-(2-{2-cyano-3-methoxy-5-[(trans-3-methoxycyclobutyl)oxy]phenyl}-1,2,3,4-tetrahydroisoquinolin-6-yl)cyclopropanecarboxylic acid | 449.2 |
| 98 | 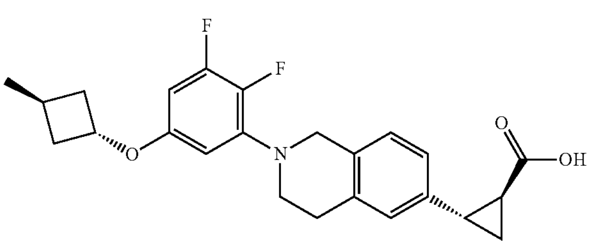 [SMILES: C[C@H]1C[C@H](Oc2cc(F)c(F)c(N3CCc4cc([C@H]5C[C@@H]5C(=O)O)ccc4C3)c2)C1] | (1S,2S)-2-(2-{2,3-difluoro-5-[(trans-3-methylcyclobutyl)oxy]phenyl}-1,2,3,4-tetrahydroisoquinolin-6-yl)-cyclopropanecarboxylic acid | 414.1 |

TABLE 3-continued

| Example | Structure | IUPAC Name | [M + H]+ |
|---|---|---|---|
| 99 | 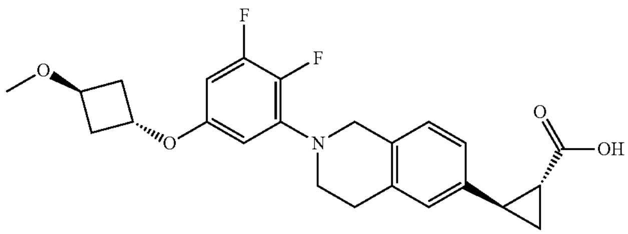 [SMILES: CO[C@H]1C[C@H](Oc2cc(F)c(F)c(N3CCc4cc([C@@H]5C[C@H]5C(=O)O)ccc4C3)c2)C1] | (1R,2R)-2-(2-{2,3-difluoro-5-[(trans-3-methoxycyclobutyl)oxy]phenyl}-1,2,3,4-tetrahydroisoquinolin-6-yl)-cyclopropanecarboxylic acid | 430.2 |
| 100 | 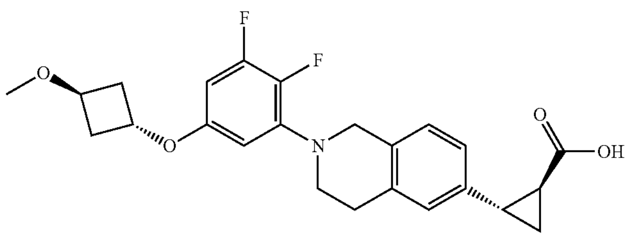 [SMILES: CO[C@H]1C[C@H](Oc2cc(F)c(F)c(N3CCc4cc([C@H]5C[C@@H]5C(=O)O)ccc4C3)c2)C1] | (1S,2S)-2-(2-{2,3-difluoro-5-[(trans-3-methoxycyclobutyl)oxy]phenyl}-1,2,3,4-tetrahydroisoquinolin-6-yl)-cyclopropanecarboxylic acid | 430.2 |
| 101 | 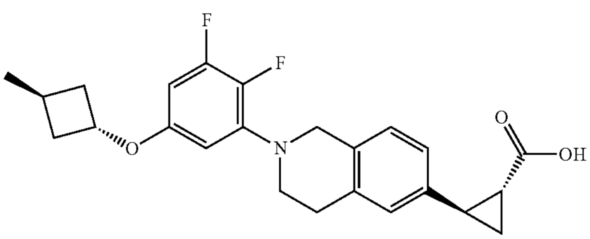 [SMILES: C[C@H]1C[C@H](Oc2cc(F)c(F)c(N3CCc4cc([C@@H]5C[C@H]5C(=O)O)ccc4C3)c2)C1] | (1R,2R)-2-(2-{2,3-difluoro-5-[(trans-3-methylcyclobutyl)oxy]phenyl}-1,2,3,4-tetrahydroisoquinolin-6-yl)-cyclopropanecarboxylic acid | 414.1 |
| 102 | 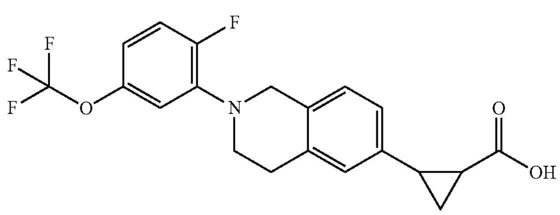 [SMILES: O=C(O)C1CC1c1ccc2c(c1)CCN(c1cc(OC(F)(F)F)ccc1F)C2] | 2-{2-[2-fluoro-5-(trifluoromethoxy)phnyl]-1,2,3,4-tetrahydroisoquinolin-6-yl}cyclopropanecarboxylic acid | 396.1 |
| 103 | 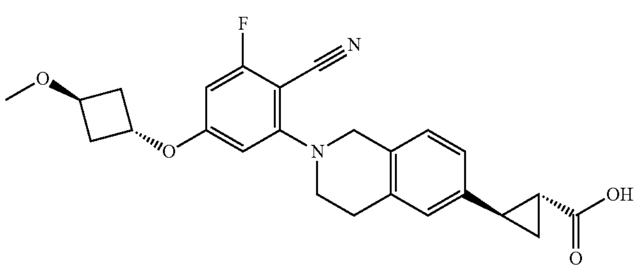 [SMILES: CO[C@H]1C[C@H](Oc2cc(F)c(C#N)c(N3CCc4cc([C@@H]5C[C@H]5C(=O)O)ccc4C3)c2)C1] | (1R,2R)-2-(2-{2-cyano-3-fluoro-5-[(trans-3-methoxycyclobutyl)oxy]phenyl}-1,2,3,4-tetrahydroisoquinolin-6-yl)cyclopropanecarboxylic acid | 437.1 |
| 104 | 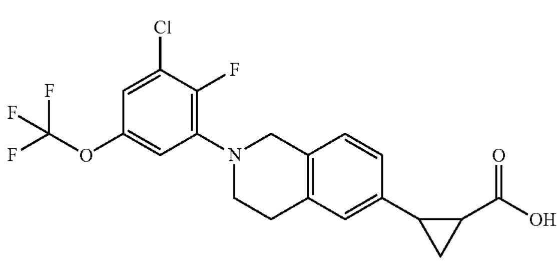 [SMILES: O=C(O)C1CC1c1ccc2c(c1)CCN(c1cc(OC(F)(F)F)cc(Cl)c1F)C2] | 2-{2-[3-chloro-2-fluoro-5-(trifluoromethoxy)phenyl]-1,2,3,4-tetrahydroisoquinolin-6-yl}cyclopropane-carboxylic acid | 430.1 |

TABLE 3-continued

| Example | Structure | IUPAC Name | [M + H]+ |
|---|---|---|---|
| 105 | 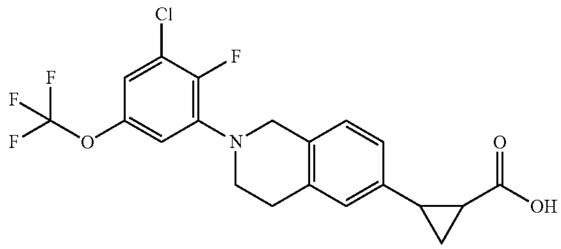 [SMILES: O=C(O)C1CC1c1ccc2c(c1)CCN(c1cc(OC(F)(F)F)cc(Cl)c1F)C2] | 2-{2-[3-chloro-2-fluoro-5-(trifluoro-methoxy)phenyl]-1,2,3,4-tetra-hydroisoquinolin-6-yl}cyclopropane-carboxylic acid | 430.1 |

Example 106

(1S,2S)-2-(2-(2,3-difluoro-5-((1r,3S)-3-methoxycyclobutoxy)phenyl)-5-fluoro-1,2,3,4-tetra-hydroisoquinolin-6-yl)cyclopropanecarboxylic acid

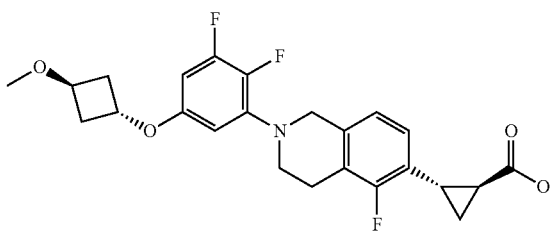

Step A. (1S,2S)-ethyl 2-(2-(2,3-difluoro-5-((1r,3S)-3-methoxycyclobutoxy) phenyl)-5-fluoro-1,2,3,4-tetrahydroisoquinolin-6-yl)cyclopropanecarboxylate To a solution of 2,3-difluoro-5-((1r,3r)-3-methoxycyclobutoxy)phenyl trifluoromethanesulfonate (200 mg, 0.552 mmol) and (1S,2S)-ethyl-2-(5-fluoro-1,2,3,4-tetrahydroisoquinolin-6-yl) cyclopropanecarboxylate (160 mg, 0.607 mmol) in 1,4-dioxane (10 ml) were added $Cs_2CO_3$ (540 mg, 1.656 mmol) and Ruphos-precatalyst (90 mg, 0.110 mmol). The mixture was stirred at 100° C. for 15 h under $N_2$. The mixture was filtered and concentrated in vacuo to give the crude product, which was purified by silica gel PTLC (PE:EA=5:1) to give the title compound. m/z 476.3 [M+H]+.

Step B. (1S,2S)-2-(2-(2,3-difluoro-5-((r,3S)-3-methoxycyclobutoxy)phenyl)-5-fluoro-1,2,3,4-tetra-hydroisoquinolin-6-yl)cyclopropanecarboxylic acid To a solution of (1S,2S)-ethyl2-(2-(2,3-difluoro-5-((1r,3S)-3-methoxycyclobutoxy)phenyl)-5-fluoro-1,2,3,4-tetrahydroisoquinolin-6-yl)cyclopropanecarboxylate (40 mg. 0.084 mmol) in MeOH (2 ml), THF (2 ml) and water (1 mL) was added LiOH hydrate (11 mg, 0.262 mmol), then the mixture was stirred at 20° C. for 15 h. The reaction mixture was acidified with 1N HCl to pH 5 and extracted with EtOAc (3×20 mL). The combined organic layers were washed with brine (10 mL), dried over $Na_2SO_4$, filtered and concentrated in vacuo. The residue was purified by reverse phase HPLC on a GILSON 281 instrument fitted with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detector wavelength: 220 nm), followed by concentration (below 50° C.) to obtain the title compound. $^1H$ NMR (400 MHz, $CDCl_3$) δ 6.77-6.87 (m, 1H), 6.13-6.22 (m, 1H), 4.71 (t, J=4.70 Hz, 1H), 4.24 (s, 2H), 4.07-4.14 (m, 1H), 3.45 (t, J=5.48 Hz, 2H), 3.27 (s, 3H), 2.92 (br. s., 2H), 2.71 (br. s., 1H), 2.33-2.45 (m, 4H), 1.87-1.95 (m, 1H), 1.61-1.70 (m, 1H), 1.38-1.48 (m, 1H); m, =448.2 [M+H]+.

Example 107

(1S,2S)-2-(2-(3-cyano-2-fluoro-5-(trifluoromethoxy)phenyl)-5-fluoro-1,2,3,4-tetrahydroisoquinolin-6-yl)cyclopropanecarboxylic acid

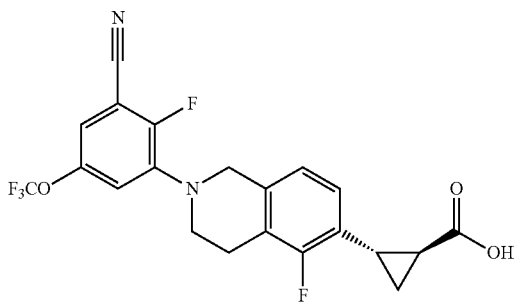 [SMILES: N#Cc1cc(OC(F)(F)F)cc(N2CCc3c(ccc([C@H]4C[C@@H]4C(=O)O)c3F)C2)c1F]

Step A. (1S,2S)-ethyl 2-(2-(3-cyano-2-fluoro-5-(trifluoromethoxy)phenyl)-5-fluoro-1,2,3,4-tetrahydroisoquinolin-6-yl)cyclopropanecarboxylate To a solution of (1S, 2S)-ethyl 2-(5-fluoro-1,2,3,4-tetrahydroisoquinolin-6-yl)cyclopropanecarboxylate (200 mg, 0.760 mmol) in 1,4-dioxane (20 mL) was added $Cs_2CO_3$ (495 mg, 1.519 mmol), 3-bromo-2-fluoro-5-(trifluoromethoxy)benzonitrile (Intermediate 44, 350 mg, 1.232 mmol), $Pd_2(dba)_3$ (696 mg, 0.760 mmol) and XANTPHOS (440 mg, 0.760 mmol). The mixture was stirred at 100° C. under $N_2$ overnight (15 h). The mixture was filtered, concentrated under vacuum and dissolved with EtOAc (2×50 mL). The combined organic layer was washed with brine (2×30 mL), and then dried over $Na_2SO_4$, filtered and concentrated in vacuo to give crude (1S,2S)-ethyl 2-(2-(3-cyano-2-fluoro-5-(trifluoro-methoxy)-phenyl)-5-fluoro-1,2, 3,4-tetra-hydroisoquinolin-6-yl)cyclopropanecarboxylate. The crude product was purified by silica gel chromatography (PE/EtOAc 30:1-20:1) to give the title compound.

Step B. (S,2S)-2-(2-(3-cyano-2-fluoro-5-(trifluoromethoxy)phenyl)-5-fluoro-1,2,3,4-tetrahydroisoquinolin-6-yl)cyclopropanecarboxylic acid To a solution of (1S,2S)-ethyl 2-(2-(3-cyano-2-fluoro-5-(trifluoromethoxy)phenyl)-5-fluoro-1,2,3,4-tetrahydroisoquinolin-6-yl)cyclopropanecarboxylate (88 mg, 0.189 mmol) in THF (5 mL) and water (2.5 mL) was added LiOH.H$_2$O (20 mg, 0.477 mmol) and the mixture was stirred at 20° C. for 15 h. The mixture was concentrated in vacuo to give crude product. The crude product was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) followed by concentration (below 50° C.) to give the title compound. $^1$HNMR (400 MHz, CH$_3$OD) δ ppm 7.31-7.22 (m, 2H) 6.99-6.86 (m, 2H) 4.35 (s, 2H) 3.54 (t, J=5.77 Hz, 2H) 3.00-2.90 (m, 2H) 2.62-2.52 (m, 1H) 1.90-1.75 (m, 1H) 1.52 (dt, J=9.29, 4.89 Hz, 1H) 1.44-1.36 (m, 1H). MS (ESI) m/z 439.1 (M+H)$^+$.

Example 108

(1S,2S)-2-(2-(2,3-difluoro-5-((1r,3S)-3-methylcyclobutoxy)phenyl)-5-fluoro-1,2,3,4-tetra-hydroisoquinolin-6-yl)cyclopropanecarboxylic acid

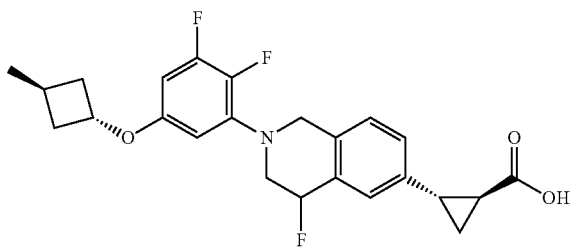 [SMILES: C[C@H]1C[C@H](Oc2cc(F)c(F)c(N3Cc4ccc([C@H]5C[C@@H]5C(=O)O)cc4C(F)C3)c2)C1]

Step A-(1S,2S)-ethyl 2-(2-(2,3-difluoro-5-((1R,3S)-3-methylcyclobutoxy)phenyl)-5-fluoro-1,2,3,4-tetrahydroisoquinolin-6-yl)cyclopropanecarboxylate To a solution of 2,3-difluoro-5-((1R,3R)-3-methylcyclobutoxy)phenyl trifluoromethanesulfonate (Intermediate 9, 200 mg, 0.578 mmol) in dioxane (5 mL) were added 2-(((S,2S)-2-(5-fluoro-1,2,34-tetra-hydroisoquinolin-6-yl)cyclopropanecarbonyl)oxy)ethan-1-ylium (167 mg, 0.635 mmol), Cs$_2$CO$_3$ (565 mg, 1.733 mmol) and RUPHOS precatalyst (94 mg, 0.116 mmol). After the addition was complete, the mixture was stirred at 90° C. for 15 h. The mixture was filtered and filtrate was diluted with water (30 ml), and extracted with EtOAc (3×30 mL). The combined organic layer was concentrated in vacuo and the residue was purified by silica gel PTLC (PE:EtOAc=10:1), to give the title compound. m/z 460.1 [M+1]$^+$.

Step-B. (1S,2S)-2-(2-(2,3-difluoro-5-((r,3S)-3-methylcyclobutoxy)phenyl)-5-fluoro-1,2,3,4-tetrahydroisoquinolin-6-yl)cyclopropanecarboxylic acid To a solution of (1S,2S)-ethyl 2-(2-(2,3-difluoro-5-((1r,3S)-3-methylcyclobutoxy)phenyl)-5-fluoro-1,2,3,4-tetrahydroisoquinolin-6-yl)cyclopropanecarboxylate (20 mg, 0.038 mmol) in MeOH (2 mL), THF (2 mL) and water (1 mL) was added LiOH hydrate (10 mg, 0.238 mmol). After the addition was complete, the mixture was stirred at rt for 15 h. The mixture was acidified by hydrochloride acid (1N) to pH-2, and concentrated in vacuo to give crude product, which was purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detector wavelength: 220 nm) then freeze dried to afford the title compound. $^1$H NMR (400 MHz, CDCl$_3$) δ 6.76-6.88 (m, 2H), 6.14-6.25 (m, 2H), 4.66 (dt, J=12.42, 6.11 Hz, 1H), 4.25 (s, 2H), 3.45 (t, J=5.67 Hz, 2H), 2.89-2.97 (m, 2H), 2.72 (t, J=9.78 Hz, 1H), 2.46 (br. s., 1H), 2.25-2.33 (m, 2H), 2.03-2.10 (m, 2H), 1.91 (dt, J=8.22, 4.50 Hz, 1H), 1.66 (dt, J=9.29, 4.55 Hz. 1H), 1.39-1.47 (m, 1H), 1.13-1.23 (m, 3H); m/z 432.4 [M+1]$^+$.

The examples in Table 4 were prepared from the appropriate starting materials described previously or commercially available starting materials available using procedures described in Examples 106-108.

TABLE 4

| Example | Structure | Name | [M + H]$^+$ |
|---------|-----------|------|-------------|
| 109 | 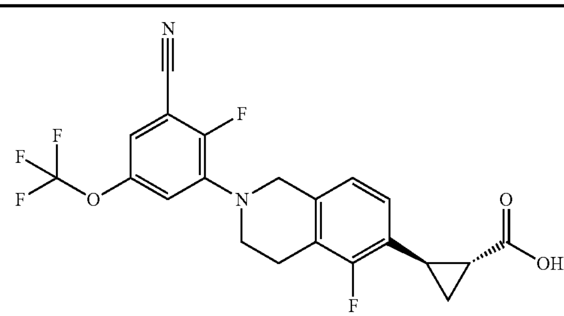 | (1R,2R)-2-{2-[3-cyano-2-fluoro-5-(trifluoromethoxy)phenyl]-5-fluoro-1,2,3,4-tetrahydroisoquinolin-6-yl}cyclopropane-carboxylic acid | 439.1 |

TABLE 4-continued

| Example | Structure | Name | [M + H]+ |
|---|---|---|---|
| 110 | 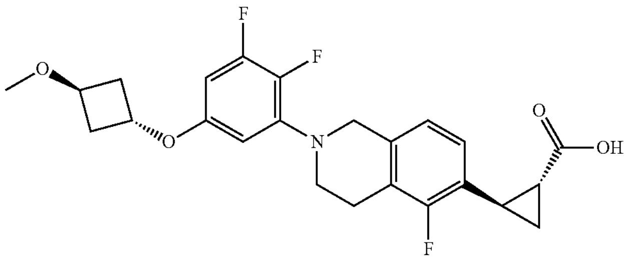 [SMILES: CO[C@H]1C[C@H](Oc2cc(F)c(F)c(N3CCc4c(ccc([C@@H]5C[C@H]5C(=O)O)c4F)C3)c2)C1] | (1R,2R)-2-(2-{2,3-difluoro-5-[(trans-3-methoxycyclobutyl)oxy]phenyl}-5-fluoro-1,2,3,4-tetrahydroisoquinolin-6-yl)-cyclopropanecarboxylic acid | 448.2 |
| 111 | 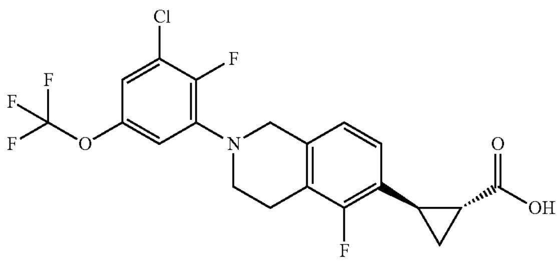 | (1R,2R)-2-{2-[3-chloro-2-fluoro-5-(trifluoromethoxy)-phenyl]-5-fluoro-1,2,3,4-tetrahydroisoquinolin-6-yl}cyclopropanecarboxylic acid | 448.0 |
| 112 | 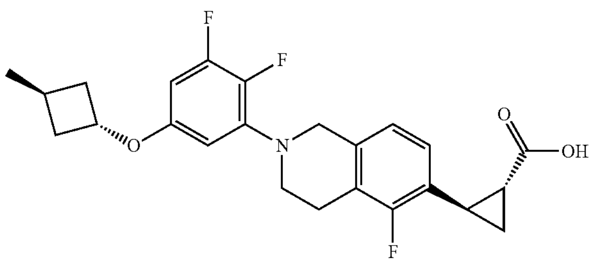 [SMILES: C[C@H]1C[C@H](Oc2cc(F)c(F)c(N3CCc4c(ccc([C@@H]5C[C@H]5C(=O)O)c4F)C3)c2)C1] | (1R,2R)-2-(2-{2,3-difluoro-5-[(trans-3-methylcyclobutyl)oxy]phenyl}-5-fluoro-1,2,3,4-tetrahydroisoquinolin-6-yl)cyclopropanecarboxylic acid | 432.4 |
| 113 | 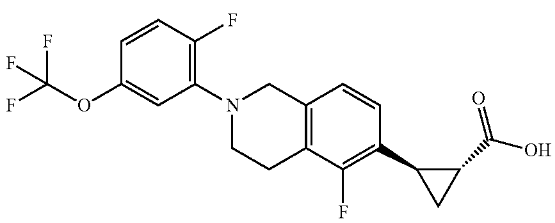 [SMILES: O=C(O)[C@@H]1C[C@H]1c1ccc2c(c1F)CCN(c1cc(OC(F)(F)F)ccc1F)C2] | (1R,2R)-2-{5-fluoro-2-[2-fluoro-5-(trifluoromethoxy)phenyl-1,2,3,4-tetrahydroisoquinolin-6-yl}cyclopropane-carboxylic acid | 414.1 |
| 114 | 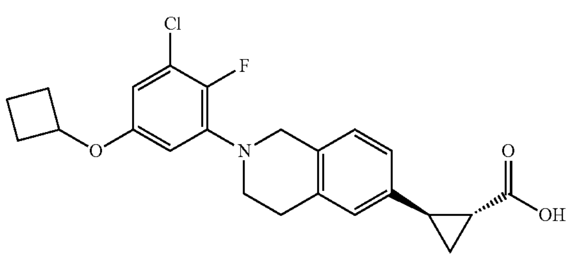 [SMILES: O=C(O)[C@@H]1C[C@H]1c1ccc2c(c1)CCN(c1cc(OC3CCC3)cc(Cl)c1F)C2] | (1R,2R)-2-{2-[3-chloro-5-(cyclobutyloxy)-2-fluorophenyl]-1,2,3,4-tetrahydroisoquinolin-6-yl}cyclopropanecarboxylic acid | 416.1 |
| 115 | 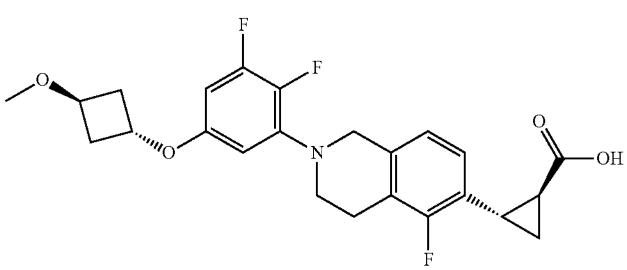 [SMILES: CO[C@H]1C[C@H](Oc2cc(F)c(F)c(N3CCc4c(ccc([C@H]5C[C@@H]5C(=O)O)c4F)C3)c2)C1] | (1S,2S)-2-(2-{2,3-difluoro-5-[(trans-3-methoxycyclobutyl)oxy]phenyl}-5-fluoro-1,2,3,4-tetrahydroisoquinolin-6-yl)-cyclopropanecarboxylic acid | 448.2 |

TABLE 4-continued

| Example | Structure | Name | [M + H]+ |
|---|---|---|---|
| 116 | 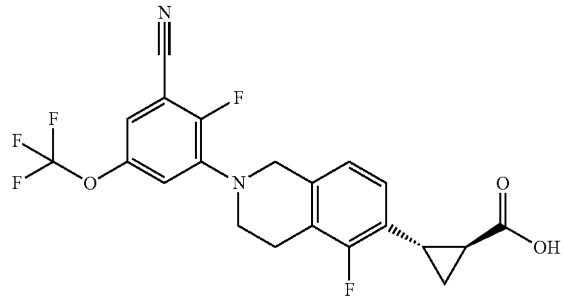 [SMILES: N#Cc1cc(OC(F)(F)F)cc(N2CCc3c(ccc([C@H]4C[C@@H]4C(=O)O)c3F)C2)c1F] | (1S,2S)-2-{2-[3-cyano-2-fluoro-5-(trifluoromethoxy)phenyl]-5-fluoro-1,2,3,4-tetrahydroisoquinolin-6-yl}cyclopropanecarboxylic acid | 439.1 |
| 117 | 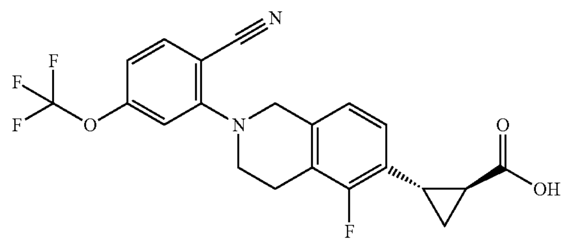 [SMILES: N#Cc1ccc(OC(F)(F)F)cc1N1CCc2c(ccc([C@H]3C[C@@H]3C(=O)O)c2F)C1] | (1S,2S)-2-{2-[2-cyano-5-(trifluoromethoxy)phenyl]-5-fluoro-1,2,3,4-tetrahydroisoquinolin-6-yl}cyclopropane-carboxylic acid | 421.1 |
| 118 | 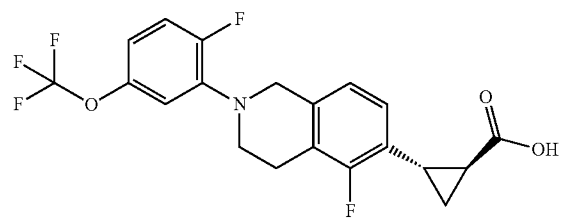 [SMILES: O=C(O)[C@H]1C[C@@H]1c1ccc2c(c1F)CCN(c1cc(OC(F)(F)F)ccc1F)C2] | (1S,2S)-2-{5-fluoro-2-[2-fluoro-5-(trifluoromethoxy)phenyl]-1,2,3,4-tetrahydroisoquinolin-6-yl}cyclopropane-carboxylic acid | 414.1 |
| 119 | 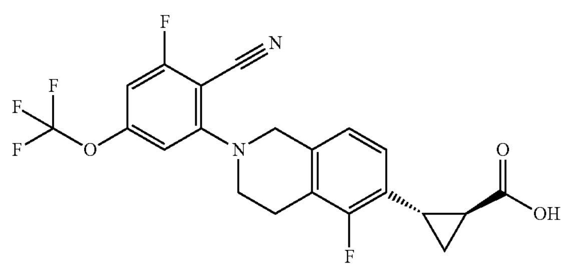 [SMILES: N#Cc1c(F)cc(OC(F)(F)F)cc1N1CCc2c(ccc([C@H]3C[C@@H]3C(=O)O)c2F)C1] | (1S,2S)-2-{2-[2-cyano-3-fluoro-5-(trifluoromethoxy)phenyl]-5-fluoro-1,2,3,4-tetrahydroisoquinolin-6-yl}cyclopropane-carboxylic acid | 439.0 |
| 120 | 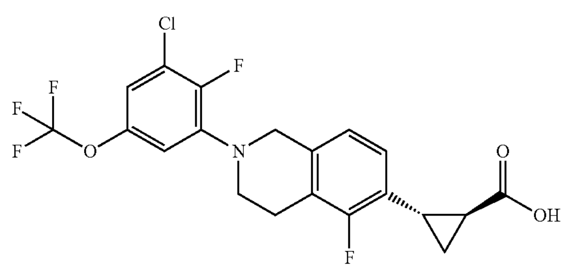 | (1S,2S)-2-{2-[3-chloro-2-fluoro-5-(trifluoromethoxy)phenyl]-5-fluoro-1,2,3,4-tetrahydroisoquinolin-6-yl}cyclopropane-carboxylic acid | 448.0 |
| 121 | 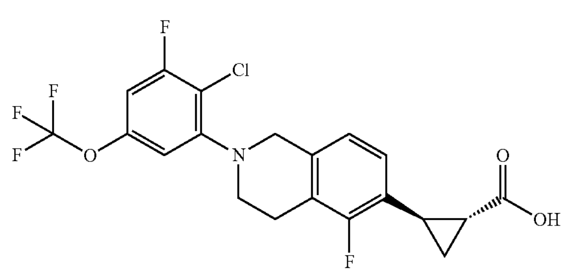 [SMILES: O=C(O)[C@@H]1C[C@H]1c1ccc2c(c1F)CCN(c1cc(OC(F)(F)F)cc(F)c1Cl)C2] | (1R,2R)-2-{2-[2-chloro-3-fluoro-5-(trifluoromethoxy)phenyl]-5-fluoro-1,2,3,4-tetrahydroisoquinolin-6-yl}cyclopropanecarboxylic acid | 448.0 |

TABLE 4-continued

| Example | Name | [M + H]+ |
|---|---|---|
| 122 | (1S,2S)-2-(2-{2,3-difluoro-5-[(trans-3-methylcyclobutyl)oxy]phenyl}-5-fluoro-1,2,3,4-tetrahydro-isoquinolin-6-yl)cyclopropane-carboxylic acid | 432.4 |
| 123 | (1R,2R)-2-{2-[3-chloro-5-(cyclobutyloxy)-2-fluorophenyl]-5-fluoro-1,2,3,4-tetrahydroisoquinolin-6-yl}cyclopropane-carboxylic acid | 434.1 |
| 124 | (1S,2S)-2-{2-[2-chloro-3-fluoro-5-(trifluoromethoxy)phenyl]-5-fluoro-1,2,3,4-tetrahydro-isoquinolin-6-yl}cyclopropane-carboxylic acid | 448.0 |
| 125 | (1S,2S)-2-{2-[3-chloro-5-(cyclobutyloxy)-2-fluorophenyl]-5-fluoro-1,2,3,4-tetrahydroisoquinolin-6-yl}cyclopropane-carboxylic acid | 434.1 |
| 126 | (1S,2S)-2-{2-[2-cyano-5-(cyclobutyloxy)-3-fluorophenyl]-5-fluoro-1,2,3,4-tetrahydroiso-quinolin-6-yl}cyclopropane-carboxylic acid | 425.1 |

Example 127

5-(2-(4-cyano-3-methyl-1-(p-tolyl)-1H-pyrazol-5-yl)-1,2,3,4-tetrahydro-isoquinolin-6-yl)pentanoic acid

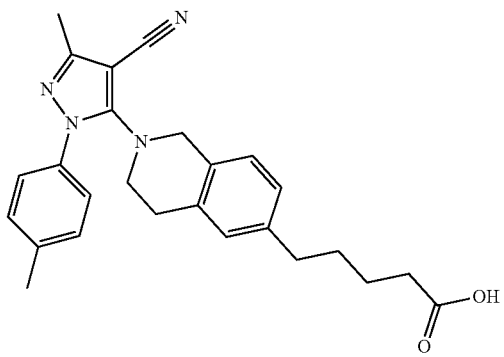 [SMILES: Cc1ccc(-n2nc(C)c(C#N)c2N2CCc3cc(CCCCC(=O)O)ccc3C2)cc1]

Step A. 2-(tert-butyl) 6-methyl 3,4-dihydroisoquinoline-2,6(1H)-dicarboxylate A stirred mixture of tert-butyl 6-bromo-3,4-dihydroisoquinoline-2(1H)-carboxylate (21 g, 67.5 mmol) in MeOH (300 mL), was added Pd(dppf)Cl$_2$ (4.9 g, 6.75 mmol) and TEA (20.45 g, 202 mmol). The mixture was stirred at 110° C. for 48 h under high pressure CO (2 MPa). Then the catalyst and salt were filtered off and the filtrate was concentrated in vacuo, followed by purification by silica gel chromatography (PE/EtOAc=50:1 to 6:1) to afford the title compound.

Step B. tert-butyl 6-(hydroxymethyl)-3,4-dihydroisoquinoline-2(1H)-carboxylate A solution of 2-tert-butyl 6-methyl 3,4-dihydroisoquinoline-2,6(1H)-dicarboxylate (15 g, 51.5 mmol) in THF (80 mL) was added dropwise to a solution of LAH (2.94 g, 77.32 mmol) in THF (80 mL) at −78° C. The reaction mixture was stirred at −78° C. for 2 h. The mixture was quenched with H$_2$O, dried over Na$_2$SO$_4$, filtered and concentrated in vacuo. The residue was purified by silica gel chromatography (PE/EtOAc=20:1∼3:1) to give the title compound.

Step C. Tert-butyl 6-formyl-3,4-dihydroisoquinoline-2(1H)-carboxylate

A stirred mixture of tert-butyl 6-(hydroxymethyl)-3,4-dihydroisoquinoline-2(1H)-carboxylate (8.0 g, 30.4 mmol) in DCM (100 mL) was added MnO$_2$(21.2 g, 243.8 mmol). The mixture was stirred under reflux for 16 h. The mixture was filtered and concentrated in vacuo, the crude product was purified by silica gel chromatography (PE/:EtOAc=100:1-10:1) to afford the title compound.

Step D. 6-formyl-3,4-dihydroisoquinoline-2(1H)-carboxylate

A solution of tert-butyl-6-formyl-3,4-dihydroisoquinoline-2(1H)-carboxylate (1.044 mg, 4 mmol) in HCl-MeOH (50 mL) was stirred under reflux for 16 h. The mixture was evaporated to obtain the title compound.

Step E. 5-(6-formyl-3,4-dihydroisoquinolin-2(1H)-yl)-3-methyl-1-(p-tolyl)-1H-pyrazole-4-carbonitrile To a solution of methyl 1,2,3,4-tetrahydroisoquinoline-6-carboxylate (197 mg, 1 mmol), in 1,4-dioxane was added 5-iodo-3-methyl-1-(p-tolyl)-1H-pyrazole-4-carbonitrile (323 mg, 1 mmol), Pd$_2$(dba)$_3$ (92 mg, 0.1 mmol), XANTPHOS (173 mg, 0.3 mmol) and Cs$_2$CO$_3$(815 mg, 3 mmol). The reaction mixture was stirred under N$_2$ and heated to 100° C. for 15 h. The mixture was quenched with H$_2$O, then extracted with EtOAc, the organic layer was washed with brine, dried over Na$_2$SO$_4$, concentrated in vacuo an purified by silica gel PTLC (PE:EA=3:1) to give the title compound.

Step F. (2E,4E)-methyl 5-(2-(4-cyano-3-methyl-1-(p-tolyl)-1H-pyrazol-5-yl)-1,2,3,4-tetra-hydroisoquinolin-6-yl)penta-2,4-dienoate A stirred mixture of ethyl methyl 4-(diethoxyphosphoryl)but-2-enoate (53 mg, 0.21 mmol) in THF (2 mL) was added NaH (12 mg, 0.28 mmol) at 0° C. The mixture was stirred for at 0° C. for 45 min, and then 5-(6-formyl-3,4-dihydroisoquinolin-2(1H)-yl)-3-methyl-1-(p-tolyl)-1H-pyrazole-4-carbonitrile (68 mg, 0.19 mmol) was added. The mixture was stirred at rt for 15 h. The mixture was poured into a solution of sat. NH$_4$Cl (10 mL) and extracted with EtOAc (10 mL×3). The organic layer was separated, washed with brine, dried and evaporated to obtain the title compound.

Step G. Methyl 5-(2-(4-cyano-3-methyl-1-(p-tolyl)-1H-pyrazol-5-yl)-1,2,3,4-tetra-hydroisoquinolin-6-yl)pentanoate To a stirred mixture of (2E,4E)-methyl 5-(2-(4-cyano-3-methyl-1-(p-tolyl)-1H-pyrazol-5-yl)-1,2,3,4-tetrahydro-isoquinolin-6-yl)penta-2,4-dienoate (80 mg, 0.182 mmol) in DCM (4 mL) was added Pd/C (20 mg). The reaction was stirred under a hydrogen atmosphere at room temperature for 6 hours. Then the reaction mixture was filtered and concentrated in vacuo to obtain the title compound.

Step H. 5-(6-formyl-3,4-dihydroisoquinolin-2(1H)-yl)-3-methyl-1-(p-tolyl)-1H-pyrazole-4-carbonitrile-5-(2-(4-cyano-3-methyl-1-(p-tolyl)-1H-pyrazol-5-yl)-1,2,3,4-tetrahydroisoquinolin-6-yl)pentanoic acid To a solution of methyl 5-(2-(4-cyano-3-methyl-1-(p-tolyl)-1H-pyrazol-5-yl)-1,2,3,4-tetrahydroisoquinolin-6-yl)pentanoate (70 mg, 0.160 mmol) in THF (2 mL), MeOH (2 mL) and (1 mL) was added LiOH.H$_2$O (44 mg, 0.8 mmol). The reaction mixture was stirred at rt overnight. The mixture was acidified with HCl, and then extracted with EtOAc. The organic layer was separated, and evaporated to give the crude product, which was purified by reverse phase HPLC on a GILSON 281 instrument fitted with a Phenomenex Synergi C18 (250*21.2 mm*4 μm) using water (0.2% Formic acid) and CH$_3$CN as eluents (Mobile phase A: water (0.2% Formic acid), Mobile phase B: CH$_3$CN. Detective wavelength: 220 nm) followed by concentration (below 50° C.) to obtain the title compound. $^1$H NMR (400 MHz, CDCl$_3$) δ=7.44 (d, J=8.2 Hz, 2H), 7.22 (d, J=8.2 Hz, 2H), 7.05-6.79 (m, 3H). 4.43 (s, 2H), 3.36 (t, J=5.9 Hz, 2H), 2.75

(t, J=5.5 Hz, 2H), 2.63-2.51 (m, 2H), 2.36 (d, J=11.7 Hz, 8H), 1.67 (d, J=3.1 Hz, 4H). m/z 439.2 [M+H]$^+$.

Example 128

5-(2-(4-cyano-3-methyl-1-(p-tolyl)-1H-pyrazol-5-yl)-1,2,3,4-tetrahydro-isoquinolin-6-yl)hexanoic acid

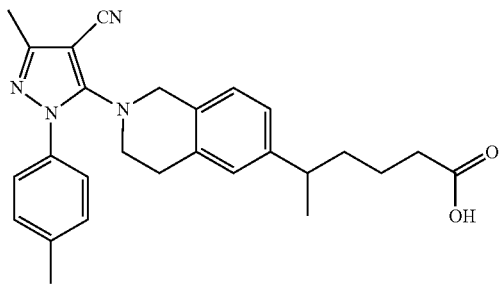 [SMILES: Cc1ccc(-n2nc(C)c(C#N)c2N2CCc3cc(C(C)CCCC(=O)O)ccc3C2)cc1]

Step A. tert-butyl 6-(((trifluoromethyl)sulfonyl)oxy)-3,4-dihydroisoquinoline-2(1H)-carboxylate To a solution of pyridine (16.22 ml, 201 mmol) and tert-butyl 6-hydroxy-3,4-dihydroisoquinoline-2(1H)-carboxylate (50.0 g, 201 mmol) in DCM (600 ml), Tf$_2$O (33.9 ml, 201 mmol) was added dropwise at 0° C. and the mixture was stirred at 0° C. for 1 h. The reaction mixture was diluted with DCM (800 mL), washed with water (2×200 mL) and brine (2×200 mL). The organic solution was dried, filtered, concentrated in vacuo and purified by silica gel chromatography (PE:EtOAc=80:1-10:1) to give the title compound.

Step B. 1-(1,2,3,4-tetrahydroisoquinolin-6-yl)ethanone hydrochloride

To a solution of 1-(vinyloxy)butane (1.576 g. 15.73 mmol), tert-butyl 6-(((trifluoromethyl)sulfonyl)oxy)-3,4-dihydroisoquinoline-2(1H)-carboxylate (1.0 g, 2.62 mmol) in DMF (15 ml) was added Pd(OAc)2 (0.059 g, 0.262 mmol) and 1,3-bis(diphenylphosphino)propane (0.108 g, 0.262 mmol), the mixture was stirred at 80° C. for 15 h. The reaction was quenched with water (25 mL), extracted with EtOAc (3×45 mL). The organic layer was separated, washed with water (3×25 mL) and brine (3×25 mL), concentrated and purified by silica gel chromatography (PE:EtOAc=20: 1~5:1) to give tert-butyl 6-acetyl-3,4-dihydroisoquinoline-2 (1H)-carboxylate. A solution of tert-butyl 6-acetyl-3,4-dihydroisoquinoline-2(1H)-carboxylate (0.5 g, 1.816 mmol) in HCl-MeOH (15 ml) was stirred at 20° C. for 1 h. Then the reaction mixture was concentrated to give the crude title compound, which was used directly in the next step without further purification.

Step C. 5-(6-acetyl-3,4-dihydroisoquinolin-2(1H)-yl)-3-methyl-1-(p-tolyl)-1H-pyrazole-4-carbonitrile A solution of potassium fluoride (0.663 g, 11.41 mmol), 5-iodo-3-methyl-1-(p-tolyl)-1H-pyrazole-4-carbonitrile (1.844 g, 5.71 mmol) and 1-(1,2,3,4-tetrahydroisoquinolin-6-yl)ethanone (1.00 g, 5.71 mmol) in DMSO (15 ml) was stirred at 110° C. for 15 h. The reaction was quenched with water, extracted with EtOAc (3×30 mL). The organic layers were washed with water (2×15 mL) and brine (2×15 mL), dried over Na$_2$SO$_4$ and filtered. The filtrate was concentrated in vacuo and purified by silica gel chromatography (PE: EtOAc=30:1-3:1) to give the title compound.

Step D. (2E,4E)-methyl 5-(2-(4-cyano-3-methyl-1-(p-tolyl)-1H-pyrazol-5-yl)-1,2,3,4-tetrahydroisoquinolin-6-yl)hexa-2,4-dienoate To a suspension of NaH (52 mg, 1.300 mmol) in THF (3 ml) was added (E)-methyl 4-(dimethoxyphosphoryl)but-2-enoate (270 mg, 1.296 mmol) at 0° C., and the mixture was stirred at 0° C. for 0.5 h. Then a solution of 5-(6-acetyl-3, 4-dihydroisoquinolin-2(1H)-yl)-3-methyl-1-(p-tolyl)-1H-pyrazole-4-carbonitrile (400 mg, 1.080 mmol) in THF (3 mL) was added dropwise to the above mixture. The reaction mixture was stirred at 0-20° C. for 6 h. The reaction was quenched with a solution of sat. NH$_4$Cl, extracted with EtOAc (3×25 mL). The combined organic layers were washed with water (2×15 mL) and brine (2×15 mL), concentrated in vacuo and purified by silica gel chromatography (PE:EtOAc=20:1~5:1) to give the title compound.

Step E. (2E,4E)-5-(2-(4-cyano-3-methyl-1-(p-tolyl)-1H-pyrazol-5-yl)-1,2,3,4-tetrahydroisoquinolin-6-yl)hexa-2,4-dienoic acid To a solution of (2E,4E)-methyl-5-(2-(4-cyano-3-methyl-1-(p-tolyl)-1H-pyrazol-5-yl)-1,2,3,4-tetrahydroisoquinolin-6-yl) hexa-2,4-dienoate (200 mg, 0.442 mmol) and LiOH hydrate (56 mg, 1.334 mmol) in THF (2.0 ml)/MeOH (2.0 ml)/Water (2.0 ml). The reaction mixture was stirred at 20° C. for 3 h. Then the reaction mixture was concentrated to give a residue, which was diluted with HCl (1 N, 5 mL) and extracted with EtOAc (3×15 mL). The combined organic layers were washed with water (2×5 mL) and brine (2×5 mL). The organic solution was dried over Na$_2$SO$_4$, filtered, and the filtrate was concentrated to give the title compound.

Step F. 5-(2-(4-cyano-3-methyl-1-(p-tolyl)-1H-pyrazol-5-yl)-1,2,3,4-tetrahydro-isoquinolin-6yl) hexanoic acid To a solution of (2E,4E)-5-(2-(4-cyano-3-methyl-1-(p-tolyl)-1H-pyrazol-5-yl)-1,2,3,4-tetrahydro-isoquinolin-6-yl) hexa-2,4-dienoic acid (180 mg, 0.410 mmol) in MeOH (5 ml) was added Pd—C (20 mg, 0.188 mmol), and the reaction was stirred at 10° C. for 15 h under H$_2$ balloon. The reaction mixture was filtered, the organic layer was concentrated in vacuo to give a residue, which was purified by reverse phase HPLC on a GILSON 281 instrument fitted with a Phenomenex Synergi C18 (250*21.2 mm*4 μm) using water (0.2% Formic acid) and CH$_3$CN as eluents (Mobile phase A: water (0.2% Formic acid), Mobile phase B: CH$_3$CN, Detective wavelength: 220 nm) followed by concentration to give to give the title compound as a racemic mixture. The enantiomers of 5-(2-(4-cyano-3-methyl-1-(p-tolyl)-1H-pyrazol-5-yl)-1,2,3,4-tetrahydro-isoquinolin-6-yl)-hexanoic acid (160 mg) were purified by SFC (Instrument: MG-II; Column: Chiralcel OJ 250×30 mm I.D., 5 um; Mobile phase: Supercritical CO$_2$/MeOH (0.1%) NH$_3$.H$_2$O=75/25 at 60 mL/min; Column Temp: 38° C.: Nozzle Pressure: 100 Bar; Nozzle Temp: 60° C.: Evaporator Temp: 20° C.; Trimmer Temp: 25° C.: Wavelength: 220 nm) to yield (R)-5-(2-(4-cyano-3-methyl-1-(p-tolyl)-1H-pyrazol-5-yl)-1,2,3,4-tetrahydroiso-quinolin-6-yl)hexanoic acid, and (S)-5-(2-(4- cyano-3-methyl-1-(p-tolyl)-1H-pyrazol-5-yl)-1,2,3,4-tetra-hydro-isoquinolin-6-yl)hexanoic acid. ¹H NMR (400 MHz, CDCl₃) δ (400 MHz, ppm): 7.43 (d, J=8.2 Hz, 2H), 7.21 (d, J=8.2 Hz, 2H), 7.00-6.91 (m, 2H), 6.88 (s, 1H), 4.43 (s, 2H), 3.34 (t, J=5.7 Hz, 2H), 2.74 (t, J=5.3 Hz, 2H), 2.68-2.57 (m, 1H), 2.37 (s, 3H), 2.34 (s, 3H), 2.32-2.25 (m, 2H), 1.64-1.42 (m, 4H), 1.20 (d, J=7.0 Hz, 3H). ESI MS m/z 443.1 [M+H]+.
¹H NMR (400 MHz, CDCl₃) δ (400 MHz, ppm): 7.44 (d, J=8.2 Hz, 2H), 7.21 (d, J=8.2 Hz, 2H), 6.99-6.92 (m, 2H), 6.88 (s, 1H), 4.43 (s, 2H), 3.35 (t, J=5.7 Hz, 2H), 2.74 (t, J=5.3 Hz, 2H), 2.68-2.56 (m, 1H), 2.37 (s, 3H), 2.34 (s, 3H), 2.32-2.26 (m, 2H), 1.66-1.42 (m, 4H), 1.21 (d, J=7.0 Hz, 3H). ESI MS m/z 443.1 [M+H]⁺.

Example 129

5-(6-hydroxy-3,4-dihydroisoquinolin-2(1H)-yl)-3-methyl-1-(p-tolyl)-1H-pyrazole-4-carbonitrile

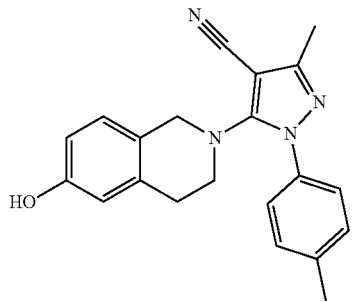 [SMILES: Cc1ccc(-n2nc(C)c(C#N)c2N2CCc3cc(O)ccc3C2)cc1]

Step A. 5-(6-methoxy-3,4-dihydroisoquinolin-2(H)-yl)-3-methyl-1-(p-tolyl)-1H-pyrazole-4-carbonitrile To a solution of 5-bromo-3-methyl-1-(p-tolyl)-1H-pyrazole-4-carbonitrile (Intermediate 11, 600 mg, 2.173 mmol) in DMSO (20 ml) was added 6-methoxy-1,2,3,4-tetrahydroisoquinoline hydrochloride (434 mg, 2.173 mmol), Cs₂CO₃ (1416 mg, 4.35 mmol) and CuI (414 mg, 2.173 mmol). The mixture was stirred at 140° C. for 18 h. The mixture was diluted with water (2×20 mL) and extracted with EtOAc (2×50 mL). The combined organic layers were dried over Na₂SO₄, filtered and concentrated in vacuo. The residue was purified by silica gel column chromatography (PE:EtOAc=50:1 to 30:1) to yield the title compound.

Step B. 5-(6-hydroxy-3,4-dihydroisoquinolin-2(1H)-yl)-3-methyl-1-(p-tolyl)-1H-pyrazole-4-carbonitrile To a solution of 5-(6-methoxy-3,4-dihydroisoquinolin-2(1H)-yl)-3-methyl-1-(p-tolyl)-1H-pyrazole-4-carbonitrile (180 mg, 0.502 mmol) in DCM (20 ml) was added BBr₃ (252 mg, 1.004 mmol) dropwise at −76° C. The mixture was stirred at −76° C. for 2 h. The mixture was diluted with water and extracted with EtOAc (2×30 mL). The combined organic layers were dried (Na₂SO₄), filtered and concentrated in vacuo. The residue was purified by reverse phase HPLC on a GILSON 281 instrument fitted with a Phenomenex Synergi C18 (250×21.2 mm×4 µm) using water (0.2% Formic acid) and CH₃CN as eluents (Mobile phase A: water (0.2% Formic acid). Mobile phase B: CH₃CN, Detective wavelength: 220 nm) followed by concentration (below 50° C.) to obtain the title compound. ¹H NMR (CDCl₃, 400 MHz, ppm): δ 7.45 (d, J=8.22 Hz, 2H) 7.23 (d, J=8.22 Hz, 2H) 6.90 (d, J=8.61 Hz, 1H) 6.65 (d, J=8.22 Hz, 1H) 6.58 (s, 1H) 4.40 (s, 2H) 3.30-3.41 (m, 2H) 2.74 (t, J=5.48 Hz, 2H) 2.31-2.44 (m. 6H). ESI MS m/z 345.1 [M+H]⁺.

Example 130

5-(6-(2-hydroxyethoxy)-3,4-dihydroisoquinolin-2(1H)-yl)-3-methyl-1-(p-tolyl)-1H-pyrazole-4-carbonitrile

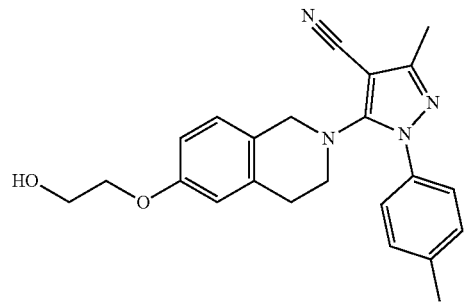 [SMILES: Cc1ccc(-n2nc(C)c(C#N)c2N2CCc3cc(OCCO)ccc3C2)cc1]

Step A. 5-(6-(2-((tert-butyldimethylsilyl)oxy)ethoxy)-3,4-dihydroisoquinolin-2(1H)-yl)-3-methyl-1-(p-tolyl)-1H-pyrazole-4-carbonitrile To a solution of (2-bromoethoxy)(tert-butyl) dimethylsilane (34 mg, 0.142 mmol) in MeCN (20 mL) was added Cs₂CO₃ (114 mg, 0.348 mmol) and the mixture was stirred at 15° C. for 30 min. Then 5-(6-hydroxy-3,4-dihydroisoquinolin-2(1H)-yl)-3-methyl-1-(p-tolyl)-1H-pyrazole-4-carbonitrile (40 mg, 0.116 mmol) was added and the mixture was stirred at 15° C. for 24 h. The mixture was washed with water (2×10 mL) and extracted with EtOAc (2×30 mL). The extract was dried over by Na₂SO₄ and concentrated in vacuo to give the crude title compound.

Step B. 5-(6-(2-hydroxyethoxy)-3,4-dihydroisoquinolin-2(1H)-yl)-3-methyl-1-(p-tolyl)-1H-pyrazole-4-carbonitrile To a stirred solution of 5-(6-(2-((tert-butyldimethyl-silyl)oxy)-ethoxy)-3,4-dihydroisoquinolin-2(1H)-yl)-3-methyl-1-(p-tolyl)-1H-pyrazole-4-carbonitrile (50 mg, 0.099 mmol) in THF (20 mL) was added TBAF (0.199 mL, 0.199 mmol) in THF (1 M), and the mixture was stirred at 15° C. for 4 h. The mixture was washed with water (2×10 mL) and extracted with EtOAc (2×30 mL). The extract was dried over by Na₂SO₄ and evaporated in vacuo. The residue was purified by reverse phase HPLC on a GILSON 281 instrument fitted with a Phenomenex Synergi C18 (250×21.2 mm×4 µm) using water (0.2% Formic acid) and CH₃CN as eluents (Mobile phase A: water (0.2% Formic acid), Mobile phase B: CH₃CN, Detector wavelength: 220 nm) followed by concentration to obtain the title compound. ¹H-NMR (400 MHz, CDCl₃) d ppm: 7.46 (d, J=8.28 Hz, 2H) 7.23 (d, J=8.28 Hz, 2H) 6.96 (d, J=8.53 Hz, 1H) 6.76 (dd, J=8.41, 2.38 Hz, 1H) 6.67 (s, 1H) 4.41 (s, 2H) 4.03-4.10 (m, 2H) 3.91-4.00 (m, 2H) 3.37 (t, J=5.77 Hz, 2H) 2.77 (t, J=5.77 Hz, 2H) 2.39 (s, 3H) 2.36 (s, 3H). m/z 389.1 [M+H]⁺.

Example 131

3-(2-(5-cyclobutoxy-2,3-difluorophenyl)-7-fluoro-1,2,3,4-tetrahydro-isoquinolin-6-yl)propanoic acid

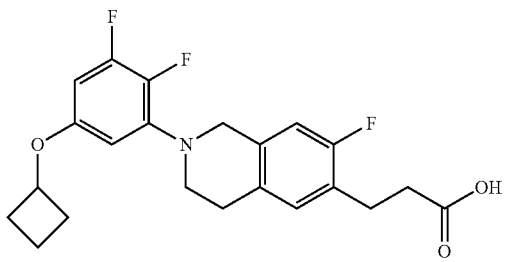 [SMILES: O=C(O)CCc1cc2c(cc1F)CN(c1cc(OC3CCC3)cc(F)c1F)CC2]

Step A. ethyl 3-(2-(5-cyclobutoxy-2,3-difluorophenyl)-7-fluoro-1,2,3,4-tetrahydro-isoquinolin-6-yl)propanoate To a solution of 5-cyclobutoxy-2,3-difluorophenyl trifluoromethanesulfonate (50 mg, 0.150 mmol) in 1,4-dioxane (5 ml) was added ethyl 3-(7-fluoro-1,2,3,4-tetrahydroisoquinolin-6-yl)propanoate (Intermediate 49, 38 mg, 0.151 mmol), $Cs_2CO_3$ (147 mg, 0.451 mmol), t-buxphos (7 mg, 0.016 mmol) and $Pd_2(dba)_3$ (14 mg, 0.015 mmol). Then the reaction mixture was placed under nitrogen and stirred at 90° C. for 16 h. The mixture was concentrated in vacuo, and water (10 mL) was added to the residue. The mixture was extracted with EtOAc (2×20 mL), and the combined organic layers were concentrated in vacuo. The crude product was purified by silica gel preparative TLC (PE/EtOAc=5:1) to give the title compound.

Step B. 3-(2-(5-cyclobutoxy-2,3-difluorophenyl)-7-fluoro-1,2,3,4-tetrahydro-isoquinolin-6-yl)propanoic acid To a solution of ethyl 3-(2-(5-cyclobutoxy-2,3-difluorophenyl)-7-fluoro-1,2,3,4-tetrahydroisoquinolin-6-yl)propanoate (20 mg, 0.046 mmol) in THF (2 ml), MeOH (2 ml) and water (1 ml) was added LiOH hydrate (4 mg, 0.095 mmol). The mixture was stirred at 15° C. for 3 h, then acidified with HCl (6 N), and extracted with EtOAc (2×20 mL). The organic layer was washed with water (20 mL), dried over anhydrous $Na_2SO_3$, and concentrated in vacuo to give the crude product. The crude product was purified with a Phenomenex Synergi C18 (250×21.2 mm×4 μm) using water (0.2% Formic acid) and $CH_3CN$ as eluents (Mobile phase A: water (0.2% Formic acid), Mobile phase B: $CH_3CN$, Detective wavelength: 220 nm) followed by concentration to obtain title compound. $^1H$ NMR (400 MHz, $CDCl_3$) δ ppm 1.61-1.73 (m, 2H) 2.13 (dd, J=19.96, 9.78 Hz, 2H) 2.39 (br. s., 2H) 2.64-2.72 (m, 2H) 2.90 (d, J=5.09 Hz, 2H) 2.92-2.98 (m, 2H) 3.42 (t, J=5.67 Hz, 2H) 4.22 (s, 2H) 4.51 (t, J=7.04 Hz, 1H) 6.20 (d, J=6.26 Hz, 2H) 6.77 (d, J=10.17 Hz, 1H) 6.98 (d, J=7.43 Hz, 1H). m/z 406.1 $[M+H]^+$.

Example 132

6-(2-(1H-tetrazol-5-yl)ethyl)-2-(2,3-difluoro-5-((1r,3r)-3-methoxylcyclobutoxy)-phenyl)-1,2,3,4-tetrahydroisoquinoline

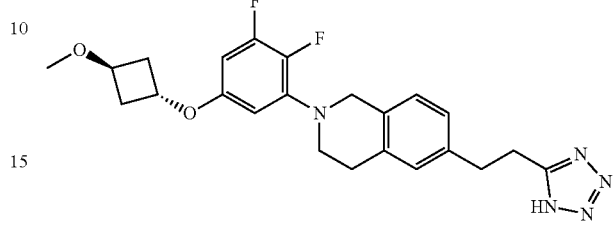

Step A. Tert-butyl 6-(3-ethoxy-3-oxopropyl)-3,4-dihydroisoquinoline-2(1H)-carboxylate To a stirred solution of ethyl 3-(1,2,3,4-tetrahydroisoquinolin-6-yl)-propanoate (Intermediate 7, 2.0 g, 8.57 mmol) in DCM (15 mL) were added $(BOC)_2O$ (2.7 g, 12.37 mmol) and $Et_3N$ (4.0 mL, 28.7 mmol) at rt. Then the reaction mixture was stirred at rt for 5 h. The solvent was removed under reduced pressure, and the resulting crude product was purified by silica gel column chromatography (PE: EtOAc=2:1) to give the title compound.

Step B. 3-(2-(tert-butoxycarbonyl)-1,2,3,4-tetrahydroisoquinolin-6-yl)propanoic acid To a stirred solution of tert-butyl 6-(3-ethoxy-3-oxopropyl)-3,4-dihydroisoquinoline-2(1H)-carboxylate (2.84 g, 8.52 mmol) in THF (6 mL), MeOH (3 mL) and water (2.5 mL) was added LiOH hydrate (1.7 g, 40.5 mmol) at rt (~8° C.). Then the reaction mixture was stirred at rt (~8° C.) for 15 h. The mixture was acidified to pH-2 with HCl (15 mL, 3 N, a.q.) and extracted with EtOAc (20 mL×2). The organic layer was removed under reduced pressure to give the crude title compound.

Step C. Tert-butyl 6-(3-amino-3-oxopropyl)-3,4-dihydroisoquinoline-2(1H)-carboxylate To a stirred solution of 3-(2-(tert-butoxycarbonyl)-1,2,3,4-tetrahydro-isoquinolin-6-yl)propanoic acid (2.46 g, 8.06 mmol) in DMF (10 mL) were added ammonium chloride (480 mg, 8.97 mmol), DIEA (4.2 mL, 24.05 mmol) and HATU (3.06 g, 8.06 mmol) at rt. Then the reaction mixture was stirred at rt for 15 h. The mixture was diluted with water (200 mL), extracted with EtOAc (30 mL×2), and the organic layer was concentrated in vacuo to give the title compound.

Step D. 3-(1,2,3,4-tetrahydroisoquinolin-6-yl)propanenitrile

A solution of tert-butyl 6-(3-amino-3-oxopropyl)-3,4-dihydroisoquinoline-2(1H)-carboxylate (2.4 g, 7.88 mmol) in phosphorus oxychloride (28.93 g, 189 mmol) was stirred at rt for 5 h. The mixture was poured into water (300 mL) slowly with stirring, then basified to pH-8 with saturated aqueous of $NaHCO_3$ (200 mL), extracted with DCM/MeOH (10:1, 50 mL×2). The organic layer was concentrated in vacuo. The resulting crude product was purified by silica gel column chromatography (DCM to DCM/MeOH=40:1 to 10:1) to give the title compound.

Step E. 3-(2-(2,3-difluoro-5-((1r,3r)-3-methoxycyclobutoxy)phenyl)-1,2,3,4-tetrahydroisoquinolin-6-yl)propanenitrile To a solution of 3-(1,2,3,4-tetrahydro-isoquinolin-6-yl)propanenitrile (100 mg, 0.537 mmol) in toluene (10 mL) were added 2,3-difluoro-5-((1R,3R)-3-methoxycyclobutoxy)phenyl trifluoromethanesulfonate (Intermediate 4, 204 mg, 0.564 mmol), Cs$_2$CO$_3$ (525 mg, 1.611 mmol), BINAP (67 mg, 0.108 mmol) and Pd(OAc)$_2$ (12 mg, 0.053 mmol) at rt. Then the reaction mixture was placed under nitrogen atmosphere and stirred at 110° C. for 15 h. The solvent was removed in vacuo, and the resulting mixture was diluted with water (20 mL) and extracted with EtOAc (20 mL×2). The organic layer was concentrated in vacuo, and the crude product was purified by silica gel PTLC (PE/EtOAc=2:1) to give the title compound. m/z 399.1 [M+H]$^+$.

Step F 6-(2-(1H-tetrazol-5-yl)ethyl)-2-(2,3-difluoro-5-((1R,3R)-3-methoxy-cyclobutoxy)phenyl)-1,2,3,4-tetrahydroisoquinoline To a solution of 3-(2-(2,3-difluoro-5-((1R,3R)-3-methoxycyclobutoxy)phenyl)-1,2,3,4-tetrahydroisoquinolin-6-yl)propane nitrile (50 mg, 0.125 mmol) in toluene (4 mL) was added azidotributyltin (0.2 mL, 0.730 mmol) at rt. Then the reaction mixture was placed under a nitrogen atmosphere and stirred at 110° C. for 40 h. The solvent was removed in vacuo, and the resulting mixture was diluted with water (10 mL), and extracted with EtOAc (10 mL×2). The organic layer was concentrated in vacuo, and the crude product was purified by silica gel column chromatography (DCM to DCM/MeOH=20:1), then purified by reverse phase HPLC on a GILSON 281 instrument fitted with a Phenomenex Synergi C18 (250×21.2 mm×4 μm) using water (0.2% Formic acid) and CH$_3$CN as eluents (Mobile phase A: water (0.2% Formic acid), Mobile phase B: CH$_3$CN, Detective wavelength: 220 nm) followed by concentration to give the title compound. $^1$HNMR (400 MHz, MeOD) δ 7.03-7.08 (m, 1H), 6.94-7.00 (m, 2H), 6.23-6.32 (m, 2H), 4.66-4.76 (m, 1H), 4.04-4.13 (m, 1H), 3.42 (t, J=5.73 Hz, 2H), 3.19-3.27 (m, 5H), 3.02-3.09 (m, 2H), 2.88 (t, J=5.51 Hz, 2H), 2.27-2.41 (m, 4H). m/z 440.2 [M−H]$^+$.

The examples in Table were prepared from the appropriate starting materials described previously or commercially available starting materials available using procedures described in Examples 127-132.

TABLE 5

| Example | Structure | Name | [M + H]$^+$ |
| --- | --- | --- | --- |
| 133 | 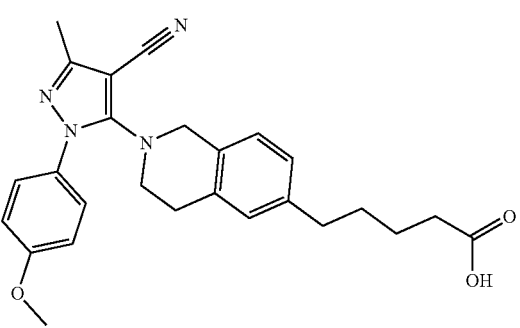 [SMILES: COc1ccc(-n2nc(C)c(C#N)c2N2CCc3cc(CCCCC(=O)O)ccc3C2)cc1] | 5-{2-[4-cyano-1-(4-methoxyphenyl)-3-methyl-1H-pyrazol-5-yl]-1,2,3,4-tetrahydroisoquinolin-6-yl}pentanoic acid | 445.1 |
| 134 | 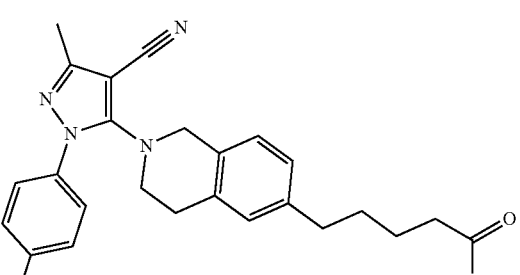 | 5-{2-[4-cyano-3-methyl-1-(4-methylphenyl)-1H-pyrazol-5-yl]-1,2,3,4-tetrahydroisoquinolin-6-yl}pentanoic acid | 429.1 |
| 135 | 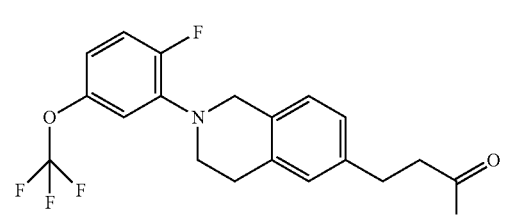 | 5-{2-[2-fluoro-5-(trifluoromethoxy)phenyl]-1,2,3,4-tetrahydroisoquinolin-6-yl}pentanoic acid | 412.1 |

TABLE 5-continued

| Example | Structure | Name | [M + H]⁺ |
|---|---|---|---|
| 136 | 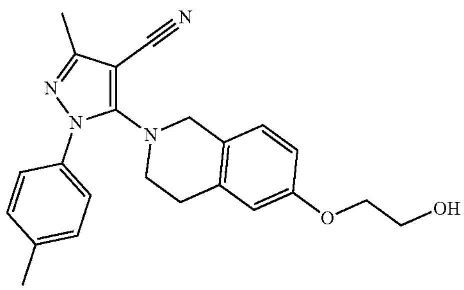 [SMILES: Cc1ccc(-n2nc(C)c(C#N)c2N2CCc3cc(OCCO)ccc3C2)cc1] | 5-[6-(2-hydroxyethoxy)-3,4-dihydro-isoquinolin-2(1H)-yl]-3-methyl-1-(4-methylphenyl)-1H-pyrazole-4-carbonitrile | 389.1 |
| 137 | 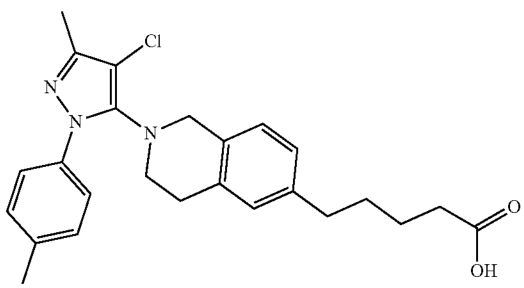 [SMILES: Cc1ccc(-n2nc(C)c(Cl)c2N2CCc3cc(CCCCC(=O)O)ccc3C2)cc1] | 5-{2-[4-chloro-3-methyl-1-(4-methylphenyl)-1H-pyrazol-5-yl]-1,2,3,4-tetrahydroisoquinolin-6-yl} pentanoic acid | 438.2 |
| 138 | 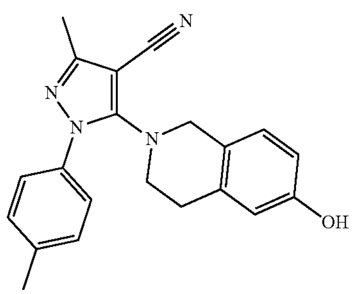 [SMILES: Cc1ccc(-n2nc(C)c(C#N)c2N2CCc3cc(O)ccc3C2)cc1] | 5-(6-hydroxy-3,4-dihydroisoquinolin-2(1H)-yl)-3-methyl-1-(4-methyl phenyl)-1H-pyrazole-4-carbonitrile | 345.1 |
| 139 | 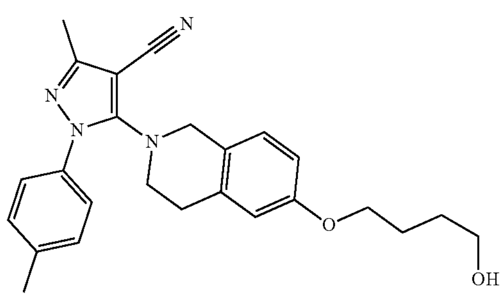 [SMILES: Cc1ccc(-n2nc(C)c(C#N)c2N2CCc3cc(OCCCCO)ccc3C2)cc1] | 5-[6-(4-hydroxybutoxy)-3,4-dihydro-isoquinolin-2(1H)-yl]-3-methyl-1-(4-methylphenyl)-1H-pyrazole-4-carbonitrile | 417.2 |
| 140 | 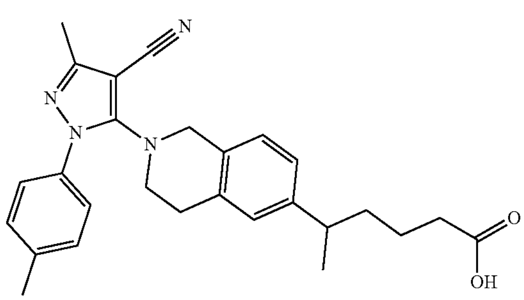 [SMILES: Cc1ccc(-n2nc(C)c(C#N)c2N2CCc3cc(C(C)CCCC(=O)O)ccc3C2)cc1] | 5-{2-[4-cyano-3-methyl-1-(4-methylphenyl)-1H-pyrazol-5-yl]-1,2,3,4-tetrahydroisoquinolin-6-yl} hexanoic acid | 443.1 |

TABLE 5-continued

| Example | Structure | Name | [M + H]+ |
|---|---|---|---|
| 141 | 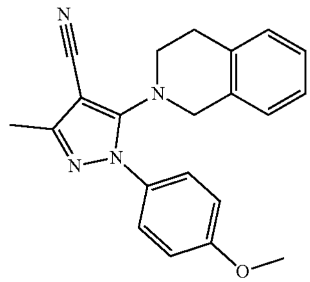 [SMILES: COc1ccc(-n2nc(C)c(C#N)c2N2CCc3ccccc3C2)cc1] | 5-(3,4-dihydroisoquinolin-2(1H)-yl)-1-(4-methoxyphenyl)-3-methyl-1H-pyrazole-4-carbonitrile | 345.1 |
| 142 | 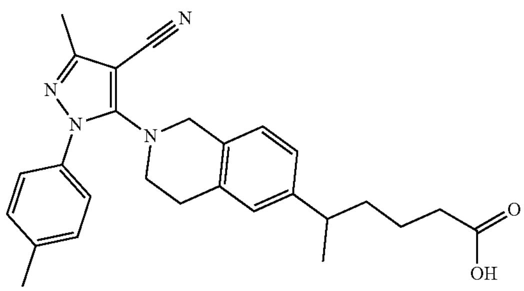 [SMILES: Cc1ccc(-n2nc(C)c(C#N)c2N2CCc3cc(C(C)CCCC(=O)O)ccc3C2)cc1] | 5-{2-[4-cyano-3-methyl-1-(4-methylphenyl)-1H-pyrazol-5-yl]-1,2,3,4-tetra-hydroisoquinolin-6-yl}hexanoic acid | 443.1 |
| 143 | 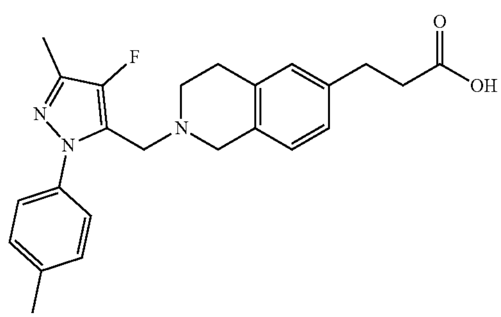 [SMILES: Cc1ccc(-n2nc(C)c(F)c2CN2CCc3cc(CCC(=O)O)ccc3C2)cc1] | 3-(2-{[4-fluoro-3-methyl-1-(4-methylphenyl)-1H-pyrazol-5-yl]methyl}-1,2,3,4-tetrahydroisoquinolin-6-yl)propanoic acid | 408.2 |
| 144 | 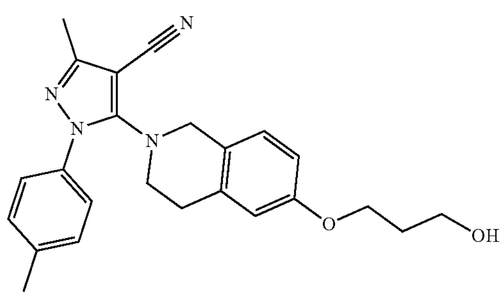 [SMILES: Cc1ccc(-n2nc(C)c(C#N)c2N2CCc3cc(OCCCO)ccc3C2)cc1] | 5-[6-(3-hydroxypropoxy)-3,4-dihydroisoquinolin-2(1H)-yl]-3-methyl-1-(4-methylphenyl)-1H-pyrazole-4-carbonitrile | 403.1 |
| 145 | 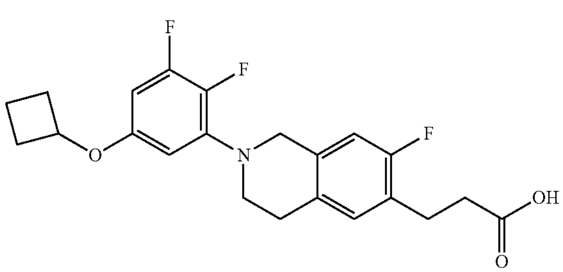 [SMILES: O=C(O)CCc1cc2c(cc1F)CN(c1cc(OC3CCC3)cc(F)c1F)CC2] | 3-{2-[5-(cyclobutyloxy)-2,3-difluoro-phenyl]-7-fluoro-1,2,3,4-tetrahydro-isoquinolin-6-yl}propanoic acid | 406.1 |

TABLE 5-continued

| Example | Structure | Name | [M + H]+ |
|---|---|---|---|
| 146 | 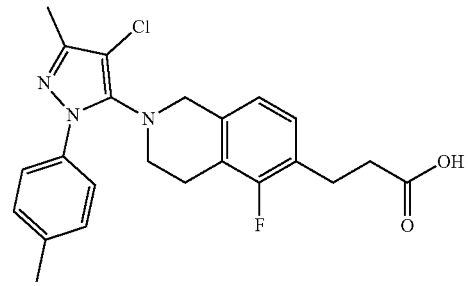 [SMILES: Cc1ccc(-n2nc(C)c(Cl)c2N2CCc3c(ccc(CCC(=O)O)c3F)C2)cc1] | 3-{2-[4-chloro-3-methyl-1-(4-methylphenyl)-1H-pyrazol-5-yl]-5-fluoro-1,2,3,4-tetrahydroisoquinolin-6-yl}propanoic acid | 428.1 |

Example 147

3-[2-(3-Cyano-4-methyl-6-thiazol-4-yl-pyridin-2-yl)-5-fluoro-1,2,3,4-tetrahydro-isoquinolin-6-yl]-propionic acid

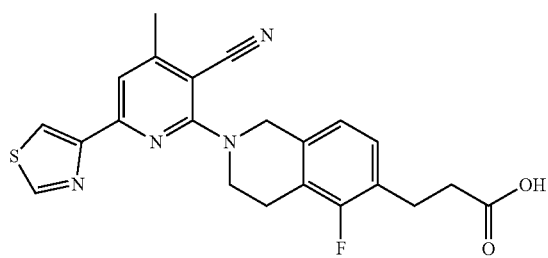 [SMILES: Cc1cc(-c2cscn2)nc(N2CCc3c(ccc(CCC(=O)O)c3F)C2)c1C#N]

Step A Ethyl 3-(2-(6-chloro-3-cyano-4-methylpyridin-2-yl)-5-fluoro-1,2,3,4-tetrahydro isoquinolin-6-yl)propanoate To a solution of 2,6-dichloro-4-methylnicotinonitrile (200 mg, 1.069 mmol), ethyl 3-(5-fluoro-1,2,3,4-tetrahydroisoquinolin-6-yl)propanoate (269 mg, 1.069 mmol) and G2-RuPHOS (41.5 mg, 0.053 mmol) in dioxane (6 ml) was added Cs$_2$CO$_3$ (697 mg, 2.139 mmol). The mixture was stirred at 90° C. for 12 h, and then water (15 ml) was added, and the mixture was extracted with EA (10 mL×2). The organic layer was separated, washed with brine (15 ml), and dried over Na$_2$SO$_4$. After filtration and concentration, the resulting residue was purified by prep-TLC (SiO$_2$, PE:EA=5:1) to afford the title compound.

Step B: Ethyl 3-(2-(3-cyano-4-methyl-6-(thiazol-4-yl)pyridin-2-yl)-5-fluoro-1,2,3,4-tetrahydroisoquinolin-6-yl)propanoate To a solution of ethyl 3-(2-(6-chloro-3-cyano-4-methylpyridin-2-yl)-5-fluoro-1,2,3,4-tetrahydroisoquinolin-6-yl)propanoate (50 mg, 0.124 mmol) and 4-(tributylstannyl)thiazole (51.2 mg, 0.137 mmol) in dioxane (3 ml) was added G2 XPhos (9.79 mg, 0.012 mmol). The mixture was stirred at 110° C. for 12 h, then quenched with 10% aqueous KF (10 ml), filtered and extracted with ethyl acetate (8 mL×3). The organic layers were combined and washed with water (15 mL), brine (10 mL), dried over Na$_2$SO$_4$, filtered and concentrated under reduced pressure to afford the title compound, which was used directly without further purification.

Step C: 3-[2-(3-Cyano-4-methyl-6-thiazol-4-yl-pyridin-2-yl)-5-fluoro-1,2,3,4-tetrahydro-isoquinolin-6-yl]-propionic acid To a solution of ethyl 3-(2-(3-cyano-4-methyl-6-(thiazol-4-yl)pyridin-2-yl)-5-fluoro-1,2,3,4-tetrahydroisoquinolin-6-yl)propanoate (50 mg, 0.111 mmol) in MeOH (2 ml), THF (2 ml) and water (1 ml) was added lithium hydroxide hydrate (46.6 mg, 1.110 mmol). The mixture was stirred at 85° C. for 5 h. The resulting mixture was acidified by HCl (1 N) to pH=6-7, then extracted with ethyl acetate (2×15 mL). The combined organic layers were washed with brine (20 mL), dried (Na$_2$SO$_4$), filtered and the solvent was evaporated under reduced pressure. The resulting residue was purified by prep-HPLC (TFA) to afford the title compound. $^1$H-NMR (400 MHz, METHANOL-d): 9.07 (d, J=1.98 Hz, 1H), 8.37 (d, J=1.98 Hz, 1H), 7.60 (s, 1H), 7.09-7.16 (m, 1H), 6.99 (d, J=7.94 Hz, 1H), 4.84 (s, 2H), 4.00 (t, J=5.73 Hz, 2H), 3.04 (t, J=5.51 Hz, 2H), 2.93 (t, J=7.61 Hz, 2H), 2.59 (t, J=7.61 Hz, 2H), 2.55 (s, 3H).

Example 148

3-(2-(6-cyclobutoxy-3-fluoro-4-methoxypyridin-2-yl)-5-fluoro-1,2,3,4-tetra-hydroisoquinolin-6-yl)propanoic acid

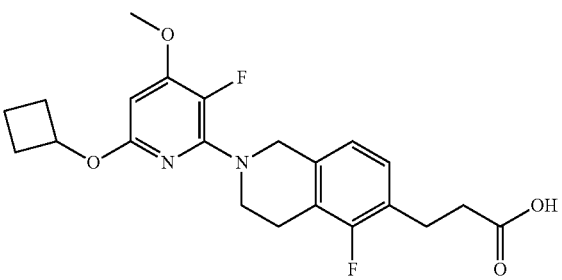 [SMILES: COc1cc(OC2CCC2)nc(N2CCc3c(ccc(CCC(=O)O)c3F)C2)c1F]

Step A Ethyl 3-(2-(6-cyclobutoxy-3-fluoro-4-methoxypyridin-2-yl)-5-fluoro-1,2,3,4-tetrahydroisoquinolin-6-yl)propanoate To a solution of 2-bromo-6-cyclobutoxy-3-fluoro-4-methoxypyridine (150 mg, 0.545 mmol) and ethyl 3-(5-fluoro-1,2,3,4-tetrahydro-isoquinolin-6-yl) propanoate (123 mg, 0.49 mmol) in dioxane (5 ml) was added Cs$_2$CO$_3$ (354 mg, 1.09 mmol), and then G2 Ruphos (28 mg, 0.03 mmol)

was added under N₂ protection. The resultant mixture was stirred at 90° C. for 10 h, then quenched with H₂O (10 mL) and extracted with EA (20 mL×3). The organic layer was washed with brine (30 mL), dried over Na₂SO₄, filtered and the filtrate was evaporated under reduced pressure to afford the title compound, which was used in the next step without further purification. MS (ESI) m/z: 447 [M+H]⁺

Step B 3-(2-(6-cyclobutoxy-3-fluoro-4-methoxy-pyridin-2-yl)-5-fluoro-1,2,3,4-tetrahydro-isoquinolin-6-yl)propanoic acid To a solution of ethyl 3-(2-(6-cyclobutoxy-3-fluoro-4-methoxypyridin-2-yl)-5-fluoro-1,2,3,4-tetrahydroisoquinolin-6-yl) propanoate (76 mg, 0.17 mmol) in MeOH (2.5 ml) and H₂O (0.5 ml) was added lithium hydroxide (20 mg, 0.85 mmol), and the resulting mixture was stirred at 18-25° C. for 6 hours. Then the reaction mixture was extracted with EA (10 mL×3). The organic layer was washed with brine (20 mL), and dried over Na₂SO₄. After filtration and concentration, the resulting residue was purified by preparative HPLC (TFA) to afford the title compound. ¹H-NMR (400 MHz, METHANOL-d4) 7.06 (t, J=7.63 Hz, 1H), 6.88 (d, J=7.83 Hz, 1H), 5.90 (d, J=3.91 Hz, 1H), 4.93-5.04 (m, 1H), 4.54 (s, 2H), 3.82 (s, 3H), 3.71 (t, J=5.87 Hz, 2H), 2.88 (t, J=7.63 Hz, 2H), 2.82 (t, J=5.48 Hz, 2H), 2.55 (t, J=7.63 Hz, 2H), 2.26-2.44 (m, 2H), 1.92-2.12 (m, 2H), 1.78 (q, J=9.91 Hz, 1H). 1.53-1.71 (m, 1H). MS (ESI) m/z: 419 [M+H]⁺

Example 149

3-(2-(3-cyano-6-cyclobutoxy-2-methylpyridin-4-yl)-5-fluoro-1,2,3,4-tetrahydroisoquinolin-6-yl)propanoic acid

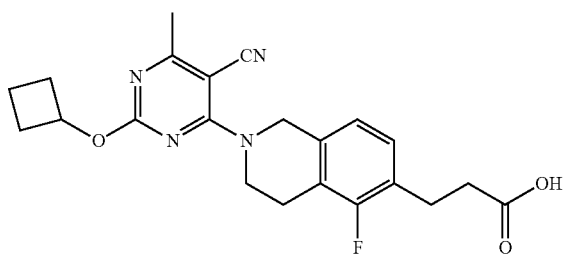 [SMILES: Cc1nc(OC2CCC2)nc(N2CCc3c(ccc(CCC(=O)O)c3F)C2)c1C#N]

Step A 6-chloro-2-methylpyridin-3-amine

A mixture of 6-chloro-2-methyl-3-nitropyridine (8.60 g, 50.00 mmol), NH₄Cl (27.00 g, 500.00 mmol) and Fe (14.00 g, 250.00 mmol) in MeOH (100 mL) was stirred at 80° C. for 5 h. The mixture was filtered and concentrated, and the resulting residue was purified by column chromatography (SiO₂, eluting with PE:EA=5:1) to afford the title compound.

Step B 4-bromo-6-chloro-2-methylpyridin-3-amine

To a solution of 6-chloro-2-methyl-pyridin-3-amine (4.97, 35.00 mmol) in CH₃CN (100 mL) was added NBS (6.23 g, 35.00 mmol) at 0° C. The resulting mixture was stirred at 26° C. for 16 h, then quenched with H₂O and extracted with EtOAc (3*100 mL). The combined organic layers were washed with brine (200 mL), and dried over Na₂SO₄. After filtration and concentration, the resulting residue was purified by column chromatography (SiO₂, eluting with PE:EA=5:1) to afford the title compound. ¹H-NMR (400 MHz, chloroform-d): 7.28 (s, 1H), 4.06 (br, 2H), 2.43 (s, 3H).

Step C: 4-bromo-6-chloro-2-methylnicotinonitrile

To a solution of CuCN (1.80 g, 20.09 mmol) in CH₃CN (20 mL) was added 3-methyl-1-nitrobutane (2.80 mL, 20.93 mmol). Then a solution of 4-bromo-6-chloro-2-methylpyridin-3-amine (3.70 g, 16.74 mmol) in CH₃CN (30 mL) was added to the mixture dropwise. The resulting reaction mixture was stirred at 65° C. for 16 h, then quenched with H₂O and extracted with EtOAc (3*50 mL). The combined organic layers were washed with brine (100 mL), and dried over Na₂SO₄. After filtration and concentration, the resulting residue was purified by column chromatography (SiO₂, eluting with PE:EA=10:1) to afford the title compound.

Step D
4-bromo-6-cyclobutoxy-2-methylnicotinonitrile

A solution of NaH (40.00 mg, 1.00 mmol) and cyclobutanol (72.00 mg, 1.00 mmol) in THF (3 mL) was cooled to −78° C. under N₂ protection. The solution was stirred at −78° C. for 30 min, and then 4-bromo-6-chloro-2-methylnicotinonitrile (230.00 mg, 1.00 mmol) was added. The resulting reaction mixture was stirred at 26° C. for 16 h, then quenched with H₂O and extracted with EtOAc (3*20 mL). The combined organic layers were washed with brine (50 mL), and dried over Na₂SO₄. After filtration and concentration, the residue was purified by column chromatography (SiO₂, eluting with PE:EA=10:1) to afford the title compound. ¹H-NMR (400 MHz, chloroform-d): 6.84 (s, 1H), 5.21-5.15 (m, 1H), 2.66 (s, 3H), 2.47-2.41 (m, 2H), 2.18-2.08 (m, 2H), 1.89-1.84 (m, 1H), 1.69-1.64 (m, 1H).

Step E Ethyl 3-(2-(3-cyano-6-cyclobutoxy-2-methylpyridin-4-yl)-5-fluoro-1,2,3,4-tetrahydroisoquinolin-6-yl)propanoate A mixture of 4-bromo-6-cyclobutoxy-2-methyl-nicotinonitrile (40.00 mg, 0.15 mmol), ethyl 3-(5-fluoro-1,2,3,4-tetrahydroisoquinolin-6-yl) propanoate (45.00 mg, 0.18 mmol), Cs₂CO₃ (147.00 mg, 0.45 mmol) and G2-Ruphos (6.00 mg, 0.0075 mmol) in 1,4-dioxane (5 mL) was stirred at 90° C. under N₂ for 16 h. Then the reaction was diluted with H₂O and extracted with EtOAc (10 mL*3). The combined organic layers were dried over Na₂SO₄, filtered and concentrated to afford the title compound, which was used in the next step without further purification. MS(ESI) m/z: 438.7 [M+H]+

Step F 3-(2-(3-cyano-6-cyclobutoxy-2-methylpyridin-4-yl)-5-fluoro-1,2,3,4-tetrahydro-isoquinolin-6-yl)propanoic acid A mixture of ethyl-3-(2-(3-cyano-6-cyclobutoxy-2-methyl-pyridin-4-yl)-5-fluoro-1,2,3,4-tetrahydroisoquinolin-6-yl)propanoate (65.00 mg, 0.15 mmol) and LiOH.H₂O (126.00 mg, 3.00 mmol) in MeOH (5 mL) and H₂O (1 mL) was stirred at 26° C. for 17 h. Then the reaction solution was adjusted with 3N HCl to pH=7, and the reaction solution was extracted with EtOAc (20 mL*3). The combined organic layers were dried over Na₂SO₄. After filtration and concentration, the resulting residue was purified by prep-HPLC (Neutral) to afford the title compound. 1H-NMR (400 MHz, chloroform-d) 7.14-7.10 (m, 1H), 6.94 (d, J=7.8 Hz, 1H), 6.15 (s, 1H), 5.14 (t, J=7.40 Hz, 1H) 4.51 (s, 2H) 3.80 (t, J=5.7 Hz, 2H), 2.99-2.89 (m, 4H), 2.59-2.54 (m, 5H), 2.45-2.43 (m, 2H), 2.14-2.09 (n, 2H), 1.85-1.68 (m, 2H). MS(ESI) m/z: 410.7 [M+H]+

The Examples in Table were prepared from the appropriate starting materials described previously or commercially available starting materials using procedures similar to those in the Examples above.

TABLE 6

| Example | Structure | Name | [M + H]+ |
|---------|-----------|------|----------|
| 150 | 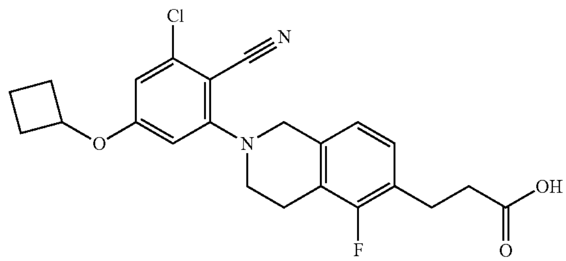 | 3-{2-[3-chloro-2-cyano-5-(cyclo butyloxy)phenyl]-5-fluoro-1,2,3,4-tetrahydroisoquinolin-6-yl} propanoic acid | 429.2 |
| 151 | 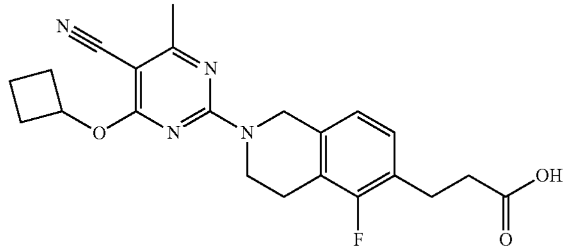 [SMILES: Cc1nc(N2CCc3c(ccc(CCC(=O)O)c3F)C2)nc(OC2CCC2)c1C#N] | 3-{2-[5-cyano-4-(cyclobutyloxy)-6-methylpyrimidin-2-yl]-5-fluoro-1,2,3,4-tetrahydroisoquino-lin-6-yl}propanoic acid | 411 |
| 152 | 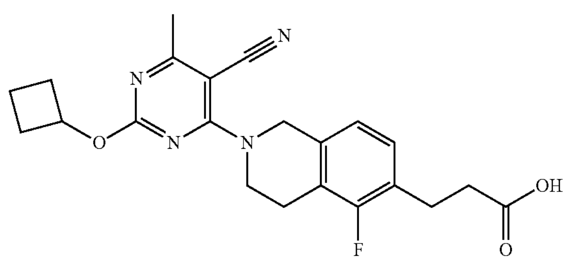 [SMILES: Cc1nc(OC2CCC2)nc(N2CCc3c(ccc(CCC(=O)O)c3F)C2)c1C#N] | 3-{2-[5-cyano-2-(cyclobutyloxy)-6-methylpyrimidin-4-yl]-5-fluoro-1,2,3,4-tetrahydroisoquino-lin-6-yl}propanoic acid | 411 |
| 153 | 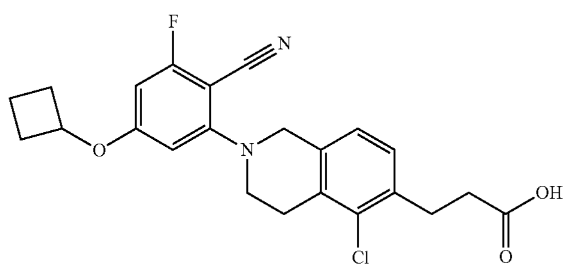 [SMILES: N#Cc1c(F)cc(OC2CCC2)cc1N1CCc2c(ccc(CCC(=O)O)c2Cl)C1] | 3-{5-chloro-2-[2-cyano-5-(cyclo butyloxy)-3-fluorophenyl]-1,2,3,4-tetrahydroisoquinolin-6-yl}-propanoic acid | 429 |
| 154 | 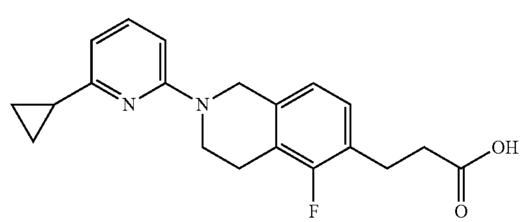 [SMILES: O=C(O)CCc1ccc2c(c1F)CCN(c1cccc(C3CC3)n1)C2] | 3-[2-(6-cyclopropylpyridin-2-yl)-5-fluoro-1,2,3,4-tetrahydroiso-quinolin-6-yl]propanoic acid | 341.2 |

TABLE 6-continued

| Example | Structure | Name | [M + H]+ |
|---|---|---|---|
| 155 | 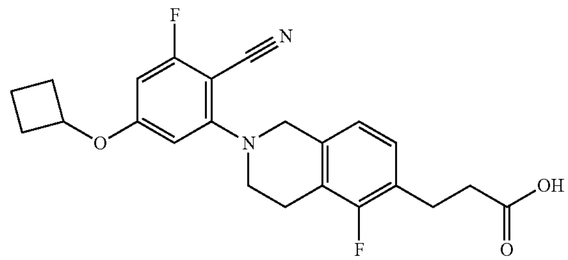 [SMILES: N#Cc1c(F)cc(OC2CCC2)cc1N1CCc2c(ccc(CCC(=O)O)c2F)C1] | 3-{2-[2-cyano-5-(cyclobutyloxy)-3-fluorophenyl]-5-fluoro-1,2,3,4-tetrahydroisoquinolin-6-yl}-propanoic acid | 413.3 |
| 156 | 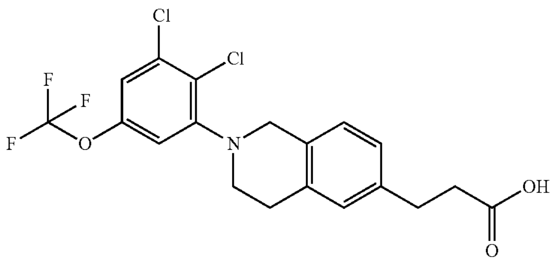 [SMILES: O=C(O)CCc1ccc2c(c1)CCN(c1cc(OC(F)(F)F)cc(Cl)c1Cl)C2] | 3-{2-[2,3-dichloro-5-(trifluoromethoxy)phenyl]-1,2,3,4-tetrahydroisoquinolin-6-yl}propanoic acid | 434 |
| 157 | 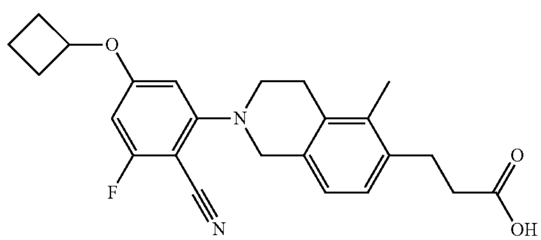 [SMILES: Cc1c(CCC(=O)O)ccc2c1CCN(c1cc(OC3CCC3)cc(F)c1C#N)C2] | 3-{2-[2-cyano-5-(cyclobutyloxy)3-fluorophenyl]-5-methyl-1,2,3,4-tetrahydroisoquinolin-6-yl}-propanoic acid | 409 |

BIOLOGICAL ASSAYS

The usefulness of the compound encompassed by formula (I) for a medicament is shown in tests described below.

Human GPR120 IP1 Assay Principle

The binding of small molecule agonists to the G-protein-coupled receptor GPR120 activates phospholipase C, and leads to the generation of inositol 1,4,5-trisphosphate (InsP3 or IP3). IP3 is subsequently de-phosphorylated to IP1, which accumulates in cells and is stable in the presence of lithium chloride.

In the present method, agonist-induced activation of the human GPR120 receptor was monitored by measuring the accumulation of IP1 in CHO-K1 cells that were stably expressing the short form of human GPR120 (Accession #NM_001195755). Following agonist addition, GPR120 activation and subsequent accumulation of IP1 was measured using a homogeneous Time Resolved Fluorescence-based ELISA commercially available from CisBio (IP-one ELISA Kit). The IP-One ELISA was a competitive immunoassay which uses IP1 labeled with HRP and a terbium cryptate-labeled anti-IP1 monoclonal antibody. Accumulation of unlabeled IP1 following GPR120 activation resulted in a loss of signal in the ELISA. The signal loss was then back calculated to IP1 concentration using an IP1 standard curve. Determination of IP1 concentration was a direct measure of GPR120 activation and was used to determine compound potency (EC50).

Generation of GPR120-Expressing Cells:

Human GPR120 stable cell-lines were generated in CHO cells. The expression plasmids were transfected using lipofectamine (Life Technologies) following manufacturer's instructions. Stable cell-lines were generated following drug selection and single cell cloning.

Inositol Phosphate Turnover (IP1) Assay:

The assay was performed in 384-well format. CHO cells stably expressing human GPR120 were plated at 20,00 cells per well in growth medium (DMEM/F12, 10% fetal calf serum). Cell plates were then incubated 16 hours at 37 degrees in a 5% $CO_2$ incubator. Measurement of Inositol Phosphate Turnover (IP1) was performed using the CisBio IP-One kit (Part number 62IPAPEB). After the 16 hour incubation, the growth media was removed by centrifugation using the BlueWasher (AusWasher GUI Ver. v1.0.1.8) Protocol #21-"Light Dry" and 10 ul of stimulation buffer (prepared as described in the kit) was added to each well. In a separate plate, compounds were diluted in DMSO (200-fold over the final concentration in the assay well) and 50 nl was acoustically transferred to the appropriate well in the assay cell plate. The plates were then incubated for 60 minutes at 37 degrees in a 5% $CO_2$ incubator. 10 ul of detection buffer (also prepared as described in the IP-One kit) was added to each well and the plates were incubated at room temperature for 60 minutes in the dark. The plates were then read in a Perkin Elmer EnVision or equivalent reader able to measure FRET. Fluorescent ratio of emission at 665 and 620 nm was then converted to the IP1 concentration by back calculating from an IP1 standard curve prepared at the time of the assay. The data was normalized to % activity using a reference compound, and the $EC_{50}$ values were determined using a standard 4-parameter fit.

The compounds of the present invention, including the compounds in Examples 1-157, have $EC_{50}$ values ≤10,000 nanomolar (nM) in the Human GPR120 IP1 Assay described above. Specific EC$_{50}$ values in the Human GPR120 IP1 Assay are provided in Table I.

Table I

Specific EC$_{50}$ values in the Human GPR120 IP1 Assay

| Example | hGPR120 EC$_{50}$ |
|---|---|
| 1 | 61 |
| 2 | 17 |
| 3 | 29 |
| 4 | 51 |
| 5 | 65 |
| 6 | 417 |
| 7 | 533 |
| 8 | 414 |
| 9 | 20 |
| 10 | 14 |
| 11 | 15 |
| 12 | 24 |
| 13 | 18 |
| 14 | 20 |
| 15 | 22 |
| 16 | 22 |
| 17 | 23 |
| 18 | 24 |
| 19 | 27 |
| 20 | 29 |
| 21 | 51 |
| 22 | 56 |
| 23 | 60 |
| 24 | 61 |
| 75 | 65 |
| 26 | 97 |
| 27 | 61 |
| 28 | 169 |
| 29 | 171 |
| 30 | 134 |
| 31 | 182 |
| 32 | 233 |
| 33 | 192 |
| 34 | 184 |
| 35 | 312 |
| 36 | 348 |
| 37 | 377 |
| 38 | 405 |
| 39 | 417 |
| 40 | 463 |
| 41 | 569 |
| 42 | 798 |
| 43 | 1466 |
| 44 | 2365 |
| 45 | 2291 |
| 46 | 5392 |
| 47 | 91 |
| 48 | 596 |
| 49 | 223 |
| 50 | 348 |
| 51 | 317 |
| 52 | 510 |
| 53 | 533 |
| 54 | 1683 |
| 55 | 25 |
| 56 | 40 |
| 57 | Isomer 1: 58; Isomer 2: 231 |
| 58 | 472 |
| 59 | 1634 |
| 60 | 60 |
| 61 | 28 |
| 62 | 3 |
| 63 | 14 |
| 64 | 15 |
| 65 | 37 |
| 66 | 41 |
| 67 | 40 |
| 68 | 58 |
| 69 | 231 |
| 70 | 472 |
| 71 | 309 |
| 72 | 1174 |
| 73 | 1634 |
| 74 | 60 |
| 75 | 358 |
| 76 | 845 |
| 77 | 5880 |
| 78 | 19 |
| 79 | 471 |
| 80 | 3123 |
| 81 | 48 |
| 82 | 25 |
| 83 | 100 |
| 84 | 118 |
| 85 | 40 |
| 86 | 61 |
| 87 | 74 |
| 88 | 110 |
| 89 | 185 |
| 90 | 250 |
| 91 | 59 |
| 92 | 482 |
| 93 | 350 |
| 94 | 473 |
| 95 | 491 |
| 96 | 834 |
| 97 | 1581 |
| 98 | 100 |
| 99 | 127 |
| 100 | 251 |
| 101 | 273 |
| 102 | 118 |
| 103 | 2999 |
| 104 | 4036 |
| 105 | 6606 |
| 106 | 83 |
| 107 | 122 |
| 108 | 122 |
| 109 | 22 |
| 110 | 42 |
| 111 | 32 |
| 112 | 42 |
| 113 | 59 |
| 114 | 61 |
| 115 | 83 |
| 116 | 107 |
| 117 | 143 |
| 118 | 215 |
| 119 | 273 |
| 120 | 299 |
| 121 | 73 |
| 122 | 121 |
| 123 | 766 |
| 124 | 824 |
| 125 | 414 |
| 126 | 9742 |
| 127 | 35 |
| 128 | Isomer 1: 312; Isomer 2: 209 |
| 129 | 92 |
| 130 | 87 |
| 131 | 174 |
| 132 | 406 |
| 133 | 50 |
| 134 | 41 |
| 135 | 77 |
| 136 | 87 |
| 137 | 93 |
| 138 | 92 |
| 139 | 187 |
| 140 | 209 |
| 141 | 288 |
| 142 | 312 |
| 143 | 395 |
| 144 | 4300 |
| 145 | 174 |

Table I-continued

Specific EC$_{50}$ values in the Human GPR120 IP1 Assay

| Example | hGPR120 EC$_{50}$ |
|---|---|
| 146 | 309 |
| 147 | 141 |
| 148 | 9 |
| 149 | 33 |
| 150 | 16 |
| 151 | 34 |
| 152 | 69 |
| 153 | 87 |
| 154 | 167 |
| 155 | 17 |
| 156 | 62 |
| 157 | 15 |

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size O hard gelatin capsule. While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound according to the formula I:

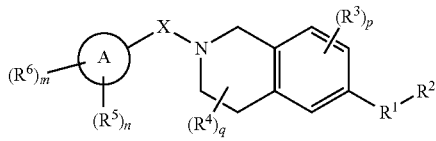

or a pharmaceutically acceptable salt thereof, wherein:

X is
 (1) bond,
 (2) (C$_{1-2}$)alkyl, or
 (3) halo(C$_{1-2}$)alkyl;
ring A is phenyl, pyridine, pyrimidine, pyrazole, pyrazine, isothiazole, or benzisoxazole;
R$^1$ is a

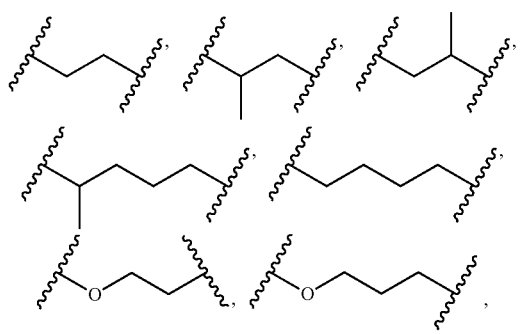

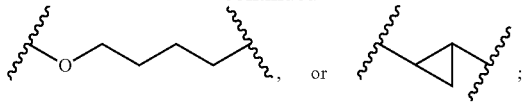

R$^2$ is
 (1) hydroxy,
 (2) COOH,
 (3) tetrazole,
 (5) hydroxyisoxazole,
 (6) triazole,
 (7) C(O)NH$_2$,
 (8) C(O)NHC$_{1-6}$alkyl,
 (9) C(O)NHC$_{3-6}$cycloalkyl,
 (10) C(O)NHC$_{2-5}$cycloheteroalkyl,
 (11) C(O)NH-aryl,
 (12) C(O)NH-heteroaryl,
 (13) SO$_2$C$_{1-6}$alkyl,
 (14) SO$_2$C$_{3-6}$cycloalkyl,
 (15) SO$_2$C$_{2-5}$cycloheteroalkyl,
 (16) SO$_2$-aryl, or
 (17) SO$_2$-heteroaryl;
R$^3$ is
 (1) hydrogen,
 (2) halogen,
 (3) cyano, or
 (4) (C$_{1-3}$)alkyl;
R$^4$ is
 (1) hydrogen,
 (2) (C$_{1-3}$)alkyl,
 (3) halo(C$_{1-3}$)alkyl, or
 (4) halogen;
R$^5$ is
 (1) cyano,
 (2) (C$_{1-3}$)alkyl,
 (3) halo(C$_{1-3}$)alkyl,
 (4) (C$_{1-3}$)alkoxy,
 (5) halo(C$_{1-3}$)alkoxy, or
 (6) halogen;
R$^6$ is
 (1) (C$_{1-3}$)alkoxy,
 (2) halo(C$_{1-3}$)alkoxy,
 (3) halo(C$_{1-3}$)alkyl,
 (4) (C$_{3-6}$)cycloalkyl,
 (5) (C$_{3-6}$)cycloalkyl-O-,
 (6) (C$_{3-6}$)cycloalkyl-S-,
 (7) (C$_{3-6}$)cycloalkyl-(C$_{1-2}$)alkyl-,
 (8) (C$_{3-6}$)cycloalkyl-halo(C$_{1-2}$)alkyl-,
 (9) phenyl,
 (10) 5- to 6-membered heteroaryl-O- wherein the heteroaryl contains 1, 2, or 3 heteroatoms independently selected from N, O and S, or
 (11) 5- to 6-membered heteroaryl- wherein the heteroaryl contains 1, 2, or 3 heteroatoms independently selected from N, O and S,
 wherein alkyl, cycloalkyl, phenyl and heteroaryl are unsubstituted or substituted with 1-3 substituents selected from (C$_{1-3}$)alkyl, halo(C$_{1-3}$)alkyl, (C$_{1-3}$)alkoxy, halo(C$_{1-3}$)alkoxy, and halogen;
n is 0, 1, 2 or 3;
m is 1;
p is 0, 1, 2 or 3; and
q is 0, 1, or 2.

2. The compound of claim 1 wherein X is
(1) bond, or
(2) $(C_{1-2})$alkyl;
or a pharmaceutically acceptable salt thereof.

3. The compound of claim 1 wherein X is a bond; or a pharmaceutically acceptable salt thereof.

4. The compound of claim 1 wherein
$R^2$ is
(1) hydroxy,
(2) COOH, or
(3) tetrazole;
or a pharmaceutically acceptable salt thereof.

5. The compound of claim 1 wherein $R^2$ is COOH; or a pharmaceutically acceptable salt thereof.

6. The compound of claim 1 wherein $R^3$ is
(1) hydrogen,
(2) halogen, or
(3) $(C_{1-3})$alkyl;
or a pharmaceutically acceptable salt thereof.

7. The compound of claim 1 wherein $R^3$ is
(1) hydrogen, or
(2) halogen;
or a pharmaceutically acceptable salt thereof.

8. The compound of claim 1 wherein $R^4$ is
(1) hydrogen, or
$(C_{1-3})$alkyl;
or a pharmaceutically acceptable salt thereof.

9. The compound of claim 1 wherein $R^4$ is hydrogen; or a pharmaceutically acceptable salt thereof.

10. The compound of claim 1 wherein $R^5$ is
(1) cyano,
(2) (C1-3)alkyl,
(3) halo(C1-3)alkyl,
(4) (C1-3)alkoxy, or
(5) halogen;
or a pharmaceutically acceptable salt thereof.

11. The compound of claim 1 wherein $R^5$ is
(1) cyano, or
(2) halogen;
or a pharmaceutically acceptable salt thereof.

12. The compound of claim 1 wherein $R^6$ is
(1) halo$(C_{1-3})$alkoxy,
(2) halo$(C_{1-3})$alkyl,
(3) $(C_{3-6})$cycloalkyl,
(4) $(C_{3-6})$cycloalkyl-O-,
(5) $(C_{3-6})$cycloalkyl-S-,
(6) $(C_{3-6})$cycloalkyl-$(C_{1-2})$alkyl-,
(7) phenyl,
(8) 5- to 6-membered heteroaryl-O- wherein the heteroaryl contains 1, 2, or 3 heteroatoms independently selected from N, O and S, or
(9) 5- to 6-membered heteroaryl- wherein the heteroaryl contains 1, 2, or 3 heteroatoms independently selected from N, O and S,
wherein alkyl, cycloalkyl, phenyl and heteroaryl are unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen; or a pharmaceutically acceptable salt thereof.

13. The compound of claim 1 wherein $R^6$ is $(C_{3-6})$ cycloalkyl-O-, wherein cycloalkyl is unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen; or a pharmaceutically acceptable salt thereof.

14. A compound according to the formula I:

wherein:
X is
(1) a bond, or
(2) $(C_{1-2})$alkyl;
ring A is phenyl, pyridine, pyrimidine, pyrazole, pyrazine, isothiaozole, or benzisoxazole;
$R^1$ is $R^2$ is
(1) hydroxy,
(2) COOH, or
(3) tetrazole;
$R^3$ is
(1) hydrogen,
(2) halogen, or
(3) $(C_{1-3})$alkyl;
$R^4$ is
(1) hydrogen, or
(2) $(C_{1-3})$alkyl;
$R^5$ is
(1) cyano,
(2) $(C_{1-3})$alkyl,
(3) halo$(C_{1-3})$alkyl,
(4) $(C_{1-3})$alkoxy, or
(5) halogen;
$R^6$ is
(1) halo$(C_{1-3})$alkoxy,
(2) halo$(C_{1-3})$alkyl,
(3) $(C_{3-6})$cycloalkyl,
(4) $(C_{3-6})$cycloalkyl-O-,
(5) $(C_{3-6})$cycloalkyl-S-,
(6) $(C_{3-6})$cycloalkyl-$(C_{1-2})$alkyl-,
(7) phenyl,
(8) 5- to 6-membered heteroaryl-O- wherein the heteroaryl contains 1, 2, or 3 heteroatoms independently selected from N, O and S, or
(9) 5- to 6-membered heteroaryl- wherein the heteroaryl contains 1, 2, or 3 heteroatoms independently selected from N, O and S, wherein alkyl, cycloalkyl, phenyl and heteroaryl are unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen;
n is 0, 1, 2 or 3;
m is 1;
p is 0, 1, 2 or 3; and
q is 0, 1, or 2, or a pharmaceutically acceptable salt thereof.

15. A compound according to the formula I:

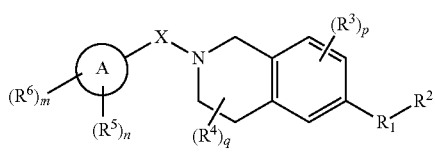

wherein:
X is a bond;
ring A is aryl;
$R^1$ is $(C_{1-6})$alkyl;
$R^2$ is COOH;
$R^3$ is
 (1) hydrogen, or
 (2) halogen;
$R^4$ is hydrogen;
$R^5$ is
 (1) cyano, or
 (2) halogen;
$R^6$ is $(C_{3-6})$cycloalkyl-O-, wherein cycloalkyl is unsubstituted or substituted with 1-3 substituents selected from $(C_{1-3})$alkyl, halo$(C_{1-3})$alkyl, $(C_{1-3})$alkoxy, halo$(C_{1-3})$alkoxy, and halogen;
n is 0, 1, 2 or 3;
m is 1;
p is 0, 1, 2 or 3; and
q is 0, 1, or 2, or a pharmaceutically acceptable salt thereof.

16. A compound selected from the group consisting of:
1) 3-(2-(2-chloro-5-cyclobutoxy-4-methoxyphenyl)-1,2,3,4-tetrahydroisoquinolin-6-yl)-propanoic acid;
2) 3-(2-(3-(difluoromethyl)-2-fluoro-5-(pyridin-2-yloxy)phenyl)-1,2,3,4-tetra-hydro-isoquinolin-6-yl)propanoic acid;
3) 3-(2-(2,3-difluoro-5-(3-methoxycyclobutoxy)phenyl)-1,2,3,4-tetrahydroiso-quinolin-6-yl)-propanoic acid;
4) 3-(2-(2-fluoro-4-methoxy-5-((5-methylthiazol-2-yl)oxy)phenyl)-1,2,3,4-tetra-hydroisoquinolin-6-yl)propanoic acid;
5) 3-(2-(6-cyclobutoxy-3-fluoropyridin-2-yl)-1,2,3,4-tetrahydroisoquinolin-6- yl)-propanoic acid;
6) 3-(2-(5-cyclobutoxy-2-fluorophenyl)-1-methyl-1,2,3,4-tetrahydroisoquinolin-6-yl)-propanoic acid;
7) 3-(2-(2-fluoro-5-(trifluoromethoxy)phenyl)-1,2,3,4-tetrahydroisoquinolin-6-yl) butanoic acid;
8) 3-(2-(2-fluoro-5-(trifluoromethoxy)phenyl)-1,2,3,4-tetrahydro-isoquinolin-6-yl)-butanoic acid;
9) 3-(2-{3-chloro-2-fluoro-5-[(5-methyl- 1,3-thiazol-2-yl)oxy]phenyl}-1,2,3,4-tetrahydro- isoquinolin-6-yl) propanoic acid;
10) 3- {2- [5-(cyclobutyloxy)-3-(difluoromethyl)-2-fluorophenyl]-1,2,3,4-tetrahydro-isoquinolin-6-yl}propanoic acid;
11) 3- {2- [5-(cyclobutyloxy)-2,3-difluorophenyl]-1,2,3,4-tetrahydroisoquinolin- 6-yl}-propanoic acid;
12) 3- {2- [3-cyano-5-(cyclobutyloxy)-2-fluorophenyl]-1,2,3,4-tetrahydroisoquinolin-6-yl}-propanoic acid;
13) 3- {2-[2-fluoro-3-methoxy-5-(trifluoromethoxy)phenyl]-1,2,3,4-tetrahydro-isoquinolin-6-yl}propanoic acid;
14) 3-(2- {3-(difluoromethyl)-2-fluoro-5-[(5-methyl- 1,3-thiazol-2-yl)oxy]phenyl}-1,2,3,4-tetrahydroisoquinolin-6-yl) propanoic acid;
15) 3- {2- [3-chloro-2-fluoro-5-(trifluoromethoxy)phenyl]-1,2,3,4-tetrahydroiso-quinolin-6-yl}propanoic acid;
16) 3-(2- {3-(difluoromethyl)-2-fluoro-5-[(5-methylpyridin-2-yl)oxy]phenyl-1,2,3,4-tetrahydroisoquinolin-6-yl}propanoic acid;
17) 3-(2-{2-fluoro-3-methoxy-5-[(5-methyl-1,3-thiazol-2-yl)oxy]phenyl}-1,2,3,4-tetrahydroisoquinolin-6-yl) propanoic acid;
18) 3-{2-[5-(cyclobutyloxy)-2-fluoro-3-methoxyphenyl]-1,2,3,4-tetrahydroiso-quinolin-6-yl}propanoic acid;
19) 3-{2- [5-(cyclobutyloxy)-2-fluorophenyl]-1,2,3,4-tetrahydroisoquinolin-6-yl}propanoic acid;
20) 3-(2-{2,3-difluoro-5-[(trans-3-methoxycyclobutyl)oxy]phenyl}-1,2,3,4-tetrahydro-isoquinolin-6-yl)propanoic acid;
21) 3-(2-{2-fluoro-4-methoxy-5-[(5-methyl-1,3-thiazol-2-yl)oxy]phenyl}-1,2,3,4-tetrahydroisoquinolin-6-yl) propanoic acid;
22) 3-{2- [4-chloro-3-methyl-1-(4-methylphenyl)-1H-pyrazol-5-yl]-1,2,3,4-tetra-hydroisoquinolin-6-yl}propanoic acid;
23) 3-{2- [5-(cyclobutylmethyl)-2-fluorophenyl]-5-fluoro-1,2,3,4-tetrahydroiso-quinolin-6-yl}propanoic acid;
24) 3-{2-[2-chloro-5-(cyclobutyloxy)-4-methoxyphenyl]-1,2,3,4-tetrahydroiso-quinolin-6-yl}propanoic acid;
25) 3-{2-[6-(cyclobutyloxy)-3-fluoropyridin-2-yl]-1,2,3,4-tetrahydroisoquinolin-6-yl}-propanoic acid;
26) 3-{2- [2-(cyclobutylsulfanyl)-5-fluoropyridin-4-yl]-1,2,3,4-tetrahydroisoquinolin-6-yl}-propanoic acid;
27) 3-{2-[2-fluoro-5-(trifluoromethoxy)phenyl]-1,2,3,4-tetrahydroisoquinolin-6-yl}-propanoic acid;
28) 3-(2-{2-fluoro-4-methoxy-5-[(5-methylpyridin-2-yl)oxy]phenyl }-1,2,3,4-tetrahydroisoquinolin-6-yl) propanoic acid;
29) 3-{2-[6-fluoro-3-(trifluoromethyl)-1,2-benzisoxazol-5-yl]-1,2,3,4-tetra-hydroisoquinolin-6-yl}propanoic acid;
30) 3-{7-fluoro-2-[2-fluoro-5-(trifluoromethoxy)phenyl]-1,2,3,4-tetrahydroiso-quinolin-6-yl}propanoic acid;
31) 3-{2- [5-(cyclobutyloxy)-2-fluoro-4-methoxyphenyl]-1,2,3,4-tetrahydroiso-quinolin-6-yl}propanoic acid;
32) 3-{2-[5-(cyclobutyloxy)-2,3-difluorophenyl]-1-methyl-1,2,3,4-tetrahydro-isoquinolin-6- yl}propanoic acid;
33) 3-{2-[2-fluoro-5-(pyrazin-2-yloxy)phenyl]-1,2,3,4-tetrahydroisoquinolin-6-yl}propanoic acid;
34) 3-(2-{3-cyano-2-fluoro-5- [(trans-3-methoxycyclobutyl)oxy]phenyl}1-1,2,3,4-tetrahydro- isoquinolin-6-yl) propanoic acid;
35) 3-(2-{3-(difluoromethyl)-2-fluoro-5-[(5-fluoropyridin-2-yl)oxy]phenyl}-1,2,3,4-tetrahydroisoquinolin-6-yl) propanoic acid;

36) 3-{2-[5-(cyclobutyloxy)-2-fluorophenyl]-1-methyl-1,2,3,4-tetrahydroisoquinolin-6-yl}-propanoic acid;
37) 3-{2-[2-chloro-5-(cyclobutyloxy)-3-fluorophenyl]-1-methyl-1,2,3,4-tetrahydro-isoquinolin-6-yl}propanoic acid;
38) 3-{2-[6-(cyclobutylsulfanyl)pyridin-2-yl]-1,2,3,4-tetrahydroisoquinolin-6-yl}-propanoic acid;
39) 3- {2-[5-(cyclobutyloxy)-2-fluorophenyl]-1-methyl-1,2,3,4-tetrahydroisoquinolin-6-yl}-propanoic acid;
40) 3- {2-[3,5-dichloro-4-(trifluoromethyl)phenyl]-1,2,3,4-tetrahydroisoquinolin-6-yl}-propanoic acid;
41) 3-{2-[6-(cyclobutyloxy)pyrazin-2-yl]-1,2,3,4-tetrahydroisoquinolin-6-yl}-propanoic acid;
42) 3-{2-[2-cyano-5-(cyclobutyloxy)-4-methoxy phenyl]-1,2,3,4-tetrahydroiso-quinolin-6-yl}-propanoic acid;
43) 3- {2-[4-cyano-1-(4-methoxy phenyl)-3-methyl-1H-pyrazol-5-yl]-1,2,3,4-tetra-hydro-isoquinolin-6-yl}propanoic acid;
44) 3-{2-[2-cyano-3-fluoro-5-(trifluoromethoxy)phenyl]-1,2,3,4-tetrahydroiso-quinolin-6-yl}propanoic acid;
45) 3-{2-[2-chloro-5-(cyclobutyloxy)-3-fluorophenyl]-1,2,3,4-tetrahydroisoquinolin-6-yl}-propanoic acid;
46) 3-{2-[2-cyano-5-(cyclobutyloxy)phenyl]-1,2,3,4-tetrahydroisoquinolin-6-yl}propanoic acid;
47) 3-{2-[4-fluoro-3-methyl-1-(4-methylphenyl)-1H-pyrazol-5-yl]-1,2,3,4-tetra-hydroisoquinolin-6-yl}propanoic acid;
48) 3-(2-{12-cyano-5-[(trans-3-methoxycyclobutyl)oxy]phenyl}-1,2,3,4-tetra-hydroisoquinolin-6-yl)-propanoic acid;
49) 3- {2- [5-(cyclobutyloxy)-2,3-difluorophenyl]-1-methyl-1,2,3,4-tetrahydro-isoquinolin-6- yl}-propanoic acid;
50) 3-(2-{[3-(4-chlorophenyl)-5-(trifluoromethyl)isothiazol-4-yl]methyl}-1,2,3,4-tetrahydroisoquinolin-6-yl) propanoic acid;
51) 3-{8-fluoro-2-[2-fluoro-5-(trifluoromethoxy)phenyl]-1,2,3,4-tetrahydroiso-quinolin-6-yl}propanoic acid;
52) 3-{2-[2-fluoro-5-(trifluoromethoxy)phenyl]-1,2,3,4-tetrahydroisoquinolin-6-yl}-2-methyl-propanoic acid;
53) 3-{2-[2-fluoro-5-(trifluoromethoxy)phenyl]-1,2,3,4-tetrahydroisoquinolin-6-yl}-butanoic acid;
54) 3- {2- [3-chloro-5-(cyclobutyloxy)-2-fluorophenyl]-1,2,3,4-tetrahydroisoquinolin-6-yl}-propanoic acid;
55) 3- {2-[2-cyano-5-(cyclobutyloxy)-3-fluorophenyl]-1,2,3,4-tetrahydroisoquinolin-6-yl}-propanoic acid;
56) 3-(2-(5-(cyclobutyldifluoromethyl)-2-fluorophenyl)-5-fluoro-1,2,3,4-tetra-hydroisoquinolin-6-yl)propanoic acid;
57) 3-(2-(3-chloro-2-fluoro-5-(trifluoromethoxy)phenyl)-5-fluoro-1,2,3,4-tetra-hydroisoquinolin-6-yl)-2-methylpropanoic acid;
58) 3-(5-fluoro-2-(2-fluoro-5-(trifluoromethoxy)phenyl)-7-methyl-1,2,3,4-tetra-hydroisoquinolin-6-yl)propanoic acid;
59) 3-(2-(3-(4-chlorophenyl)-5-(trifluoromethyl)isothiazol-4-yl)-5-fluoro-1,2,3,4-tetra-hydro-isoquinolin-6-yl)propanoic acid;
60) 3-(2-(5-(cyclobutylmethyl)-2-fluorophenyl)-5-fluoro-1,2,3,4-tetrahydroiso-quinolin-6-yl)-propanoic acid;
61) 3-(2-(5-cyclobutoxy-2-fluorophenyl)-5-fluoro-1,2,3,4-tetrahydroisoquinolin-6-yl)-propanoic acid;
62) 3-(2-{3-chloro-2-fluoro-5-[(5-methyl-1,3-thiazol-2-yl)oxy]phenyl}-5-fluoro-1,2,3,4-tetrahydroisoquinolin-6-yl)propanoic acid;
63) 3- {2- [6-(cyclobutyloxy)-3-fluoropyridin-2-yl]-5-fluoro-1,2,3,4-tetrahydro-isoquinolin-6-yl}propanoic acid;
64) 3- {2- [5-(cyclobutyloxy)-2,3-difluorophenyl]-5-fluoro-1,2,3,4-tetrahydroiso-quinolin-6-yl}propanoic acid;
65) 3-{2-[3-chloro-2-fluoro-5-(trifluoromethoxy)phenyl]-5-fluoro-1,2,3,4-tetra-hydroisoquinolin-6-yl}propanoic acid;
66) 3-(2- {2,3-difluoro-5- [(trans-3-methoxycyclobutyl)oxy]phenyl}-5-fluoro-1,2,3,4-tetra- hydroisoquinolin-6-yl)propanoic acid;
67) 3-(2-{5-[cyclobutyl(difluoro)methyl]-2-fluorophenyl}-5-fluoro-1,2,3,4-tetrahydroisoquinolin-6-yl) propanoic acid;
68) 3-{2-[3-chloro-2-fluoro-5-(trifluoromethoxy)phenyl]-5-fluoro-1,2,3,4-tetrahydroisoquinolin-6-yl}-2-methylpropanoic acid;
69) 3-{2-[3-chloro-2-fluoro-5-(trifluoromethoxy)phenyl]-5-fluoro-1,2,3,4-tetrahydroisoquinolin-6-yl}-2-methylpropanoic acid;
70) 3-{5-fluoro-2-[2-fluoro-5-(trifluoromethoxy)phenyl]-7-methyl-1,2,3,4-tetra-hydro-isoquinolin-6-yl}propanoic acid;
71) 3-{2 [4-chloro-3-methyl-1-(4-methylphenyl)-1H-pyrazol-5-yl]-5-fluoro-1,2,3,4-tetra-hydroisoquinolin-6-yl}propanoic acid;
72) 3-{5-chloro-2-[2-fluoro-5-(trifluoromethoxy)phenyl]-1,2,3,4-tetrahydro-isoquinolin-6- yl}propanoic acid;
73) 3-{2 [3-(4-chlorophenyl)-5-(trifluoromethyl)isothiazol-4-yl]-5-fluoro-1,2,3,4-tetrahydro-isoquinolin-6-yl}propanoic acid;
74) 3-{2 [5-(cyclobutylmethyl)-2-fluorophenyl]-fluoro-1,2,3,4-tetrahydro-isoquinolin-6-yl}propanoic acid;
75) 3 [2-(5-{[3-(difluoromethyl)cyclobutyl]oxy}-2,3-difluorophenyl)-5-fluoro-1,2,3,4-tetra- hydroisoquinolin-6-yl]propanoic acid;
76) 3-{2-[2-cyano-5-(cyclobutyloxy)phenyl]-5-fluoro-1,2,3,4-tetrahydroisoquinolin-6-yl}propanoic acid;
77) 3-{5-fluoro-2-[2-fluoro-5-(trifluoromethoxy)phenyl]-1,2,3,4-tetrahydroiso-quinolin-6-yl}-2-methylpropanoic acid;
78) 3-{2-[2-cyano-5-(trifluoromethoxy)phenyl]-5-fluoro-1,2,3,4-tetrahydroiso-quinolin-6-yl}propanoic acid;
79) 3-(2-(2-cyano-5-cyclobutoxy-3-fluorophenyl)-5-fluoro-1,2,3,4-tetrahydro-isoquinolin-6- yl)-2-methyl-propanoic acid;
80) 3-{5-fluoro-2-[2-fluoro-5-(trifluoromethoxy)phenyl]-1,2,3,4-tetrahydroiso-quinolin-6-yl}propanoic acid;
81) 3-{2- [5-(cyclobutyloxy)-2-fluorophenyl]-5-fluoro-1,2,3,4-tetrahydroisoquinolin-6-yl}-propanoic acid;
82) 3-{2- [2-cyano-5-(cyclobutyloxy)-3-fluorophenyl]-1,2,3,4-tetrahydroisoquinolin-6-yl}-propanoic acid;
83) (1S,2S)-2-(2-(2,3-difluoro-5-((1R,3S)-3-methylcyclobutoxy)phenyl)-1,2,3,4-tetrahydro- isoquinolin-6-yl)cyclopropanecarboxylic acid;
84) 2-(2-(2-fluoro-5-(trifluoromethoxy)phenyl)-1,2,3,4-tetrahydroisoquinolin-6-yl)-cyclo-propanecarboxylic acid;
85) (1R,2R)-2-{2-[5-(cyclobutyloxy)-2,3-difluorophenyl]-1,2,3,4-tetrahydroiso-quinolin-6-yl}cyclopropane- carboxylic acid;
86) (1R,2R)-2-{2-[3-chloro-5-(cyclobutyloxy)-2-fluorophenyl]-1,2,3,4-tetra-hydroisoquinolin-6-yl}cyclopropanecarboxylic acid;

87) (1R,2R)-2-{2-[2-fluoro-5-(trifluoromethoxy)phenyl]-1,2,3,4-tetrahydroiso-quinolin-6-yl}cyclopropanecarboxylic acid;
88) (1S,2S)-2-{2-[2-fluoro-5-(trifluoromethoxy)phenyl]-1,2,3,4-tetrahydroiso-quinolin-6-yl}cyclopropanecarboxylic acid;
89) (1R,2R)-2-(2-{3-cyano-2-fluoro-5-[(trans-3-methoxycyclobutyl)oxy]phenyl}-1,2,3,4-tetrahydroisoquinolin-6-yl)cyclopropanecarboxylic acid;
90) (1S,2S)-2-{2-[2-fluoro-5-(trifluoromethoxy)benzyl]-1,2,3,4-tetrahydroiso-quinolin-6-yl}cyclopropanecarboxylic acid;
91) (1S,2S)-2-{2-[3-chloro-5-(cyclobutyloxy)-2-fluorophenyl]-1,2,3,4-tetra-hydroisoquinolin-6-yl}cyclopropanecarboxylic acid;
92) 2-{2-[4-fluoro-1-(4-fluorophenyl)-3-methyl-1H-pyrazol-5-yl]-1,2,3,4-tetra-hydroisoquinolin-6-yl}cyclopropanecarboxylic acid;
93) (1S,2S)-2-{2-[3-chloro-2-fluoro-5-(trifluoromethyl)benzyl]-1,2,3,4-tetra-hydroisoquinolin-6-yl}cyclopropanecarboxylic acid;
94) 2-{2-[4-fluoro-3-methyl-1-(4-methylphenyl)-1H-pyrazol-5-yl]-1,2,3,4-tetra-hydroisoquinolin-6-yl}cyclopropanecarboxylic acid;
95) 2-{2-[4-fluoro-1-(4-fluorophenyl)-3-methyl-1H-pyrazol-5-yl]-1,2,3,4-tetra-hydroisoquinolin-6-yl}cyclopropanecarboxylic acid;
96) 2-{2-[4-fluoro-3-methyl-1-(4-methylphenyl)-1H-pyrazol-5-yl]-1,2,3,4-tetrahydroisoquinolin-6-yl}cyclopropanecarboxylic acid;
97) (1S,2S)-2-(2-{2-cyano-3-methoxy-5-[(trans-3-methoxycyclobutyl)oxy]-phenyl}-1,2,3,4-tetrahydroisoquinolin-6-yl)cyclopropanecarboxylic acid;
98) (1S,2S)-2-(2-{2,3-difluoro-5-[(trans-3-methylcyclobutyl)oxy]phenyl}-1,2,3,4-tetra-hydroisoquinolin-6-yl) cyclopropanecarboxylic acid;
99) (1R,2R)-2-(2-{2,3-difluoro-5-[(trans-3-methoxycyclobutyl)oxy]phenyl}-1,2,3,4-tetrahydroisoquinolin-6-yl)cyclopropanecarboxylic acid;
100) (1S,2S)-2-(2-{2,3-difluoro-5-[(trans-3-methoxycyclobutyl)oxy]phenyl}-1,2,3,4-tetrahydroisoquinolin-6-yl)cyclopropanecarboxylic acid;
101) (1R,2R)-2-(2-{2,3-difluoro-5-[(trans-3-methylcyclobutyl)oxy]phenyl}-1,2,3,4-tetrahydroisoquinolin-6-yl)cyclopropanecarboxylic acid;
102) 2-{2-[2-fluoro-5-(trifluoromethoxy)phenyl]-1,2,3,4-tetrahydroisoquinolin-6-yl}-cyclopropanecarboxylic acid;
103) (1R,2R)-2-(2-{2-cyano-3-fluoro-5-[(trans-3-methoxycyclobutyl)oxy]phenyl}-1,2,3,4-tetrahydroisoquinolin-6-yl)cyclopropanecarboxylic acid;
104) 2-{2-[3-chloro-2-fluoro-5-(trifluoromethoxy)phenyl]-1,2,3,4-tetrahydroiso-quinolin-6-yl}cyclopropanecarboxylic acid;
105) 2-{2-[3-chloro-2-fluoro-5-(trifluoromethoxy)phenyl]-1,2,3,4-tetrahydroiso-quinolin-6-yl}cyclopropanecarboxylic acid;
106) (1S,2S)-2-(2-(2,3-difluoro-5-((1r,3S)-3-methoxycyclobutoxy)phenyl)-5-fluoro-1,2,3,4-tetrahydroisoquinolin-6-yl)cyclopropanecarboxylic acid;
107) (1S,2S)-2-(2-(3-cyano-2-fluoro-5-(trifluoromethoxy)phenyl)-5-fluoro-1,2,3,4-tetrahydroisoquinolin-6-yl)cyclopropanecarboxylic acid;
108) (1S,2S)-2-(2-(2,3-difluoro-5-((1r,3S)-3-methylcyclobutoxy)phenyl)-4-fluoro-1,2,3,4-tetrahydroisoquinolin-6-yl)cyclopropanecarboxylic acid;
109) (1R,2R)-2-{2-[3-cyano-2-fluoro-5-(trifluoromethoxy)phenyl]-5-fluoro-1,2,3,4-tetrahydroisoquinolin-6-yl}cyclopropanecarboxylic acid;
110) (1R,2R)-2-(2-{2,3-difluoro-5-[(trans-3-methoxycyclobutyl)oxy]phenyl}-5-fluoro-1,2,3,4-tetrahydroisoquinolin-6-yl)cyclopropanecarboxylic acid;
111) (1R,2R)-2-{2-[3-chloro-2-fluoro-5-(trifluoromethoxy)phenyl]-5-fluoro-1,2,3,4-tetra-hydroisoquinolin-6-yl}cyclopropanecarboxylic acid;
112) (1R,2R)-2-(2-{2,3-difluoro-5-[(trans-3-methylcyclobutyl)oxy]phenyl}-5-fluoro-1,2,3,4-tetrahydroisoquinolin-6-yl)cyclopropanecarboxylic acid;
113) (1R,2R)-2-{5-fluoro-2-[2-fluoro-5-(trifluoromethoxy)phenyl]-1,2,3,4-tetrahydro-isoquinolin-6-yl}cyclopropanecarboxylic acid;
114) (1R,2R)-2-{2-[3-chloro-5-(cyclobutyloxy)-2-fluorophenyl]-1,2,3,4-tetra-hydroisoquinolin-6-yl}cyclopropanecarboxylic acid;
115) (1S,2S)-2-(2-{2,3-difluoro-5-[(trans-3-methoxycyclobutyl)oxy]phenyl}-5-fluoro-1,2,3,4-tetrahydroisoquinolin-6-yl)cyclopropanecarboxylic acid;
116) (1S,2S)-2-{2-[3-cyano-2-fluoro-5-(trifluoromethoxy)phenyl]-5-fluoro-1,2,3,4-tetrahydroisoquinolin-6-yl}cyclopropanecarboxylic acid;
117) (1S,2S)-2-{2-[2-cyano-5-(trifluoromethoxy)phenyl]-5-fluoro-1,2,3,4-tetra-hydroisoquinolin-6-yl}cyclopropanecarboxylic acid;
118) (1S,2S)-2-{5-fluoro-2-[2-fluoro-5-(trifluoromethoxy)phenyl]-1,2,3,4-tetrahydro-isoquinolin-6-yl}cyclopropanecarboxylic acid;
119) (1S,2S)-2-{2-[2-cyano-3-methoxy-5-(trifluoromethoxy)phenyl]-5-fluoro-1,2,3,4-tetrahydroisoquinolin-6-yl}cyclopropanecarboxylic acid;
120) (1S,2S)-2-{2-[3-chloro-2-fluoro-5-(trifluoromethoxy)phenyl]-5-fluoro-1,2,3,4-tetrahydroisoquinolin-6-yl}cyclopropanecarboxylic acid;
121) (1R,2R)-2-{2-[2-chloro-3-fluoro-5-(trifluoromethoxy)phenyl]-5-fluoro-1,2,3,4-tetrahydroisoquinolin-6-yl}cyclopropanecarboxylic acid;
122) (1S,2S)-2-(2-{2,3-difluoro-5-[(trans-3-methylcyclobutyl)oxy]phenyl}-5-fluoro-1,2,3,4-tetrahydroisoquinolin-6-yl)cyclopropanecarboxylic acid;
123) (1R,2R)-2-{2-[3-chloro-5-(cyclobutyloxy)-2-fluorophenyl]-5-fluoro-1,2,3,4-tetra hydroisoquinolin-6-yl}cyclopropanecarboxylic acid;
124) (1S,2S)-2-{2-[2-chloro-3-fluoro-5-(trifluoromethoxy)phenyl]-5-fluoro-1,2,3,4-tetrahydroisoquinolin-6-yl}cyclopropanecarboxylic acid;
125) (1S,2S)-2-{2-[3-chloro-5-(cyclobutyloxy)-2-fluorophenyl]-5-fluoro-1,2,3,4-tetrahydroisoquinolin-6-yl}cyclopropanecarboxylic acid;
126) (1S,2S)-2-{2-[2-cyano-5-(cyclobutyloxy)-3-fluorophenyl]-5-fluoro-1,2,3,4-tetrahydroisoquinolin-6-yl}cyclopropanecarboxylic acid;
127) 5-(2-(4-cyano-3-methyl-1-(p-tolyl)-1H-pyrazol-5-yl)-1,2,3,4-tetrahydro-isoquinolin-6-yl)pentanoic acid;
128) 5-(2-(4-cyano-3-methyl-1-(p-tolyl)-1H-pyrazol-5-yl)-1,2,3,4-tetrahydroiso-quinolin-6-yl)hexanoic acid;
129) 5-(6-hydroxy-3,4-dihydroisoquinolin-2(1H)-yl)-3-methyl-1-(p-tolyl)-1H-pyrazole-4-carbonitrile;
130) 5-(6-(2-hydroxyethoxy)-3,4-dihydroisoquinolin-2(1H)-yl)-3-methyl-1-(p-tolyl)-1H-pyrazole-4-carbonitrile;
131) 3-(2-(5-cyclobutoxy-2,3-difluorophenyl)-7-fluoro-1,2,3,4-tetrahydroiso-quinolin-6-yl)-propanoic acid;

132) 6-(2-(1H-tetrazol-5-yl)ethyl)-2-(2,3-difluoro-5-((1r,3r)-3-methoxylcyclo-butoxy)-phenyl)-1,2,3,4-tetrahydroisoquinoline;

133) 5-{2-[4-cyano-1-(4-methoxyphenyl)-3-methyl-1H-pyrazol-5-yl]-1,2,3,4-tetrahydro-isoquinolin-6-yl}pentanoic acid;

134) 5-{2-[4-cyano-3-methyl-1-(4-methylphenyl)-1H-pyrazol-5-yl]-1,2,3,4-tetra-hydroisoquinolin-6-yl}pentanoic acid;

135) 5-{2-[2-fluoro-5-(trifluoromethoxy)phenyl]-1,2,3,4-tetrahydroisoquinolin-6-yl}-pentanoic acid;

136) 5-[6-(2-hydroxyethoxy)-3,4-dihydroisoquinolin-2(1H)-yl]-3-methyl-1-(4-methylphenyl)-1H-pyrazole-4-carbonitrile;

137) 5-{2-[4-chloro-3-methyl-1-(4-methylphenyl)-1H-pyrazol-5-yl]-1,2,3,4-tetra-hydroisoquinolin-6-yl}pentanoic acid;

138) 5-(6-hydroxy-3,4-dihydroisoquinolin-2(1H)-yl)-3-methyl-1-(4-methylphenyl)-1H-pyrazole-4-carbonitrile;

139) 5-[6-(4-hydroxybutoxy)-3,4-dihydroisoquinolin-2(1H)-yl]-3-methyl-1-(4-methylphenyl)-1H-pyrazole-4-carbonitrile;

140) 5-{2-[4-cyano-3-methyl-1-(4-methylphenyl)-1H-pyrazol-5-yl]-1,2,3,4-tetrahydro-isoquinolin-6-yl}hexanoic acid;

141) 5-(3,4-dihydroisoquinolin-2(1H)-yl)-1-(4-methoxyphenyl)-3-methyl-1H-pyrazole-4-carbonitrile;

142) 5-{2-[4-cyano-3-methyl-1-(4-methylphenyl)-1H-pyrazol-5-yl]-1,2,3,4-tetrahydro-isoquinolin-6-yl}hexanoic acid;

143) 3-(2-1[4-fluoro-3-methyl-1-(4-methyl phenyl)-1H-pyrazol-5-yl]methyl}-1,2,3,4-tetrahydroisoquinolin-6-yl) propanoic acid;

144) 5-[6-(3-hydroxypropoxy)-3,4-dihydroisoquinolin-2(1H)-yl]-3-methyl-1-(4-methylphenyl)-1H-pyrazole-4-carbonitrile;

145) 3-2-[5-(cyclobutyloxy)-2,3-difluorophenyl]-7-fluoro-1,2,3,4-tetrahydroiso-quinolin-6-yl}propanoic acid;

146) 3-2-[4-chloro-3-methyl-1-(4-methylphenyl)-1H-pyrazol-5-yl]-5-fluoro-1,2,3,4-tetrahydro- isoquinolin-6-yl}propanoic acid;

147) 3-2-[3-chloro-2-cyano-5-(cyclobutyloxy)phenyl]-5-fluoro-1,2,3,4-tetra-hydroisoquinolin-6-yl}propanoic acid;

148) 3-{2-[5-cyano-4-(cyclobutyloxy)-6-methylpyrimidin-2-yl]-5-fluoro-1,2,3,4-tetrahydroisoquinolin-6-yl}propanoic acid;

149) 3-{2-[5-cyano-2-(cyclobutyloxy)-6-methylpyrimidin-4-yl]-5-fluoro-1,2,3,4-tetrahydroisoquinolin-6-yl}propanoic acid;

150) 3-{5-chloro-2-[2-cyano-5-(cyclobutyloxy)-3-fluorophenyl]-1,2,3,4-tetra-hydroisoquinolin-6-yl}propanoic acid;

151) 342-(6-cyclopropylpyridin-2-yl)-5-fluoro-1,2,3,4-tetrahydroisoquinolin-6-yl}-propanoic acid;

152) 3-{2-[2-cyano-5-(cyclobutyloxy)-3-fluorophenyl]-5-fluoro-1,2,3,4-tetra-hydroisoquinolin-6-yl}propanoic acid;

153) 3-{2-[2,3-dichloro-5-(trifluoromethoxy)phenyl]-1,2,3,4-tetrahydroisoquinolin-6-yl}propanoic acid;

154) 3-{2-[2-cyano-5-(cyclobutyloxy)-3-fluorophenyl]-5-methyl-1,2,3,4-tetra-hydroisoquinolin-6-yl}propanoic acid;

155) 3-{2-[6-(cyclobutyloxy)-3-fluoro-4-methoxypyridin-2-yl]-5-fluoro-1,2,3,4-tetrahydroisoquinolin-6-yl}propanoic acid;

156) 3-{2-[3-cyano-6-(cyclobutyloxy)-2-methylpyridin-4-yl]-5-fluoro-1,2,3,4-tetrahydroisoquinolin-6-yl}propanoic acid; and 157) 3-{2-[3-cyano-4-methyl-6-(1,3-thiazol-4-yl)pyridin-2-yl]-5-fluoro-1,2,3,4-tetrahydroisoquinolin-6-yl}propanoic acid;

or a pharmaceutically acceptable salt thereof.

17. A pharmaceutical composition comprising a compound of claim 1 in combination with a pharmaceutically acceptable carrier.

* * * * *